US006627624B1

(12) United States Patent
DeSimone et al.

(10) Patent No.: US 6,627,624 B1
(45) Date of Patent: Sep. 30, 2003

(54) ARYL FUSED AMINOALKYL-IMIDAZOLE DERIVATIVES: SELECTIVE MODULATORS OF GABAA RECEPTORS

(75) Inventors: Robert W. DeSimone, Durham, CT (US); Alan Hutchison, Madison, CT (US); Kenneth Shaw, Weston, CT (US); Daniel L. Rosewater, Golden, CO (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/541,797

(22) Filed: Mar. 31, 2000

Related U.S. Application Data

(60) Provisional application No. 60/127,526, filed on Apr. 2, 1999.

(51) Int. Cl.[7] ............... C07D 471/04; C07D 235/14; A61K 31/437; A61K 31/4184; A61P 25/00
(52) U.S. Cl. ............... 514/183; 546/19; 546/273.4; 546/144; 546/199; 540/480; 540/603; 548/200; 548/309.7; 548/304.7; 548/305.1; 514/278; 514/365; 514/394; 514/339; 514/322; 514/234.5; 514/217.09; 514/307; 514/228.2; 544/62; 544/139
(58) Field of Search ............... 546/19, 273.4, 546/199, 144; 514/278, 365, 394, 339, 322, 234.5, 217.09, 228.2, 183, 307; 548/200, 309.7, 304.7, 305.1; 544/139, 62; 540/603, 480

(56) References Cited

U.S. PATENT DOCUMENTS

| | | | |
|---|---|---|---|
| 3,255,202 A | 6/1966 | Johnson | 260/309.2 |
| 3,455,940 A | 7/1969 | Stecker | 260/295 |
| 3,905,990 A | 9/1975 | Ehrmann et al. | 260/309.2 |
| 3,941,788 A | 3/1976 | Hankovsky et al. | 260/256.4 |
| 3,995,044 A | * 11/1976 | Kabbe et al. | 424/263 |
| 5,066,576 A | 11/1991 | Ichijima et al. | 430/558 |
| 5,296,339 A | 3/1994 | Fujita et al. | 430/389 |
| 5,789,428 A | 8/1998 | Shibata et al. | 514/367 |
| 5,877,195 A | 3/1999 | Lukenheimer et al. | 514/394 |

FOREIGN PATENT DOCUMENTS

| | | |
|---|---|---|
| EP | 0 598 962 | 6/1994 |
| EP | 0 616 807 | 9/1994 |
| EP | 0 882 718 A | 12/1998 |
| FR | 1 501 151 | 10/1966 |
| JP | 7-133224 | 5/1995 |
| WO | WO 96/00730 | 1/1996 |
| WO | WO 96/33191 | 10/1996 |
| WO | WO 96/33194 | 10/1996 |
| WO | WO 96/39404 | 12/1996 |
| WO | WO 97/24119 | 7/1997 |
| WO | WO 98/17651 | 4/1998 |
| WO | WO 98/45295 | 10/1998 |
| WO | WO 99/37303 | 7/1999 |
| WO | WO 99/47131 | 9/1999 |
| WO | WO 99/47142 | 9/1999 |
| WO | WO 99/47171 | 9/1999 |

OTHER PUBLICATIONS

V.M. Aryuzina et al., "The Synthesis of Substitution Products of 4H–Imidazo[5,1–b]Benzimidazole, V*. Some Substitution Reactions of 1,4,–Dimethyl and 1–Phenyl–4–Methylimidazo[5,1–b]Benzimidazoles", *Chemistry of Heterocyclic Compounds*, 1970, vol. 4, pp. 526–528.
V.M. Aryuzina et al., "Synthesis of 4H–Imidazo[5,1–a] Benzimidazole Substituents, VIII*, Synthesis of 1–Phenyl–4–Benzylimidazo[5,1–a]Benzimidazole and Some of Its 3–Substituents", *Chemistry of Heterocyclic Compounds*, No. 3, 1973, pp. 395–397.
*Chemical Abstracts*, vol. 73, No. 17, abstract No. 87845h. (Oct. 26, 1970).
*Chemical Abstracts*, vol. 127, No. 3, abstract No. 34242m, col. 650. (Jul. 21, 1997).
Horvath et al., U.S. patent application Ser. No. 09/285,327, Filed Apr. 2, 1999. Abn.
DeSimone et al., U.S. patent application Ser. No. 09/285, 415, Filed Apr. 2, 1999. Abn.
DeSimone et al., U.S. patent application No. 09/285,357, Filed Apr. 2, 1999. Abn.
Cristos T.E. et al., "Corticotrophin–releasing factor receptor antagonists", *Expert Opinion on Therapeutic Patents*, vol. 8, No. 2, Feb. 1998, pp. 143–152, XP002109498.

* cited by examiner

*Primary Examiner*—Mukund J. Shah
*Assistant Examiner*—Hong Liu
(74) *Attorney, Agent, or Firm*—McDonnell Boehnen Hulbert & Berghoff

(57) ABSTRACT

Disclosed are compounds of the formula:

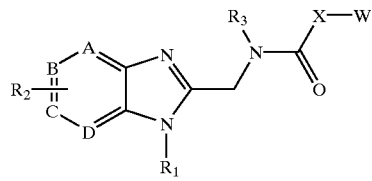

or the pharmaceutically acceptable non-toxic salts thereof wherein the A, B, C, D, X, $R_1$, $R_2$, $R_3$, $R_4$, $R_5$, and $R_6$, are variables defined herein, which compounds are highly selective agonists, antagonists or inverse agonists for GABAa brain receptors or prodrugs of agonists, antagonists or inverse agonists for GABAa brain receptors, and are therefore useful in the diagnosis and treatment of anxiety, Down Syndrome, sleep, cognitive and seizure disorders, depression, overdose with benzodiazepine drugs, and enhancement of memory and alertness.

33 Claims, No Drawings

ARYL FUSED AMINOALKYL-IMIDAZOLE DERIVATIVES: SELECTIVE MODULATORS OF GABAA RECEPTORS

This application claims the benefit of U.S. Provisional Application No. 60/127,526, filed Apr. 2, 1999.

FIELD OF THE INVENTION

This invention relates to certain aryl fused aminoalkylimidazole derivatives which when appropriately substituted selectively bind to $GABA_A$ receptors. This invention also relates to pharmaceutical compositions comprising such compounds and to the use of such compounds in enhancing alertness and treating anxiety, overdoses of benzodiazepine-type drugs, Down Syndrome, depression, sleep, seizure and cognitive disorders both in human as well as domestic pets and livestock.

The compounds of this invention are also useful as probes for the localization of cell surface receptors.

BACKGROUND

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when when used in combination with $GABA_A$ selective ligands than when used alone.

SUMMARY OF THE INVENTION

This invention relates to aryl fused aminoalkyl-derivatives. Preferred compounds of the invention that bind with high affinity to the benzodiazepine site of the $GABA_A$ receptor, including human $GABA_A$ receptors. Preferred compounds of the invention also bind with high selectivity to the benzodiazepine site of the $GABA_A$ receptor.

The invention provides compounds of Formula I (shown below), and pharmaceutical compositions comprising compounds of Formula I.

The invention further comprises methods of treating patients suffering from certain CNS disorders with an effective amount of a compound of the invention. The patient may be a human or other mammal. Treatment of humans, domesticated companion animals (pets) or livestock animals suffering such conditions with an effective amount of a compound of the invention is contemplated by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections. Such probes are useful for in vitro studies, such as binding assays and autoradiography of tissue sections and for in vivo techniques such as PET and SPECT scans.

Packaged pharmaceutical compositions including instructions for use of the composition are also included.

In a separate aspect, the invention provides a method of potentiating the actions of other CNS active compounds. This method comprises administering an effective amount of a compound of the invention with another CNS active compound.

The invention furthermore provides methods of using compounds of this invention as positive controls in assays for receptor activity and using appropriately labeled compounds of the invention as probes for the localization of receptors, particularly $GABA_A$ receptors, in tissue sections. Such probes are useful for in vitro studies, such as binding assays and autoradiography of tissue sections and for in vivo techniques such as PET and SPECT scans.

Accordingly, a broad embodiment of the invention is directed to compounds of Formula I:

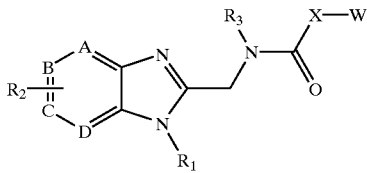

or the pharmaceutically acceptable non-toxic salts thereof wherein:

W represents

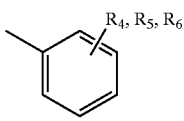 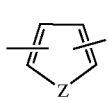 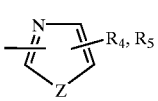

where Z is O, or S:

$R_1$ represents phenyl, $C_1$–$C_6$ alkyl, cyclopentyl, cyclohexyl, benzyl, 3-fluorobenzyl, or cyclopropylmethyl;

$R_2$ represents hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring;

$R_3$ represents $C_1$–$C_6$ alkyl, allyl, cyclopropylmethyl, cyclopentyl; or benzyl optionally mono-, di-, or trisubstituted independently with halogen, nitro, trifluoromethyl, trifluoromethoxy, cyano, hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring, additional substitution on the benzyl ring can be directly bound or $O(CH_2)_n$ (where n=1,2,3,4) linked $SO_2R_8$, $NHSO_2R_8$, $SO_2NHR_8$, $SO_2NHCOR_8$, $CONHSO_2R_8$, as well as tetrazole, triazole, imidazole, thiazole, oxazole, thiophene, and pyridyl;

$R_4$, $R_5$ and $R_6$ are the same or different and represent hydrogen, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring, $C_1$–$C_6$ alkylthio, or halogen, or $O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms, additionally $R_8$ and $R_9$ can be a 5,6,7 member heterocyclic ring, additionally $R_4$ and $R_5$ can form a 1,3-dioxolene ring;

X represents a bond, $CH_2$, or CHCH;

A,B,C,D are the same or different and represent CH or N with the proviso that not more than two of A,B,C, or D represent N.

Preferred compounds of the invention are highly selective agonists, antagonists or inverse agonists for $GABA_A$ brain receptors or prodrugs of agonists, antagonists or inverse agonists for GABAa brain receptors, the benzodiazepine receptor. These compounds are useful in the diagnosis and treatment of anxiety, Down Syndrome, depression, sleep and seizure disorders, cognitive disorders overdose with benzodiazepine drugs, and enhancement of alertness, both in human and non-human animals and domestic pets, especially dogs and cats and farm animals such as sheep, swine and cattle.

Thus, the invention also provides methods and compositions for treating and diagnosing anxiety, Down Syndrome, depression, sleep, cognitive and seizure disorders, and overdose with benzodiazepine drugs.

In another aspect, the invention encompasses compounds that are intermediates in the synthesis of the compounds of Formula I.

DETAILED DESCRIPTION OF THE INVENTION

The compounds encompassed by the instant invention are represented by the general formula I:

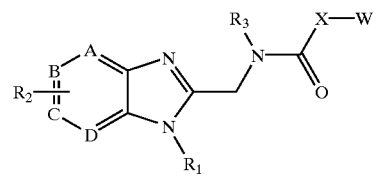

or pharmaceutically acceptable non-toxic salts thereof wherein:

W represents

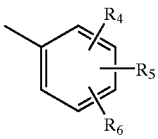 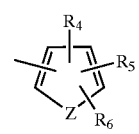 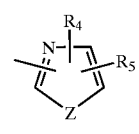

where

Z is O, or S;

$R_1$ represents phenyl, $C_1$–$C_6$ alkyl, cyclopentyl, cyclohexyl, benzyl, 3-fluorobenzyl, or cyclopropylmethyl;

$R_2$ represents
hydroxyl;
$C_1$–$C_6$ alkyl or $C_1$–$C_6$ alkoxy, each of which are optionally substituted with amino, mono or di($C_1$–$C_6$) alkylamino, a $C_5$–$C_7$ heterocycloalkyl group where the heteroatom is nitrogen and the nitrogen is attached to the parent alkyl portion;
$O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl; or
$NR_8R_9$ forms a 5-, 6-, or 7-membered heterocyclic ring;

$R_3$ represents
  $C_1$–$C_6$ alkyl, allyl, cyclopropylmethyl, cyclopentyl; or benzyl optionally mono-, di-, or trisubstituted independently with
    halogen, nitro, trifluoromethyl, trifluoromethoxy, cyano, or hydroxy;
    $C_1$–$C_6$ alkyl or $C_1$–$C_6$ alkoxy, each of which is optionally substituted with amino, mono or di($C_1$–$C_6$) alkylamino, a $C_5$–$C_7$ heterocycloalkyl group where the heteroatom is nitrogen and the nitrogen is attached to the parent alkyl portion;
    $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl;
    $NR_8R_9$ forms a 5-, 6-, 7-membered heterocyclic ring;
    $SO_2R_8$, $NHSO_2R_8$, $SO_2NHR_8$, $SO_2NHCOR_8$, $CONHSO_2R_8$ where $R_8$ is defined as above;
    $O(CH_2)_n$—G where n=1,2,3,4 and G is $SO_2R_8$, $NHSO_2R_8$, $SO_2NHR_8$, $SO_2NHCOR_8$, or $CONHSO_2R_8$, where $R_8$ is as defined above; or
    tetrazole, triazole, imidazole, thiazole, oxazole, thiophene, or pyridyl;
$R_4$, $R_5$ and $R_6$ are the same or different and represent hydrogen; or
  $C_1$–$C_6$ alkyl or $C_1$–$C_6$ alkoxy, each of which is optionally substituted with amino, mono or di($C_1$–$C_6$) alkylamino, a $C_5$–$C_7$ heterocycloalkyl group where the heteroatom is nitrogen and the nitrogen is attached to the parent alkyl portion, $C_1$–$C_6$ alkylthiol, or halogen;
  $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl;
  $NR_8R_9$ forms a 5-, 6-, or 7-membered heterocyclic ring; or
  $R_4$ and $R_5$ can form a 1,3-dioxolene ring;
X represents a bond, $CH_2$, or CHCH; and
A, B, C, and D are the same or different and represent CH or N with the proviso that not more than two of A,B,C, or D represent N.
In formula I, $R_2$ may also represent hydrogen or a group of the formula

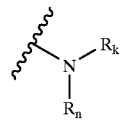

where
  $R_n$ and $R_k$ independently represent $C_1$–$C_6$ alkyl, $C_2$–$C_6$ alkenyl, $C_1$–$C_6$ cycloalkyl($C_1$–$C_6$)alkyl, benzoyl where the phenyl portion is optionally substituted with halgoen, $C_1$–$C_6$ alkyl, or $C_1$–$C_6$ alkoxy;
a group of the formula IV-a

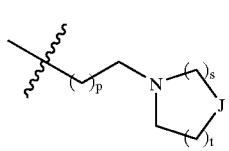

where p, s, and t independently represent 1 or 2;
J is CH, N, O, S, or a carbon atom substituted with $C_1$–$C_6$ alkyl; or $NR_kR_n$ represents

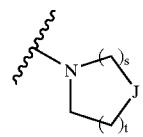

where s, t, and J are as defined above.
Preferred compounds of the invention are represented by Formula II.

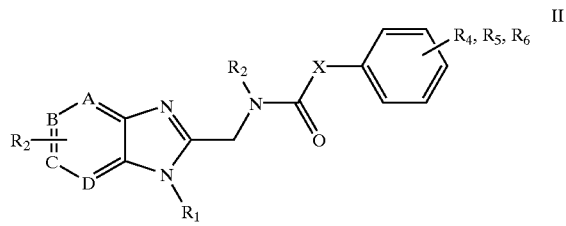

$R_1$ represents phenyl, $C_1$–$C_6$ alkyl, cyclopentyl, cyclohexyl, benzyl, 3-fluorobenzyl, or cyclopropylmethyl;
$R_2$ represents hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring;
$R_3$ represents $C_1$–$C_6$ alkyl, allyl, cyclopropylmethyl, cyclopentyl; or benzyl optionally mono-, di-, or trisubstituted independently with halogen, nitro, trifluoromethyl, trifluoromethoxy, cyano, hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_nCO_2R_8$ where n=1,2,3, 4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring, additional substitution on the benzyl ring can be directly bound or $O(CH_2)_n$ (where n=1,2,3,4) linked $SO_2R_8$, $NHSO_2R_8$, $SO_2NHR_8$, $SO_2NHCOR_8$, $CONHSO_2R_8$, as well as tetrazole, triazole, imidazole, thiazole, oxazole, thiophene, and pyridyl;
$R_4$, $R_5$ and $R_6$ are the same or different and represent hydrogen, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring, $C_1$–$C_6$ alkylthiol, or halogen, or $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms, additionally $R_8$ and $R_9$ can be a 5,6,7 member heterocyclic ring, additionally $R_4$ and $R_5$ can form a 1,3-dioxolene ring;
X represents a bond, $CH_2$, CHCH;
A,B,C,D are the same or different and represent CH or N with the proviso that not more than two of A,B,C, or D represent N.

Other preferred compounds of the invention are represented by Formula III.

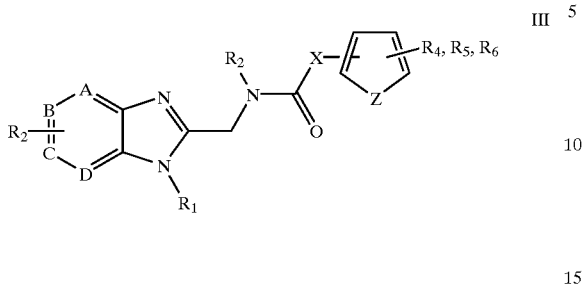

where Z is O, or S;

$R_1$ represents phenyl, $C_1$–$C_6$ alkyl, cyclopentyl, cyclohexyl, benzyl, 3-fluorobenzyl, or cyclopropylmethyl;

$R_2$ represents hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_n CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring;

$R_3$ represents $C_1$–$C_6$ alkyl, allyl, cyclopropylmethyl, cyclopentyl; or benzyl optionally mono-, di-, or trisubstituted independently with halogen, nitro, trifluoromethyl, trifluoromethoxy, cyano, hydroxyl, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring; or $O(CH_2)_nCO_2R_8$ where n=1,2,3, 4, $NR_8COR_9$, $COR_8$, $CONR_8R_9$ or $CO_2R_8$ where $R_8$ and $R_9$ are the same or different and represent hydrogen or $C_1$–$C_6$ alkyl, additionally $R_8$ and $R_9$ can be a 5,6,7 member heterocyclic ring, additional substitution on the benzyl ring can be directly bound or $O(CH_2)_n$ (where n=1,2,3,4) linked $SO_2R_8$, $NHSO_2R_8$, $SO_2NHR_8$, $SO_2NHCOR_8$, $CONHSO_2R_8$, as well as tetrazole, triazole, imidazole, thiazole, oxazole, thiophene, and pyridyl;

$R_4$, $R_5$ and $R_6$ are the same or different and represent hydrogen, $C_1$–$C_6$ alkyl or $C_1$–$C_6$ alkoxy, either of which could be substituted with amino or mono or di($C_1$–$C_6$) alkylamino, additionally the alkyl portion can form a 5,6,7 member ring, $C_1$–$C_6$ alkylthiol, or halogen, or $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms, additionally $R_8$ and $R_9$ can be a 5,6,7 member heterocyclic ring, additionally $R_4$ and $R_5$ can form a 1,3-dioxolene ring;

X represents a bond, $CH_2$, CHCH;

A,B,C,D are the same or different and represent CH or N with the proviso that not more than two of A,B,C, or D represent N.

More preferred compounds of Formula I are represented by Formula IV

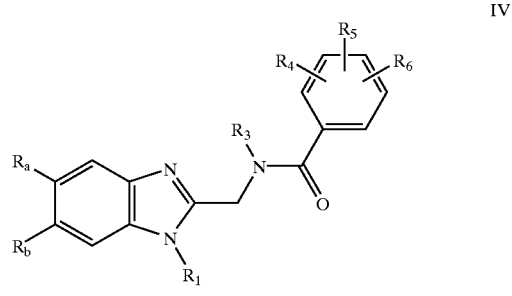

where $R_4$, $R_5$, and $R_6$ are as defined above for Formula I;

$R_1$ and $R_3$ are independently $C_1$–$C_6$ alkyl;

and $R_a$ and $R_b$ are independently
hydrogen or
a group of the formula

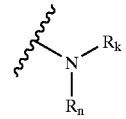

where
$R_n$ and $R_k$ independently represent $C_1$–$C_6$ alkyl, $C_2$–$C_6$ alkenyl, $C_1$–$C_6$ cycloalkyl ($C_1$–$C_6$)alkyl, benzoyl where the phenyl portion is optionally substituted with halgoen, $C_1$–$C_6$ alkyl, or $C_1$–$C_6$ alkoxy;

a group of the formula IV-a

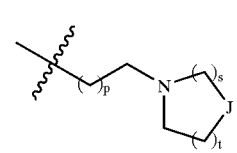

where p, s, and t independently represent 1 or 2;
J is CH, N, O, or a carbon atom substituted with $C_1$–$C_6$ alkyl; or $NR_kR_n$ represents

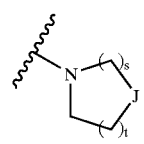

where s, t, and J are as defined above.

Preferred compounds of Formula IV include those where $R_1$ is propyl and $R_3$ is $C_3$–$C_5$ alkyl, preferably isobutyl. More preferred compounds of IV are those where $R_b$ is hydrogen and $R_a$ is —$NHR_n$ where $R_n$ is defined as above or —$NR_kR_n$ where both $R_n$ and $R_k$ are allyl or $C_1$–$C_6$ alkyl.

Preferred —$NR_kR_n$ groups include diallylamino, dimethylamino, diethylamino, and N-ethyl-N-cyclopropylmethylamino.

Preferred NHR$_n$ groups include those where R$_n$ is allyl, C$_1$–C$_6$ alkyl, or a group of IV-a. Preferred IV-a groups include pyrrolidinyl, morpholinyl and piperidinyl.

Particularly preferred compounds of IV are those where R$_1$ is propyl, R$_3$ is isobutyl, R$_b$ is hydrogen, and R$_a$ is In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl" or "lower alkyl" in the present invention is meant C$_1$–C$_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred C$_1$–C$_6$ alkyl groups are methyl, ethyl, propyl, butyl, cyclopropyl or cyclopropylmethyl.

By "alkoxy" or "lower alkoxy" in the present invention is meant C$_1$–C$_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By (hetero) cyclic ring is meant a ring that is either aliphatic or aromatic and optionally contains at least one hetero atom. Hetero atoms include nitrogen, sulfur, and oxygen. Examples of such (hetero) cyclic rings are cyclohexyl, cyclopenyl, cyclohexyl, piperidinyl, piperazinyl, pyrrolidinyl, morpholinyl, etc.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, imidazolyl, (iso)quinolinyl, naphthyridinyl, benzimidazolyl, and benzoxazolyl.

Specific examples of heteroaryl groups are the following:

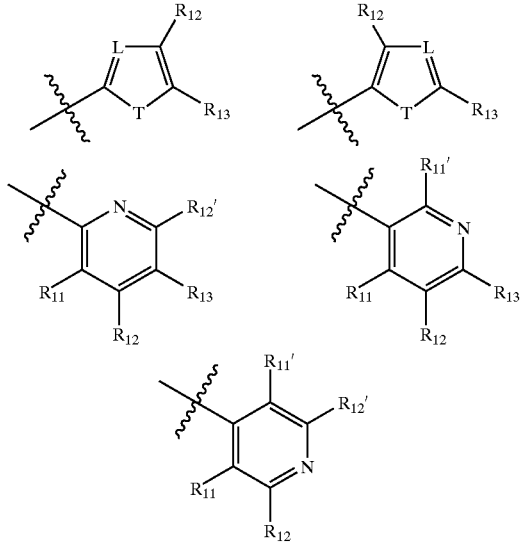

L is nitrogen or —CR$^{11}$;
T is —NR$^{19}$, oxygen, or sulfur;
R$^{11}$ and R$^{11i}$ are the same or different and are selected from hydrogen, halogen, hydroxy, C$_1$–C$_6$ alkyl, (C$_1$–C$_6$)alkoxy, amino, or mono- or di(C$_1$–C$_6$) alkylamino;
R$^{12}$, R$^{12i}$, and R$^{13}$ are the same or different and are selected from hydrogen, halogen, (C$_1$–C$_6$)alkyl, (C$_1$–C$_6$)alkoxy, amino, mono- or di(C$_1$–C$_6$) alkylamino, hydroxy, or trifluoromethyl; and
R$^{19}$ is hydrogen, lower alkyl having 1–6 carbon atoms.

The invention encompasses all possible tautomers and rotamers represented by Formula I.

By the term "halogen" in the present invention is meant fluorine, bromine, chlorine, and iodine.

Aryl and heteroaryl fused aminoalkyl-imidazoles of Formula I and their salts are suitable for the diagnosis and treatment of anxiety, Down Syndrome, sleep and seizure disorders, overdoses of benzodiazepine-type drugs, depression and cognitive disorders and for the enhancement of alertness, both in human and non-human animals and domestic pets, especially dogs and cats and farm animals such as sheep, swine and cattle. These interactions result in the pharmacological activites of these compounds.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety or depression a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously. Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to $GABA_A$ receptor modulation, e.g., treatment of cognitive deficits, anxiety or depression by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

The present invention also pertains to methods for altering the signal-tranducing activity of $GABA_A$ receptors, said method comprising exposing cells expressing such receptor to an effective amount of a compound of the invention.

A method of inhibiting the binding of a benzodiazepine compound to the benzodiazepine site of the $GABA_A$ receptor, comprising contacting a compound of Formula I with cells expressing such a receptor in the presence of a the benzodiazepine compound, wherein the compound is present at a concentration sufficient to inhibit benzodiazepine compound binding to cells expressing a cloned human $GABA_A$ receptor in vitro is provided by a separate aspect of the invention.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5-HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in an analogous fashion to that disclosed in Da-Rocha, et al., *J. Psychopharmacology* (1997) 11(3) 211–218; Smith, et al., *Am. J. Psychiatry* (1998) 155(10) 1339–45; and Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The disclosures of all articles and references mentioned in in this application, including patents, are incorporated herein by reference.

The invention is illustrated further by the following examples which are not to be construed as limiting the invention in scope or spirit to the specific procedures described in them. Compounds of the invention can be prepared using the reactions depicted in Schemes I to VI.

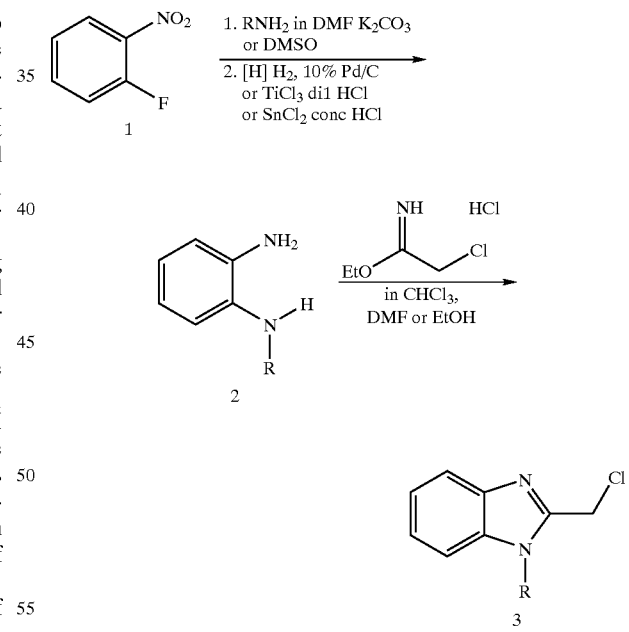

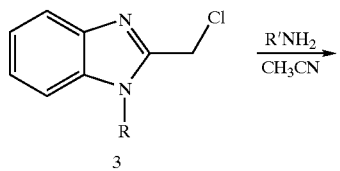

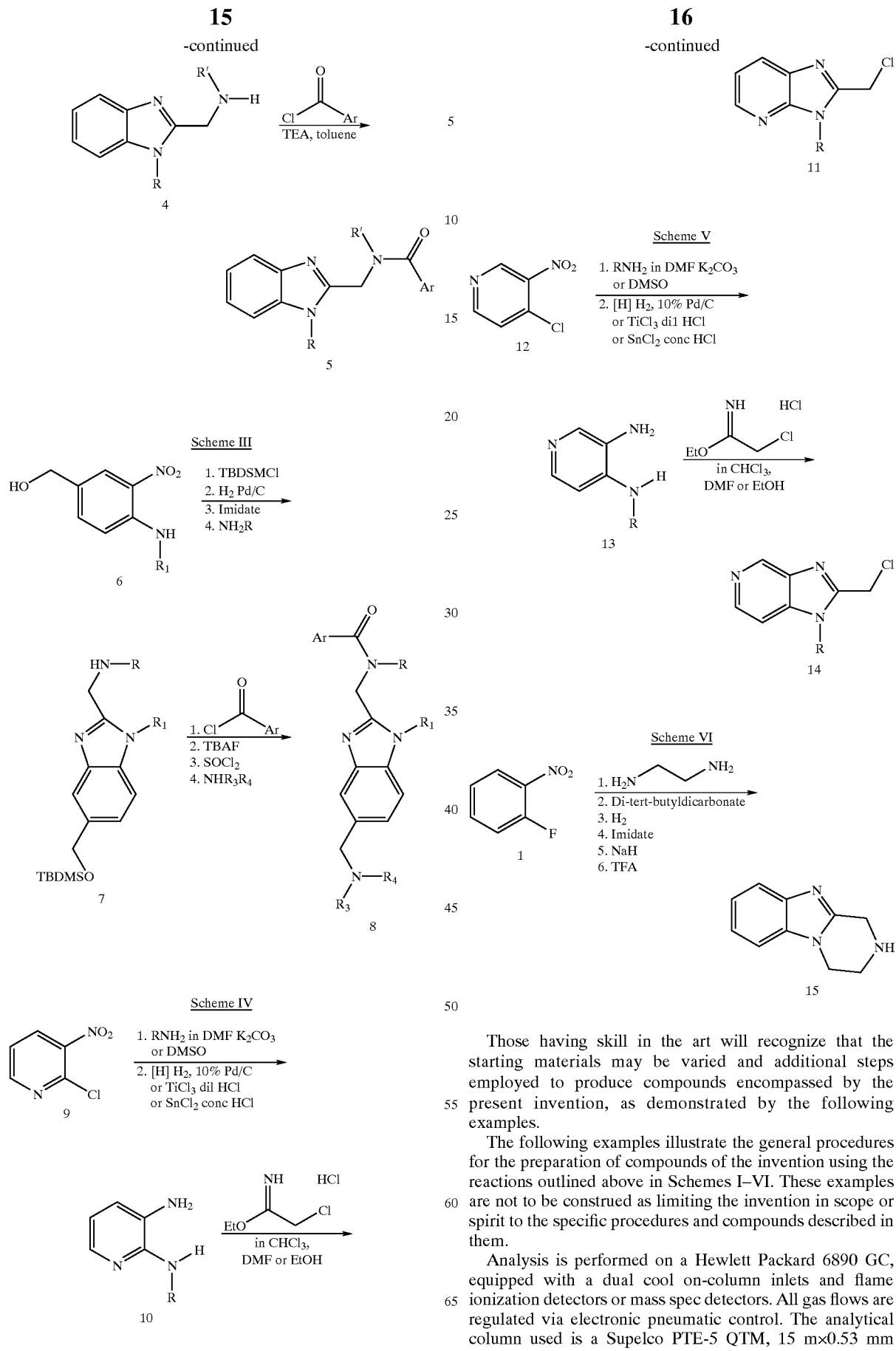

Those having skill in the art will recognize that the starting materials may be varied and additional steps employed to produce compounds encompassed by the present invention, as demonstrated by the following examples.

The following examples illustrate the general procedures for the preparation of compounds of the invention using the reactions outlined above in Schemes I–VI. These examples are not to be construed as limiting the invention in scope or spirit to the specific procedures and compounds described in them.

Analysis is performed on a Hewlett Packard 6890 GC, equipped with a dual cool on-column inlets and flame ionization detectors or mass spec detectors. All gas flows are regulated via electronic pneumatic control. The analytical column used is a Supelco PTE-5 QTM, 15 m×0.53 mm ID×0.50 μm film. GC instrument control and data collection are handled using a Perkin Elmer TurboChrom Client/Server data system. GC conditions: On-column injector 163 C for 2.5 min., ramp at 40 C/min to 323 C. Oven program 100 C for 1 minute, ramp at 40 C/min to 320 C. Detector temperature is set at 325 C. GC conditions: for compounds 7–12 initial temperature 200 C, ramp to 300 C at 20 C/min on a 12 m, DB-5 column.

EXAMPLE 1

General Procedure for the Preparation of Chloromethylbenzimidazoles as Outlined in Scheme I 1. Imidate hydrochloride:

A solution of 150 mL (2.37 mole) of chloroacetonitrile, 139 mL (2.37 mole) of ethanol in 1,200 mL of dry benzene is cooled to 0° C. in an ice/ethanol bath. Dry HCl gas is bubbled through the vigorously stirred solution for approximately 30 min. while the internal temperature is maintained below 10° C. The solution is allowed to stand at rt. overnight. The resulting solid is filtered and washed with 2L of dry ether and allowed to air dry to afford 328 g (88%) of imidate hydrochloride.

2. 1-n-Propyl-2-(chloromethyl)-5-fluorobenzimidazole:

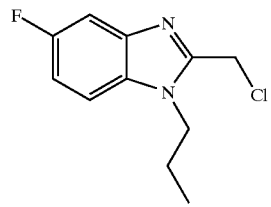

A solution of 11.25 g (0.07 mole) of 2-n-Propyl-5-fluorophenelyenediamine in 200 mL of anhydrous CHCl₃ is treated with 11.06 g (0.07 mole) of imidate at room temperature. The heterogeneous reaction mixture is allowed to stir for 45 min. at which time no starting material is detectable by TLC. 100 mL of saturated NaHCO₃ is added and extracted 3×50 mL of CH₂Cl₂. The extracts are dried over anhydrous MgSO₄, the solvent removed in vacuo, and the residue chromatgraphed (SiO₂) with 50% ethyl acetate/hexane to afford 15 g (95%) of 1-n-Propyl-2-(chloromethyl)-5-fluorobenzimidazole.

EXAMPLE 2

General Procedure for the Preparation of Benzimidazoles as shown in Scheme II

N-[benzoyl]-N-methyl-1-n-propyl-2-(methanamine)-5-fluorobenzimidazole

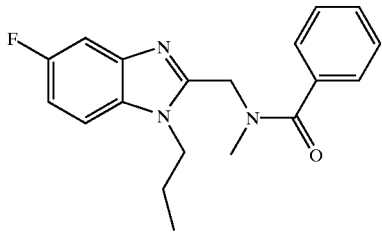

A solution of 8 mmole of 1-n-Propyl-2-(chloromethyl)-5-fluorobenzimidazole (alternatively named 2-(chloromethyl)-5-fluoro-1-propylbenzimidazole) in 20 mL of dry Acetonitrile is treated with 10 mL of 40% aqueous methylamine for 16 hr at room temperature. The solvent is removed in vacuo and the residue is partitioned between 30 mL of ethyl acetate and 10 mL of 1 N NaOH. The ethyl acetate layer is dried over anhydrous Na₂SO₄ and solvent removed in vacuo to afford 1.68 g 95% of 1-n-Propyl-2-(methanamine)-5-fluorobenzimidazole. Benzoylchloride 1.5 eq is treated with of 1-n-Propyl-2-(methanamine)-5-fluorobenzimidazole 1.0 eq in dichloromethane at room temperature for 1 hr. The reaction is quenched with 1 N NaOH and partitioned between dichloromethane and water. The organic layer is dried with Na₂SO₄ and the solvent removed in vacuo. The residue is chromatographed (SiO₂) with ethyl acetate to afford 95% of N-[benzoyl]-N-methyl-1-n-propyl-2-(methanamine)-5-fluorobenzimidazole [alternatively named N-((5-fluorobenzimidazol-2-yl)methyl)-N-methylbenzamide] (Compound A1).

EXAMPLE 3

General Procedure for the Preparation of Benzimidazoles as shown in Scheme 3

(2,5-difluorophenyl)-N-{[5-(morpholin-4-ylmethyl)-1-propylbenzimidazol-2-yl]methyl}-N-propylcarboxamide

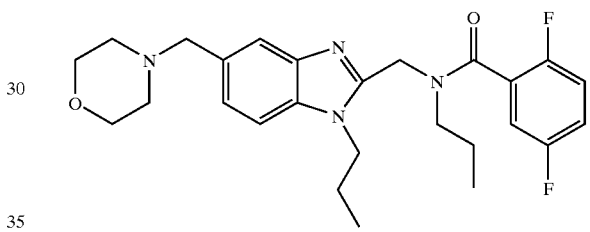

A solution of 20 g (0.095 mole) of [3-nitro-4-(propylamino)phenyl]methan-1-ol and 19.2 g (0.28 mole) of imidazole in 200 mL of anhydrous DMF is treated with 19 g (0.13 mole) of t-butyldimethylsilyl chloride at room temperature for 30 min. The resulting mixture is diluted with 400 mL of ethyl acetate and washed 3×200 mL of water and 1×200 mL of brine. The resulting orgainc layer is dried over anhydrous Na₂SO₄ and the solvent removed in vacuo. The resulting oil is column chromatographed 5% ethyl acetate/hexanes to afford 11 g (35%) of {2-nitro-4-[(1,1,2,2-tetramethy-1-silapropoxy)methyl]phenyl}propylamine.

A solution of 11 g (0.033 mole) of {2-nitro-4-[(1,1,2,2-tetramethy-1-silapropoxy)methyl]phenyl}propylamine in 100 mL of ethanol and 1 g 10% Pd/C is treated with 50 psi of H₂ at room temperature for 2 hr. The resulting mixture is filtered through celite, washed with 200 mL of ethanol and the solvent removed in vacuo. The crude material is treated with 9.7 g (0.06 mole) of imidate hydrochloride in 250 mL of chloroform at room temperature for 1 hr. The reaction mixture is partitioned between 200 mL sat NaHCO₃ and 200 mL of chloroform. The organic layer is dried over anhydrous anhydrous Na₂SO₄ and the solvent removed in vacuo. The resulting oil is column chromatographed 50% ethyl acetate/hexanes to afford 6 g (52% for 2 steps) of 1-{[2-(chloromethyl)-1-propylbenzimidazol-5-yl]methoxy}-1,1,2,2-tetramethyl-1-silapropane.

A solution of 2.0 g (5.6 mmole) of 1-{[2-(chloromethyl)-1-propylbenzimidazol-5-yl]methoxy}-1,1,2,2-tetramethyl-1-silapropane in 20 mL of anhydrous acetonitrile is treated with 10 mL of propylamine for 16 hr at room temperature.

The solvent is removed in vacuo and the residue is partitioned between 30 mL of ethyl acetate and 10 mL of 1 N NaOH. The ethyl acetate layer is dried over anhydrous Na$_2$SO$_4$ and solvent removed in vacuo to afford 2.1 g (99%) of propyl({1-propyl-5-[(1,1,2,2-tetramethyl-1-silapropoxy) methyl]benzimidazol-2-yl}methyl)amine.

2,5-difluorobenzoylchloride 1.5 eq is treated with 1.0 eq 1.25 g (3.3 mmole) of propyl({1-propyl-5-[(1,1,2,2-tetramethyl-1-silapropoxy)methyl]benzimidazol-2-yl}methyl) amine in dichloromethane at room temperature for 1 hr. The reaction is quenched with 1 N NaOH and partitioned between dichloromethane and water. The organic layer is dried over anhydrous Na$_2$SO$_4$ and the solvent removed in vacuo. The residue is chromatographed (SiO$_2$) with ethyl acetate to afford 74% of (2,5-difluorophenyl)-N-propyl-N-({1-propyl-5-[(1,1,2,2-tetramethyl-1-silapropoxy) methyl]benzimidazol-2-yl}methyl)carboxamide.

A solution 1.25 g (2.4 mmole) of (2,5-difluorophenyl)-N-propyl-N-({1-propyl-5-[(1,1,2,2-tetramethyl-1-silapropoxy)methyl]benzimidazol-2-yl}methyl) carboxamide in 20 mL of THF is treated at room temperature with 3 mL of 1M tetrabutylammonium fluoride for 1 hr. The reaction solution is diluted with 20 mL of sat NaHCO$_3$ and extracted with 3×100 mL of dichloromethane. The organic extracts are dried over anhydrous Na$_2$SO$_4$ and the solvent removed in vacuo to afford 0.96 g (99%) of (2,5-difluorophenyl)-N-{[5-(hydroxymethyl)-1-propylbenzimidazol-2-yl]methyl}-N-propylcarboxamide.

(2,5-difluorophenyl)-N-{[5-(hydroxymethyl)-1-propylbenzimidazol-2-yl]methyl}-N-propylcarboxamide 0.96 g (2.3 mmole) is treated with 30 mL of thionyl chloride for 15 min a room temperature. The resulting mixture is concentrated in vacuo and partitioned between 100 mL sat NaHCO$_3$ and 100 mL of ethyl acetate. The ethyl acetate layer is dried over anhydrous Na$_2$SO$_4$ and concentrated in vacuo. The resulting oil is chroamtographed 50% ethyl acetate/hexanes to afford 0.9 g (93%) of (2,5-difluorophenyl)-N-{[5-(chloromethyl)-1-propylbenzimidazol-2-yl]methyl}-N-propylcarboxamide.

A solution of 0.2 mL of 0.2M (2,5-difluorophenyl)-N-{[5-(chloromethyl)-1-propylbenzimidazol-2-yl]methyl}-N-propylcarboxamide in 1-methyl-2-pyrrolidinone is treated at room temperature for 16 hr with 0.3 mL of 0.2M solution of morpholine in toluene. The resulting mixture is diluted with 2 mL of ethyl acetate and washed 2×2 mL of water 1×2 mL brine. The ethyl acetate layer is dried over anhydrous Na$_2$SO$_4$ and concentrated in vacuo to afford 70% of (2,5-difluorophenyl)-N-{[5-(morpholin-4-ylmethyl)-1-propylbenzimidazol-2-yl]methyl}-N-propylcarboxamide.

EXAMPLE 4

The following compounds are prepared essentially according to the procedure described in Examples 1–5, and as shown in Schemes 1–6:

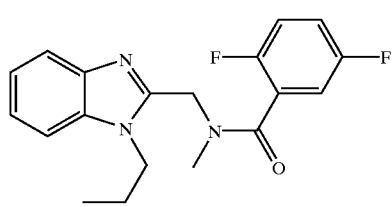

(a) (2,5-difluorodifluorophenyl)-N-methyl-N-((1-propylbenzimidazol-2-yl)methyl)carboxamide (Compound A5); GC retention time=5.26 minutes.

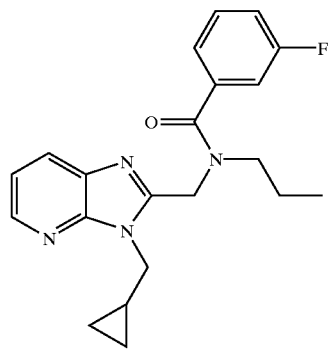

(b) N-((3-cyclopropylmethylimidazolo[5,4-b]pyridin-2-yl)methyl) (3-fluorophenyl)-N-propylcarboxamide (Compound A6); GC retention time=5.07 minutes.

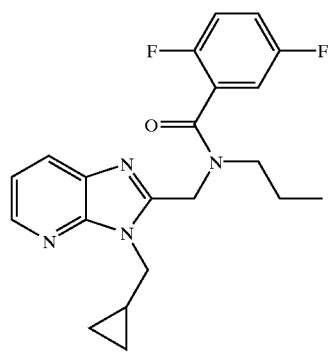

(c) N-[(3-cyclopropylmethylimidazolo[5,4-b]pyridin-2-yl)methyl](2,5-difluorophenyl)-N-propylcarboxamide (Compound A7); GC retention time=4.80 minutes.

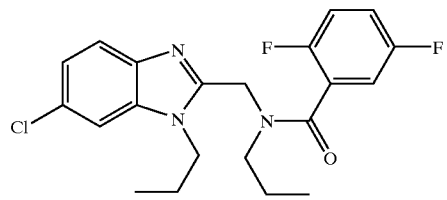

(d) N-[(6-chloro-1-propylbenzimidazol-2-yl)methyl](2,5-difluorophenyl)-N-propylcarboxamide (Compound A8); GC retention time=MS (CI) M+ 453 amu.

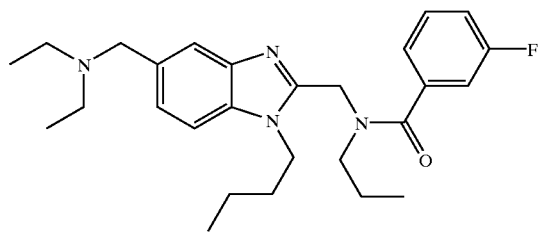

(e) N-({5-(diethylamino)methyl]-1-butylbenzimidazol-2-yl}methyl) (3-fluorophenyl)-N-propylcarboxamide (Compound A9); GC retention time=5.96 minutes.

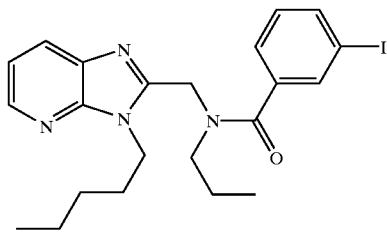

(f) N-((3-n-butyl-imidazolo[5,4-b]pyridin-2-yl)methyl] (3-iodophenyl)-N-propylcarboxamide (Compound A10); GC retention time=6.12 minutes.

(g) N-[(7-chloro-1-propylbenzimidazol-2-yl)methyl](3-fluorophenyl)-N-methylcarboxamide M+ 361 amu (h) N-[(7-chloro-1-propylbenzimidazol-2-yl)methyl](3-fluorophenyl)-N-propylcarboxamide M+ 389 amu (i) N-[(6-chloro-1-propylbenzimidazol-2-yl)methyl]{3-[(methylamino)methyl]phenyl}-N-propylcarboxamide M+ 414 amu (j) (3-fluorophenyl)-N-[(4-fluoro-1-propylbenzimidazol-2-yl)methyl]-N-propylcarboxamide M+ 372 amu (k) (2,5-difluorophenyl)-N-{[1-(cyclopropylmethyl) benzimidazol-2-yl]methyl}-N-propylcarboxamide M+ 384 amu (l) N-{[5-(N,N-diethylcarbamoyl)-1-propylbenzimidazol-2-yl]methyl}(3-fluorophenyl)-N-propylcarboxamide M+ 454 amu (m) (2,5-difluorophenyl)-N-[(4-fluoro-1-propylbenzimidazol-2-yl)methyl]-N-propylcarboxamide M+ 391 amu (n) N-{[6-chloro-1-(cyclopropylmethyl)benzimidazol-2-yl]methyl}(3-fluorophenyl)-N-propylcarboxamide M+ 401 amu (o) (2,5-difluorophenyl)-N-({5-[(ethylamino)methyl]-1-propylbenzimidazol-2-yl}methyl)-N-propylcarboxamide M+ 430 amu (p) (2,5-difluorophenyl)-N-propyl-N-({1-propyl-5-[(propylamino)methyl]benzimidazol-2-yl}methyl) carboxamide M+ 444 amu (q) (2,5-difluorophenyl)-N-({5-[(methylamino)methyl]-1-propylbenzimidazol-2-yl}methyl)-N-propylcarboxamide M+ 416 amu (r) N-[(6-chloro-1-propylbenzimidazol-2-yl)methyl]{4-[2-(ethylamino)ethoxy]phenyl}-N-(3-methylbutyl) carboxamide M+ 486 amu (s) N-[(6-chloro-1-propylbenzimidazol-2-yl)methyl]-N-(3-methylbutyl){4-[2-(propylamino)ethoxy] phenyl}carboxamide M+ 500 amu (t) N-[(6-chloro-1-propylbenzimidazol-2-yl)methyl](2-methyl(1,3-thiazol-4-yl))-N-(2-methylpropyl)carboxamide M+ 406 amu (u) (5-bromo(2-thienyl))-N-[(6-chloro-1-propylbenzimidazol-2-yl)methyl]-N-(2-methylpropyl) carboxamide M+ 470 amu (v) [3-(2-bromoethoxy)phenyl]-N-[(6-chloro-1-propylbenzimidazol-2-yl)methyl]-N-(2-methylpropyl) carboxamide M+ 508 amu (w) N-[(6-chloro-1-propylbenzimidazol-2-yl)methyl]-N-(2-methylpropyl){3-[2-(propylamino)ethoxy] phenyl}carboxamide M+ 486 amu (x) N-[(6-chloro-1-propylbenzimidazol-2-yl)methyl](3-{2-[(2-methoxyethyl)amino]ethoxy}phenyl)-N-(2-methylpropyl)carboxamide M+ 502 amu (y) N-[(6-chloro-1-propylbenzimidazol-2-yl)methyl](3-{2-[(2-ethoxyethyl)amino]propoxy}phenyl)-N-(2-methylpropyl)carboxamide M+ 530 amu (z) N-[(6-chloro-1-propylbenzimidazol-2-yl)methyl](3-(2-{[2-(methylethoxy)ethyl]amino}propoxy)phenyl]-N-(2-methylpropyl)carboxamide M+ 544 amu

EXAMPLES 5–41

The compounds of Examples 5–41 are prepared essentially according to the procedure described in Examples 1–3, and as shown in Schemes 1–6. These compounds are represented by the formulae presented in each of the examples with the definitions of the substituents found within the table. It is noted for the reader that the $R_2$ and $R_3$ groups used in these formulae are not the same $R_2$ and $R_3$ groups used in Formula I.

Structures for the compounds of Examples 5–42 are shown in Appendices 1 and 2 hereto.

EXAMPLE 5

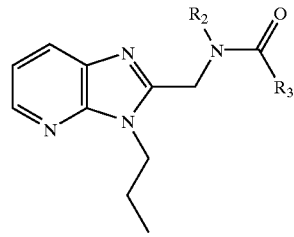

For each compound, the definitions of $R_2$ and $R_3$ are specified in the following table.

| Compound No. | $R_2$ | $R_3$ |
| --- | --- | --- |
| 1 | Methyl | 3-Fluorophenyl |
| 2 | Allyl | 3-Fluorophenyl |
| 3 | Propyl | 3-Fluorophenyl |
| 4 | Allyl | 3-Fluorophenyl |
| 5 | Propyl | 3-Fluorophenyl |
| 6 | Propyl | 3,4-Difluorophenyl |
| 7 | Allyl | 2,5-Difluorophenyl |
| 8 | Propyl | 2,5-Difluorophenyl |
| 9 | Propyl | 1,3-Benzodioxol-5-yl |
| 10 | Allyl | 3-Chloro-4-fluorophenyl |
| 11 | Propyl | 3-Chloro-4-fluorophenyl |
| 12 | Methyl | 5-Chloro-2-methoxyphenyl |
| 13 | 3-Methylbutyl | 3-{2-[(3-Methoxypropyl)amino]ethoxy}phenyl |
| 14 | 3-Methylbutyl | Ethoxypropyl)amino]ethoxy}phenyl |
| 15 | 3-Methylbutyl | 3-{2-[(3-Ethoxypropyl)amino]ethoxy}phenyl |
| 16 | 3-Methylbutyl | 3-[2-(Benzylamino)ethoxy]phenyl |
| 17 | 3-Methylbutyl | 3-[2-(Benzylamino)ethoxy]phenyl |
| 18 | 2-Methylpropyl | 3-{2-[(3-Propoxypropyl)amino]ethoxy}phenyl |
| 19 | 3-Methylbutyl | 3-{2-[(3-i-Propoxypropyl)amino]ethoxy}phenyl |
| 20 | Benzyl | 3-Chloro-2-thienyl |
| 21 | 4-Fluorobenzyl | 3-Chloro-2-thienyl |

-continued

| Compound No. | R₂ | R₃ |
|---|---|---|
| 22 | Benzyl | 3-Chloro-4-methylphenyl |
| 23 | 2-Fluorobenzyl | 3-Chloro-4-methylphenyl |
| 24 | 4-Fluorobenzyl | 3-Chloro-4-methylphenyl |
| 25 | 4-Fluorobenzyl | 2-Fluoro-6-trifluoromethyl phenyl |
| 26 | 4-Fluorobenzyl | 3,5-Dibromophenyl |
| 27 | Pentyl | 3-Bromophenyl |
| 28 | 3-Methylbutyl | 3-Bromophenyl |
| 29 | 2-Methylpropyl | 4-Bromophenyl |
| 30 | 3-Methylbutyl | 4-Bromophenyl |
| 31 | Butyl | 2-Bromophenyl |
| 32 | Pentyl | 2-Bromophenyl |
| 33 | 3-Methylbutyl | 2-Bromophenyl |
| 34 | 3-Methylbutyl | 3-Methoxyphenyl |
| 35 | 3-Methylbutyl | 2-Methoxyphenyl |
| 36 | 3-Methylbutyl | 3-Chlorophenyl |
| 37 | 3-Methylbutyl | 2-Chlorophenyl |
| 38 | 3-Methylbutyl | 2-Chlorophenyl |
| 39 | Ethyl | 5-Chloro-2-methoxyphenyl |
| 40 | Allyl | 5-Chloro-2-methoxyphenyl |
| 41 | Propyl | 5-Chloro-2-methoxyphenyl |
| 42 | Methyl | 2,5-Dichlorophenyl |
| 43 | Allyl | 2,5-Dichlorophenyl |
| 44 | Propyl | 2,5-Dichlorophenyl |
| 45 | Propyl | 5-Methyl-2-thienyl |
| 46 | Propyl | Phenyl |
| 47 | Propyl | 3-Methylphenyl |
| 48 | Propyl | 3-Fluoro-4-methylphenyl |
| 49 | Allyl | 5-Fluoro-2-methylphenyl |
| 50 | Propyl | 5-Fluoro-2-methylphenyl |
| 51 | Benzyl | 2,3,5,6-Tetrafluoro phenyl |
| 52 | 4-Fluorobenzyl | 2,3,5,6-Tetrafluoro phenyl |
| 53 | Benzyl | 2,4,6-Trifluoro phenyl |
| 54 | Benzyl | 2,3,6-Trifluoro phenyl |
| 55 | 4-Fluorobenzyl | 2,3,6-Trifluoro phenyl |
| 56 | 4-Fluorobenzyl | 2-Chloro-6-fluorophenyl |
| 57 | Benzyl | 2-Fluoro-6-trifluoromethyl phenyl |
| 58 | 2-Methylpropyl | 3-(2-{[(4-Methylphenyl)methyl]amino}ethoxy)phenyl |
| 59 | 3-Methylbutyl | 3-{2-[(2-Cyclohex-1-enylethyl)amino]ethoxy}phenyl |
| 60 | 2-Methylpropyl | 3-(2-{[(2-Methylphenyl)methyl]amino}ethoxy)phenyl |
| 61 | 2-Methylpropyl | 3-(2-{[(3-Methylphenyl)methyl]amino}ethoxy)phenyl |
| 62 | 2-Methylpropyl | 3-(2-{[(2-Methoxyphenyl)methyl]amino}ethoxy)phenyl |
| 63 | 2-Fluorobenzyl | 3-Iodo-4-methylphenyl |
| 64 | 4-Fluorobenzyl | 3-Iodo-4-methylphenyl |
| 65 | 4-Fluorobenzyl | 2-Thienyl |
| 66 | Benzyl | 2-Thienyl |
| 67 | 4-Fluorobenzyl | 2-Thienyl |
| 68 | Benzyl | 3-Methyl-2-thienyl |
| 69 | 4-Fluorobenzyl | 3-Methyl-2-thienyl |
| 70 | Benzyl | 5-Methyl-2-thienyl |
| 71 | 2-Fluorobenzyl | 5-Methyl-2-thienyl |
| 72 | 4-Fluorobenzyl | 5-Methyl-2-thienyl |
| 73 | 4-Fluorobenzyl | 4,5-Dimethyl-2-furyl |
| 74 | 2-Methylpropyl | 3,4-Dichlorophenyl |
| 75 | Pentyl | 3,4-Dichlorophenyl |
| 76 | 3-Methylbutyl | 3,4-Dichlorophenyl |
| 77 | 3-Methylbutyl | 3,5-Dichlorophenyl |
| 78 | 3-Methylbutyl | 2,3-Dichlorophenyl |
| 79 | Butyl | 2,5-Dichlorophenyl |
| 80 | 2-Methylpropyl | 2,5-Dichlorophenyl |
| 81 | Pentyl | 2,5-Dichlorophenyl |
| 82 | 3-Methylbutyl | 2,5-Dichlorophenyl |
| 83 | Butyl | 2,4-Dichlorophenyl |
| 84 | 2-Methylpropyl | 2,4-Dichlorophenyl |
| 85 | 3-Methylbutyl | 2,4-Dichlorophenyl |
| 86 | Allyl | 3-Chlorophenyl |
| 87 | Propyl | 3-Chlorophenyl |
| 88 | Propyl | 2,3,6-Trifluorophenyl |
| 89 | Methyl | 5-Chloro-2-methoxyphenyl |
| 90 | Ethyl | 5-Chloro-2-methoxyphenyl |
| 91 | Allyl | 5-Chloro-2-methoxyphenyl |
| 92 | Methyl | 2,5-Dichlorophenyl |
| 93 | Methyl | 3-Bromophenyl |
| 94 | Ethyl | 3-Bromophenyl |
| 95 | Propyl | 3-Bromophenyl |
| 96 | Methyl | 3-Bromo-4-fluorophenyl |
| 97 | Methyl | 3-Iodophenyl |
| 98 | 3-Methylbutyl | 3-(2-{[(2-Methoxyphenyl)methyl]amino}ethoxy)phenyl |
| 99 | 2-Methylpropyl | 3-(2-{[(3-Methoxyphenyl)methyl]amino}ethoxy)phenyl |
| 100 | 2-Methylpropyl | 3-(2-{[(4-Methoxyphenyl)methyl]amino}ethoxy)phenyl |
| 101 | 2-Methylpropyl | 3-(2-{[(2-Chlorophenyl)methyl]amino}ethoxy)phenyl |
| 102 | Benzyl | 2,5-Dimethoxyphenyl |
| 103 | 2-Fluorobenzyl | 2,5-Dimethoxyphenyl |
| 104 | 4-Fluorobenzyl | 2,5-Dimethoxyphenyl |
| 105 | Butyl | 4-Pentylphenyl |
| 106 | 2-Methylpropyl | 4-Pentylphenyl |
| 107 | 3-Methylbutyl | 4-Pentylphenyl |
| 108 | Butyl | 3-Bromophenyl |
| 109 | 2-Methylpropyl | 3-Bromophenyl |
| 110 | Pentyl | 3-Bromophenyl |
| 111 | 3-Methylbutyl | 3-Bromophenyl |
| 112 | 2-Methylpropyl | 4-Bromophenyl |
| 113 | 3-Methylbutyl | 4-Bromophenyl |
| 114 | Butyl | 2-Bromophenyl |
| 115 | Pentyl | 2-Bromophenyl |
| 116 | 3-Methylbutyl | 2-Bromophenyl |
| 117 | Ethyl | 3-Iodophenyl |
| 118 | Allyl | 3-Iodophenyl |
| 119 | Propyl | 3-Chloro-4-methylphenyl |
| 120 | Propyl | 5-Bromo-2-thienyl |
| 121 | Ethyl | Phenyl |
| 122 | Allyl | Phenyl |
| 123 | Propyl | Phenyl |
| 124 | Allyl | 3-Methylphenyl |
| 125 | Propyl | 3-Methylphenyl |
| 126 | Propyl | 4-Methylphenyl |
| 127 | Methyl | 3-Fluorophenyl |
| 128 | Propyl | 3-Fluorophenyl |
| 129 | Butyl | 3-Chloro-4-methoxyphenyl |
| 130 | 2-Methylpropyl | 3-Chloro-4-methoxyphenyl |
| 131 | 3-Methylbutyl | 3-Chloro-4-methoxyphenyl |
| 132 | Butyl | 5-Chloro-2-methoxyphenyl |
| 133 | 2-Methylpropyl | 5-Chloro-2-methoxyphenyl |
| 134 | Pentyl | 5-Chloro-2-methoxyphenyl |
| 135 | 3-Methylbutyl | 5-Chloro-2-methoxyphenyl |
| 136 | Butyl | 3-Trifluoromethylphenyl |
| 137 | Pentyl | 3-Trifluoromethylphenyl |
| 138 | 3-Methylbutyl | 3-Trifluoromethylphenyl |
| 139 | 3-Methylbutyl | 2-Trifluoromethylphenyl |
| 140 | Butyl | 3,4-Dichlorophenyl |
| 141 | Propyl | 4-Fluorophenyl |
| 142 | Methyl | 2-Fluorophenyl |
| 143 | Allyl | 2-Fluorophenyl |
| 144 | Propyl | 2-Fluorophenyl |
| 145 | Propyl | 3-Fluoro-4-methylphenyl |
| 146 | Methyl | 5-Fluoro-2-methylphenyl |
| 147 | Propyl | 5-Fluoro-2-methylphenyl |
| 148 | Methyl | 3-Chlorophenyl |
| 149 | Allyl | 3-Chlorophenyl |
| 150 | Propyl | 3-Chlorophenyl |

-continued

| Compound No. | R₂ | R₃ |
|---|---|---|
| 151 | 3-Methylbutyl | 4-Hexylphenyl |
| 152 | 3-Methylbutyl | 2-Fluoro-3-trifluoromethylphenyl |
| 153 | Butyl | 2,5-Dichlorophenyl |
| 154 | 2-Methylpropyl | 2,5-Dichlorophenyl |
| 155 | Pentyl | 2,5-Dichlorophenyl |
| 156 | 3-Methylbutyl | 2,5-Dichlorophenyl |
| 157 | Butyl | 2,4-Dichlorophenyl |
| 158 | 2-Methylpropyl | 2,4-Dichlorophenyl |
| 159 | 3-Methylbutyl | 2,4-Dichlorophenyl |
| 160 | Butyl | 4-Pentylphenyl |
| 161 | 2-Methylpropyl | 4-Pentylphenyl |
| 162 | 3-Methylbutyl | 4-Pentylphenyl |
| 163 | Butyl | 3-Bromophenyl |
| 164 | 2-Methylpropyl | 3-Bromophenyl |
| 165 | 2-Methylpropyl | 3-Bromo-4-methylphenyl |
| 166 | 3-Methylbutyl | 3-Bromo-4-methylphenyl |
| 167 | Butyl | 3-Bromo-4-fluorophenyl |
| 168 | 2-Methylpropyl | 3-Bromo-4-fluorophenyl |
| 169 | 3-Methylbutyl | 3-Bromo-4-fluorophenyl |
| 170 | Butyl | 3-Iodophenyl |
| 171 | 2-Methylpropyl | 3-Iodophenyl |
| 172 | Pentyl | 3-Iodophenyl |
| 173 | 3-Methylbutyl | 3-Iodophenyl |
| 174 | 2-Methylpropyl | 4-Iodophenyl |
| 175 | 3-Methylbutyl | 3-Iodo-4-methylphenyl |
| 176 | Butyl | 2-Thienyl |
| 177 | Pentyl | 2-Thienyl |
| 178 | 3-Methylbutyl | 2-Thienyl |
| 179 | Butyl | 3-Thienyl |
| 180 | Pentyl | 3-Thienyl |
| 181 | 3-Methylbutyl | 3-Thienyl |
| 182 | 3-Methylbutyl | Benzyl |
| 183 | Butyl | 3-Methyl-2-thienyl |
| 184 | Pentyl | 3-Methyl-2-thienyl |
| 185 | 3-Methylbutyl | 3-Methyl-2-thienyl |
| 186 | Pentyl | 3-Methyl-5-thienyl |
| 187 | 3-Methylbutyl | 3-Methyl-5-thienyl |
| 188 | 3-Methylbutyl | 3-Methylphenyl |
| 189 | 2-Methylpropyl | 5-Chloro-2-methoxyphenyl |
| 190 | Pentyl | 5-Chloro-2-methoxyphenyl |
| 191 | 3-Methylbutyl | 5-Chloro-2-methoxyphenyl |
| 192 | Butyl | 3-Trifluoromethylphenyl |
| 193 | Pentyl | 3-Trifluoromethylphenyl |
| 194 | 3-Methylbutyl | 3-Trifluoromethylphenyl |
| 195 | 3-Methylbutyl | 2-Trifluoromethylphenyl |
| 196 | Butyl | 3,4-Dichlorophenyl |
| 197 | 2-Methylpropyl | 3,4-Dichlorophenyl |
| 198 | 3-Methylbutyl | 3,4-Dichlorophenyl |
| 199 | 3-Methylbutyl | 3,5-Dichlorophenyl |
| 200 | 3-Methylbutyl | 2,3-Dichlorophenyl |
| 201 | Butyl | Phenyl |
| 202 | Pentyl | Phenyl |
| 203 | 3-Methylbutyl | Phenyl |
| 204 | Pentyl | 3-Methylphenyl |
| 205 | 3-Methylbutyl | 3-Methylphenyl |
| 206 | 2-Methylpropyl | 4-Methylphenyl |
| 207 | 3-Methylbutyl | 4-Methylphenyl |
| 208 | Pentyl | 2-Methylphenyl |
| 209 | 3-Methylbutyl | 2-Methylphenyl |
| 210 | Butyl | 3-Fluorophenyl |
| 211 | 2-Methylpropyl | 3-Fluorophenyl |
| 212 | Pentyl | 3-Fluorophenyl |
| 213 | 3-Methylbutyl | 3-Fluorophenyl |
| 214 | Pentyl | 4-Fluorophenyl |
| 215 | 3-Methylbutyl | 4-Fluorophenyl |
| 216 | Pentyl | 2-Fluorophenyl |
| 217 | 3-Methylbutyl | 2-Fluorophenyl |
| 218 | 2-Methylpropyl | 3,4-Dimethylphenyl |
| 219 | 3-Methylbutyl | 3,4-Dimethylphenyl |
| 220 | Pentyl | 2,5-Dimethylphenyl |
| 221 | 3-Methylbutyl | 2,5-Dimethylphenyl |
| 222 | 2-Methylpropyl | 2,4-Dimethylphenyl |
| 223 | 3-Methylbutyl | 2,4-Dimethylphenyl |
| 224 | 2-Methylpropyl | 3-Methoxyphenyl |
| 225 | Pentyl | 3-Methoxyphenyl |
| 226 | 3-Methylbutyl | 3-Methoxyphenyl |
| 227 | 2-Methylpropyl | 4-Methoxyphenyl |
| 228 | 3-Methylbutyl | 4-Methoxyphenyl |
| 229 | Pentyl | 2-Methoxyphenyl |
| 230 | 3-Methylbutyl | 2-Methoxyphenyl |
| 231 | 2-Methylpropyl | 3-Fluoro-4-methylphenyl |
| 232 | Pentyl | 3-Fluoro-4-methylphenyl |
| 233 | 3-Methylbutyl | 3-Fluoro-4-methylphenyl |
| 234 | 3-Methylbutyl | 3-Fluoro-2-methylphenyl |
| 235 | 2-Methylpropyl | 5-Fluoro-2-methylphenyl |
| 236 | Pentyl | 5-Fluoro-2-methylphenyl |
| 237 | 2-Methylpropyl | 3-Chloro-4-Fluorophenyl |
| 238 | Pentyl | 3-Chloro-4-Fluorophenyl |
| 239 | 3-Methylbutyl | 3-Chloro-4-Fluorophenyl |
| 240 | 3-Methylbutyl | 3,4,5-TriFluorophenyl |
| 241 | 3-Methylbutyl | 4-Butylphenyl |
| 242 | Pentyl | 4-i-propylphenyl |
| 243 | 3-Methylbutyl | 4-i-propylphenyl |
| 244 | Butyl | 4-Ethylthiophenyl |
| 245 | 2-Methylpropyl | 4-Ethylthiophenyl |
| 246 | 3-Methylbutyl | 4-Ethylthiophenyl |
| 247 | 3-Methylbutyl | 3-Chloro-4-methoxyphenyl |
| 248 | Butyl | 5-Chloro-2-methoxyphenyl |
| 249 | 3-Methylbutyl | 5-Fluoro-2-methylphenyl |
| 250 | 2-Methylpropyl | 2-Fluoro-3-methylphenyl |
| 251 | Pentyl | 2-Fluoro-3-methylphenyl |
| 252 | 3-Methylbutyl | 2-Fluoro-3-inethylphenyl |
| 253 | 2-Methylpropyl | 3-Chlorophenyl |
| 254 | Pentyl | 3-Chlorophenyl |
| 255 | 3-Methylbutyl | 3-Chlorophenyl |
| 256 | 2-Methylpropyl | 4-Chlorophenyl |
| 257 | 3-Methylbutyl | 4-Chlorophenyl |
| 258 | 3-Methylbutyl | 2-Chlorophenyl |
| 259 | 3-Methylbutyl | 3,4-Difluorophenyl |
| 260 | 3-Methylbutyl | i,2-Difluorophenyl |
| 261 | Pentyl | 2,5-Difluorophenyl |
| 262 | 3-Methylbutyl | 2,5-Difluorophenyl |
| 263 | Pentyl | 2,4-Difluorophenyl |
| 264 | 3-Methylbutyl | 2,4-Difluorophenyl |
| 265 | 3-Methylbutyl | 4-Propylphenyl |
| 266 | Pentyl | 1,3-Benzodioxol-5-yl |
| 267 | 3-Methylbutyl | 1,3-Benzodioxol-5-yl |
| 268 | 3-Methylbutyl | 4-Methylthio phenyl |
| 269 | 3-Methylbutyl | 3-Fluoro-4-methoxyphenyl |
| 270 | 2-Methylpropyl | 4-Chloro-3-methylphenyl |
| 271 | 3-Methylbutyl | 4-Chloro-3-methylphenyl |
| 272 | Butyl | 3-Chloro-4-Fluorophenyl |

EXAMPLE 6

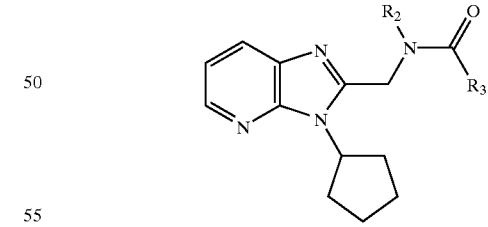

For each compound, the definitions of R₂ and R₃ are specified in the following table.

| Compound No. | R₂ | R₃ |
|---|---|---|
| 273 | 2-Methylpropyl | 2,4,6-Trifluorophenyl |
| 274 | 3-Methylbutyl | 2,4,6-Trifluorophenyl |
| 275 | 2-Methylpropyl | 2,3,6-Trifluorophenyl |

| Compound No. | R₂ | R₃ |
| --- | --- | --- |
| 276 | Pentyl | 2,3,6-Trifluorophenyl |
| 277 | 3-Methylbutyl | 2,3,6-Trifluorophenyl |
| 278 | Pentyl | 2-Chloro-6-fluorophenyl |
| 279 | 3-Methylbutyl | 2-Chloro-6-fluorophenyl |
| 280 | Pentyl | 2-Fluoro-6-trifluoromethylphenyl |
| 281 | 3-Methylbutyl | 2-Fluoro-6-trifluoromethylphenyl |
| 282 | Pentyl | 3-Bromo-4-fluorophenyl |
| 283 | 2-Methylpropyl | 4-Hexylphenyl |
| 284 | Butyl | 4-Pentoxyphenyl |
| 285 | 2-Methylpropyl | 4-Pentoxyphenyl |
| 286 | Butyl | 2-Fluoro-3-trifluoromethylphenyl |
| 287 | 2-Methylpropyl | 2-Fluoro-3-trifluoromethylphenyl |
| 288 | 3-Methylbutyl | 3-Bromo-4-fluorophenyl |
| 289 | 2-Methylpropyl | 4-heptylphenyl |
| 290 | Butyl | 3-Iodophenyl |
| 291 | 2-Methylpropyl | 3-Iodophenyl |
| 292 | Pentyl | 3-Iodophenyl |
| 293 | 3-Methylbutyl | 3-Iodophenyl |
| 294 | Butyl | 4-Iodophenyl |
| 295 | 2-Methylpropyl | 4-Iodophenyl |
| 296 | 2-Methylpropyl | 4-Pentylphenyl |
| 297 | 3-Methylbutyl | 2-Fluoro-3-trifluoromethylphenyl |
| 298 | Butyl | 3-Bromo-4-methylphenyl |
| 299 | 2-Methylpropyl | 3-Bromo-4-methylphenyl |
| 300 | Pentyl | 3-Bromo-4-methylphenyl |
| 301 | 3-Methylbutyl | 3-Bromo-4-methylphenyl |
| 302 | Butyl | 3-Bromo-4-fluorophenyl |
| 303 | 2-Methylpropyl | 3-Bromo-4-fluorophenyl |
| 304 | 3-Methylbutyl | 3,4-Dichlorophenyl |
| 305 | Butyl | 2,3-Dichlorophenyl |
| 306 | 2-Methylpropyl | 2,3-Dichlorophenyl |
| 307 | 3-Methylbutyl | 2,3-Dichlorophenyl |
| 308 | Butyl | 2,5-Dichlorophenyl |
| 309 | Butyl | 3-Bromophenyl |
| 310 | 2-Methylpropyl | 3-Bromophenyl |
| 311 | Pentyl | 3-Bromophenyl |
| 312 | 3-Methylbutyl | 3-Bromophenyl |
| 313 | Butyl | 4-Bromophenyl |
| 314 | 2-Methylpropyl | 4-Bromophenyl |
| 315 | 3-Methylbutyl | 4-Bromophenyl |
| 316 | Butyl | 2-Bromophenyl |
| 317 | Pentyl | 2-Bromophenyl |
| 318 | 3-Methylbutyl | 2-Bromophenyl |
| 319 | Pentyl | 4-Hexylphenyl |
| 320 | 2-Methylpropyl | 4-Chloro-2-methoxyphenyl |
| 321 | 2-Methylpropyl | 2,5-Dichlorophenyl |
| 322 | Pentyl | 2,5-Dichlorophenyl |
| 323 | 3-Methylbutyl | 2,5-Dichlorophenyl |
| 324 | Butyl | 2,4-Dichlorophenyl |
| 325 | 2-Methylpropyl | 2,4-Dichlorophenyl |
| 326 | Pentyl | 2,4-Dichlorophenyl |
| 327 | 3-Methylbutyl | 2,4-Dichlorophenyl |
| 328 | 2-Methylpropyl | 2,5-Dimethoxyphenyl |
| 329 | Pentyl | 2,5-Dimethoxyphenyl |
| 330 | 3-Methylbutyl | 2,5-Dimethoxyphenyl |
| 331 | 2-Methylpropyl | 2,4-Dimethoxyphenyl |
| 332 | 3-Methylbutyl | 2,4-Dimethoxyphenyl |
| 333 | Pentyl | 4-Chloro-2-methoxyphenyl |
| 334 | 3-Methylbutyl | 4-Chloro-2-methoxyphenyl |
| 335 | Butyl | 3-Trifluoromethylphenyl |
| 336 | 2-Methylpropyl | 3-Trifluoromethylphenyl |
| 337 | Pentyl | 3-Trifluoromethylphenyl |
| 338 | 3-Methylbutyl | 3-Trifluoromethylphenyl |
| 339 | 2-Methylpropyl | 4-Trifluoromethylphenyl |
| 340 | Butyl | 2-Trifluoromethylphenyl |
| 341 | 3-Methylbutyl | 2-Trifluoromethylphenyl |
| 342 | Butyl | 3,4-Dichlorophenyl |
| 343 | 2-Methylpropyl | 3,4-Dichlorophenyl |
| 344 | Butyl | 4-Methylthio phenyl |
| 345 | Butyl | 3-Chloro-4-methoxyphenyl |
| 346 | 2-Methylpropyl | 3-Chloro-4-methoxyphenyl |
| 347 | 3-Methylbutyl | 3-Chloro-4-methoxyphenyl |
| 348 | Butyl | 5-Chloro-2-methoxyphenyl |
| 349 | 2-Methylpropyl | 5-Chloro-2-methoxyphenyl |
| 350 | Pentyl | 5-Chloro-2-methoxyphenyl |
| 351 | 3-Methylbutyl | 5-Chloro-2-methoxyphenyl |
| 352 | Butyl | 2,5-Difluorophenyl |
| 353 | 2-Methylpropyl | 2,5-Difluorophenyl |
| 354 | Pentyl | 2,5-Difluorophenyl |
| 355 | 3-Methylbutyl | 2,5-Difluorophenyl |
| 356 | Butyl | 2,4-Difluorophenyl |
| 357 | 2-Methylpropyl | 4-Methylthio phenyl |
| 358 | Butyl | 3-Fluoro-4-methoxyphenyl |
| 359 | 2-Methylpropyl | 3-Fluoro-4-methoxyphenyl |
| 360 | 3-Methylbutyl | 3-Fluoro-4-methoxyphenyl |
| 361 | 2-Methylpropyl | 4-Chloro-3-methylphenyl |
| 362 | Butyl | 3-Chloro-4-fluorophenyl |
| 363 | 2-Methylpropyl | 3-Chloro-4-fluorophenyl |
| 364 | Pentyl | 3-Chloro-4-fluorophenyl |
| 365 | 3-Methylbutyl | 3-Chloro-4-fluorophenyl |
| 366 | 2-Methylpropyl | 4-Ethylthiophenyl |
| 367 | Butyl | 2,5-Dimethoxyphenyl |
| 368 | Butyl | 2-Chlorophenyl |
| 369 | 2-Methylpropyl | 2,4-Difluorophenyl |
| 370 | Pentyl | 2,4-Difluorophenyl |
| 371 | 3-Methylbutyl | 2,4-Difluorophenyl |
| 372 | Butyl | 1,3-Benzodioxol-5-yl |
| 373 | 2-Methylpropyl | 1,3-Benzodioxol-5-yl |
| 374 | Pentyl | 1,3-Benzodioxol-5-yl |
| 375 | 3-Methylbutyl | 1,3-Benzodioxol-5-yl |
| 376 | 3-Methylbutyl | 3-Fluoro-2-methylphenyl |
| 377 | Butyl | 5-Fluoro-2-methylphenyl |
| 378 | 2-Methylpropyl | 5-Fluoro-2-methylphenyl |
| 379 | Pentyl | 5-Fluoro-2-methylphenyl |
| 380 | 3-Methylbutyl | 5-Fluoro-2-methylphenyl |
| 381 | 2-Methylpropyl | 2-Chlorophenyl |
| 382 | Pentyl | 2-Chlorophenyl |
| 383 | 3-Methylbutyl | 2-Chlorophenyl |
| 384 | Butyl | 3,4-Difluorophenyl |
| 385 | 2-Methylpropyl | 3,4-Difluorophenyl |
| 386 | Pentyl | 3,4-Difluorophenyl |
| 387 | 3-Methylbutyl | 3,4-Difluorophenyl |
| 388 | Butyl | 2,3-Difluorophenyl |
| 389 | 2-Methylpropyl | 2,3-Difluorophenyl |
| 390 | Pentyl | 2,3-Difluorophenyl |
| 391 | 3-Methylbutyl | 2,3-Difluorophenyl |
| 392 | 2-Methylpropyl | 4-Methoxyphenyl |
| 393 | Butyl | 3-Chlorophenyl |
| 394 | 2-Methylpropyl | 3-Chlorophenyl |
| 395 | Pentyl | 3-Chlorophenyl |
| 396 | 3-Methylbutyl | 3-Chlorophenyl |
| 397 | Butyl | 4-Chlorophenyl |
| 398 | 2-Methylpropyl | 4-Chlorophenyl |
| 399 | 3-Methylbutyl | 4-Chlorophenyl |
| 400 | Butyl | 2,5-Dimethylphenyl |
| 401 | 2-Methylpropyl | 2,5-Dimethylphenyl |
| 402 | Pentyl | 2,5-Dimethylphenyl |
| 403 | 3-Methylbutyl | 2,5-Dimethylphenyl |
| 404 | Butyl | 2,4-Dimethylphenyl |
| 405 | 3-Methylbutyl | 4-Methoxyphenyl |
| 406 | Butyl | 2-Methoxyphenyl |
| 407 | 2-Methylpropyl | 2-Methoxyphenyl |
| 408 | Pentyl | 2-Methoxyphenyl |
| 409 | 3-Methylbutyl | 2-Methoxyphenyl |
| 410 | Butyl | 3-Fluoro-4-methylphenyl |
| 411 | 2-Methylpropyl | 3-Fluoro-4-methylphenyl |
| 412 | Pentyl | 3-Fluoro-4-methylphenyl |
| 413 | 3-Methylbutyl | 3-Fluoro-4-methylphenyl |
| 414 | Butyl | 3-Fluoro-2-methylphenyl |
| 415 | 2-Methylpropyl | 3-Fluoro-2-methylphenyl |
| 416 | Butyl | 4-Fluorophenyl |
| 417 | 2-Methylpropyl | 2,4-Dimethylphenyl |
| 418 | 3-Methylbutyl | 2,4-Dimethylphenyl |
| 419 | Butyl | 3-Methoxyphenyl |
| 420 | 2-Methylpropyl | 3-Methoxyphenyl |
| 421 | Pentyl | 3-Methoxyphenyl |
| 422 | 3-Methylbutyl | 3-Methoxyphenyl |
| 423 | Butyl | 4-Methoxyphenyl |
| 424 | 3-Methylbutyl | 3-Methylphenyl |
| 425 | Butyl | 4-Methylphenyl |
| 426 | 2-Methylpropyl | 4-Methylphenyl |
| 427 | Pentyl | 4-Methylphenyl |
| 428 | 3-Methylbutyl | 4-Methylphenyl |
| 429 | 2-Methylpropyl | 4-Fluorophenyl |

-continued

| Compound No. | R$_2$ | R$_3$ |
|---|---|---|
| 430 | Pentyl | 4-Fluorophenyl |
| 431 | 3-Methylbutyl | 4-Fluorophenyl |
| 432 | Butyl | 2-Fluorophenyl |
| 433 | 2-Methylpropyl | 2-Fluorophenyl |
| 434 | Pentyl | 2-Fluorophenyl |
| 435 | 3-Methylbutyl | 2-Fluorophenyl |
| 436 | 2-Methylpropyl | 4-Ethylphenyl |
| 437 | Butyl | 3,4-Dimethylphenyl |
| 438 | 2-Methylpropyl | 3,4-Dimethylphenyl |
| 439 | 3-Methylbutyl | 3,4-Dimethylphenyl |
| 440 | Butyl | 2-Methylphenyl |
| 441 | Pentyl | 2-Methylphenyl |
| 442 | 3-Methylbutyl | 2-Methylphenyl |
| 443 | Butyl | 3-Fluorophenyl |
| 444 | 2-Methylpropyl | 3-Fluorophenyl |
| 445 | Pentyl | 3-Fluorophenyl |
| 446 | 3-Methylbutyl | 3-Fluorophenyl |
| 447 | Butyl | Phenyl |
| 448 | 2-Methylpropyl | Phenyl |
| 449 | Pentyl | Phenyl |
| 450 | 3-Methylbutyl | Phenyl |
| 451 | Butyl | 3-Methylphenyl |
| 452 | 2-Methylpropyl | 3-Methylphenyl |
| 453 | Pentyl | 3-Methylphenyl |

EXAMPLE 7

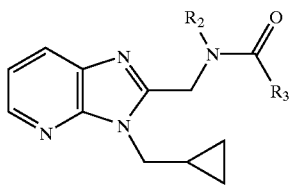

For each compound, the definitions of R$_2$ and R$_3$ are specified in the following table.

| Compound No. | R$_2$ | R$_3$ |
|---|---|---|
| 454 | Allyl | 2,5-Dichlorophenyl |
| 455 | Propyl | 2,5-Dichlorophenyl |
| 456 | Propyl | 2,4-Dichlorophenyl |
| 457 | Propyl | 4-Pentylphenyl |
| 458 | Allyl | 3-Bromophenyl |
| 459 | Propyl | 3-Bromophenyl |
| 460 | Propyl | 4-Bromophenyl |
| 461 | Propyl | 2-Chlorophenyl |
| 462 | Methyl | Phenyl |
| 463 | Propyl | Phenyl |
| 464 | Methyl | 3-Methylphenyl |
| 465 | Propyl | 3-Methylphenyl |
| 466 | Propyl | 2-Chlorophenyl |
| 467 | Propyl | 3,4-Difluorophenyl |
| 468 | Methyl | 2,3-Difluorophenyl |
| 469 | Propyl | 2,3-Difluorophenyl |
| 470 | Methyl | 2,5-Difluorophenyl |
| 471 | Allyl | 2,5-Difluorophenyl |
| 472 | Propyl | 2,5-Difluorophenyl |
| 473 | Propyl | 2,4-Difluorophenyl |
| 474 | Allyl | 1,3-Benzodioxol-5-yl |
| 475 | Propyl | 1,3-Benzodioxol-5-yl |
| 476 | Propyl | 4-Methylthiophenyl |
| 477 | Propyl | 4-Chloro-3-methylphenyl |
| 478 | Propyl | 4-Methylphenyl |
| 479 | Propyl | 3-Fluorophenyl |
| 480 | Propyl | 4-Fluorophenyl |
| 481 | Methyl | 2-Fluorophenyl |
| 482 | Allyl | 2-Fluorophenyl |
| 483 | Propyl | 2-Fluorophenyl |
| 484 | Propyl | 3,4-Dimethylphenyl |
| 485 | Propyl | 3-Fluoro-4-methylphenyl |
| 486 | Propyl | 2-Fluoro-3-niethylphenyl |
| 487 | Allyl | 3-Chlorophenyl |
| 488 | Propyl | 3-Chlorophenyl |
| 489 | Propyl | 4-Chlorophenyl |
| 490 | 2-Methylpropyl | 3-Chloro-2-thienyl |
| 491 | Pentyl | 3-Chloro-2-thienyl |
| 492 | 3-Methylbutyl | 3-Chloro-2-thienyl |
| 493 | Butyl | 3-Ethoxy-2-thienyl |
| 494 | Pentyl | 3-Ethoxy-2-thienyl |
| 495 | 3-Methylbutyl | 2-Methoxybenzyl |
| 496 | 3-Methylbutyl | 2-(2-Fluorophenyl)ethenyl |
| 497 | 2-Methylpropyl | 2-(2-ChlorOphenyl)ethenyl |
| 498 | 3-Methylbutyl | 2-(2-Chlorophenyl)ethenyl |
| 499 | Pentyl | 2-Fluoro-6-trifluoromethylphenyl |
| 500 | 3-Methylbutyl | 3-Ethoxy-2-thienyl |
| 501 | Butyl | 5-Methylthio-2-thienyl |
| 502 | 2-Methylpropyl | 5-Methylthio-2-thienyl |
| 503 | 3-Methylbutyl | 5-Methylthio-2-thienyl |
| 504 | 3-Methylbutyl | 4-Fluorophenyl |
| 505 | 3-Methylbutyl | 2-Fluorophenyl |
| 506 | 3-Methylbutyl | 3-Methoxyphenyl |
| 507 | 3-Methylbutyl | 2,3,5,6-Tetrafluorophenyl |
| 508 | 2-Methylpropyl | 2,4,6-Trifluorophenyl |
| 509 | 3-Methylbutyl | 2,4,6-Trifluorophenyl |
| 510 | Butyl | 2,3,6-Trifluorophenyl |
| 511 | 2-Methylpropyl | 2,3,6-Trifluorophenyl |
| 512 | 3-Methylbutyl | 2-Fluoro-6-trifluoromethylphenyl |
| 513 | 2-Methylpropyl | 2,4,6-Trichlorophenyl |
| 514 | Pentyl | 2,5-Dimethyl-3-furyl |
| 515 | 3-Methylbutyl | 4,5-Dimethyl-2-furyl |
| 516 | Butyl | 3,4-Dimethyl-2-furyl |
| 517 | 2-Methylpropyl | 3,4-Ditnethyl-2-furyl |
| 518 | Pentyl | 3,4-Dimethyl-2-furyl |
| 519 | 3-Methylbutyl | 3,4-Dimethyl-2-furyl |
| 520 | Butyl | 4-Methoxy-3-thienyl |
| 521 | 3-Methylbutyl | 4-Methoxy-3-thienyl |
| 522 | Butyl | 3-Chloro-2-thienyl |
| 523 | Allyl | 3-Bromo-4-fluorophenyl |
| 524 | Propyl | 3-Bromo-4-fluorophenyl |
| 525 | Methyl | 3-Iodophenyl |
| 526 | Ethyl | 3-Iodophenyl |
| 527 | Allyl | 3-Iodophenyl |
| 528 | Propyl | 3-Iodophenyl |
| 529 | Propyl | 3-Methyl-2-thienyl |
| 530 | Propyl | 3-Fluorobenzyl |
| 531 | Pentyl | 2,3,6-Trifluorophenyl |
| 532 | 3-Methylbutyl | 2,3,6-Trifluorophenyl |
| 533 | Butyl | 2-Chloro-6-fluorophenyl |
| 534 | 2-Methylpropyl | 2-Chloro-6-fluorophenyl |
| 535 | Pentyl | 2-Chloro-6-fluorophenyl |
| 536 | 3-Methylbutyl | 2-Chloro-6-fluorophenyl |
| 537 | Butyl | 2-Fluoro-6-trifluoromethylphenyl |
| 538 | 3-Methylbutyl | 3-Chlorobenzyl |
| 539 | 2-Methylpropyl | 4-Chlorobenzyl |
| 540 | 3-Methylbutyl | 2-Chlorobenzyl |
| 541 | Butyl | 2,3,5,6-Tetrafluorophenyl |
| 542 | 2-Methylpropyl | 2,3,5,6-Tetrafluorophenyl |
| 543 | Pentyl | 2,3,5,6-Tetrafluorophenyl |
| 544 | Allyl | 3-Chloro-4-fluorophenyl |
| 545 | Propyl | 3-Chloro-4-fluorophenyl |
| 546 | Propyl | 4-Butylphenyl |
| 547 | Propyl | 3-Chloro-4-methoxyphenyl |
| 548 | Allyl | 5-Chloro-2-methoxyphenyl |
| 549 | Propyl | 5-Chloro-2-methoxyphenyl |
| 550 | Propyl | 3,4-Dichlorophenyl |
| 551 | Propyl | 4-Hexylphenyl |
| 552 | Methyl | 3-Bromo-4-methylphenyl |

EXAMPLE 8

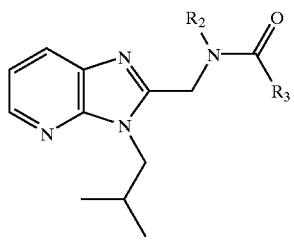

For each compound, the definitions of $R_2$ and $R_3$ are specified in the following table.

| Compound No. | $R_2$ | $R_3$ |
| --- | --- | --- |
| 557 | Propyl | 3-Chlorophenyl |
| 558 | Propyl | Phenyl |
| 559 | Allyl | 2-Fluorophenyl |
| 560 | Propyl | 2-Fluorophenyl |
| 561 | Propyl | 3-Fluoro-4-methylphenyl |
| 562 | Methyl | 2,5-Dichlorophenyl |
| 563 | Propyl | 2,5-Dichlorophenyl |
| 564 | Propyl | 4-Pentylphenyl |
| 565 | Propyl | 3-Bromophenyl |
| 566 | Propyl | 3-Methyl-2-thienyl |

Compound No. 567: (5-Chloro-2-methoxyphenyl)-N-({3-[(2-chlorophenyl)methyl]imidazolo[5,4-b]pyridin-2-yl}methyl-N-pentylcarboxamide.

EXAMPLE 9

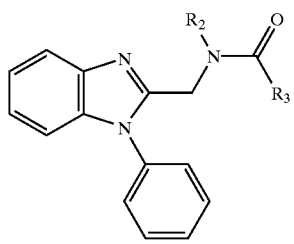

For each compound, the definitions of $R_2$ and $R_3$ are specified in the following table.

| Compound No. | $R_2$ | $R_3$ |
| --- | --- | --- |
| 568 | Methyl | Phenyl |
| 569 | Methyl | 3-Chlorophenyl |
| 570 | Butyl | 2,5-Dimethylphenyl |
| 571 | Butyl | 5-Fluoro-2-methylphenyl |
| 572 | Butyl | 2,3-Dimethylphenyl |
| 573 | Propyl | 3-Fluorophenyl |
| 574 | Butyl | 3-Methylphenyl |
| 575 | Butyl | 4-Fluorophenyl |
| 576 | Butyl | 3-Methoxyphenyl |
| 577 | Butyl | 2,5-Difluorophenyl |
| 578 | Methyl | 2-Fluorophenyl |
| 579 | Butyl | 4-Methylphenyl |
| 580 | Butyl | 2-Fluorophenyl |
| 581 | Butyl | 4-Methoxyphenyl |
| 582 | Butyl | 3-Chlorophenyl |
| 583 | Methyl | 2,5-Dimethylphenyl |
| 584 | Butyl | 2-Methylphenyl |
| 585 | Butyl | 4-Ethylphenyl |
| 586 | Butyl | 2-Methoxyphenyl |
| 587 | Butyl | 3-Chlorophenyl |
| 588 | Propyl | 3-Fluoro-4-methylphenyl |
| 589 | Butyl | 3-Fluorophenyl |
| 590 | Butyl | 3,4-Dimethylphenyl |
| 591 | Butyl | 3-Fluoro-4-methylphenyl |
| 592 | Butyl | 3,4-Difluorophenyl |
| 593 | Propyl | 2,4-Dimethoxyphenyl |
| 594 | Methyl | 2,5-Dichlorophenyl |
| 595 | Butyl | 5-Chloro-2-methoxyphenyl |
| 596 | Butyl | 3-Methyl-2-thienyl |
| 597 | Butyl | 3-Methylphenyl |
| 598 | Pentyl | 3-Fluorophenyl |
| 599 | Pentyl | 2,5-Dimethylphenyl |
| 600 | Propyl | 2,5-Dichlorophenyl |
| 601 | Butyl | 3-Methyl-2-thienyl |
| 602 | Pentyl | 3-Methylphenyl |
| 603 | Butyl | 2-Fluorophenyl |
| 604 | Pentyl | 3-Methoxyphenyl |
| 605 | Methyl | 3-Bromophenyl |
| 606 | Butyl | 3-Iodophenyl |
| 607 | Butyl | 4-Fluorophenyl |
| 608 | 2-Methylpropyl | 4-Methylphenyl |
| 609 | 2-Methylpropyl | 2-Fluorophenyl |
| 610 | 2-Methylpropyl | 4-Methoxyphenyl |
| 611 | Propyl | 3-Bromophenyl |
| 612 | Allyl | 4-Octylphenyl |
| 613 | Butyl | Phenyl |
| 614 | Pentyl | 2-Methylphenyl |
| 615 | Pentyl | 2-Fluorophenyl |
| 616 | Butyl | 2-Methoxyphenyl |
| 617 | Butyl | 3-Chloro-4-methoxyphenyl |
| 618 | Propyl | 4-Octylphenyl |
| 619 | Pentyl | Phenyl |
| 620 | Butyl | 3-Fluorophenyl |
| 621 | 2-Methylpropyl | 3,4-Dimethylphenyl |
| 622 | Pentyl | 2-Methoxyphenyl |
| 623 | Butyl | 3-Fluoro-4-methylphenyl |
| 624 | Butyl | 2-Fluoro-3-methylphenyl |
| 625 | 2-Methylpropyl | 4-Chlorophenyl |
| 626 | 2-Methylpropyl | 2,3-Difluorophenyl |
| 627 | 2-Methylpropyl | 1,3-Benzodioxol-5-yl |
| 628 | 2-Methylpropyl | 3-Chloro-4-methoxyphenyl |
| 629 | 2-Methylpropyl | 3-Fluoro-4-methylphenyl |
| 630 | Pentyl | 2-Fluoro-3-methylphenyl |
| 631 | Pentyl | 2-Chlorophenyl |
| 632 | Pentyl | 2,3-Difluorophenyl |
| 633 | Butyl | 4-Methylthiophenyl |
| 634 | 2-Methylpropyl | 3-Chloro-4-methoxyphenyl |
| 635 | Butyl | 5-Fluoro-2-methylphenyl |
| 636 | Butyl | 3-Chlorophenyl |
| 637 | Butyl | 3,4-Difluorophenyl |
| 638 | Butyl | 2,5-Difluorophenyl |
| 639 | Butyl | 3-Chloro-4-fluorophenyl |
| 640 | Butyl | 5-Chloro-2-methoxyphenyl |
| 641 | 2-Methylpropyl | 5-Fluoro-2-methylphenyl |
| 642 | 2-Methylpropyl | 3-Chlorophenyl |
| 643 | 2-Methylpropyl | 3,4-Difluorophenyl |
| 644 | Pentyl | 2,5-Difluorophenyl |
| 645 | 2-Methylpropyl | 4-Ethylthiophenyl |
| 646 | 2-Methylpropyl | 5-Chloro-2-methoxyphenyl |
| 647 | Pentyl | 5-Fluoro-2-methylphenyl |
| 648 | Pentyl | 3-Chlorophenyl |

-continued

| Compound No. | $R_2$ | $R_3$ |
| --- | --- | --- |
| 553 | Allyl | 3-Bromo-4-methylphenyl |
| 554 | Propyl | 3-Bromo-4-methylphenyl |
| 555 | Methyl | 3-Bromo-4-fluorophenyl |
| 556 | Butyl | 2-Methoxybenzyl |

-continued

| Compound No. | R₂ | R₃ |
|---|---|---|
| 649 | Butyl | 2,3-Difluorophenyl |
| 650 | 2-Methylpropyl | 2,4-Difluorophenyl |
| 651 | Butyl | 3-Chloro-4-methoxyphenyl |
| 652 | Pentyl | 5-Chloro-2-methoxyphenyl |
| 653 | 3-Methylbutyl | 5-Chloro-2-methoxyphenyl |
| 654 | 3-Methylbutyl | 2,5-Dichlorophenyl |
| 655 | 2-Methylpropyl | 4-Bromophenyl |
| 656 | Butyl | 2-Thienyl |
| 657 | 3-Methylbutyl | 3-Thienyl |
| 658 | 2-Methylpropyl | 3-Methyl-2-thienyl |
| 659 | 3-Methylbutyl | 3-Trifluoromethylphenyl |
| 660 | Butyl | 3-Bromophenyl |
| 661 | 3-Methylbutyl | 2-Bromophenyl |
| 662 | Pentyl | 2-Thienyl |
| 663 | Butyl | 5-Methyl-2-thienyl |
| 664 | 3-Methylbutyl | 3-Methyl-2-thienyl |
| 665 | 2-Methylpropyl | 3,4-Dichlorophenyl |
| 666 | 2-Methylpropyl | 3-Bromophenyl |
| 667 | 3-Methylbutyl | 3-Bromo-4-fluorophenyl |
| 668 | 3-Methylbutyl | 2-Thienyl |
| 669 | Pentyl | 5-Methyl-2-thienyl |
| 670 | Butyl | 3-Fluorophenyl |
| 671 | Butyl | 2,5-Dichlorophenyl |
| 672 | Pentyl | 3-Bromophenyl |
| 673 | Pentyl | 3-Iodophenyl |
| 674 | Butyl | 3-Thienyl |
| 675 | 3-Methylbutyl | 5-Methyl-2-thienyl |
| 676 | 3-Methylbutyl | 3-Fluorophenyl |
| 677 | Pentyl | 2,5-Dichlorophenyl |
| 678 | 3-Methylbutyl | 3-Bromophenyl |
| 679 | 3-Methylbutyl | 3-Iodophenyl |
| 680 | Pentyl | 3-Thienyl |
| 681 | Butyl | 3-Methyl-2-thienyl |
| 682 | 2-Methylpropyl | 2-Chlorophenyl |
| 815 | 2-Methylpropyl | 3,5-Difluorophenyl |
| 816 | 3-Methylbutyl | 3,5-Difluorophenyl |
| 817 | Butyl | 3,5-Difluorophenyl |
| 2238 | Benzyl | 3-Fluorophenyl |
| 2242 | Benzyl | 2-Fluorophenyl |
| 2253 | Benzyl | 2-Methoxyphenyl |
| 2257 | Benzyl | 5-Fluoro-2-methylphenyl |
| 2260 | Benzyl | 3-Chlorophenyl |
| 2268 | Benzyl | 2,3-Difluorophenyl |
| 2271 | Benzyl | 2,5-Difluorophenyl |

EXAMPLE 10

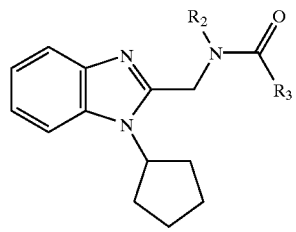

For each compound, the definitions of R₂ and R₃ are specified in the following table.

| Compound No. | R₂ | R₃ |
|---|---|---|
| 683 | Allyl | 3-Fluorophenyl |
| 684 | Allyl | 3,4-Difluorophenyl |
| 685 | Propyl | 1,3-Benzodioxol-5-yl |
| 686 | Allyl | 5-Chloro-2-methoxyphenyl |
| 687 | Propyl | 3-Methyl-2-Thienyl |
| 688 | Propyl | 3-Fluoro-4-methylphenyl |

-continued

| Compound No. | R₂ | R₃ |
|---|---|---|
| 689 | Propyl | 3-Fluorophenyl |
| 690 | Propyl | 3,4-Difluorophenyl |
| 691 | Allyl | 3-Chloro-4-fluorophenyl |
| 692 | Propyl | 5-Chloro-2-methoxyphenyl |
| 693 | Allyl | Phenyl |
| 694 | Allyl | 5-Fluoro-2-methylphenyl |
| 695 | Propyl | 4-Fluorophenyl |
| 696 | Allyl | 2,5-Difluorophenyl |
| 697 | Propyl | 3-Chloro-4-fluorophenyl |
| 698 | Methyl | 2,5-Dichlorophenyl |
| 699 | Propyl | Phenyl |
| 700 | Propyl | 5-Fluoro-2-methylphenyl |
| 701 | Allyl | 2-Fluorophenyl |
| 702 | Propyl | 2,5-Difluorophenyl |
| 703 | Methyl | 5-Chloro-2-methoxyphenyl |
| 704 | Allyl | 2,5-Dichlorophenyl |
| 705 | Allyl | 3-Methylphenyl |
| 706 | Allyl | 3-Chlorophenyl |
| 707 | Propyl | 2-Fluorophenyl |
| 708 | Allyl | 1,3-Benzodioxol-5-yl |
| 709 | Ethyl | 5-Chloro-2-methoxyphenyl |
| 710 | Propyl | 2,5-Dichlorophenyl |
| 711 | Propyl | 3-Methylphenyl |
| 712 | Propyl | 3-Chlorophenyl |
| 713 | Propyl | 4-Methylthio phenyl |
| 714 | Propyl | 3-Iodo-4-methylphenyl |
| 887 | Propyl | 2,3,6-Trifluorophenyl |
| 2306 | 3-Methylbutyl | 2,3,6-Trifluorophenyl |
| 2347 | 3-Methylbutyl | 3-(2-1,2,3,4-Teterahydro isoquinolinylmethyl) phenyl |
| 2348 | 3-Methylbutyl | 3-(Diethylaminomethyl)phenyl |
| 2349 | 3-Methylbutyl | 3-(Hexylmethylaminomethyl)phenyl |
| 2351 | 3-Methylbutyl | 3-(Dibutylaminomethyl)phenyl |
| 2364 | 3-Methylbutyl | 3-[(1-methylethyl) methylaminomethyl]phenyl |
| 2365 | 3-Nethylbutyl | 3-(Cyclohexyl ethylamino methyl)phenyl |
| 2367 | 3-Methylbutyl | 3-[bis(2-Methoxyethyl) aminomethyl]phenyl |
| 2369 | 3-Methylbutyl | 3-[(3,3,5-Trimethylaza perhydroepinyl)methyl]phenyl |

EXAMPLE 11

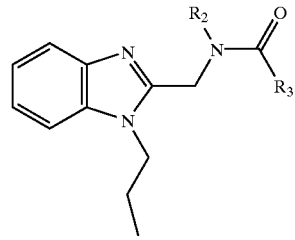

For each compound, the definitions of R₂ and R₃ are specified in the following table.

| Compound No. | R₂ | R₃ |
|---|---|---|
| 715 | Methyl | 3-Fluorophenyl |
| 716 | Methyl | 5-Fluoro-2-methylphenyl |
| 717 | Methyl | 3-Chlorophenyl |
| 718 | Methyl | 5-Chloro-2-methoxyphenyl |
| 839 | 2-Methylpropyl | 2,3,6-Trifluorophenyl |
| 840 | Pentyl | 2,3,6-Trifluorophenyl |
| 841 | 3-Methylbutyl | 2,3,6-Trifluorophenyl |

| Compound No. | $R_2$ | $R_3$ |
|---|---|---|
| 938 | Butyl | Phenyl |
| 939 | 2-Methylpropyl | Phenyl |
| 940 | Pentyl | Phenyl |
| 941 | 3-Methylbutyl | Phenyl |
| 942 | Butyl | 3-Methylphenyl |
| 943 | 2-Methylpropyl | 3-Methylphenyl |
| 944 | 3-Methylbutyl | 3-Methylphenyl |
| 945 | 2-Methylpropyl | 4-Methylphenyl |
| 946 | Butyl | 3-Fluorophenyl |
| 947 | Pentyl | 3-Fluorophenyl |
| 948 | 3-Methylbutyl | 3-Fluorophenyl |
| 949 | 3-Methylbutyl | 4-Fluorophenyl |
| 950 | Butyl | 2-Fluorophenyl |
| 951 | 2-Methylpropyl | 2-Fluorophenyl |
| 952 | Pentyl | 2-Fluorophenyl |
| 953 | 3-Methylbutyl | 2-Fluorophenyl |
| 954 | 2-Methylpropyl | 3,4-Dimethylphenyl |
| 1002 | Butyl | 2-Chlorophenyl |
| 1003 | Pentyl | 2-Chlorophenyl |
| 1004 | 3-Methylbutyl | 2-Chlorophenyl |
| 1005 | Butyl | 3,4-Difluorophenyl |
| 1006 | 2-Methylpropyl | 3,4-Difluorophenyl |
| 1007 | Pentyl | 3,4-Difluorophenyl |
| 1008 | 3-Methylbutyl | 3,4-Difluorophenyl |
| 1009 | Butyl | 2,3-Difluorophenyl |
| 1010 | 2-Methylpropyl | 2,3-Difluorophenyl |
| 1011 | Pentyl | 2,3-Difluorophenyl |
| 1012 | 3-Methylbutyl | 2,3-Difluorophenyl |
| 1013 | Butyl | 2,5-Difluorophenyl |
| 1014 | 2-Methylpropyl | 2,5-Difluorophenyl |
| 1015 | Pentyl | 2,5-Difluorophenyl |
| 1016 | 3-Methylbutyl | 2,5-Difluorophenyl |
| 1017 | Butyl | 2,4-Difluorophenyl |
| 1018 | 2-Methylpropyl | 2,4-Difluorophenyl |
| 1019 | 3-Methylbutyl | 2,4-Difluorophenyl |
| 1020 | 2-Methylpropyl | 3-Ethoxyphenyl |
| 1021 | Butyl | 1,3-Benzodioxol-5-yl |
| 1022 | 2-Methylpropyl | 1,3-Benzodioxol-5-yl |
| 1023 | 3-Methylbutyl | 1,3-Benzodioxol-5-yl |
| 1024 | 2-Methylpropyl | 4-Methylthio phenyl |
| 1025 | 3-Methylbutyl | 4-Methylthio phenyl |
| 1026 | 2-Methylpropyl | 3-Fluoro-4-methoxyphenyl |
| 1027 | 3-Methylbutyl | 3-Fluoro-4-methoxyphenyl |
| 1028 | 2-Methylpropyl | 4-Chloro-3-methylphenyl |
| 1029 | Butyl | 3-Chloro-4-fluorophenyl |
| 1030 | 2-Methylpropyl | 3-Chloro-4-fluorophenyl |
| 1031 | Pentyl | 3-Chloro-4-fluorophenyl |
| 1032 | 3-Methylbutyl | 3-Chloro-4-fluorophenyl |
| 1033 | 2-Methylpropyl | 3,4,5-Trifluorophenyl |
| 1034 | 3-Methylbutyl | 3,4,5-Trifluorophenyl |
| 1035 | 2-Methylpropyl | 4-Butylphenyl |
| 1036 | 2-Methylpropyl | 4-Ethylthiophenyl |
| 1109 | Cyclopropyl methyl | Phenyl |
| 1110 | Cyclopropyl Methyl | 3-Methylphenyl |
| 1111 | Cyclopropyl Methyl | 4-Methylphenyl |
| 1112 | Cyclopropyl Methyl | 3-Fluorophenyl |
| 1113 | Cyclopropyl Methyl | 2-Fluorophenyl |
| 1114 | Cyclopropyl Methyl | 3-Methoxyphenyl |
| 1115 | Cyclopropyl Methyl | 3-Fluoro-4-methylphenyl |
| 1116 | Cyclopropyl Methyl | 5-Fluoro-2-methylphenyl |
| 1130 | Cyclopropyl Methyl | 5-Chloro-2-methoxyphenyl |
| 1131 | Cyclopropyl Methyl | 2,5-Dichlorophenyl |
| 1132 | Cyclopropyl Methyl | 3-Bromophenyl |
| 1133 | 3-Methylbutyl | 5-Chloro-2-methoxyphenyl |
| 1134 | Butyl | 2,5-Dichlorophenyl |
| 1135 | 2-Methylpropyl | 2,5-Dichlorophenyl |
| 1136 | Pentyl | 2,5-Dichlorophenyl |
| 1137 | 3-Methylbutyl | 2,5-Dichlorophenyl |
| 1138 | 2-Methylpropyl | 2,4-Dichlorophenyl |
| 1139 | 2-Methylpropyl | 4-Pentylphenyl |
| 1140 | Butyl | 3-Bromophenyl |
| 1141 | 2-Methylpropyl | 3-Bromophenyl |
| 1142 | Pentyl | 3-Bromophenyl |
| 1143 | 3-Methylbutyl | 3-Bromophenyl |
| 1144 | 2-Methylpropyl | 4-Bromophenyl |
| 1256 | Cyclopropyl Methyl | 3,4-Difluorophenyl |
| 1257 | Cyclopropyl Methyl | 2,4-Difluorophenyl |
| 1258 | Propyl | 1,3-Benzodioxol-5-yl |
| 1259 | Cyclopropyl Methyl | 1,3-Benzodioxol-5-yl |
| 1260 | Cyclopropyl Methyl | 3-Chloro-4-fluorophenyl |
| 1261 | 3-Methylbutyl | 3-Iodo-4-methylphenyl |
| 1262 | 3-Methylbutyl | 2-Thienyl |
| 1263 | 3-Methylbutyl | 3-Thienyl |
| 1264 | 2-Methylpropyl | 5-Methyl-2-thienyl |
| 1265 | Pentyl | 5-Methyl-2-thienyl |
| 1266 | 3-Methylbutyl | 5-Methyl-2-thienyl |
| 1267 | 3-Methylbutyl | 3-Fluorobenzyl |
| 1448 | Methyl | 2,5-Difluorophenyl |
| 1449 | Methyl | 2,5-Dichlorophenyl |
| 2005 | 3-Methylbutyl | 5-Bromo-2-thienyl |
| 2239 | Benzyl | 3-Fluorophenyl |
| 2243 | Benzyl | 2-Fluorophenyl |
| 2245 | Benzyl | 3,4-Dimethylphenyl |
| 2251 | Benzyl | 3-Methoxyphenyl |
| 2254 | Benzyl | 2-Methoxyphenyl |
| 2258 | Benzyl | 5-Fluoro-2-methylphenyl |
| 2261 | Benzyl | 3-Chlorophenyl |
| 2266 | Benzyl | 3,4-Difluorophenyl |
| 2269 | Benzyl | 2,3-Difluorophenyl |
| 2272 | Benzyl | 2,5-Difluorophenyl |
| 2281 | Benzyl | 5-Chloro-2-methoxyphenyl |
| 2289 | Benzyl | 2,5-Dichlorophenyl |
| 2292 | Benzyl | 3-Bromophenyl |
| 2295 | Benzyl | 2-Bromophenyl |
| 2298 | Benzyl | 3-Iodophenyl |
| 2302 | Benzyl | 2,5-Dimethylpyrrol-3-yl |
| 2305 | Benzyl | 3-Methylbutyl |
| 2320 | 3-Methylbutyl | 3-(Methylaminomethyl)phenyl |
| 2321 | 3-Methylbutyl | 3-(Ethylaminomethyl)phenyl |
| 2322 | 3-Methylbutyl | 3-(Cyclobutylaminomethyl)phenyl |
| 2323 | 3-Methylbutyl | 3-[(1-Methylpropyl)aminomethyl]phenyl |
| 2324 | 3-Methylbutyl | 3-(Cyclopentylaminomethyl)phenyl |
| 2350 | 3-Methylbutyl | 3-(Dibutylaminomethyl)phenyl |
| 2366 | 3-Methylbutyl | 3-[bis(2-Methoxyethyl)aminomethyl]phenyl |
| 2368 | 3-Methylbutyl | 3-[(3,3,5-Trimethylazaperhydroepinyl)methyl]phenyl |
| 2391 | Methyl | 2,5-Difluorophenyl |

EXAMPLE 12

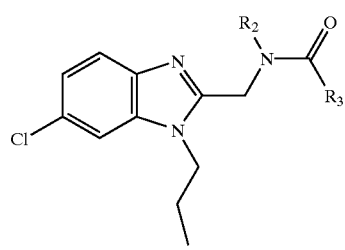

For each compound, the definitions of $R_2$ and $R_3$ are specified in the following table.

| Compound No. | R₂ | R₃ |
|---|---|---|
| 719 | Propyl | 3-Fluorophenyl |
| 720 | Propyl | 1,3-Benzodioxol-5-yl |
| 721 | Propyl | 5-Fluoro-2-methylphenyl |
| 722 | Allyl | 2-Fluorophenyl |
| 723 | Propyl | 3-Chloro-4-fluorophenyl |
| 724 | Propyl | 3-Chlorophenyl |
| 725 | Propyl | 2-Fluorophenyl |
| 726 | Allyl | 5-Chloro-2-methoxyphenyl |
| 727 | Allyl | 3-Chlorophenyl |
| 728 | Methyl | 3-Fluorophenyl |
| 729 | Methyl | 2,5-Difluorophenyl |
| 730 | Propyl | Phenyl |
| 731 | Propyl | 3-Chlorophenyl |
| 732 | Allyl | 3-Fluorophenyl |
| 733 | Propyl | 2,5-Difluorophenyl |
| 734 | Propyl | 3-Fluoro-4-methylphenyl |
| 735 | Propyl | 4-Methylthio phenyl |
| 736 | 3-Methylbutyl | 3-Fluorophenyl |
| 737 | 2-Methylpropyl | 2-Fluorophenyl |
| 738 | Butyl | 3,4-Difluorophenyl |
| 739 | 2-Methylpropyl | 2,5-Difluorophenyl |
| 740 | 3-Methylbutyl | 1,3-Benzodioxol-5-yl |
| 741 | Butyl | 4-Fluorophenyl |
| 742 | Pentyl | 2-Fluorophenyl |
| 743 | 2-Methylpropyl | 3,4-Difluorophenyl |
| 744 | Pentyl | 2,5-Difluorophenyl |
| 745 | Butyl | 3-Chloro-4-fluorophenyl |
| 746 | Butyl | 3-Fluorophenyl |
| 747 | 2-Methylpropyl | 4-Fluorophenyl |
| 748 | 3-Methylbutyl | 2-Fluorophenyl |
| 749 | Pentyl | 3,4-Difluorophenyl |
| 750 | 3-Methylbutyl | 2,5-Difluorophenyl |
| 751 | 2-Methylpropyl | 3-Chloro-4-fluorophenyl |
| 752 | 2-Methylpropyl | 3-Chlorophenyl |
| 753 | 3-Methylbutyl | 4-Fluorophenyl |
| 754 | 2-Methylpropyl | 2,5-Dimethylphenyl |
| 755 | 3-Methylbutyl | 3,4-Difluorophenyl |
| 756 | Butyl | 1,3-Benzodioxol-5-yl |
| 757 | Pentyl | 3-Chloro-4-fluorophenyl |
| 758 | Pentyl | 3-Fluorophenyl |
| 759 | Butyl | 2-Fluorophenyl |
| 760 | 3-Methylbutyl | 2,5-Dimethylphenyl |
| 761 | Butyl | 2,5-Difluorophenyl |
| 762 | 2-Methylpropyl | 1,3-Benzodioxol-5-yl |
| 763 | 3-Methylbutyl | 3-Chloro-4-fluorophenyl |
| 764 | Butyl | 5-Chloro-2-methoxyphenyl |
| 765 | 2-Methylpropyl | 2,5-Dichlorophenyl |
| 766 | Pentyl | 5-Methyl-2-thienyl |
| 767 | 3-Methylbutyl | Phenyl |
| 768 | 2-Methylpropyl | 2-Methylphenyl |
| 769 | 3-Methylbutyl | 5-Fluoro-2-methylphenyl |
| 770 | 2-Methylpropyl | 5-Chloro-2-methoxyphenyl |
| 771 | Pentyl | 2,5-Dichlorophenyl |
| 772 | 3-Methylbutyl | 5-Methyl-2-thienyl |
| 773 | Butyl | 3-Methylphenyl |
| 774 | 3-Methylbutyl | 2-Methylphenyl |
| 775 | Butyl | 3-Chlorophenyl |
| 776 | Pentyl | 5-Chloro-2-methoxyphenyl |
| 777 | 3-Methylbutyl | 2,5-Dichlorophenyl |
| 778 | Butyl | Phenyl |
| 779 | 2-Methylpropyl | 3-Methylphenyl |
| 780 | 2-Methylpropyl | 3-Fluoro-4-methylphenyl |
| 781 | 2-Methylpropyl | 3-Chlorophenyl |
| 782 | 3-Methylbutyl | 5-Chloro-2-methoxyphenyl |
| 783 | Butyl | 5-Methyl-2-thienyl |
| 784 | 2-Methylpropyl | Phenyl |
| 785 | Pentyl | 3-Methylphenyl |
| 786 | 3-Methylbutyl | 3-Fluoro-4-methylphenyl |
| 787 | Pentyl | 3-Chlorophenyl |
| 788 | Butyl | 2,5-Dichlorophenyl |
| 789 | 2-Methylpropyl | 5-Methyl-2-thienyl |
| 790 | Pentyl | Phenyl |
| 791 | 3-Methylbutyl | 3-Methylphenyl |
| 792 | Pentyl | 5-Fluoro-2-methylphenyl |
| 793 | 3-Methylbutyl | 3-Chlorophenyl |
| 794 | 2-Methylpropyl | 4-Methylthio phenyl |
| 795 | 2-Methylpropyl | 3-Fluoro-4-methoxyphenyl |
| 796 | 3-Methylbutyl | 3-Fluoro-4-methoxyphenyl |
| 797 | 2-Methylpropyl | 2,4,6-Trifluorophenyl |
| 798 | Butyl | 2,3,6-Trifluorophenyl |
| 799 | 2-Methylpropyl | 2,3,6-Trifluorophenyl |
| 885 | Methyl | 2,3,6-Trifluorophenyl |
| 886 | Propyl | 2,3,6-Trifluorophenyl |
| 933 | Propyl | Phenyl |
| 934 | Propyl | 3-Fluorophenyl |
| 935 | Propyl | 4-Fluorophenyl |
| 936 | Allyl | 2-Fluorophenyl |
| 937 | Propyl | 2-Fluorophenyl |
| 1037 | Butyl | 3-Chlorophenyl |
| 1038 | 2-Methylpropyl | 3-Chlorophenyl |
| 1039 | Pentyl | 3-Chlorophenyl |
| 1040 | 3-Methylbutyl | 3-Chlorophenyl |
| 1041 | Butyl | 3,4-Difluorophenyl |
| 1042 | 2-Methylpropyl | 3,4-Difluorophenyl |
| 1043 | Pentyl | 3,4-Difluorophenyl |
| 1044 | 3-Methylbutyl | 3,4-Difluorophenyl |
| 1045 | Butyl | 2,3-Difluorophenyl |
| 1046 | 2-Methylpropyl | 2,3-Difluorophenyl |
| 1047 | Pentyl | 2,3-Difluorophenyl |
| 1048 | 3-Methylbutyl | 2,3-Difluorophenyl |
| 1049 | Butyl | 2,5-Difluorophenyl |
| 1050 | 2-Methylpropyl | 2,5-Difluorophenyl |
| 1051 | Pentyl | 2,5-Difluorophenyl |
| 1052 | 3-Methylbutyl | 2,5-Difluorophenyl |
| 1053 | Butyl | 2,4-Difluorophenyl |
| 1054 | 2-Methylpropyl | 2,4-Difluorophenyl |
| 1055 | Pentyl | 2,4-Difluorophenyl |
| 1056 | 3-Methylbutyl | 2,4-Difluorophenyl |
| 1057 | 2-Methylpropyl | 4-Propylphenyl |
| 1058 | 2-Methylpropyl | 4-Ethoxyphenyl |
| 1059 | Butyl | 1,3-Benzodioxol-5-yl |
| 1060 | 2-Methylpropyl | 1,3-Benzodioxol-5-yl |
| 1061 | Pentyl | 1,3-Benzodioxol-5-yl |
| 1062 | 3-Methylbutyl | 1,3-Benzodioxol-5-yl |
| 1063 | Butyl | 4-Methylothio phenyl |
| 1064 | 2-Methylpropyl | 4-Methylothio phenyl |
| 1065 | Butyl | 3-Fluoro-4-methoxyphenyl |
| 1066 | 2-Methylpropyl | 3-Fluoro-4-methoxyphenyl |
| 1067 | 3-Methylbutyl | 3-Fluoro-4-methoxyphenyl |
| 1068 | 2-Methylpropyl | 4-Chloro-3-methylphenyl |
| 1069 | 3-Methylbutyl | 4-Chloro-3-methylphenyl |
| 1070 | Butyl | 3-Chloro-4-fluorophenyl |
| 1071 | 2-Methylpropyl | 3-Chloro-4-fluorophenyl |
| 1072 | Pentyl | 3-Chloro-4-fluorophenyl |
| 1073 | 3-Methylbutyl | 3-Chloro-4-fluorophenyl |
| 1074 | 2-Methylpropyl | 3,4,5-Trifluorophenyl |
| 1075 | 3-Methylbutyl | 3,4,5-Trifluorophenyl |
| 1076 | 2-Methylpropyl | 4-Ethylthiophenyl |
| 1077 | 3-Methylbutyl | 2,3,6-Trifluorophenyl |
| 1078 | Allyl | 5-Chloro-2-methoxyphenyl |
| 1079 | Propyl | 5-Chloro-2-methoxyphenyl |
| 1080 | Propyl | 3-Trifluoromethylphenyl |
| 1081 | Allyl | 2,5-Dichlorophenyl |
| 1082 | Propyl | 2,5-Dichlorophenyl |
| 1083 | Methyl | 3-Bromophenyl |
| 1084 | Allyl | 3-Bromophenyl |
| 1085 | Propyl | 3-Bromo-4-fluorophenyl |
| 1086 | Methyl | 3-Iodophenyl |
| 1087 | Allyl | 3-Iodophenyl |
| 1088 | Propyl | 3-Iodophenyl |
| 1089 | 2-Methoxyethyl | 2,5-Difluorophenyl |
| 1090 | 2-Methoxyethyl | 2,5-Dichlorophenyl |
| 1091 | 2-Methoxyethyl | 3-Bromophenyl |
| 1145 | 2-Methylpropyl | 3-Chloro-4-methoxyphenyl |
| 1146 | 3-Methylbutyl | 3-Chloro-4-methoxyphenyl |
| 1147 | 2-Methylpropyl | 5-Chloro-2-methoxyphenyl |
| 1148 | Pentyl | 5-Chloro-2-methoxyphenyl |
| 1149 | 3-Methylbutyl | 5-Chloro-2-methoxyphenyl |
| 1150 | Pentyl | 3-Trifluoromethylphenyl |
| 1151 | 3-Methylbutyl | 3-Trifluoromethylphenyl |
| 1152 | Butyl | 2-Trifluoromethylphenyl |

-continued

| Compound No. | R₂ | R₃ |
|---|---|---|
| 1153 | 3-Methylbutyl | 2-Trifluoromethylphenyl |
| 1154 | Butyl | 3,4-Dichlorophenyl |
| 1155 | 2-Methylpropyl | 3,4-Dichlorophenyl |
| 1156 | 3-Methylbutyl | 3,4-Dichlorophenyl |
| 1157 | 2-Methylpropyl | 2,5-Dichlorophenyl |
| 1158 | Pentyl | 2,5-Dichlorophenyl |
| 1159 | 3-Methylbutyl | 2,5-Dichlorophenyl |
| 1160 | 2-Methylpropyl | 2,4-Dichlorophenyl |
| 1161 | 2-Methylpropyl | 3-Bromophenyl |
| 1162 | Pentyl | 3-Bromophenyl |
| 1163 | 3-Methylbutyl | 3-Bromophenyl |
| 1164 | 2-Methylpropyl | 4-Bromophenyl |
| 1165 | 2-Methylpropyl | 2-Bromophenyl |
| 1166 | Pentyl | 2-Bromophenyl |
| 1167 | 3-Methylbutyl | 2-Bromophenyl |
| 1194 | 2-Methylpropyl | 3-Phenoxyphenyl |
| 1195 | 2-Methylpropyl | 4-Phenoxyphenyl |
| 1196 | Butyl | 3-Bromo-4-methylphenyl |
| 1197 | 2-Methylpropyl | 3-Bromo-4-methylphenyl |
| 1198 | Butyl | 3-Bromo-4-fluorophenyl |
| 1199 | 2-Methylpropyl | 3-Bromo-4-fluorophenyl |
| 1200 | Pentyl | 3-Bromo-4-fluorophenyl |
| 1201 | 3-Methylbutyl | 3-Bromo-4-fluorophenyl |
| 1202 | Butyl | 3-Iodophenyl |
| 1203 | Pentyl | 3-Iodophenyl |
| 1204 | 3-Methylbutyl | 3-Iodophenyl |
| 1205 | 2-Methylpropyl | 4-Iodophenyl |
| 1206 | Methyl | 3-Iodophenyl |
| 1239 | Cyclopentyl | 4-Methylphenyl |
| 1240 | Cyclopentyl | 3-Fluoro-4-methylphenyl |
| 1241 | Cyclopropyl Methyl | 5-Chloro-2-methoxyphenyl |
| 1242 | Cyclopropyl Methyl | 3-Trifluoromethylphenyl |
| 1243 | Cyclopropyl Methyl | 2,5-Dichlorophenyl |
| 1244 | Cyclopropyl Methyl | 3-Bromophenyl |
| 1245 | Cyclopentyl | 3-Methoxybenzyl |
| 1246 | Cyclopentyl | 2-(2-Chlorophenyl)ethenyl |
| 1247 | Cyclopropyl Methyl | 3-Bromo-4-methylphenyl |
| 1248 | Cyclopropyl Methyl | 3-Bromo-4-fluorophenyl |
| 1249 | Cyclopropyl Methyl | 3-Iodophenyl |
| 1253 | Cyclopentyl | 3-Chloro-4-methoxyphenyl |
| 1254 | Cyclopropyl Methyl | 5-Chloro-2-methoxyphenyl |
| 1255 | Cyclopentyl | 2,4-Dichlorophenyl |
| 1268 | Cyclopentyl | 3-Fluorobenzyl |
| 1269 | Cyclopentyl | 2-(2-Trifluoromethylphenyl)ethenyl |
| 1270 | Cyclopentyl | 2-(2-Bromophenyl)ethenyl |
| 1271 | Cyclopropyl Methyl | 2,3,6-Trifluorophenyl |
| 1274 | Cyclopentyl | 3-Chloro-4-methylphenyl |
| 1275 | Cyclopropyl Methyl | 2,4,5-Trifluorophenyl |
| 1425 | Propyl | 3-Fluoro-4-methylphenyl |
| 1426 | Propyl | 3-Chlorophenyl |
| 1427 | Allyl | 3-Bromo-4-fluorophenyl |
| 1428 | Propyl | 3-Bromo-4-fluorophenyl |
| 1429 | Allyl | 3-Iodophenyl |
| 1430 | Propyl | 3-Iodophenyl |
| 1431 | Propyl | 3-Iodo-4-methylphenyl |
| 1433 | Propyl | 3,4-Difluorophenyl |
| 1434 | Propyl | 2,3-Difluorophenyl |
| 1435 | Propyl | 2,4-Difluorophenyl |
| 1436 | Propyl | 1,3-Benzadioxol-5-yl |
| 1437 | Propyl | 3-Chloro-4-fluorophenyl |
| 1438 | Propyl | 5-Chloro-2-methoxyphenyl |
| 1439 | Methyl | 2,5-Dichlorophenyl |
| 1440 | Allyl | 2,5-Dichlorophenyl |
| 1441 | Propyl | 2,5-Dichlorophenyl |
| 1442 | Propyl | 2,4-Dichlorophenyl |
| 1443 | Methyl | 3-Bromophenyl |
| 1444 | Allyl | 3-Bromophenyl |

-continued

| Compound No. | R₂ | R₃ |
|---|---|---|
| 1445 | Propyl | 3-Bromophenyl |
| 1446 | Propyl | 5-Methyl-2-thienyl |
| 1447 | Propyl | 2,6-Difluorophenyl |
| 1977 | 3-Methylbutyl | 4,5-Dimethyl-2-furyl |
| 1978 | 3-Methylbutyl | 3-Chloro-4-methylphenyl |
| 1980 | 3-Methylbutyl | 2,4,5-Trifluorophenyl |
| 1982 | 3-Methylbutyl | 2,6-Difluorophenyl |
| 1983 | 3-Methylbutyl | 2-Bromo-5-methoxyphenyl |
| 1984 | 3-Methylbutyl | 3,5-Difluorophenyl |
| 2006 | 3-Methylbutyl | 5-Bromo-2-thienyl |
| 2008 | 3-Methylbutyl | 3-Bromo-2-thienyl |

EXAMPLE 13

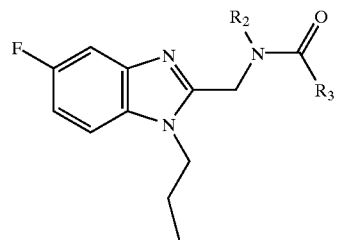

For each compound, the definitions of R₂ and R₃ are specified in the following table.

| Compound No. | R₂ | R₃ |
|---|---|---|
| 800 | Propyl | Phenyl |
| 801 | Methyl | 3-Chlorophenyl |
| 802 | Allyl | 3-Chlorophenyl |
| 803 | Propyl | 3-Chlorophenyl |
| 804 | Propyl | 5-Chloro-2-methoxyphenyl |
| 805 | Propyl | 3-Trifluoromethylphenyl |
| 806 | Propyl | 2,5-Dichlorophenyl |
| 807 | Propyl | 3-Bromophenyl |
| 808 | Propyl | 3-Bromo-4-fluorophenyl |
| 809 | Methyl | 3-Iodophenyl |
| 810 | Allyl | 3-Iodophenyl |
| 811 | Propyl | 3-Iodophenyl |
| 888 | Allyl | 5-Chloro-2-methoxyphenyl |
| 931 | Propyl | 3-Fluorophenyl |
| 932 | Propyl | 2-Fluorophenyl |
| 1092 | Propyl | 3-Fluorophenyl |
| 1093 | Propyl | 2-Fluorophenyl |
| 1094 | Allyl | 2,5-Difluorophenyl |
| 1095 | Propyl | 2,5-Difluorophenyl |
| 1096 | Propyl | 1,3-Benzodioxol-5-yl |
| 1097 | Methyl | 5-Chloro-2-methoxyphenyl |
| 1098 | Allyl | 5-Chloro-2-methoxyphenyl |
| 1099 | Methyl | 2,5-Dichlorophenyl |
| 1168 | Methyl | 5-Chloro-2-methoxyphenyl |
| 1169 | Allyl | 5-Chloro-2-methoxyphenyl |
| 1170 | Propyl | 5-Chloro-2-methoxyphenyl |
| 1171 | Propyl | 3,4-Dichlorophenyl |
| 1172 | Allyl | 2,5-Dichlorophenyl |
| 1173 | Propyl | 2,5-Dichlorophenyl |
| 1174 | Propyl | 2,4-Dichlorophenyl |
| 1175 | Methyl | 3-Bromophenyl |
| 1176 | Allyl | 3-Bromophenyl |
| 1177 | Propyl | 3-Bromophenyl |
| 1178 | Cyclopropyl methyl | 5-Chloro-2-methoxyphenyl |
| 1179 | Cyclopropyl methyl | 2,5-Dichlorophenyl |
| 1180 | Propyl | 3-Bromophenyl |

-continued

| Compound No. | $R_2$ | $R_3$ |
|---|---|---|
| 1181 | Cyclopropyl methyl | 3-Bromophenyl |
| 1182 | Pentyl | 3-Bromo-4-fluorophenyl |
| 1183 | 3-Methylbutyl | 3-Bromo-4-fluorophenyl |
| 1184 | Pentyl | 3-Iodophenyl |
| 1185 | Cyclopropyl Methyl | 3-Bromo-4-fluorophenyl |
| 1186 | Cyclopropyl Methyl | 3-Iodophenyl |
| 1756 | Butyl | 2-Thienyl |
| 1757 | 2-Methylpropyl | 2-Thienyl |
| 1758 | Pentyl | 2-Thienyl |
| 1759 | 3-Methylbutyl | 2-Thienyl |
| 1760 | Buty1 | 3-Thienyl |
| 1761 | 2-Methylpropyl | 3-Thienyl |
| 1762 | Pentyl | 3-Thienyl |
| 1763 | 3-Methylbutyl | 3-Thienyl |
| 1764 | 3-Methylbutyl | Benzyl |
| 1765 | Butyl | 5-Methyl-2-thienyl |
| 1766 | 2-Methylpropyl | 5-Methyl-2-thienyl |
| 1767 | Pentyl | 5-Methyl-2-thienyl |
| 1768 | 3-Methylbutyl | 5-Methyl-2-thienyl |
| 1769 | 3-Methylbutyl | 3-Fluorobenzyl |
| 1770 | 3-Methylbutyl | 4-Fluorobenzyl |
| 1771 | 3-Methylbutyl | 3-Methoxybenzyl |
| 1787 | 3-Methylbutyl | 2,3,6-Trifluorophenyl |
| 1788 | 2-Methylpropyl | 2,3,6-Trifluorophenyl |
| 1789 | 3-Methylbutyl | 2,3,6-Trifluorophenyl |
| 1790 | 3-Methylbutyl | 2-Chloro-6-fluorophenyl |
| 1791 | Butyl | Phenyl |
| 1792 | 2-Methylpropyl | Phenyl |
| 1793 | Pentyl | Phenyl |
| 1794 | 3-Methylbutyl | Phenyl |
| 1795 | Butyl | 3-Methylphenyl |
| 1796 | 2-Methylpropyl | 3-Methylphenyl |
| 1797 | Pentyl | 3-Methylphenyl |
| 1798 | 3-Methylbutyl | 3-Methylphenyl |
| 1799 | Butyl | 4-Methylphenyl |
| 1800 | 2-Methylpropyl | 4-Methylphenyl |
| 1801 | Butyl | 3-Fluorophenyl |
| 1802 | 2-Methylpropyl | 3-Fluorophenyl |
| 1803 | Pentyl | 3-Fluorophenyl |
| 1804 | 3-Methylbutyl | 3-Fluorophenyl |
| 1805 | Butyl | 4-Fluorophenyl |
| 1806 | 3-Methylbutyl | 4-Fluorophenyl |
| 1807 | Butyl | 2-Fluorophenyl |
| 1808 | 2-Methylpropyl | 2-Fluorophenyl |
| 1809 | Pentyl | 2-Fluorophenyl |
| 1810 | 3-Methylbutyl | 2-Fluorophenyl |
| 1811 | 2-Methylpropyl | 4-Ethylphenyl |
| 1812 | 2-Methylpropyl | 3,4-Dimethylphenyl |
| 1813 | 3-Methylbutyl | 3-Methoxyphenyl |
| 1814 | 2-Methylpropyl | 3-Fluoro-4-methylphenyl |
| 1815 | 3-Methylbutyl | 3-Fluoro-4-methylphenyl |
| 1816 | 2-Methylpropyl | 5-Fluoro-2-methylphenyl |
| 1817 | Pentyl | 5-Fluoro-2-methylphenyl |
| 1818 | 3-Methylbutyl | 5-Fluoro-2-methylphenyl |
| 1857 | Butyl | 2,5-Dichlorophenyl |
| 1858 | 2-Methylpropyl | 2,5-Dichlorophenyl |
| 1859 | Pentyl | 2,5-Dichlorophenyl |
| 1860 | 3-Methylbutyl | 2,5-Dichlorophenyl |
| 1861 | 2-Methylpropyl | 4-Pentylphenyl |
| 1862 | Butyl | 3-Bromophenyl |
| 1863 | 2-Methylpropyl | 3-Bromophenyl |
| 1864 | Pentyl | 3-Bromophenyl |
| 1865 | 3-Methylbutyl | 3-Bromophenyl |
| 1866 | 2-Methylpropyl | 4-Bromophenyl |
| 1922 | Butyl | 3,4-Dimethylphenyl |
| 1923 | 2-Methylpropyl | 3-Iodo-4-methylphenyl |
| 1924 | 3-Methylbutyl | 3-Iodo-4-methylphenyl |
| 1986 | Butyl | 4,5-Dimethyl-2-furyl |
| 1987 | 2-Methylpropyl | 4,5-Dimethyl-2-furyl |
| 1988 | 3-Methylbutyl | 4,5-Dimethyl-2-furyl |
| 1989 | 3-Methylbutyl | 4-Methoxy-3-thienyl |
| 1990 | Butyl | 3-Chloro-2-thienyl |
| 1991 | 2-Methylpropyl | 3-Chloro-2-thienyl |
| 1992 | Pentyl | 3-Chloro-2-thienyl |
| 1993 | 3-Methylbutyl | 3-Chloro-2-thienyl |
| 1994 | 2-Methylpropyl | 3-Chloro-4-methylphenyl |
| 1995 | 3-Methylbutyl | 3-Chloro-4-methylphenyl |
| 1996 | 3-Methylbutyl | 2,4,5-Trifluorophenyl |
| 1997 | Pentyl | 2,6-Difluorophenyl |
| 1998 | 3-Methylbutyl | 2,6-Difluorophenyl |
| 1999 | Pentyl | 2-Bromo-5-methoxyphenyl |
| 2000 | 3-Methylbutyl | 2-Bromo-5-methoxyphenyl |
| 2001 | 3-Methylbutyl | 3,5-Difluorophenyl |
| 2002 | 2-Methylpropyl | 5-Bromo-2-thienyl |
| 2003 | 3-Methylbutyl | 5-Bromo-2-thienyl |
| 2009 | Butyl | 5-Ethyl-2-thienyl |
| 2010 | 2-Methylpropyl | 5-Ethyl-2-thienyl |
| 2011 | 3-Methylbutyl | 5-Ethyl-2-thienyl |
| 2012 | 2-Methylpropyl | 5-Propyl-2-thienyl |
| 2013 | 2-Methylpropyl | 5-Butyl-2-thienyl |
| 2014 | 2-Methylpropyl | 5-Pentyl-2-thienyl |
| 2015 | 2-Methylpropyl | 5-Hexyl-2-thienyl |

EXAMPLE 14

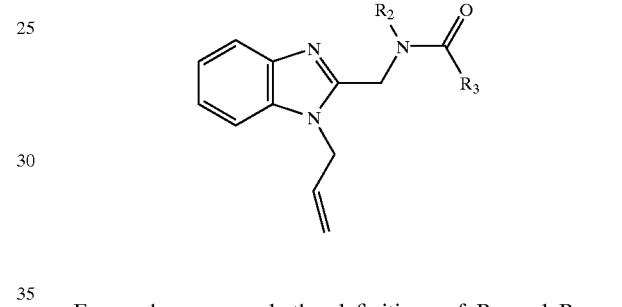

For each compound, the definitions of $R_2$ and $R_3$ are specified in the following table.

| Compound No. | $R_2$ | $R_3$ |
|---|---|---|
| 889 | Methyl | 2,5-Difluorophenyl |
| 890 | Methyl | 215-Dichlorophenyl |
| 891 | Propyl | 3-Bromophenyl |
| 892 | Methyl | 3-Iodophenyl |
| 893 | Allyl | 3-Iodophenyl |
| 894 | Propyl | 3-Iodophenyl |
| 1126 | Propyl | 2,5-Dichlorophenyl |
| 1127 | Methyl | 3-Bromophenyl |
| 1128 | Allyl | 3-Bromophenyl |
| 1432 | Propyl | 3-Bromo-4-fluorophenyl |
| 1517 | 2-Methylpropyl | 3-Fluorophenyl |
| 1518 | 2-Methylpropyl | 3,4-Dimethylphenyl |
| 1519 | 2-Methylpropyl | 3-Methoxyphenyl |
| 1520 | 2-Methylpropyl | 3-Fluoro-4-methylphenyl |
| 1521 | Cyclopentyl | 3-Fluoro-4-methylphenyl |
| 1522 | 2-Methylpropyl | 5-Fluoro-2-methylphenyl |
| 1523 | 2-Methylpropyl | 2-Fluoro-3-methylphenyl |
| 1524 | 2-Methylpropyl | 3-Chlorophenyl |
| 1525 | 2-Methylpropyl | 4-Chlorophenyl |
| 1567 | 2-Methylpropyl | 1,3-Benzodioxol-5-yl |
| 1568 | Cyclopentyl | 4-Methoxyphenyl |
| 1569 | Cyclopentyl | 4-Butylphenyl |
| 1570 | 3-Methylbutyl | 3-Chloro-4-methoxyphenyl |
| 1571 | Cyclopentyl | 3-Chloro-4-methoxyphenyl |
| 1572 | 2-Methylpropyl | 3,4-Dichlorophenyl |
| 1573 | 3-Methylbutyl | 2,5-Dichlorophenyl |
| 1574 | Cyclopentyl | 2,4-Dichlorophenyl |
| 1575 | Cyclopentyl | 4-Pentylphenyl |
| 1576 | 3-Methylbutyl | 3-Bromophenyl |
| 1619 | 2-Methylpropyl | 4-Hexylphenyl |
| 1620 | Cyclopentyl | 4-Hexylphenyl |

-continued

| Compound No. | R₂ | R₃ |
|---|---|---|
| 1621 | 2-Methylpropyl | 3-Bromo-4-methylphenyl |
| 1622 | 2-Methylpropyl | 3-Bromo-4-fluorophenyl |
| 1623 | 3-Methylbutyl | 3-Bromo-4-fluorophenyl |
| 1624 | 2-Methylpropyl | 3-Iodophenyl |
| 1625 | 3-Methylbutyl | 3-Iodophenyl |
| 1653 | 2-Methylpropyl | 3-Iodo-4-methylphenyl |
| 1654 | 3-Methylbutyl | 2-Thienyl |
| 1655 | 3-Methylbutyl | Benzyl |
| 1656 | 2-Methylpropyl | 5-Methyl-2-thienyl |
| 1657 | 3-Methylbutyl | 5-Methyl-2-thienyl |
| 1658 | 3-Methylbutyl | 3-Fluorobenzyl |
| 1659 | Cyclopentyl | 3-Fluorobenzyl |
| 1678 | Cyclopentyl | 2-Chlorobenzyl |
| 1682 | 2-Methylpropyl | 2-(2-Chlorophenyl)ethenyl |
| 1683 | Cyclopentyl | 2-(2-Chlorophenyl)ethenyl |
| 1701 | 2-Methylpropyl | 2,3,6-Trifluorophenyl |
| 1702 | 2-Methylpropyl | 4,5-Dimethyl-2-furyl |

-continued

| Compound No. | R₂ | R₃ |
|---|---|---|
| 898 | Propyl | 3-Iodophenyl |
| 899 | Propyl | 3-Iodo-4-methylphenyl |
| 900 | Methyl | 2-Thienyl |
| 901 | Methyl | 5-Methyl-2-thienyl |
| 923 | Propyl | 3-Methylphenyl |
| 1117 | Propyl | 5-Chloro-2-methoxyphenyl |
| 1118 | Propyl | 2,5-Dichlorophenyl |
| 1119 | Propyl | 3-Bromophenyl |
| 1979 | 3-Methylbutyl | 3-Chloro-4-methylphenyl |
| 1981 | 3-Methylbutyl | 2,4,5-Trifluorophenyl |
| 1985 | 3-Methylbutyl | 3,5-Difluorophenyl |
| 2007 | 3-Methylbutyl | 5-Bromo-2-thienyl |
| 2386 | 2-(2-Fluorophenyl)ethyl | 2,5-Dichlorophenyl |
| 2387 | 2-(2-Fluorophenyl)ethyl | 3-Bromophenyl |
| 2388 | 2-(2-Fluorophenyl)ethyl | 3-Iodophenyl |

EXAMPLE 15

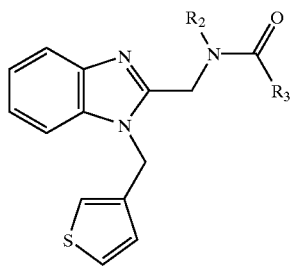

For each compound, the definitions of R₂ and R₃ are specified in the following table.

| Compound No. | R₂ | R₃ |
|---|---|---|
| 895 | Propyl | 5-Bromo-2-thienyl |
| 993 | Propyl | 1,3-Benzodioxol-5-yl |

EXAMPLE 16

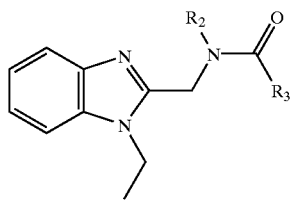

For each compound, the definitions of R₂ and R₃ are specified in the following table.

| Compound No. | R₂ | R₃ |
|---|---|---|
| 896 | Propyl | 3-Bromo-4-fluorophenyl |
| 897 | Allyl | 3-Iodophenyl |

EXAMPLE 17

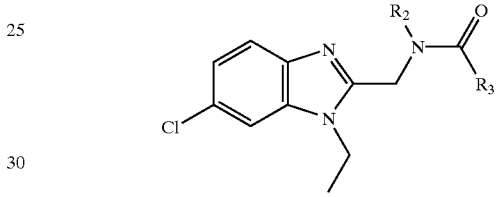

For each compound, the definitions of R₂ and R₃ are specified in the following table.

| Compound No. | R₂ | R₃ |
|---|---|---|
| 902 | Allyl | 3-Bromo-4-methylphenyl |
| 903 | Propyl | 3-Bromo-4-methylphenyl |
| 904 | Allyl | 3-Bromo-4-fluorophenyl |
| 905 | Propyl | 3-Bromo-4-fluorophenyl |
| 906 | Methyl | 3-Iodophenyl |
| 907 | Allyl | 3-Iodophenyl |
| 908 | Propyl | 3-Iodophenyl |
| 909 | Propyl | 3-Iodo-4-methylphenyl |
| 910 | Methyl | 2-Thienyl |
| 911 | Methyl | 3-Thienyl |
| 912 | Methyl | 3-Methyl-2-thienyl |
| 913 | Propyl | 5-Methyl-2-thienyl |
| 914 | Propyl | Phenyl |
| 915 | Methyl | 3-Methylphenyl |
| 916 | Propyl | 3-Fluorophenyl |
| 917 | Propyl | 2-Fluorophenyl |
| 918 | Methyl | 5-Fluoro-2-methylphenyl |
| 919 | Allyl | 5-Fluoro-2-methylphenyl |
| 920 | Methyl | 3-Chlorophenyl |
| 921 | Propyl | 3-Chlorophenyl |
| 976 | Propyl | 2-Chlorophenyl |
| 977 | Allyl | 3,4-Difluorophenyl |
| 978 | Propyl | 3,4-Difluorophenyl |
| 979 | Methyl | 2,3-Difluorophenyl |
| 980 | Allyl | 2,3-Difluorophenyl |
| 981 | Propyl | 2,3-Difluorophenyl |
| 982 | Methyl | 2,5-Difluorophenyl |
| 983 | Allyl | 2,5-Difluorophenyl |
| 984 | Propyl | 2,5-Difluorophenyl |
| 985 | Propyl | 2,4-Difluorophenyl |
| 986 | Propyl | 1,3-Benzodioxol-5-yl |
| 987 | Allyl | 3-Chloro-4-fluorophenyl |
| 988 | Propyl | 3-Chloro-4-fluorophenyl |

-continued

| Compound No. | R₂ | R₃ |
|---|---|---|
| 1120 | Allyl | 5-Chloro-2-methoxyphenyl |
| 1121 | Propyl | 5-Chloro-2-methoxyphenyl |
| 1122 | Allyl | 2,5-Dichlorophenyl |
| 1123 | Propyl | 2,5-Dichlorophenyl |
| 1124 | Allyl | 3-Bromophenyl |
| 1125 | Propyl | 3-Bromophenyl |
| 1516 | Methyl | 5-Ethoxy-2-thienyl |
| 1706 | 2-Methylpropyl | 2,4,6-Trifluorophenyl |
| 1707 | 2-Methylpropyl | 2,3,6-Trifluorophenyl |
| 1708 | 3-Methylbutyl | 2,3,6-Trifluorophenyl |
| 1709 | 2-Methylpropyl | 4,5-Dimethyl-2-furyl |
| 1710 | 3-Methylbutyl | 4,5-Dimethyl-2-furyl |
| 1711 | 2-Methylpropyl | 3-Chloro-2-thienyl |
| 1712 | 3-Methylbutyl | 3-Chloro-2-thienyl |
| 1713 | 2-Methylpropyl | 5-Methylthio-2-thienyl |
| 1719 | 2-Methylpropyl | 3-Chlorophenyl |
| 1720 | 3-Methylbutyl | 2,4,5-Trifluorophenyl |
| 1725 | 2-Methylpropyl | 2,6-Difluorophenyl |
| 1727 | 3-Methylbutyl | Phenyl |
| 1728 | 2-Methylpropyl | 3-Methylphenyl |
| 1729 | 3-Methylbutyl | 3-Methylphenyl |
| 1730 | 2-Methylpropyl | 4-Methylphenyl |
| 1731 | 3-Methylbutyl | 4-Methylphenyl |
| 1732 | 2-Methylpropyl | 2-Methylphenyl |
| 1733 | 3-Methylbutyl | 2-Methylphenyl |
| 1734 | 2-Methylpropyl | 3-Fluorophenyl |
| 1735 | 3-Methylbutyl | 3-Fluorophenyl |
| 1736 | 2-Methylpropyl | 3-Fluorophenyl |
| 1737 | 3-Methylbutyl | 4-Fluorophenyl |
| 1738 | 2-Methylpropyl | 2-Fluorophenyl |
| 1739 | 3-Methylbutyl | 2-Fluorophenyl |
| 1740 | 2-Methylpropyl | 4-Ethylphenyl |
| 1741 | 2-Methylpropyl | 3,4-Dimethylphenyl |
| 1742 | 2-Methylpropyl | 3-Fluoro-4-methylphenyl |
| 1743 | Cyclopentyl | 3-Fluoro-4-methylphenyl |
| 1744 | 2-Methylpropyl | 4-Chlorophenyl |
| 1745 | Cyclopentyl | 4-Methoxyphenyl |
| 1746 | 3-Methylbutyl | 3-Chloro-4-fluorophenyl |
| 1747 | 3-Methylbutyl | 2-Thienyl |

EXAMPLE 18

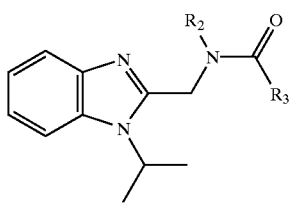

For each compound, the definitions of R₂ and R₃ are specified in the following table.

| Compound No. | R₂ | R₃ |
|---|---|---|
| 812 | Methyl | 2,5-Difluorophenyl |
| 813 | Propyl | 2,5-Dichlorophenyl |
| 814 | Propyl | 3-Iodophenyl |

EXAMPLE 19

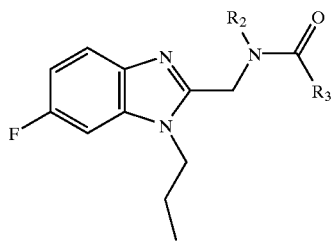

For each compound, the definitions of R₂ and R₃ are specified in the following table.

| Compound No. | R₂ | R₃ |
|---|---|---|
| 818 | Propyl | 3-Fluorophenyl |
| 819 | Propyl | 2-Fluorophenyl |
| 820 | Propyl | 3,4-Difluorophenyl |
| 821 | Methyl | 2,5-Difluorophenyl |
| 822 | Allyl | 2,5-Difluorophenyl |
| 823 | Propyl | 2,5-Difluorophenyl |
| 824 | Propyl | 1,3-Benzodioxol-5-yl |
| 825 | Propyl | 3-Chloro-4-fluorophenyl |
| 826 | Methyl | 5-Chloro-2-methoxyphenyl |
| 827 | Ethyl | 5-Chloro-2-methoxyphenyl |
| 828 | Allyl | 5-Chloro-2-methoxyphenyl |
| 829 | Propyl | 5-Chloro-2-methoxyphenyl |
| 830 | Methyl | 2,5-Dichlorophenyl |
| 831 | Allyl | 2,5-Dichlorophenyl |
| 832 | Propyl | 2,5-Dichlorophenyl |
| 833 | Propyl | Phenyl |
| 834 | Propyl | 3-Fluoro-4-methylphenyl |
| 835 | Propyl | 5-Fluoro-2-methylphenyl |
| 836 | Methyl | 3-Chlorophenyl |
| 837 | Allyl | 3-Chlorophenyl |
| 838 | Propyl | 3-Chlorophenyl |
| 842 | Methyl | 5-Chloro-2-methoxyphenyl |
| 843 | Ethyl | 5-Chloro-2-methoxyphenyl |
| 844 | Allyl | 5-Chloro-2-methoxyphenyl |
| 845 | Propyl | 5-Chloro-2-methoxyphenyl |
| 846 | Methyl | 3-Trifluorophenyl |
| 847 | Propyl | 3-Trifluorophenyl |
| 848 | Methyl | 2,5-Dichlorophenyl |
| 849 | Allyl | 2,5-Dichlorophenyl |
| 850 | Propyl | 2,5-Dichlorophenyl |
| 851 | Methyl | 3-Bromophenyl |
| 852 | Allyl | 3-Bromophenyl |
| 853 | Propyl | 3-Bromophenyl |
| 854 | Propyl | 3-Bromo-4-fluorophenyl |
| 855 | Methyl | 3-Iodophenyl |
| 856 | Allyl | 3-Iodophenyl |
| 857 | Propyl | 3-Iodophenyl |
| 859 | Allyl | 2-Fluorophenyl |
| 860 | Propyl | 2-Fluorophenyl |
| 861 | Propyl | 2-Chlorophenyl |
| 862 | Propyl | 3,4-Difluorophenyl |
| 863 | Propyl | 2,3-Difluorophenyl |
| 864 | Methyl | 2,5-Difluorophenyl |
| 865 | Propyl | 4-Methylthio phenyl |
| 866 | Propyl | 3-Fluoro-4-methoxyphenyl |
| 867 | Propyl | 4-Chloro-3-methylphenyl |
| 868 | Methyl | 3-Chloro-4-fluorophenyl |
| 869 | Allyl | 3-Chloro-4-fluorophenyl |
| 870 | Propyl | 3-Chloro-4-fluorophenyl |
| 871 | Propyl | 3,4,5-Trifluorophenyl |
| 872 | Propyl | 4-Butylphenyl |
| 873 | Propyl | 4-Methylthio phenyl |
| 1772 | Butyl | 2-Thienyl |
| 1773 | 2-Methylpropyl | 2-Thienyl |
| 1774 | Pentyl | 2-Thienyl |
| 1775 | 3-Methylbutyl | 2-Thienyl |

-continued

| Compound No. | R₂ | R₃ |
|---|---|---|
| 1776 | Butyl | 3-Thienyl |
| 1777 | 2-Methylpropyl | 3-Thienyl |
| 1778 | Pentyl | 3-Thienyl |
| 1779 | 3-Methylbutyl | 3-Thienyl |
| 1780 | 3-Methylbutyl | Benzyl |
| 1781 | Butyl | 5-Methyl-2-thienyl |
| 1782 | 2-Methylpropyl | 5-Methyl-2-thienyl |
| 1783 | Pentyl | 5-Methyl-2-thienyl |
| 1784 | 3-Methylbutyl | 5-Methyl-2-thienyl |
| 1785 | 3-Methylbutyl | 3-Fluorobenzyl |
| 1786 | 3-Methylbutyl | 3-Methoxybenzyl |
| 1819 | Butyl | Phenyl |
| 1820 | 2-Methylpropyl | Phenyl |
| 1821 | Pentyl | Phenyl |
| 1822 | 3-Methylbutyl | Phenyl |
| 1823 | Butyl | 3-Methylphenyl |
| 1824 | 2-Methylpropyl | 3-Methylphenyl |
| 1825 | Pentyl | 3-Methylphenyl |
| 1826 | 3-Methylbutyl | 3-Methylphenyl |
| 1827 | Butyl | 4-Methylphenyl |
| 1828 | 2-Methylpropyl | 4-Methylphenyl |
| 1829 | 3-Methylbutyl | 4-Methylphenyl |
| 1830 | Butyl | 3-Fluorophenyl |
| 1831 | 2-Methylpropyl | 3-Fluorophenyl |
| 1832 | Pentyl | 3-Fluorophenyl |
| 1833 | 3-Methylbutyl | 3-Fluorophenyl |
| 1834 | Butyl | 4-Fluorophenyl |
| 1835 | 2-Methylpropyl | 4-Fluorophenyl |
| 1836 | Pentyl | 4-Fluorophenyl |
| 1837 | 3-Methylbutyl | 4-Fluorophenyl |
| 1838 | Butyl | 2-Fluorophenyl |
| 1839 | 2-Methylpropyl | 2-Fluorophenyl |
| 1840 | Pentyl | 2-Fluorophenyl |
| 1841 | 3-Methylbutyl | 2-Fluorophenyl |
| 1842 | 2-Methylpropyl | 4-Ethylphenyl |
| 1843 | 2-Methylpropyl | 3,4-Dimethylphenyl |
| 1844 | 3-Methylbutyl | 2,5-Dimethylphenyl |
| 1845 | 2-Methylpropyl | 2,4-Dimethylphenyl |
| 1846 | 2-Methylpropyl | 3-Methoxyphenyl |
| 1847 | 3-Methylbutyl | 3-Methoxyphenyl |
| 1848 | 3-Methylbutyl | 2-Methoxyphenyl |
| 1849 | 2-Methylpropyl | 3-Fluoro-4-methylphenyl |
| 1850 | 3-Methylbutyl | 3-Fluoro-4-methylphenyl |
| 1851 | Butyl | 5-Fluoro-2-methylphenyl |
| 1852 | 2-Methylpropyl | 5-Fluoro-2-methylphenyl |
| 1853 | Pentyl | 5-Fluoro-2-methylphenyl |
| 1854 | 3-Methylbutyl | 5-Fluoro-2-methylphenyl |
| 1855 | 2-Methylpropyl | 4-Chlorophenyl |
| 1856 | 3-Methylbutyl | 4-Chlorophenyl |
| 1867 | 2-Methylpropyl | 2,5-Dichlorophenyl |
| 1868 | Pentyl | 2,5-Dichlorophenyl |
| 1869 | 3-Methylbutyl | 2,5-Dichlorophenyl |
| 1870 | 2-Methylpropyl | 4-Pentylphenyl |
| 1871 | 2-Methylpropyl | 3-Bromophenyl |
| 1872 | Pentyl | 3-Bromophenyl |
| 1873 | 3-Methylbutyl | 3-Bromophenyl |
| 1925 | 2-Methylpropyl | 3-Iodo-4-methylphenyl |
| 1926 | 3-Methylbutyl | 3-Iodo-4-methylphenyl |
| 1928 | Butyl | 2-Chlorophenyl |
| 1929 | 2-Methylpropyl | 2-Chlorophenyl |
| 1930 | Pentyl | 2-Chlorophenyl |
| 1931 | Butyl | 3,4-Difluorophenyl |
| 1932 | 2-Methylpropyl | 3,4-Difluorophenyl |
| 1933 | Pentyl | 3,4-Difluorophenyl |
| 1934 | 3-Methylbutyl | 3,4-Difluorophenyl |
| 1935 | Butyl | 2,3-Difluorophenyl |
| 1936 | 2-Methylpropyl | 2,3-Difluorophenyl |
| 1937 | Pentyl | 2,3-Difluorophenyl |
| 1938 | 3-Methylbutyl | 2,3-Difluorophenyl |
| 1939 | Butyl | 2,5-Difluorophenyl |
| 1940 | 2-Methylpropyl | 2,5-Difluorophenyl |
| 1941 | Pentyl | 2,5-Difluorophenyl |
| 1942 | 3-Methylbutyl | 2,5-Difluorophenyl |
| 1943 | Butyl | 2,4-Difluorophenyl |
| 1944 | 2-Methylpropyl | 2,4-Difluorophenyl |
| 1945 | Pentyl | 2,4-Difluorophenyl |
| 1946 | 3-Methylbutyl | 2,4-Difluorophenyl |
| 1947 | 2-Methylpropyl | 4-Propylphenyl |
| 1948 | 2-Methylpropyl | 4-i-Propylphenyl |
| 1949 | Butyl | 1,3-Benzodioxol-5-yl |
| 1950 | 2-Methylpropyl | 1,3-Benzodioxol-5-yl |
| 1951 | Pentyl | 1,3-Benzodioxol-5-yl |
| 1952 | 3-Methylbutyl | 1,3-Benzodioxol-5-yl |
| 1953 | Butyl | 3-Bromo-4-methylphenyl |
| 1954 | 2-Methylpropyl | 3-Bromo-4-methylphenyl |
| 1955 | Pentyl | 3-Bromo-4-methylphenyl |
| 1956 | 3-Methylbutyl | 3-Brom6-4-methylphenyl |
| 1957 | 2-Methylpropyl | 4-Heptylphenyl |
| 1958 | Butyl | 3-Iodophenyl |
| 1959 | 2-Methylpropyl | 3-Iodophenyl |
| 1960 | Pentyl | 3-Iodophenyl |
| 1961 | 3-Methylbutyl | 3-Iodophenyl |
| 1962 | 2-Methylpropyl | 4-Iodophenyl |
| 2016 | Butyl | 5-Ethyl-2-thienyl |
| 2017 | 2-Methylpropyl | 5-Ethyl-2-thienyl |
| 2018 | 3-Methylbutyl | 5-Ethyl-2-thienyl |
| 2019 | 2-Methylpropyl | 5-Propyl-2-thienyl |

EXAMPLE 20

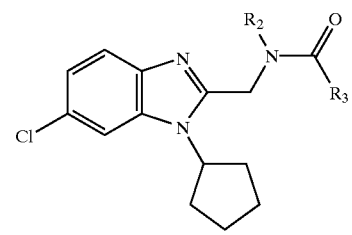

For each compound, the definitions of R₂ and R₃ are specified in the following table.

| Compound No. | R₂ | R₃ |
|---|---|---|
| 874 | Methyl | 3-Fluorophenyl |
| 875 | Allyl | 3-Fluorophenyl |
| 876 | Propyl | 3-Fluorophenyl |
| 877 | Propyl | 4-Fluorophenyl |
| 878 | Methyl | 3-Chloro-4-methylphenyl |
| 879 | Allyl | 3-Chloro-4-methylphenyl |
| 880 | Propyl | 3-Chloro-4-methylphenyl |
| 881 | Allyl | 5-Bromo-2-thienyl |
| 882 | Propyl | 5-Bromo-2-thienyl |
| 883 | Propyl | 3-Fluoro-4-methylphenyl |
| 884 | Propyl | 5-Fluoro-2-methylphenyl |
| 922 | Propyl | 3-Methoxyphenyl |
| 1450 | Propyl | 3-Bromo-4-methylphenyl |
| 1451 | Allyl | 3-Bromo-4-fluorophenyl |
| 1452 | Propyl | 3-Bromo-4-fluorophenyl |
| 1453 | Allyl | 3-Iodophenyl |
| 1454 | Propyl | 3-Iodophenyl |
| 1455 | Allyl | 5-Chloro-2-methoxyphenyl |
| 1456 | Propyl | 5-Chloro-2-methoxyphenyl |
| 1457 | Propyl | 3,4-Dichlorophenyl |
| 1458 | Ethyl | 2,5-Dichlorophenyl |
| 1459 | Allyl | 2,5-Dichlorophenyl |
| 1460 | Propyl | 2,5-Dichlorophenyl |
| 1461 | Propyl | 2,4-Dichlorophenyl |
| 1462 | Ethyl | 3-Bromophenyl |
| 1463 | Allyl | 3-Bromophenyl |
| 1464 | Propyl | 3-Bromophenyl |
| 1465 | Propyl | 5-Methyl-2-thienyl |
| 1466 | Propyl | 4-Chloro-3-methylphenyl |
| 1467 | Propyl | 3-Chloro-4-fluorophenyl |

| Compound No. | R₂ | R₃ |
|---|---|---|
| 1526 | 2-Methylpropyl | Phenyl |
| 1527 | 3-Methylbutyl | Phenyl |
| 1528 | 2-Methylpropyl | 3-Methylphenyl |
| 1529 | 3-Methylbutyl | 3-Methylphenyl |
| 1530 | 2-Methylpropyl | 4-Methylphenyl |
| 1531 | Cyclopentyl | 4-Methylphenyl |
| 1532 | 2-Methylpropyl | 2-Methylphenyl |
| 1533 | 3-Methylbutyl | 2-Methylphenyl |
| 1534 | 2-Methylpropyl | 3-Fluorophenyl |
| 1535 | 3-Methylbutyl | 3-Fluorophenyl |
| 1536 | 2-Methylpropyl | 4-Fluorophenyl |
| 1537 | 3-Methylbutyl | 4-Fluorophenyl |
| 1538 | 2-Methylpropyl | 2-Fluorophenyl |
| 1539 | Cyclopentyl | 2-Fluorophenyl |
| 1540 | 2-Methylpropyl | 4-Ethylphenyl |
| 1541 | 2-Methylpropyl | 3,4-Dimethylphenyl |
| 1542 | 2-Methylpropyl | 2,3-Dimethylphenyl |
| 1543 | 2-Methylpropyl | 2,5-Dimethylphenyl |
| 1544 | 3-Methylbutyl | 2,5-Dimethylphenyl |
| 1545 | 2-Methylpropyl | 2,4-Dimethylphenyl |
| 1546 | 3-Methylbutyl | 2,4-Dimethylphenyl |
| 1547 | Cyclopentyl | 2,4-Dimethylphenyl |
| 1548 | 2-Methylpropyl | 3-Methoxyphenyl |
| 1549 | 3-Methylbutyl | 3-Methoxyphenyl |
| 1550 | 2-Methylpropyl | 4-Methoxyphenyl |
| 1551 | 3-Methylbutyl | 4-Methoxyphenyl |
| 1552 | Cyclopentyl | 4-Methoxyphenyl |
| 1553 | 2-Methylpropyl | 2-Methoxyphenyl |
| 1554 | 3-Methylbutyl | 2-Methoxyphenyl |
| 1555 | 2-Methylpropyl | 3-Fluoro-4-methylphenyl |
| 1556 | Cyclopentyl | 3-Fluoro-4-methylphenyl |
| 1557 | 2-Methylpropyl | 3-Fluoro-2-methylphenyl |
| 1558 | 3-Methylbutyl | 3-Fluoro-2-methylphenyl |
| 1559 | 2-Methylpropyl | 5-Fluoro-2-methylphenyl |
| 1560 | 3-Methylbutyl | 5-Fluoro-2-methylphenyl |
| 1561 | 2-Methylpropyl | 2-Fluoro-3-methylphenyl |
| 1562 | 2-Methylpropyl | 3-Chlorophenyl |
| 1563 | 3-Methylbutyl | 3-Chlorophenyl |
| 1564 | Cyclopentyl | 3-Chlorophenyl |
| 1565 | 2-Methylpropyl | 4-Chlorophenyl |
| 1566 | Cyclopentyl | 4-Chlorophenyl |
| 1577 | 3-Methylbutyl | 2-Chlorophenyl |
| 1578 | Cyclopentyl | 2-Chlorophenyl |
| 1579 | 2-Methylpropyl | 3,4-Difluorophenyl |
| 1580 | 3-Methylbutyl | 3,4-Difluorophenyl |
| 1581 | 2-Methylpropyl | 2,3-Difluorophenyl |
| 1582 | 3-Methylbutyl | 2,3-Difluorophenyl |
| 1583 | Cyclopentyl | 2,3-Difluorophenyl |
| 1584 | 2-Methylpropyl | 2,5-Difluorophenyl |
| 1585 | 3-Methylbutyl | 2,5-Difluorophenyl |
| 1586 | 2-Methylpropyl | 2,4-Difluorophenyl |
| 1587 | 3-Methylbutyl | 2,4-Difluorophenyl |
| 1588 | Cyclopentyl | 2,4-Difluorophenyl |
| 1589 | 2-Methylpropyl | 1,3-Benzodioxol-5-yl |
| 1590 | 3-Methylbutyl | 1,3-Benzodioxol-5-yl |
| 1591 | Cyclopentyl | 1,3-Benzodioxol-5-yl |
| 1592 | 2-Methylpropyl | 4-Methylthiophenyl |
| 1593 | Cyclopentyl | 4-Methylthiophenyl |
| 1594 | Cyclopentyl | 3-Fluoro-4-methoxy |
| 1595 | Cyclopentyl | 4-Butylphenyl |
| 1596 | Cyclopentyl | 4-Ethylthiophenyl |
| 1597 | 2-Methylpropyl | 3-Chloro-4-methoxyphenyl |
| 1598 | 3-Methylbutyl | 3-Chloro-4-methoxyphenyl |
| 1599 | Cyclopentyl | 3-Chloro-4-methoxyphenyl |
| 1600 | 2-Methylpropyl | 2-Trifluoromethylphenyl |
| 1601 | 3-Methylbutyl | 2-Trifluoromethylphenyl |
| 1602 | 2-Methylpropyl | 3,4-Dichlorophenyl |
| 1603 | 3-Methylbutyl | 3,4-Dichlorophenyl |
| 1604 | 2-Methylpropyl | 2,3-Dichlorophenyl |
| 1605 | 2-Methylpropyl | 2,5-Dichlorophenyl |
| 1606 | 3-Methylbutyl | 2,5-Dichlorophenyl |
| 1607 | 2-Methylpropyl | 2,4-Dichlorophenyl |
| 1608 | Cyclopentyl | 2,4-Dichlorophenyl |
| 1609 | 2-Methylpropyl | 3-Bromophenyl |
| 1610 | 3-Methylbutyl | 3-Bromophenyl |
| 1611 | Cyclopentyl | 3-Bromophenyl |
| 1612 | 2-Methylpropyl | 4-Bromophenyl |
| 1613 | Cyclopentyl | 4-Bromophenyl |
| 1614 | 2-Methylpropyl | 2-Bromophenyl |
| 1615 | 3-Methylbutyl | 2-Bromophenyl |
| 1626 | 2-Methylpropyl | 3-Bromo-4-methylphenyl |
| 1627 | 3-Methylbutyl | 3-Bromo-4-methylphenyl |
| 1628 | Cyclopentyl | 3-Bromo-4-methylphenyl |
| 1629 | 2-Methylpropyl | 3-Bromo-4-fluorophenyl |
| 1630 | 3-Methylbutyl | 3-Bromo-4-fluorophenyl |
| 1631 | 2-Methylpropyl | 3-Iodophenyl |
| 1632 | 3-Methylbutyl | 3-Iodophenyl |
| 1633 | 2-Methylpropyl | 4-Iodophenyl |
| 1660 | 2-Methylpropyl | 3-Iodo-4-methylphenyl |
| 1661 | 2-Methylpropyl | 4-Iodobenzyl |
| 1662 | 2-Methylpropyl | 2-Thienyl |
| 1663 | 3-Methylbutyl | 2-Thienyl |
| 1664 | 2-Methylpropyl | Benzyl |
| 1665 | 3-Methylbutyl | Benzyl |
| 1666 | Cyclopentyl | Benzyl |
| 1667 | 2-Methylpropyl | 5-Methyl-2-thienyl |
| 1668 | 3-Methylbutyl | 5-Methyl-2-thienyl |
| 1669 | Cyclopentyl | 5-Methyl-2-thienyl |
| 1670 | Cyclopentyl | 3-Methylbenzyl |
| 1671 | 2-Methylpropyl | 3-Fluorobenzyl |
| 1672 | 3-Methylbutyl | 3-Fluorobenzyl |
| 1673 | Cyclopentyl | 3-Fluorobenzyl |
| 1679 | 3-Methylbutyl | 2-Methoxybenzyl |
| 1680 | Cyclopentyl | 1-(4-Fluorophenyl)ethyl |
| 1681 | Cyclopentyl | 2-Chlorobenzyl |
| 1684 | Cyclopentyl | 2-(2-Chlorophenyl)ethenyl |
| 1703 | 2-Methylpropyl | 2,4,6-Trifluorophenyl |
| 1704 | 2-Methylpropyl | 2,3,6-Trifluorophenyl |
| 1705 | 2-Methylpropyl | 2-Chloro-6-fluorophenyl |
| 1714 | 2-Methylpropyl | 3-Chloro-4-methylphenyl |

EXAMPLE 21

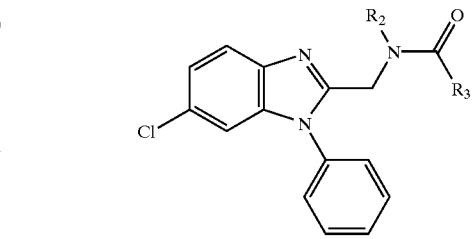

For each compound, the definitions of R₂ and R₃ are specified in the following table.

| Compound No. | R₂ | R₃ |
|---|---|---|
| 923 | Propyl | Phenyl |
| 924 | Propyl | 3-Methylphenyl |
| 925 | Propyl | 4-Methylphenyl |
| 926 | Propyl | 3-Fluorophenyl |
| 927 | Methyl | 2-Fluorophenyl |
| 928 | Allyl | 2-Fluorophenyl |
| 929 | Propyl | 2-Fluorophenyl |
| 1000 | Methyl | 2,3-Difluorophenyl |
| 1001 | Methyl | 2,5-Difluorophenyl |
| 1129 | Ethyl | 5-Chloro-2-methoxyphenyl |
| 2307 | 3-Methylbutyl | 2,3,6-Trifluorophenyl |

EXAMPLE 22

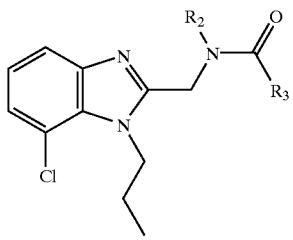

For each compound, the definitions of $R_2$ and $R_3$ are specified in the following table.

| Compound No. | $R_2$ | $R_3$ |
| --- | --- | --- |
| 955 | Methyl | Phenyl |
| 956 | Propyl | Phenyl |
| 957 | Methyl | 3-Methylphenyl |
| 958 | Propyl | 3-Methylphenyl |
| 959 | Methyl | 3-Fluorophenyl |
| 960 | Propyl | 3-Fluorophenyl |
| 961 | Methyl | 2-Fluorophenyl |
| 962 | Allyl | 2-Fluorophenyl |
| 963 | Propyl | 2-Fluorophenyl |
| 964 | Methyl | 5-Fluoro-2-methylphenyl |
| 965 | Methyl | 3-Chlorophenyl |
| 966 | Propyl | 3-Chlorophenyl |
| 989 | Propyl | 3-Chloro-4-fluorophenyl |
| 994 | Methyl | 2-Thienyl |
| 995 | Propyl | 2-Thienyl |
| 996 | Methyl | 3-Thienyl |
| 997 | Methyl | 3-Methyl-2-thienyl |
| 998 | Methyl | 5-Methyl-2-thienyl |
| 999 | Propyl | 5-Methyl-2-thienyl |
| 1100 | Propyl | 5-Chloro-2-methoxyphenyl |
| 1101 | Methyl | 3-Bromophenyl |
| 1102 | Propyl | 3-Bromophenyl |
| 975 | Propyl | 3-Chlorophenyl |
| 990 | Propyl | 1,3-Benzodioxol-5-yl |
| 991 | Allyl | 3-Chloro-4-fluorophenyl |
| 992 | Propyl | 3-Chloro-4-fluorophenyl |
| 1103 | Propyl | 5-Chloro-2-methoxyphenyl |
| 1104 | Propyl | 3-Trifluoromethylphenyl |
| 1105 | Propyl | 3,4-Dichlorophenyl |
| 1106 | Allyl | 2,5-Dichlorophenyl |
| 1107 | Allyl | 3-Bromophenyl |
| 1108 | Propyl | 3-Bromophenyl |
| 1187 | Propyl | 3-Bromo-4-methylphenyl |
| 1188 | Methyl | 3-Bromo-4-fluorophenyl |
| 1189 | Allyl | 3-Bromo-4-fluorophenyl |
| 1190 | Propyl | 3-Bromo-4-fluorophenyl |
| 1191 | Methyl | 3-Iodophenyl |
| 1192 | Allyl | 3-Iodophenyl |
| 1193 | Propyl | 3-Iodophenyl |
| 1207 | Propyl | 3-Bromo-4-fluorophenyl |
| 1208 | Methyl | 3-Bromo-4-fluorophenyl |
| 1209 | Allyl | 3-Bromo-4-fluorophenyl |
| 1210 | Propyl | 3-Bromo-4-fluorophenyl |
| 1211 | Methyl | 3-Iodophenyl |
| 1212 | Ethyl | 3-Iodophenyl |
| 1213 | Allyl | 3-Iodophenyl |
| 1214 | Propyl | 3-Iodophenyl |
| 1215 | Propyl | 3-Iodo-4-methylphenyl |
| 1216 | Methyl | 2-Thienyl |
| 1217 | Propyl | 2-Thienyl |
| 1218 | Allyl | 5-Methyl-2-thienyl |
| 1219 | Propyl | 5-Methyl-2-thienyl |

EXAMPLE 23

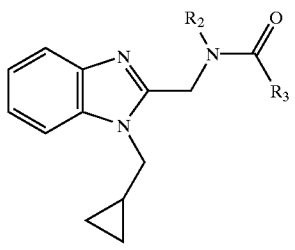

For each compound, the definitions of $R_2$ and $R_3$ are specified in the following table.

| Compound No. | $R_2$ | $R_3$ |
| --- | --- | --- |
| 967 | Propyl | Phenyl |
| 968 | Propyl | 3-Methylphenyl |
| 969 | Propyl | 4-Methylphenyl |
| 970 | Propyl | 3-Fluorophenyl |
| 971 | Propyl | 2-Fluorophenyl |
| 972 | Propyl | 5-Fluoro-2-methylphenyl |
| 973 | Ethyl | 3-Chlorophenyl |
| 974 | Allyl | 3-Chlorophenyl |

EXAMPLE 24

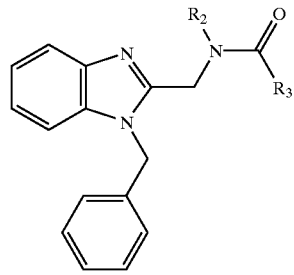

For each compound, the definitions of $R_2$ and $R_3$ are specified in the following table.

| Compound No. | $R_2$ | $R_3$ |
| --- | --- | --- |
| 1220 | 2-Methylpropyl | Phenyl |
| 1221 | 2-Methylpropyl | 3-Methylphenyl |
| 1222 | 2-Methylpropyl | 4-Methylphenyl |
| 1223 | 2-Methylpropyl | 2-Fluorophenyl |
| 1224 | 2-Methylpropyl | 4-Ethylphenyl |
| 1225 | 2-Methylpropyl | 3,4-Dimethylphenyl |
| 1227 | 2-Methylpropyl | 2,5-Difluorophenyl |
| 1228 | 2-Methylpropyl | 2,4-Difluorophenyl |
| 1229 | 2-Methylpropyl | 1,3-Benzodioxol-5-yl |
| 1230 | 2-Methylpropyl | 4-Bromophenyl |
| 1251 | 2-Methylpropyl | 3-Bromo-4-methylphenyl |
| 1272 | 2-Methylpropyl | 3-Chloro-4-methylphenyl |
| 1273 | 2-Methylpropyl | 2,4,5-Trifluorophenyl |

EXAMPLE 25

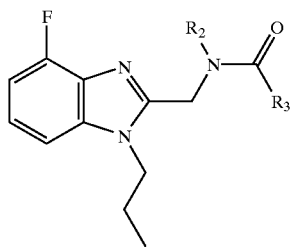

For each compound, the definitions of $R_2$ and $R_3$ are specified in the following table.

| Compound No. | $R_2$ | $R_3$ |
| --- | --- | --- |
| 1226 | Propyl | 2-Fluorophenyl |
| 1231 | Allyl | 5-Chloro-2-methoxyphenyl |
| 1232 | Propyl | 5-Chloro-2-methoxyphenyl |
| 1233 | Methyl | 2,5-Dichlorophenyl |
| 1234 | Allyl | 2,5-Dichlorophenyl |
| 1235 | Propyl | 2,5-Dichlorophenyl |
| 1236 | Methyl | 3-Bromophenyl |
| 1237 | Allyl | 3-Bromophenyl |
| 1238 | Propyl | 3-Bromophenyl |
| 1252 | Propyl | 3-Iodophenyl |
| 1748 | 2-Methylpropyl | 2,3,6-Trifluorophenyl |
| 1749 | 3-Methylbutyl | 2,3,6-Trifluorophenyl |
| 1750 | 2-Methylpropyl | 3-Chloro-4-phenyl |
| 1751 | 3-Methylbutyl | 3-Chloro-4-phenyl |
| 1752 | 2-Methylpropyl | 2,4,5-Trifluorophenyl |
| 1753 | 3-Methylbutyl | 2,4,5-Trifluorophenyl |
| 1754 | 2-Methylpropyl | 2,6-Difluorophenyl |
| 1755 | 3-Nethylbutyl | 2,6-Difluorophenyl |
| 1881 | Butyl | Phenyl |
| 1882 | 2-Methylpropyl | Phenyl |
| 1883 | Pentyl | Phenyl |
| 1884 | 3-Methylbutyl | Phenyl |
| 1885 | Butyl | 3-Methylphenyl |
| 1886 | 2-Methylpropyl | 3-Methylphenyl |
| 1887 | Pentyl | 3-Methylphenyl |
| 1888 | 3-Methylbutyl | 3-Methylphenyl |
| 1889 | 2-Methylpropyl | 4-Methylphenyl |
| 1890 | 3-Methylbutyl | 4-Methylphenyl |
| 1891 | Butyl | 3-Fluorophenyl |
| 1892 | 2-Methylpropyl | 3-Fluorophenyl |
| 1893 | Pentyl | 3-Fluorophenyl |
| 1894 | 3-Methylbutyl | 3-Fluorophenyl |
| 1895 | 2-Methylpropyl | 4-Fluorophenyl |
| 1896 | 3-Methylbutyl | 4-Fluorophenyl |
| 1897 | Butyl | 2-Fluorophenyl |
| 1898 | 2-Methylpropyl | 2-Fluorophenyl |
| 1899 | Pentyl | 2-Fluorophenyl |
| 1900 | 3-Methylbutyl | 2-Fluorophenyl |
| 1901 | 2-Methylpropyl | 3,4-Dimethylphenyl |
| 1902 | Butyl | 2-Chlorophenyl |
| 1903 | 2-Methylpropyl | 2-Chlorophenyl |
| 1904 | Pentyl | 2-Chlorophenyl |
| 1905 | 3-Methylbutyl | 2-Chlorophenyl |
| 1906 | Butyl | 3,4-Difluorophenyl |
| 1907 | 2-Methylpropyl | 3,4-Difluorophenyl |
| 1908 | Pentyl | 3,4-Difluorophenyl |
| 1909 | 3-Methylbutyl | 3,4-Difluorophenyl |
| 1910 | Butyl | 2,3-Difluorophenyl |
| 1911 | 2-Methylpropyl | 2,3-Difluorophenyl |
| 1912 | Pentyl | 2,3-Difluorophenyl |
| 1913 | 3-Methylbutyl | 2,3-Difluorophenyl |
| 1914 | Butyl | 2,5-Difluorophenyl |
| 1915 | 2-Methylpropyl | 2,5-Difluorophenyl |
| 1916 | Pentyl | 2,5-Difluorophenyl |
| 1917 | 3-Methylbutyl | 2,5-Difluorophenyl |
| 1918 | 2-Methylpropyl | 2,4-Difluorophenyl |
| 1919 | 3-Methylbutyl | 2,4-Difluorophenyl |
| 1920 | 2-Methylpropyl | 1,3-Benzodioxol-5-yl |
| 1921 | 3-Methylbutyl | 1,3-Benzodioxol-5-yl |
| 1927 | 3-Methylbutyl | 3-Iodo-4-methylphenyl |
| 1963 | 2-Methylpropyl | 2-(2-Chlorophenyl)ethenyl |
| 1964 | Butyl | 2-Thienyl |
| 1965 | Pentyl | 2-Thienyl |
| 1966 | 3-Methylbutyl | 2-Thienyl |
| 1967 | Pentyl | 3-Thienyl |
| 1968 | 3-Methylbutyl | 3-Thienyl |
| 1969 | 3-Methylbutyl | Benzyl |
| 1970 | Butyl | 5-Methyl-2-thienyl |
| 1971 | 2-Methylpropyl | 5-Methyl-2-thienyl |
| 1972 | Pentyl | 5-Methyl-2-thienyl |
| 1973 | 3-Methylbutyl | 5-Methyl-2-thienyl |
| 1974 | 3-Methylbutyl | 3-Fluorobenzyl |
| 1975 | 3-Methylbutyl | 3-Methoxybenzyl |

EXAMPLE 26

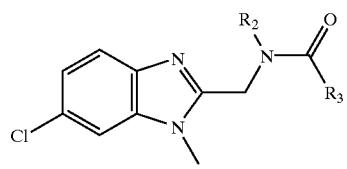

For each compound, the definitions of $R_2$ and $R_3$ are specified in the following table.

| Compound No. | $R_2$ | $R_3$ |
| --- | --- | --- |
| 1250 | Propyl | 3-Iodophenyl |
| 1616 | 2-Methylpropyl | 3-Chloro-4-fluorophenyl |
| 1617 | 2-Methylpropyl | 3-Bromophenyl |
| 1618 | 3-Methylbutyl | 3-Bromophenyl |
| 1634 | 2-Methylpropyl | 3-Bromo-4-methylphenyl |
| 1635 | 2-Methylpropyl | 3-Bromo-4-fluorophenyl |
| 1636 | 3-Methylbutyl | 3-Bromo-4-fluorophenyl |
| 1637 | 2-Methylpropyl | 3-Iodophenyl |
| 1638 | 3-Methylbutyl | 3-Bromo-4-fluorophenyl |
| 1639 | 2-Methylpropyl | Phenyl |
| 1640 | 3-Methylbutyl | Phenyl |
| 1641 | 2-Methylpropyl | 3-Methylphenyl |
| 1642 | 3-Methylbutyl | 3-Methylphenyl |
| 1643 | 2-Methylpropyl | 4-Methylphenyl |
| 1644 | 2-Methylpropyl | 3-Fluorophenyl |
| 1645 | 3-Methylbutyl | 3-Fluorophenyl |
| 1646 | 2-Methylpropyl | 4-Fluorophenyl |
| 1647 | 2-Methylpropyl | 2-Fluorophenyl |
| 1648 | 3-Methylbutyl | 2-Fluorophenyl |
| 1649 | 2-Methylpropyl | 3,4-Dimethylphenyl |
| 1650 | 2-Methylpropyl | 3-Fluoro-4-methylphenyl |
| 1651 | 2-Methylpropyl | 3-Chlorophenyl |
| 1652 | 3-Methylbutyl | 3-Chlorophenyl |
| 1674 | 2-Methylpropyl | 3-Iodo-4-methylphenyl |
| 1675 | 2-Methylpropyl | 5-Methyl-2-thienyl |
| 1676 | 3-Methylbutyl | 5-Methyl-2-thienyl |
| 1677 | 3-Methylbutyl | 3-Fluorobenzyl |
| 1715 | 2-Methylpropyl | 3-Chloro-4-methylphenyl |
| 1716 | 2-Methylpropyl | 2,4,5-Trifluorophenyl |
| 1874 | Butyl | 3,4-Dimethylphenyl |
| 1875 | 2-Methylpropyl | 3,4-Dimethylphenyl |
| 1876 | 3-Methylbutyl | 3,4-Dimethylphenyl |
| 1877 | 3-Methylbutyl | 2,3-Dimethylphenyl |
| 1878 | 2-Methylpropyl | 2,5-Dimethylphenyl |
| 1879 | 3-Methylbutyl | 2,5-Dimethylphenyl |
| 1880 | 2-Methylpropyl | 1,3-Benzodioxol-5-yl |
| 1976 | 3-Methylbutyl | 3-Methaxybenzyl |
| 2262 | Benzyl | 3-Chlorophenyl |
| 2282 | Benzyl | 5-Chloro-2-methoxyphenyl |
| 2293 | Benzyl | 3-Bromophenyl |
| 2299 | Benzyl | 3-Iodophenyl |

EXAMPLE 27

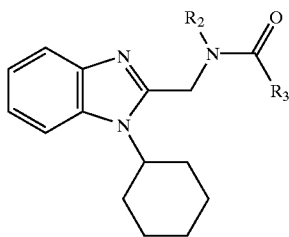

For each compound, the definitions of $R_2$ and $R_3$ are specified in the following table.

| Compound No. | $R_2$ | $R_3$ |
|---|---|---|
| 1276 | 2-Methylpropyl | Phenyl |
| 1277 | Pentyl | Phenyl |
| 1278 | 3-Methylbutyl | Phenyl |
| 1279 | 3-Methylbutyl | 3-Methylphenyl |
| 1280 | 2-Methylpropyl | 4-Methylphenyl |
| 1281 | 2-Methylpropyl | 3-Fluorophenyl |
| 1282 | 3-Methylbutyl | 3-Fluorophenyl |
| 1283 | 2-Methylpropyl | 4-Fluorophenyl |
| 1284 | Butyl | 2-Fluorophenyl |
| 1285 | 2-Methylpropyl | 2-Fluorophenyl |
| 1286 | Pentyl | 2-Fluorophenyl |
| 1287 | 3-Methylbutyl | 2-Fluorophenyl |
| 1288 | 2-Methylpropyl | 3-Methoxyphenyl |
| 1289 | 3-Methylbutyl | 3-Methoxyphenyl |
| 1290 | 3-Methylbutyl | 4-Methoxyphenyl |
| 1291 | 2-Methylpropyl | 3-Fluoro-4-methylphenyl |
| 1292 | 3-Methylbutyl | 2-Fluoro-3-methylphenyl |
| 1293 | Butyl | 3-Chlorophenyl |
| 1294 | 2-Methylpropyl | 3-Chlorophenyl |
| 1295 | Pentyl | 3-Chlorophenyl |
| 1296 | 3-Methylbutyl | 3-Chlorophenyl |
| 1297 | 2-Methylpropyl | 3,4-Difluorophenyl |
| 1298 | 2-Methylpropyl | 2,3-Difluorophenyl |
| 1299 | 3-Methylbutyl | 2,3-Difluorophenyl |
| 1300 | 3-Methylbutyl | 2,5-Difluorophenyl |
| 1301 | 2-Methylpropyl | 1,3-Benzodioxol-5-yl |
| 1302 | 2-Methylpropyl | 1,3-Benzodioxol-5-yl |
| 1386 | 3-Methylbutyl | 5-Chloro-2-methoxyphenyl |
| 1387 | 3-Methylbutyl | 3-Bromophenyl |
| 1388 | 2-Methylpropyl | 4-Bromophenyl |
| 1389 | 2-Methylpropyl | 5-Methyl-2-thienyl |
| 1390 | 3-Methylbutyl | 5-Methyl-2-thienyl |
| 1685 | 3-Methylbutyl | 2,3,6-Trifluorophenyl |

EXAMPLE 28

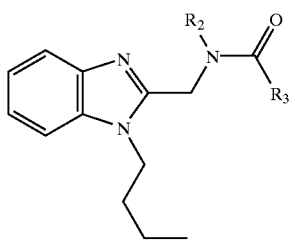

For each compound, the definitions of $R_2$ and $R_3$ are specified in the following table.

| Compound No. | $R_2$ | $R_3$ |
|---|---|---|
| 1303 | Butyl | Phenyl |
| 1304 | 2-Methylpropyl | Phenyl |
| 1305 | Pentyl | Phenyl |
| 1306 | 3-Methylbutyl | Phenyl |
| 1307 | Butyl | 3-Methylphenyl |
| 1308 | 2-Methylpropyl | 3-Methylphenyl |
| 1309 | Pentyl | 3-Methylphenyl |
| 1310 | 3-Methylbutyl | 3-Methylphenyl |
| 1311 | Butyl | 4-Methylphenyl |
| 1312 | 2-Methylpropyl | 4-Methylphenyl |
| 1313 | 3-Methylbutyl | 4-Methylphenyl |
| 1314 | 3-Methylbutyl | 2-Methylphenyl |
| 1315 | Butyl | 3-Fluorophenyl |
| 1316 | 2-Methylpropyl | 3-Fluorophenyl |
| 1317 | Pentyl | 3-Fluorophenyl |
| 1318 | 3-Methylbutyl | 3-Fluorophenyl |
| 1319 | 2-Methylpropyl | 4-Fluorophenyl |
| 1320 | 3-Methylbutyl | 4-Fluorophenyl |
| 1321 | Butyl | 2-Fluorophenyl |
| 1322 | 2-Methylpropyl | 2-Fluorophenyl |
| 1323 | Pentyl | 2-Fluorophenyl |
| 1324 | 3-Methylbutyl | 2-Fluorophenyl |
| 1325 | 2-Methylpropyl | 4-Ethylphenyl |
| 1326 | Butyl | 3,4-Dimethylphenyl |
| 1327 | 2-Methylpropyl | 3,4-Dimethylphenyl |
| 1328 | 3-Methylbutyl | 3,4-Dimethylphenyl |
| 1329 | 2-Methylpropyl | 2,4-Dimethylphenyl |
| 1330 | Butyl | 3-Methoxyphenyl |
| 1331 | 2-Methylpropyl | 3-Methoxyphenyl |
| 1332 | Pentyl | 3-Methoxyphenyl |
| 1333 | 3-Methylbutyl | 3-Methoxyphenyl |
| 1334 | Butyl | 4-Methoxyphenyl |
| 1335 | 2-Methylpropyl | 4-Methoxyphenyl |
| 1336 | 3-Methylbutyl | 4-Methoxyphenyl |
| 1337 | Pentyl | 2-Methoxyphenyl |
| 1338 | 3-Methylbutyl | 2-Methoxyphenyl |
| 1339 | Butyl | 3-Fluoro-4-methylphenyl |
| 1340 | Pentyl | 3-Fluoro-4-methylphenyl |
| 1341 | 3-Methylbutyl | 3-Fluoro-4-methylphenyl |
| 1342 | 3-Methylbutyl | 3-Fluoro-2-methylphenyl |
| 1343 | Butyl | 2-Fluoro-3-methylphenyl |
| 1344 | 2-Methylpropyl | 2-Fluoro-3-methylphenyl |
| 1345 | Pentyl | 2-Fluoro-3-methylphenyl |
| 1346 | 3-Methylbutyl | 2-Fluoro-3-methylphenyl |
| 1347 | Butyl | 3-Chlorophenyl |
| 1348 | 2-Methylpropyl | 3-Chlorophenyl |
| 1349 | Pentyl | 3-Chlorophenyl |
| 1350 | 3-Methylbutyl | 3-Chlorophenyl |
| 1351 | 2-Methylpropyl | 4-Chlorophenyl |
| 1352 | Pentyl | 4-Chlorophenyl |
| 1353 | 3-Methylbutyl | 4-Chlorophenyl |
| 1354 | Butyl | 2-Chlorophenyl |
| 1355 | 2-Methylpropyl | 2-Chlorophenyl |
| 1356 | Pentyl | 2-Chlorophenyl |
| 1357 | 3-Methylbutyl | 2-Chlorophenyl |
| 1358 | Butyl | 3,4-Difluorophenyl |
| 1359 | 2-Methylpropyl | 3,4-Difluorophenyl |
| 1360 | Pentyl | 3,4-Difluorophenyl |
| 1361 | 3-Methylbutyl | 3,4-Difluorophenyl |
| 1362 | Butyl | 2,3-Difluorophenyl |
| 1363 | 2-Methylpropyl | 2,3-Difluorophenyl |
| 1364 | Pentyl | 2,3-Difluorophenyl |
| 1365 | 3-Methylbutyl | 2,3-Difluorophenyl |
| 1366 | Butyl | 2,5-Difluorophenyl |
| 1367 | 2-Methylpropyl | 2,5-Difluorophenyl |
| 1368 | Pentyl | 2,5-Difluorophenyl |
| 1369 | 3-Methylbutyl | 2,5-Difluorophenyl |
| 1370 | Butyl | 2,4-Difluorophenyl |
| 1371 | 2-Methylpropyl | 2,4-Difluorophenyl |
| 1372 | Pentyl | 2,4-Difluorophenyl |
| 1373 | 3-Methylbutyl | 2,4-Difluorophenyl |
| 1374 | 2-Methylpropyl | 3-Ethoxyphenyl |
| 1375 | 3-Methylbutyl | 3-Ethoxyphenyl |
| 1376 | Butyl | 1,3-Benzodioxol-5-yl |
| 1377 | 2-Methylpropyl | 1,3-Benzodioxol-5-yl |
| 1378 | Pentyl | 1,3-Benzodioxol-5-yl |
| 1379 | 3-Methylbutyl | 1,3-Benzodioxol-5-yl |
| 1380 | Butyl | 4-Methylthiophenyl |
| 1381 | 2-Methylpropyl | 4-Methylthiophenyl |
| 1382 | 3-Methylbutyl | 3-Fluoro-4-methoxyphenyl |

-continued

| Compound No. | R₂ | R₃ |
|---|---|---|
| 1383 | Butyl | 3-Chloro-4-fluorophenyl |
| 1384 | 2-Methylpropyl | 3-Chloro-4-fluorophenyl |
| 1385 | 3-Methylbutyl | 3-Chloro-4-fluorophenyl |
| 1391 | 3-Methylbutyl | 3-Chloro-4-methoxyphenyl |
| 1392 | Pentyl | 5-Chloro-2-methoxyphenyl |
| 1393 | 3-Methylbutyl | 5-Chloro-2-methoxyphenyl |
| 1394 | 2-Methylpropyl | 3,4-Dichlorophenyl |
| 1395 | 3-Methylbutyl | 3,4-Dichlorophenyl |
| 1396 | Butyl | 2,5-Dichlorophenyl |
| 1397 | 2-Methylpropyl | 2,5-Dichlorophenyl |
| 1398 | Pentyl | 2,5-Dichlorophenyl |
| 1399 | 3-Methylbutyl | 2,5-Dichlorophenyl |
| 1400 | 2-Methylpropyl | 2,4-Dichlorophenyl |
| 1401 | 3-Methylbutyl | 2,4-Dichlorophenyl |
| 1402 | Butyl | 3-Bromophenyl |
| 1403 | 2-Methylpropyl | 3-Bromophenyl |
| 1404 | Pentyl | 3-Bromophenyl |
| 1405 | 3-Methylbutyl | 3-Bromophenyl |
| 1406 | 2-Methylpropyl | 4-Bromophenyl |
| 1407 | 3-Methylbutyl | 4-Bromophenyl |
| 1408 | 3-Methylbutyl | 2-Bromophenyl |
| 1409 | 3-Methylbutyl | 3-Bromo-4-methylphenyl |
| 1410 | Butyl | 3-Bromo-4-fluorophenyl |
| 1411 | 2-Methylpropyl | 3-Bromo-4-fluorophenyl |
| 1412 | Pentyl | 3-Bromo-4-fluorophenyl |
| 1413 | 3-Methylbutyl | 3-Bromo-4-fluorophenyl |
| 1414 | Butyl | 3-Iodophenyl |
| 1415 | 2-Methylpropyl | 3-Iodophenyl |
| 1416 | Pentyl | 3-Iodophenyl |
| 1417 | 3-Methylbutyl | 3-Iodophenyl |
| 1418 | Butyl | 5-Methyl-2-thienyl |
| 1419 | 2-Methylpropyl | 5-Methyl-2-thienyl |
| 1420 | Pentyl | 5-Methyl-2-thienyl |
| 1421 | 3-Methylbutyl | 5-Methyl-2-thienyl |
| 1422 | 3-Methylbutyl | 3-Fluorobenzyl |
| 1423 | 3-Methylbutyl | 3-Methoxybenzyl |
| 1424 | 3-Methylbutyl | 2-Methoxybenzyl |
| 1686 | 2-Methylpropyl | 2,4,6-Trifluorophenyl |
| 1687 | Butyl | 2,3,6-Trifluorophenyl |
| 1688 | 2-Methylpropyl | 2,3,6-Trifluorophenyl |
| 1689 | Pentyl | 2,3,6-Trifluorophenyl |
| 1690 | 3-Methylbutyl | 2,3,6-Trifluorophenyl |
| 1691 | 3-Methylbutyl | 2,5-Dimethyl-3-furyl |
| 1692 | Butyl | 4,5-Dimethyl-2-furyl |
| 1693 | 2-Methylpropyl | 4,5-Dimethyl-2-furyl |
| 1694 | Pentyl | 4,5-Dimethyl-2-furyl |
| 1695 | 3-Methylbutyl | 4,5-Dimethyl-2-furyl |
| 1696 | 2-Methylpropyl | 2-(3-Thienyl)ethenyl |
| 1697 | Pentyl | 3-Chloro-2-thienyl |
| 1698 | 3-Methylbutyl | 3-Chloro-2-thienyl |
| 1699 | 2-Methylpropyl | 5-Methylthio-2-thienyl |
| 1700 | 3-Methylbutyl | 5-Methylthio-2-thienyl |
| 1721 | Butyl | 3-Chloro-4-methylphenyl |
| 1722 | 2-Methylpropyl | 3-Chloro-4-methylphenyl |
| 1723 | 3-Methylbutyl | 3-Chloro-4-methylphenyl |
| 1724 | 2-Methylpropyl | 2,4,5-Trichlorophenyl |

| Compound No. | R₂ | R₃ |
|---|---|---|
| 1468 | Methyl | Phenyl |
| 1469 | Allyl | Phenyl |
| 1470 | Propyl | Phenyl |
| 1471 | Methyl | 3-Methylphenyl |
| 1472 | Allyl | 3-Methylphenyl |
| 1473 | Propyl | 3-Methylphenyl |
| 1474 | Propyl | 4-Methylphenyl |
| 1475 | Methyl | 3-Fluorophenyl |
| 1476 | Allyl | 3-Fluorophenyl |
| 1477 | Propyl | 3-Fluorophenyl |
| 1478 | Propyl | 4-Fluorophenyl |
| 1479 | Methyl | 2-Fluorophenyl |
| 1480 | Allyl | 2-Fluorophenyl |
| 1481 | Propyl | 2-Fluorophenyl |
| 1482 | Propyl | 3,4-Dimethylphenyl |
| 1483 | Propyl | 3-Methoxyphenyl |
| 1484 | Propyl | 3-Fluoro-4-methylphenyl |
| 1485 | Allyl | 3-Chlorophenyl |
| 1486 | Propyl | 3-Chlorophenyl |
| 1487 | Propyl | 2-Chlorophenyl |
| 1488 | Propyl | 3,4-Difluorophenyl |
| 1489 | Methyl | 2,3-Difluorophenyl |
| 1490 | Propyl | 2,3-Difluorophenyl |
| 1491 | Methyl | 2,5-Difluorophenyl |
| 1492 | Allyl | 2,5-Difluorophenyl |
| 1493 | Propyl | 2,5-Difluorophenyl |
| 1494 | Propyl | 2,4-Difluorophenyl |
| 1495 | Propyl | 1,3-Benzodioxol-5-yl |
| 1496 | Propyl | 3-Chloro-4-fluorophenyl |
| 1497 | Methyl | 5-Chloro-2-methoxyphenyl |
| 1498 | Methyl | 3-Trifluoromethylphenyl |
| 1499 | Propyl | 3-Trifluoromethylphenyl |
| 1500 | Methyl | 2,5-Dichlorophenyl |
| 1501 | Propyl | 2,5-Dichlorophenyl |
| 1502 | Methyl | 3-Brolnophenyl |
| 1503 | Allyl | 3-Bromophenyl |
| 1504 | Propyl | 3-Bromophenyl |
| 1505 | Propyl | 3-Bromo-4-methylphenyl |
| 1506 | Methyl | 3-Bromo-4-fluorophenyl |
| 1507 | Allyl | 3-Bromo-4-fluorophenyl |
| 1508 | Propyl | 3-Bromo-4-fluorophenyl |
| 1509 | Methyl | 3-Iodophenyl |
| 1510 | Ethyl | 3-Iodophenyl |
| 1511 | Allyl | 3-Iodophenyl |
| 1512 | Propyl | 3-Iodophenyl |
| 1513 | Propyl | 5-Methyl-2-thienyl |
| 1514 | Propyl | 3-Fluorobenzyl |
| 1515 | Methyl | 5-Ethoxy-2-thienyl |

EXAMPLE 29

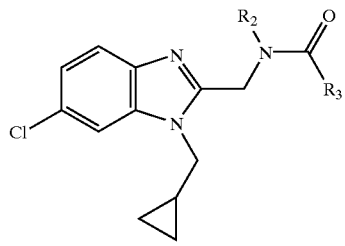

For each compound, the definitions of R₂ and R₃ are specified in the following table.

EXAMPLE 30

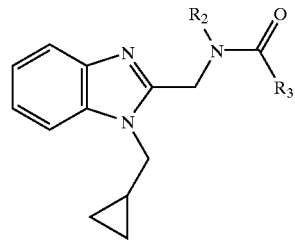

For each compound, the definitions of R₂ and R₃ are specified in the following table.

| Compound No. | R₂ | R₃ |
|---|---|---|
| 1717 | Propyl | 3-Chloro-4-methylphenyl |
| 1718 | Propyl | 2,4,5-Trifluorophenyl |
| 2237 | Benzyl | Phenyl |

-continued

| Compound No. | R$_2$ | R$_3$ |
|---|---|---|
| 2240 | Benzyl | 3-Fluorophenyl |
| 2241 | Benzyl | 4-Fluorophenyl |
| 2244 | Benzyl | 2-Fluorophenyl |
| 2246 | Benzyl | 3,4-Dimethylphenyl |
| 2247 | Benzyl | 3,5-Dimethylphenyl |
| 2248 | Benzyl | 2,3-Dimethylphenyl |
| 2249 | Benzyl | 2,5-Dimethylphenyl |
| 2250 | Benzyl | 2,4-Dimethylphenyl |
| 2252 | Benzyl | 3-Methoxyphenyl |
| 2255 | Benzyl | 2-Methoxyphenyl |
| 2256 | Benzyl | 3-Fluoro-4-methylphenyl |
| 2259 | Benzyl | 5-Fluoro-2-methylphenyl |
| 2263 | Benzyl | 3-Chlorophenyl |
| 2264 | Benzyl | 4-Chlorophenyl |
| 2265 | Benzyl | 2-Chlorophenyl |
| 2267 | Benzyl | 3,4-Difluorophenyl |
| 2270 | Benzyl | 2,3-Difluorophenyl |
| 2273 | Benzyl | 2,5-Difluorophenyl |
| 2274 | Benzyl | 2,4-Difluorophenyl |
| 2275 | Benzyl | 3-Ethoxyphenyl |
| 2276 | Benzyl | 1,3-Benzodioxol-5-yl |
| 2277 | Benzyl | 4-Chloro-3-methylphenyl |
| 2278 | Benzyl | 3-Chloro-4-fluorophenyl |
| 2279 | Benzyl | 3,4,5-Trifluorophenyl |
| 2280 | Benzyl | 2,5-Dimethoxyphenyl |
| 2283 | Benzyl | 5-Chloro-2-methoxyphenyl |
| 2284 | Benzyl | 4-Chloro-2-methoxyphenyl |
| 2285 | Benzyl | 3-Trifluoromethylphenyl |
| 2286 | Benzyl | 2-Trifluoromethylphenyl |
| 2287 | Benzyl | 3,4-Dichlorophenyl |
| 2288 | Benzyl | 2,3-Dichlorophenyl |
| 2290 | Benzyl | 2,5-Dichlorophenyl |
| 2291 | Benzyl | 2,4-Dichlorophenyl |
| 2294 | Benzyl | 3-Bromophenyl |
| 2296 | Benzyl | 2-Bromophenyl |
| 2297 | Benzyl | 3-Bromo-4-fluorophenyl |
| 2300 | Benzyl | 3-Iodophenyl |
| 2301 | Benzyl | 2-Methoxyphenyl |
| 2303 | Benzyl | 2,5-Dimethylpyrrol-3-yl |
| 2308 | Benzyl | 2,3,6-Trifluorphenyl |
| 2309 | 3-Methylbutyl | 2-Chloro-6-fluorophenyl |
| 2325 | 3-Methylbutyl | 3-(Methylamino methyl)phenyl |
| 2326 | 3-Methylbutyl | 3-(Ethylamino methyl)phenyl |
| 2327 | 3-Methylbutyl | 3-(allylamino methyl)phenyl |
| 2328 | 3-Methylbutyl | 3-(propylamino methyl)phenyl |
| 2329 | 3-Methylbutyl | 3-[(Cyclopropyl methyl)aminomethyl]phenyl |
| 2330 | 3-Methylbutyl | 3-(butylamino methyl)phenyl |
| 2331 | 3-Methylbutyl | 3-[(2-Methylpropyl) aminomethyl]phenyl |
| 2332 | 3-Methylbutyl | 3-(Pentylamino methyl)phenyl |
| 2333 | 3-Methylbutyl | 3-[(3-Methylbutyl) aminomethyl]phenyl |
| 2334 | 3-Methylbutyl | 3-[(2-Methylbutyl) aminomethyl]phenyl |
| 2335 | 3-Methylbutyl | 3-(Hexylamino methyl)phenyl |
| 2336 | 3-Methylbutyl | 3-(Cyclopropyl aminomethyl)phenyl |
| 2337 | 3-Methylbutyl | 3-[(1-Methylethyl) aminomethyl]phenyl |
| 2338 | 3-Methylbutyl | 3-(Cyclobutyl aminomethyl)phenyl |
| 2339 | 3-Methylbutyl | 3-[(1-Methylpropyl) aminomethyl]phenyl |
| 2340 | 3-Methylbutyl | 3-[(1,1-Dimethylethyl) aminomethyl]phenyl |
| 2341 | 3-Methylbutyl | 3-(Cyclopentyl aminomethyl)phenyl |
| 2342 | 3-Methylbutyl | 3-[(1-Methylbutyl) aminomethyl]phenyl |

-continued

| Compound No. | R$_2$ | R$_3$ |
|---|---|---|
| 2343 | 3-Methylbutyl | 3-[(1,2-Dimethylpropyl) aminomethyl]phenyl |
| 2344 | 3-Methylbutyl | 3-[(1-Ethylpropyl) aminomethyl]phenyl |
| 2345 | 3-Methylbutyl | 3-[(1,1-Dimethylpropyl) aminomethyl]phenyl |
| 2346 | 3-Methylbutyl | 3-(Cyclohexyl aminomethyl)phenyl |
| 2352 | 3-Methylbutyl | 3-(Piperidyl methyl)phenyl |
| 2353 | 3-Methylbutyl | 3-(Morpholin-4-yl methyl)phenyl |
| 2354 | 3-Methylbutyl | 3-(Azaperhydro epinylmethyl)phenyl |
| 2355 | 3-Methylbutyl | 3-(Azaperhydro ocinylmethyl)phenyl |
| 2356 | 3-Methylbutyl | 3-(2-1,2,3,4-Teterahydro isoquinolinylmethyl)phenyl |
| 2357 | 3-Methylbutyl | 3-(Methylpropyl aminomethyl)phenyl |
| 2358 | 3-Methylbutyl | 3-(i-propylethyl aminomethyl)phenyl |
| 2359 | 3-Methylbutyl | 3-(Diethyl aminomethyl)phenyl |
| 2360 | 3-Methylbutyl | 3-(Butylethyl aminomethyl)phenyl |
| 2361 | 3-Methylbutyl | 3-[(Cyclopropylmethyl)propyl aminomethyl]phenyl |
| 2362 | 3-Methylbutyl | 3-(Hexylmethyl aminomethyl)phenyl |
| 2363 | 3-Methylbutyl | 3-(Dibutyl aminomethyl)phenyl |
| 2370 | 3-Methylbutyl | 3-[(1-methylethyl) methylaminomethyl]phenyl |
| 2371 | 3-Methylbutyl | 3-[(2-Methyl piperidyl)methyl]phenyl |
| 2372 | 3-Methylbutyl | 3-[Ethyl(2-Methylprop-2-enyl)amino methyl]phenyl |
| 2373 | 3-Methylbutyl | 3-[(2-Ethyl piperidyl)methyl]phenyl |
| 2374 | 3-Methylbutyl | 3-(Cyclohexyl ethylaminomethyl)phenyl |
| 2375 | 3-Methylbutyl | 3-[bis(2-Methoxyethyl) aminomethyl]phenyl |
| 2376 | 3-Methylbutyl | 3-[(3,3,5-Trimethylaza perhydroepinyl)methyl]phenyl |
| 2377 | 3-Methylbutyl | 3-[(8-Aza-1,4-dioxaspiro[4.5]dec-8-yl)methyl]phenyl |
| 2378 | 3-Methylbutyl | 3-(Dipentylamino methyl)phenyl |
| 2379 | 3-Methylbutyl | 3-(Dihexylamino methyl)phenyl |

EXAMPLE 31

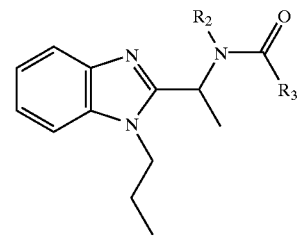

For each compound, the definitions of R$_2$ and R$_3$ are specified in the following table.

| Compound No. | R$_2$ | R$_3$ |
|---|---|---|
| 2004 | 2-Methylpropyl | 2-(4-Chlorophenyl) ethenyl |

EXAMPLE 32

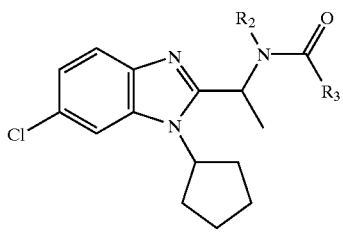

For each compound, the definitions of $R_2$ and $R_3$ are specified in the following table.

| Compound No. | $R_2$ | $R_3$ |
|---|---|---|
| 2020 | Methyl | 3-Thienyl |
| 2021 | i-Propyl | 3-Methyl-2-thienyl |
| 2022 | Methyl | 4-Methylbenzyl |
| 2023 | Methyl | 2-Methylbenzyl |
| 2024 | Methyl | 3-Fluorobenzyl |

EXAMPLE 33

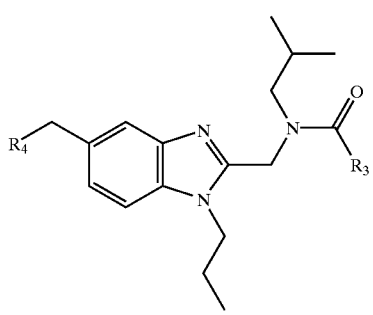

For each compound, the definitions of $R_2$ and $R_3$ are specified in the following table.

| Compound No. | $R_4$ | $R_3$ |
|---|---|---|
| 2025 | 3-Pyrrolinyl | 2,5-Difluorophenyl |
| 2026 | 3-Pyrrolinyl | 3-Fluorophenyl |
| 2027 | Pyrrolidinyl | 2,5-Difluorophenyl |
| 2028 | Pyrrolidinyl | 3-Fluorophenyl |
| 2029 | 1,2,5,6-Tetrahydro pyridyl | 2,5-Difluorophenyl |
| 2030 | 1,2,5,6-Tetrahydro pyridyl | 3-Fluorophenyl |
| 2031 | Piperidyl | 2,5-Difluorophenyl |
| 2032 | Piperidyl | 3-Fluorophenyl |
| 2039 | Morpholinyl | 2,5-Difluorophenyl |
| 2040 | Morpholinyl | 3-Fluorophenyl |
| 2043 | 4-Methyl piperidyl | 2,5-Difluorophenyl |
| 2044 | 4-Methyl piperidyl | 3-Fluorophenyl |
| 2046 | Azaperhydro epinyl | 2,5-Difluorophenyl |
| 2047 | Azaperhydro Epinyl | 3-Fluorophenyl |
| 2049 | 1,4-Thiazaper hydroin-4-yl | 2,5-Difluorophenyl |
| 2050 | 1,4-Thiazaper hydroin-4-yl | 3-Fluorophenyl |
| 2053 | 3,3-dimethyl piperidyl | 2,5-Difluorophenyl |
| 2054 | 3,3-dimethyl piperidyl | 3-Fluorophenyl |
| 2057 | Azaperhydro ocinyl | 2,5-Difluorophenyl |
| 2058 | Azaperhydro Ocinyl | 3-Fluorophenyl |
| 2061 | 2-(1,2,3,4-Tetrahydroiso quinolyl) | 2,5-Difluorophenyl |
| 2062 | 2-(1,2,3,4-Tetrahydroiso quinolyl) | 3-Fluorophenyl |
| 2065 | Methylprop-2-enylamino | 2,5-Difluorophenyl |
| 2066 | Methylprop-2-enylamino | 3-Fluorophenyl |
| 2068 | Diethylamino | 2,5-Difluorophenyl |
| 2069 | Diethylamino | 3-Fluorophenyl |
| 2072 | Methylpropyl amino | 2,5-Difluorophenyl |
| 2073 | Methylpropyl Amino | 3-Fluorophenyl |
| 2076 | Butylmethyl amino | 2,5-Difluorophenyl |
| 2077 | Butylmethyl Amino | 3-Fluorophenyl |
| 2080 | i-Propylethyl amino | 2,5-Difluorophenyl |
| 2081 | i-Propylethyl amino | 3-Fluorophenyl |
| 2084 | Diallylamino | 2,5-Difluorophenyl |
| 2085 | Diallylamino | 3-Fluorophenyl |
| 2088 | Dipropylamino | 2,5-Difluorophenyl |
| 2089 | Dipropylamino | 3-Fluorophenyl |
| 2092 | Butylethyl Amino | 2,5-Difluorophenyl |
| 2093 | Butylethyl Amino | 3-Fluorophenyl |
| 2096 | (Cyclo propylmethyl) propyl amino | 2,5-Difluorophenyl |
| 2097 | (Cyclo propylmethyl) propyl amino | 3-Fluorophenyl |
| 2100 | Hexylmethyl amino | 2,5-Difluorophenyl |
| 2101 | Hexylmethyl Amino | 3-Fluorophenyl |
| 2104 | Dibutylamino | 2,5-Difluorophenyl |
| 2105 | Dibutylamino | 3-Fluorophenyl |
| 2107 | Methylamino | 2,5-Difluorophenyl |
| 2108 | Methylamino | 3-Fluorophenyl |
| 2110 | Ethylamino | 2,5-Difluorophenyl |
| 2111 | Ethylamino | 3-Fluorophenyl |
| 2114 | Allylamino | 2,5-Difluorophenyl |
| 2115 | Allylamino | 3-Fluorophenyl |
| 2118 | Propylamino | 2,5-Difluorophenyl |
| 2119 | Propylamino | 3-Fluorophenyl |
| 2122 | (Cyclopropyl methyl)amino | 2,5-Difluorophenyl |
| 2123 | (Cyclopropyl methyl)amino | 3-Fluorophenyl |
| 2126 | Butyl | 2,5-Difluorophenyl |
| 2127 | Butyl | 3-Fluorophenyl |
| 2130 | (2-Methylpropyl) amino | 2,5-Difluorophenyl |
| 2131 | (2-Methylpropyl) amino | 3-Fluorophenyl |
| 2134 | Pentylamino | 2,5-Difluorophenyl |
| 2135 | Pentylamino | 3-Fluorophenyl |
| 2138 | (3-Methylbutyl) amino | 2,5-Difluorophenyl |
| 2139 | (3-Methylbutyl) amino | 3-Fluorophenyl |
| 2141 | (2-Methylbutyl) amino | 2,5-Difluorophenyl |
| 2142 | (2-Methylbutyl) amino | 3-Fluorophenyl |
| 2145 | Hexylamino | 2,5-Difluorophenyl |
| 2146 | Hexylamino | 3-Fluorophenyl |
| 2148 | [2-(Dimethyl amino)ethyl] amino | 2,5-Difluorophenyl |

-continued

| Compound No. | R4 | R3 |
|---|---|---|
| 2149 | [2-(Dimethyl amino)ethyl]amino | 3-Fluorophenyl |
| 2150 | [3-(Dimethyl amino)propyl]amino | 2,5-Difluorophenyl |
| 2151 | [3-(Dimethyl amino)propyl]amino | 3-Fluorophenyl |
| 2153 | (2-Pyrrolidinyl ethyl)amino | 2,5-Difluorophenyl |
| 2154 | (2-Pyrrolidinyl ethyl)amino | 3-Fluorophenyl |
| 2157 | [2-(Diethyl amino)ethyl]amino | 2,5-Difluorophenyl |
| 2158 | [2-(Diethyl amino)ethyl]amino | 3-Fluorophenyl |
| 2161 | (2-Piperidyl ethyl)amino | 2,5-Difluorophenyl |
| 2162 | (2-Piperidyl ethyl)amino | 3-Fluorophenyl |
| 2164 | [2-(1-Methyl pyrrolidin-2-yl)ethyl]amino | 2,5-Difluorophenyl |
| 2165 | [2-(1-Methyl pyrrolidin-2-yl)ethyl]amino | 3-Fluorophenyl |
| 2168 | [2-(Diethyl amino)propyl]amino | 2,5-Difluorophenyl |
| 2169 | [2-(Diethyl amino)propyl]amino | 3-Fluorophenyl |
| 2172 | (2-Morpholin-4-yl ethyl)amino | 2,5-Difluorophenyl |
| 2173 | (2-Morpholin-4-yl ethyl)amino | 3-Fluorophenyl |
| 2176 | (3-Morpholin-4-yl propyl)amino | 2,5-Difluorophenyl |
| 2177 | (3-Morpholin-4-yl propyl)amino | 3-Fluorophenyl |
| 2180 | [3-(2-Methyl piperidyl)propyl]amino | 2,5-Difluorophenyl |
| 2181 | [3-(2-Methyl piperidyl)propyl]amino | 3-Fluorophenyl |
| 2184 | [3-(2-Oxo pyrrolidinyl)propyl]amino | 2,5-Difluorophenyl |
| 2185 | [3-(2-Oxo pyrrolidinyl)propyl]amino | 3-Fluorophenyl |

EXAMPLE 34

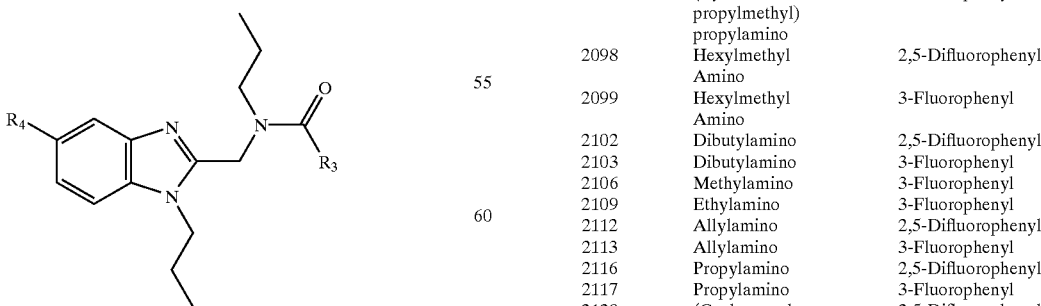

For each compound, the definitions of R2 and R3 are specified in the following table.

| Compound No. | R4 | R3 |
|---|---|---|
| 2033 | Pyrrolidinyl | 2,5-Difluorophenyl |
| 2034 | Pyrrolidinyl | 3-Fluorophenyl |
| 2035 | 1,2,5,6-Tetrahydropyridyl | 2,5-Difluorophenyl |
| 2036 | 1,2,5,6-Tetrahydropyridyl | 3-Fluorophenyl |
| 2037 | Piperidyl | 2,5-Difluorophenyl |
| 2038 | Morpholinyl | 3-Fluorophenyl |
| 2041 | 4-Methyl piperidyl | 2,5-Difluorophenyl |
| 2042 | 4-Methyl piperidyl | 3-Fluorophenyl |
| 2045 | Azaperhydro Epinyl | 3-Fluorophenyl |
| 2048 | 1,4-Thiazaper hydroin-4-yl | 3-Fluorophenyl |
| 2051 | 3,3-dimethyl piperidyl | 2,5-Difluorophenyl |
| 2052 | 3,3-dimethyl piperidyl | 3-Fluorophenyl |
| 2055 | Azaperhydro ocinyl | 2,5-Difluorophenyl |
| 2056 | Azaperhydro Ocinyl | 3-Fluorophenyl |
| 2059 | 2-(1,2,3,4-Tetrahydroiso quinolyl) | 2,5-Difluorophenyl |
| 2060 | 2-(1,2,3,4-Tetrahydroiso quinolyl) | 3-Fluorophenyl |
| 2063 | Methylprop-2-enylamino | 2,5-Difluorophenyl |
| 2064 | Methylprop-2-enylamino | 3-Fluorophenyl |
| 2067 | Diethylamino | 3-Fluorophenyl |
| 2070 | Methylpropyl amino | 2,5-Difluorophenyl |
| 2071 | Methylpropyl Amino | 3-Fluorophenyl |
| 2074 | Butylmethyl amino | 2,5-Difluorophenyl |
| 2075 | Butylmethyl Amino | 3-Fluorophenyl |
| 2078 | i-Propylethyl amino | 2,5-Difluorophenyl |
| 2079 | i-Propylethyl amino | 3-Fluorophenyl |
| 2082 | Diallylamino | 2,5-Difluorophenyl |
| 2083 | Diallylamino | 3-Fluorophenyl |
| 2086 | Dipropylamino | 2,5-Difluorophenyl |
| 2087 | Dipropylamino | 3-Fluorophenyl |
| 2090 | Butylethyl Amino | 2,5-Difluorophenyl |
| 2091 | Butylethyl Amino | 3-Fluorophenyl |
| 2094 | (Cyclo propylmethyl) propylamino | 2,5-Difluorophenyl |
| 2095 | (Cyclo propylmethyl) propylamino | 3-Fluorophenyl |
| 2098 | Hexylmethyl Amino | 2,5-Difluorophenyl |
| 2099 | Hexylmethyl Amino | 3-Fluorophenyl |
| 2102 | Dibutylamino | 2,5-Difluorophenyl |
| 2103 | Dibutylamino | 3-Fluorophenyl |
| 2106 | Methylamino | 3-Fluorophenyl |
| 2109 | Ethylamino | 3-Fluorophenyl |
| 2112 | Allylamino | 2,5-Difluorophenyl |
| 2113 | Allylamino | 3-Fluorophenyl |
| 2116 | Propylamino | 2,5-Difluorophenyl |
| 2117 | Propylamino | 3-Fluorophenyl |
| 2120 | (Cyclopropyl methyl)amino | 2,5-Difluorophenyl |
| 2121 | (Cyclopropyl methyl)amino | 3-Fluorophenyl |

| Compound No. | R₄ | R₃ |
|---|---|---|
| 2124 | Butyl | 2,5-Difluorophenyl |
| 2125 | Butyl | 3-Fluorophenyl |
| 2128 | (2-Methylpropyl)amino | 2,5-Difluorophenyl |
| 2129 | (2-Methylpropyl)amino | 3-Fluorophenyl |
| 2132 | Pentylamino | 2,5-Difluorophenyl |
| 2133 | Pentylamino | 3-Fluorophenyl |
| 2136 | (3-Methylbutyl)amino | 2,5-Difluorophenyl |
| 2137 | (3-Methylbutyl)amino | 3-Fluorophenyl |
| 2140 | (2-Methylbutyl)amino | 3-Fluorophenyl |
| 2143 | Hexylamino | 2,5-Difluorophenyl |
| 2144 | Hexylamino | 3-Fluorophenyl |
| 2152 | (2-Pyrrolidinylethyl)amino | 3-Fluorophenyl |
| 2155 | [2-(Diethylamino)ethyl]amino | 2,5-Difluorophenyl |
| 2156 | [2-(Diethylamino)ethyl]amino | 3-Fluorophenyl |
| 2159 | (2-Piperidylethyl)amino | 2,5-Difluorophenyl |
| 2160 | (2-Piperidylethyl)amino | 3-Fluorophenyl |
| 2163 | [2-(1-Methylpyrrolidin-2-yl)ethyl]amino | 3-Fluorophenyl |
| 2166 | [2-(Diethylamino)propyl]amino | 2,5-Difluorophenyl |
| 2167 | [2-(Diethylamino)propyl]amino | 3-Fluorophenyl |
| 2170 | (2-Morpholin-4-ylethyl)amino | 2,5-Difluorophenyl |
| 2171 | (2-Morpholin-4-ylethyl)amino | 3-Fluorophenyl |
| 2174 | (3-Morpholin-4-ylpropyl)amino | 2,5-Difluorophenyl |
| 2175 | (3-Morpholin-4-ylpropyl)amino | 3-Fluorophenyl |
| 2178 | [3-(2-Methylpiperidyl)propyl]amino | 2,5-Difluorophenyl |
| 2179 | [3-(2-Methylpiperidyl)propyl]amino | 3-Fluorophenyl |
| 2182 | [3-(2-Oxopyrrolidinyl)propyl]amino | 2,5-Difluorophenyl |
| 2183 | [3-(2-Oxopyrrolidinyl)propyl]amino | 3-Fluorophenyl |

EXAMPLE 35

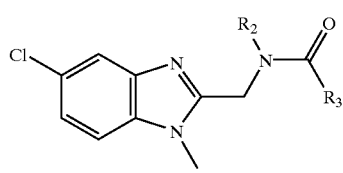

For each compound, the definitions of R₂ and R₃ are specified in the following table.

| Compound No. | R₂ | R₃ |
|---|---|---|
| 2147 | 3-Methylbutyl | 3-Chlorophenyl |
| 2219 | 3-Methylbutyl | 3-Trifluoromethylphenyl |
| 2220 | Butyl | 3-Bromophenyl |
| 2221 | 2-Methylpropyl | 3-Bromophenyl |
| 2222 | 3-Methylbutyl | 3-Bromophenyl |

EXAMPLE 36

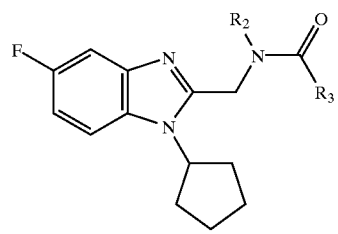

For each compound, the definitions of R₂ and R₃ are specified in the following table.

| Compound No. | R₂ | R₃ |
|---|---|---|
| 2186 | Butyl | 2,5-Dimethoxyphenyl |
| 2187 | 2-Methylpropyl | 2,5-Dimethoxyphenyl |
| 2188 | 3-Methylbutyl | 2,5-Dimethoxyphenyl |
| 2189 | Butyl | 3-Chloro-4-methoxyphenyl |
| 2190 | 2-Methylpropyl | 3-Chloro-4-methoxyphenyl |
| 2191 | 3-Methylbutyl | 3-Chloro-4-methoxyphenyl |
| 2192 | Butyl | 5-Chloro-2-methoxyphenyl |
| 2193 | 2-Methylpropyl | 5-Chloro-2-methoxyphenyl |
| 2194 | 3-Methylbutyl | 5-Chloro-2-methoxyphenyl |
| 2195 | 2-Methylpropyl | 4-Chloro-2-methoxyphenyl |
| 2196 | Butyl | 3-Trifluoromethylphenyl |
| 2197 | 2-Methylpropyl | 3-Trifluoromethylphenyl |
| 2198 | 3-Methylbutyl | 3-Trifluoromethylphenyl |
| 2199 | Butyl | 2-Trifluoromethylphenyl |
| 2200 | 3-Methylbutyl | 2-Trifluoromethylphenyl |
| 2201 | Butyl | 3,4-Dichlorophenyl |
| 2202 | 2-Methylpropyl | 3,4-Dichlorophenyl |
| 2203 | 3-Methylbutyl | 3,4-Dichlorophenyl |
| 2204 | Butyl | 2,5-Dichlorophenyl |
| 2205 | 2-Methylpropyl | 2,5-Dichlorophenyl |
| 2206 | Pentyl | 2,5-Dichlorophenyl |
| 2207 | 3-Methylbutyl | 2,5-Dichlorophenyl |
| 2208 | Butyl | 2,4-Dichlorophenyl |
| 2209 | 2-Methylpropyl | 2,4-Dichlorophenyl |
| 2210 | 3-Methylbutyl | 2,4-Dichlorophenyl |
| 2211 | Butyl | 3-Bromophenyl |
| 2212 | 2-Methylpropyl | 3-Bromophenyl |
| 2213 | Pentyl | 3-Bromophenyl |
| 2214 | 3-Methylbutyl | 3-Bromophenyl |
| 2215 | 2-Methylpropyl | 4-Bromophenyl |
| 2216 | Butyl | 2-Bromophenyl |
| 2217 | 2-Methylpropyl | 2-Bromophenyl |
| 2218 | 3-Methylbutyl | 2-Bromophenyl |
| 2223 | 2-Methylpropyl | 3-Phenoxyphenyl |
| 2224 | 2-Methylpropyl | 4-Phenoxyphenyl |
| 2225 | 2-Methylpropyl | 3-Bromo-4-methylphenyl |
| 2226 | Pentyl | 3-Bromo-4-methylphenyl |
| 2227 | 3-Methylbutyl | 3-Bromo-4-methylphenyl |
| 2228 | Butyl | 3-Bromo-4-methylphenyl |
| 2229 | 2-Methylpropyl | 3-Bromo-4-methylphenyl |
| 2230 | Pentyl | 3-Bromo-4-methylphenyl |
| 2231 | 3-Methylbutyl | 3-Bromo-4-methylphenyl |
| 2232 | Butyl | 3-Iodophenyl |
| 2233 | 2-Methylpropyl | 3-Iodophenyl |
| 2234 | Pentyl | 3-Iodophenyl |
| 2235 | 3-Methylbutyl | 3-Iodophenyl |
| 2236 | 2-Methylpropyl | 4-Iodophenyl |
| 2310 | 2-Methylpropyl | 2,3,5,6-Tetrafluorophenyl |
| 2311 | 2-Methylpropyl | 2,4,6-Trifluorophenyl |
| 2312 | Butyl | 2,3,6-Trifluorophenyl |
| 2313 | 2-Methylpropyl | 2,3,6-Trifluorophenyl |

-continued

| Compound No. | R₂ | R₃ |
|---|---|---|
| 2314 | Pentyl | 2,3,6-Trifluorophenyl |
| 2315 | 3-Methylbutyl | 2,3,6-Trifluorophenyl |
| 2316 | Butyl | 3-Chloro-6-fluorophenyl |
| 2317 | Pentyl | 3-Chloro-6-fluorophenyl |
| 2318 | 3-Methylbutyl | 3-Chloro-6-fluorophenyl |
| 2319 | Butyl | 2-Fluoro-6-trifluoromethylphenyl |

EXAMPLE 37

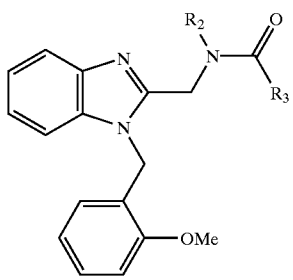

For each compound, the definitions of $R_2$ and $R_3$ are specified in the following table.

| Compound No. | R₂ | R₃ |
|---|---|---|
| 2304 | 2-Methylpropyl | 5-Methyl-2-thienyl |

EXAMPLE 38

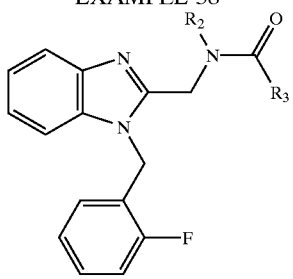

For each compound, the definitions of $R_2$ and $R_3$ are specified in the following table.

| Compound No. | R₂ | R₃ |
|---|---|---|
| 2380 | 2-Methylpropyl | 2,4-Difluorophenyl |
| 2381 | 2-Methylpropyl | 2H-Benzo[d]1,3-dioxolane |
| 2382 | 2-Methylpropyl | 3-Chloro-4-methylphenyl |

EXAMPLE 39

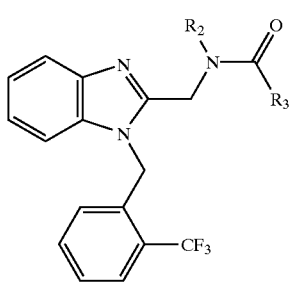

For each compound, the definitions of $R_2$ and $R_3$ are specified in the following table.

| Compound No. | R₂ | R₃ |
|---|---|---|
| 2390 | 2-Methylpropyl | 5-Methyl-2-thienyl |

EXAMPLE 40

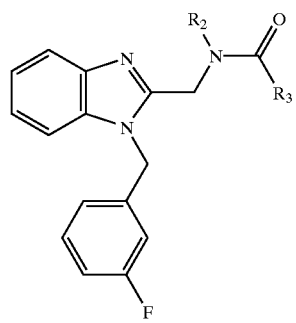

For each compound, the definitions of $R_2$ and $R_3$ are specified in the following table.

| Compound No. | R₂ | R₃ |
|---|---|---|
| 2383 | 2-Methylpropyl | 3-Chloro-4-methylphenyl |
| 2384 | 2-Methylpropyl | 2,4-Difluorophenyl |
| 2385 | 2-Methylpropyl | 2H-Benzo[d]1,3-dioxolane |

EXAMPLE 41

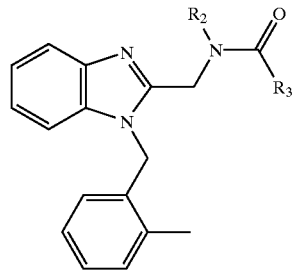

For each compound, the definitions of $R_2$ and $R_3$ are specified in the following table.

| Compound No. | R₂ | R₃ |
|---|---|---|
| 2389 | Pentyl | 3-Fluoro-4-methylphenyl |

EXAMPLE 42

Assay for GABA$_A$ Receptor Binding

The following assay is a standard assay for GABA$_A$ receptor binding.

The high affinity and high selectivity of compounds of this invention for the benzodiazepine site of the GABA$_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000× g for 20 minutes. The supernatant is decanted, the pellet rehomogenized in the same volume of buffer, and centrifuged again at 20,000× g. The supernatant of this centrifugation step is decanted and the pellet stored at −20° C. overnight. The pellet is then thawed and resuspended in 25 volumes of Buffer A (original wt/vol), centrifuged at 20,000× g and the supernatant decanted. This wash step is repeated once. The pellet is finally resuspended in 50 volumes of Buffer A.

Incubations containi 100 $\mu$l of tissue homogenate, 100 $\mu$l of radioligand, (0.5 nM $^3$H-Ro15-1788 [$^3$H-Flumazenil], specific activity 80 Ci/mmol), and test compound or control (see below), and are brought to a total volume of 500 $\mu$l with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 $\mu$M Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. When tested in this assay compounds of the invention exihibit $K_i$ values of less than 1 uM, preferred compounds of the invention have $K_i$ values of less than 500 nM and more compounds of the invention have $K_i$ values of less than 100 nM.

EXAMPLE 43

Assay for GABA$_A$ Receptor Functional Activity

Electrophysiology

The following assay is used to determine if a compound of the invention act as an agonist, an antagonist, or an inverse agonist at the benzodiazepine site of the GABA$_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis oocytes* are enzymatically isolated and injected with non-polyadenylated cRNA mixed in a ratio of 4:1:4 for $\alpha$, $\beta$ and $\gamma$ subunits, respectively. Of the nine combinations of $\alpha$, $\beta$ and $\gamma$ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 $\mu$M GABA is applied.

Compounds are evaluated against a GABA concentration that evokes <10% of the maximal evokable GABA current (e.g. 1 $\mu$M–9 $\mu$M). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 $\mu$M RO15-1788, followed by exposure to GABA+1 $\mu$M RO15-1788+test compound. Percent change due to addition of compound is calculated as described above. Any percent change observed in the presence of RO15-1788 is subtracted from the percent changes in current amplitude observed in the absence of 1 $\mu$M RO15-1788. These net values are used for the calculation of average efficacy and EC$_{50}$ values by standard methods. To evaluate average efficacy and EC$_{50}$ values, the concentration/effect data are averaged across cells and fit to the logistic equation.

EXAMPLE 44

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 45

Use of Compounds of the Invention as Probes for GABA$_A$ Receptors in Cultured Cells and Tissue Samples Receptor autoradiography (receptor mapping) of NK-3 or GABA$_A$ receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

Appendix 1
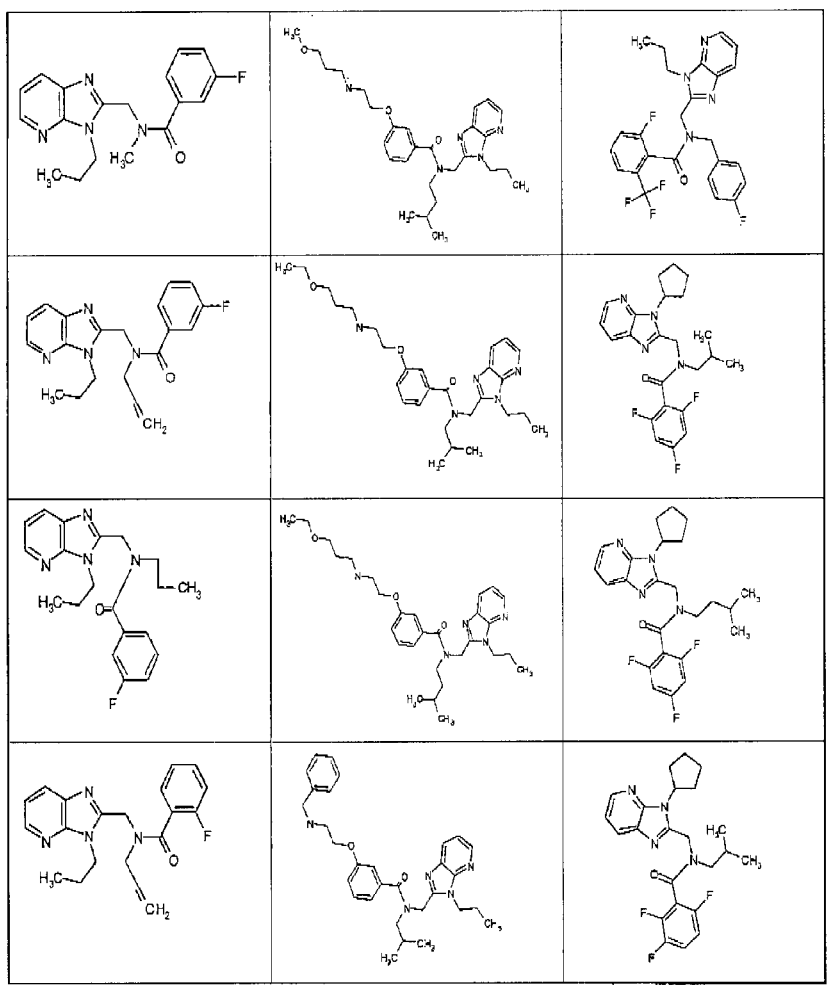

Appendix 1
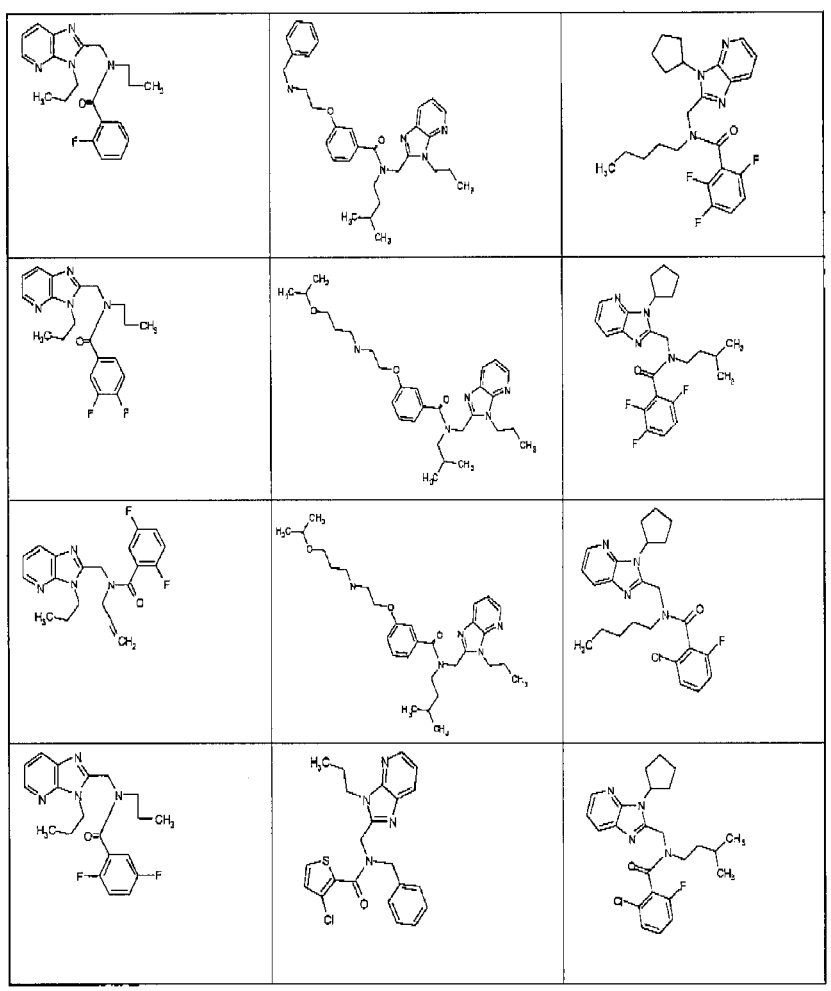

Appendix 1
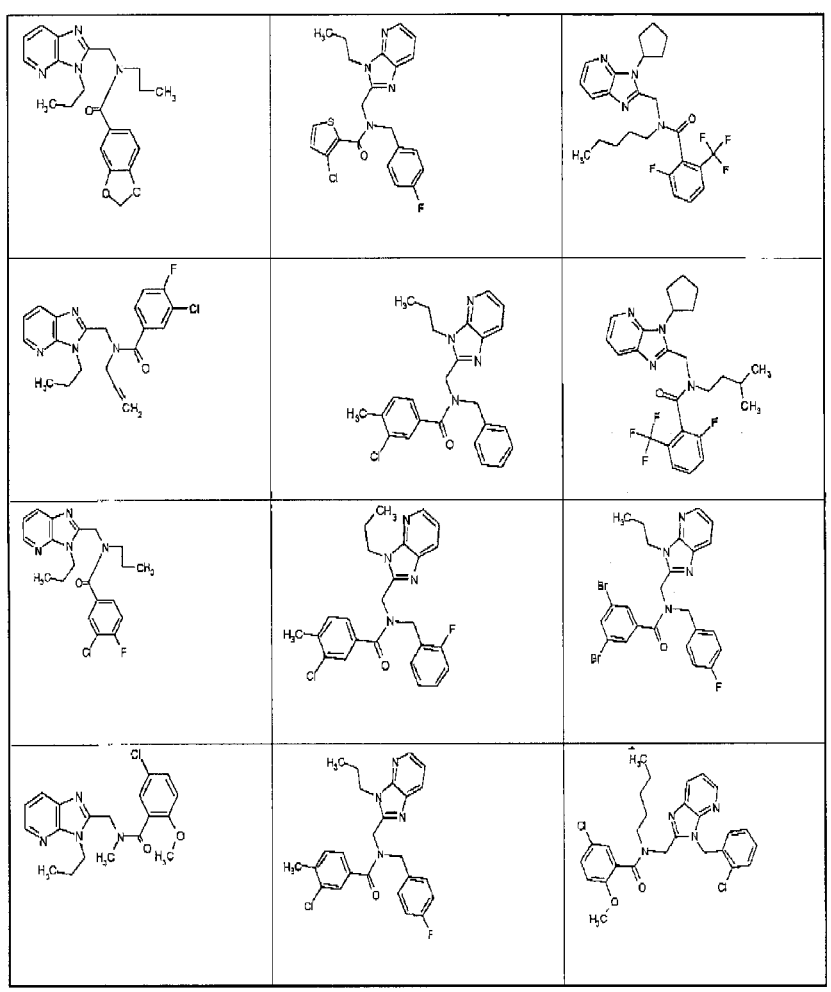

Appendix 1
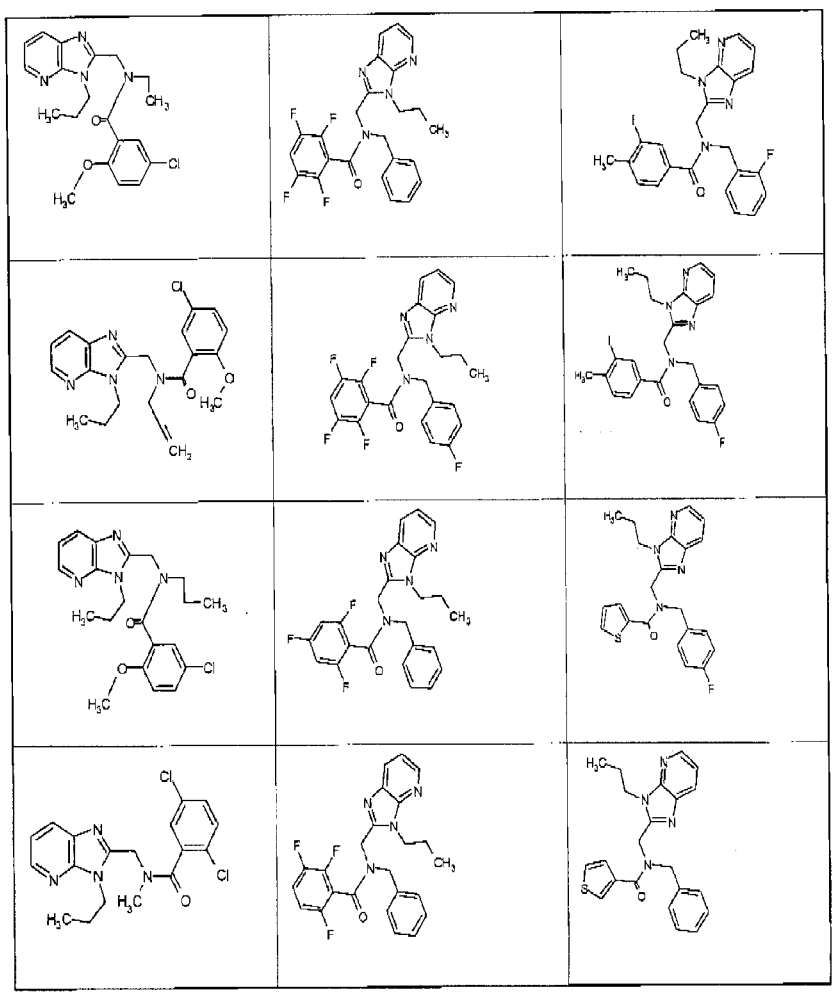

Appendix 1
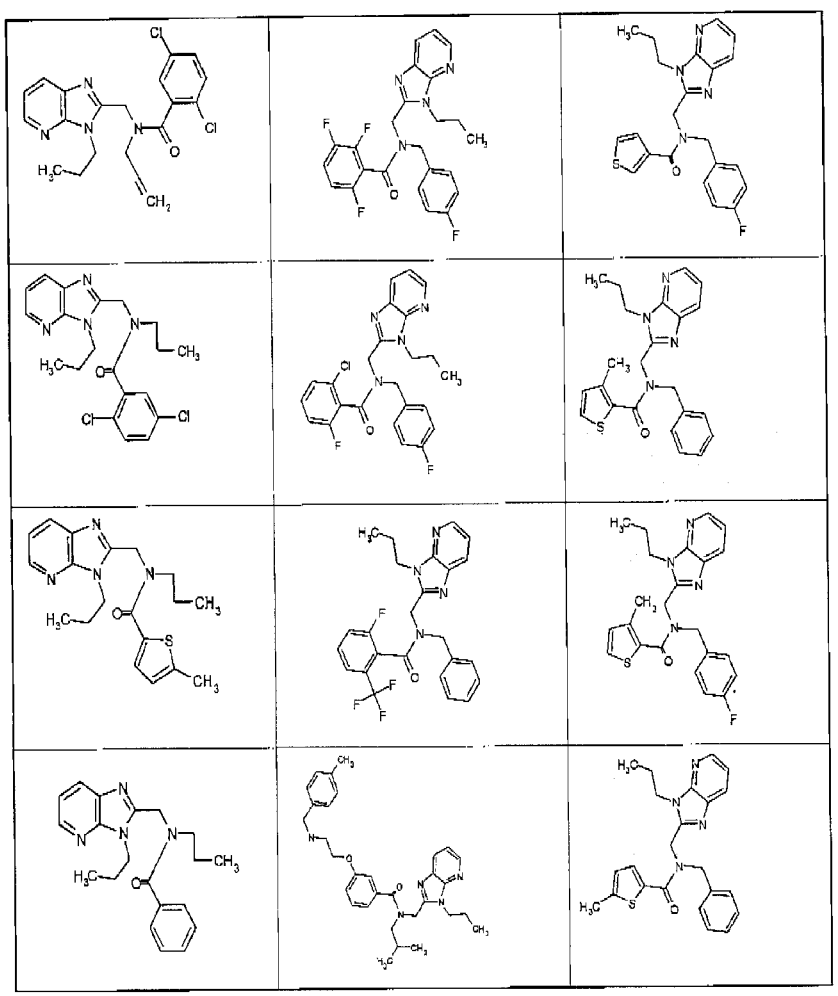

Appendix 1
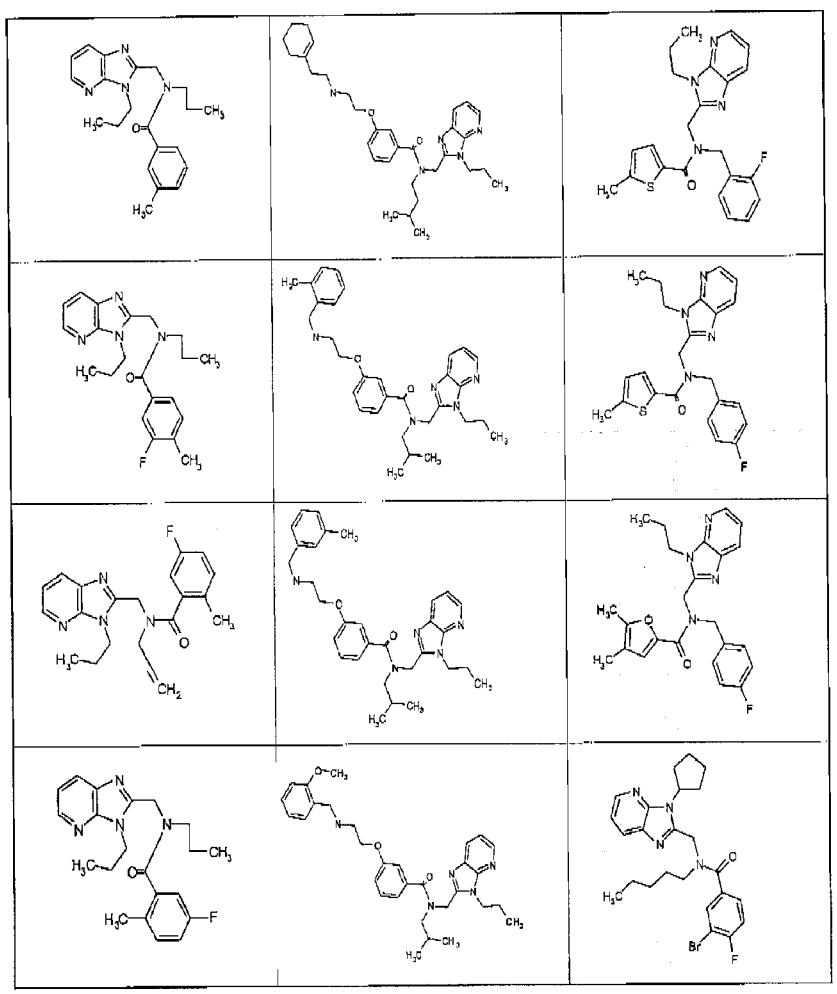

Appendix 1
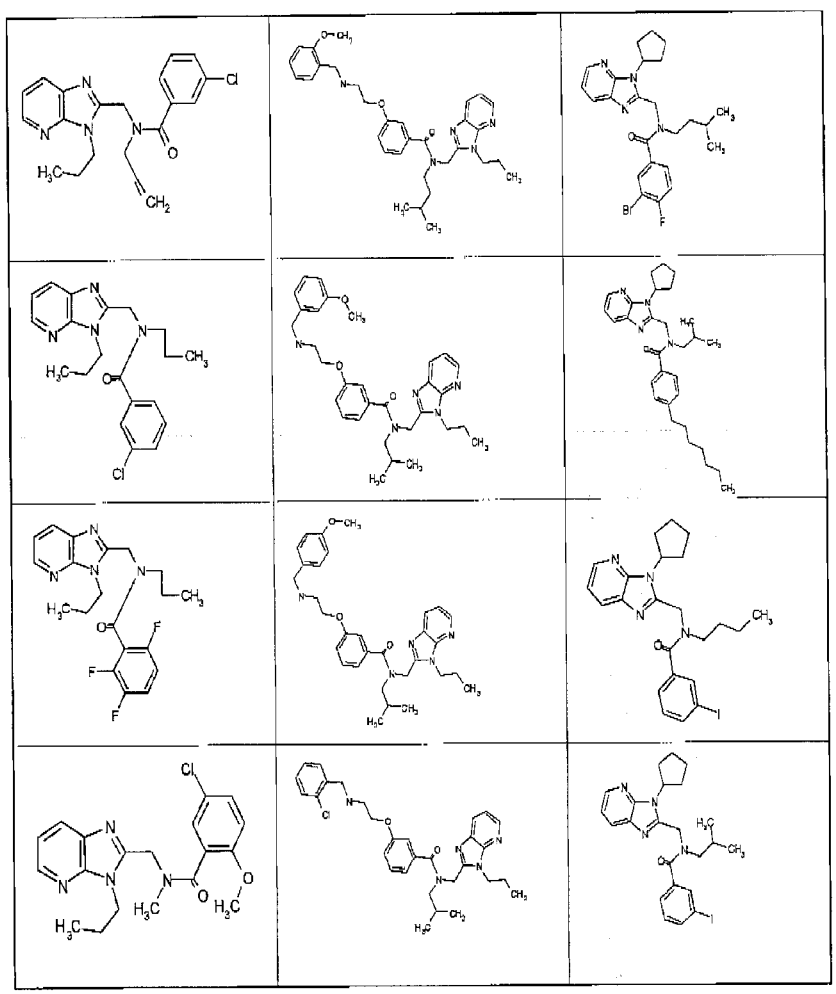

Appendix 1
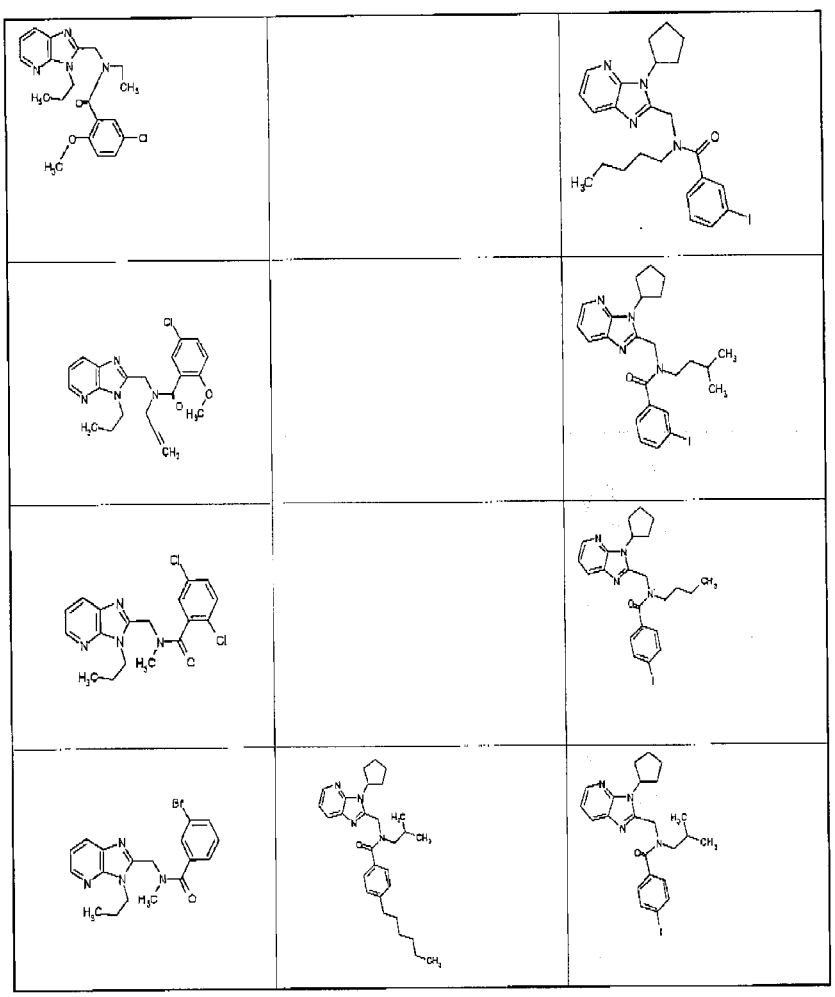

Appendix 1
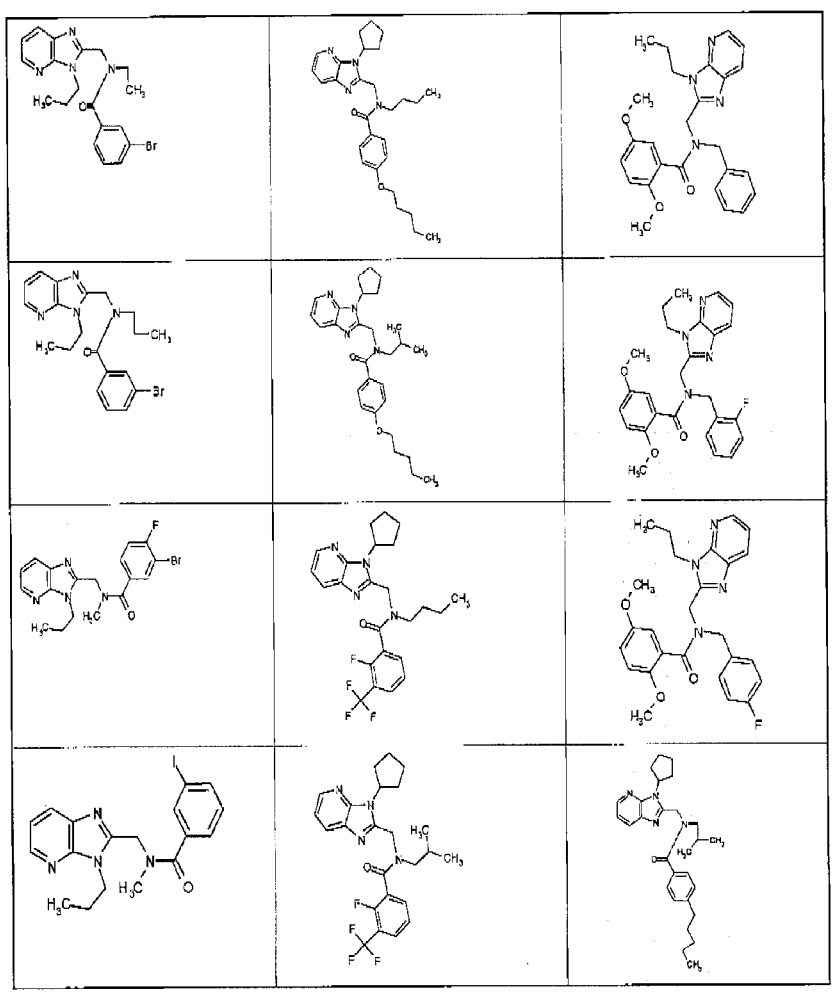

Appendix 1
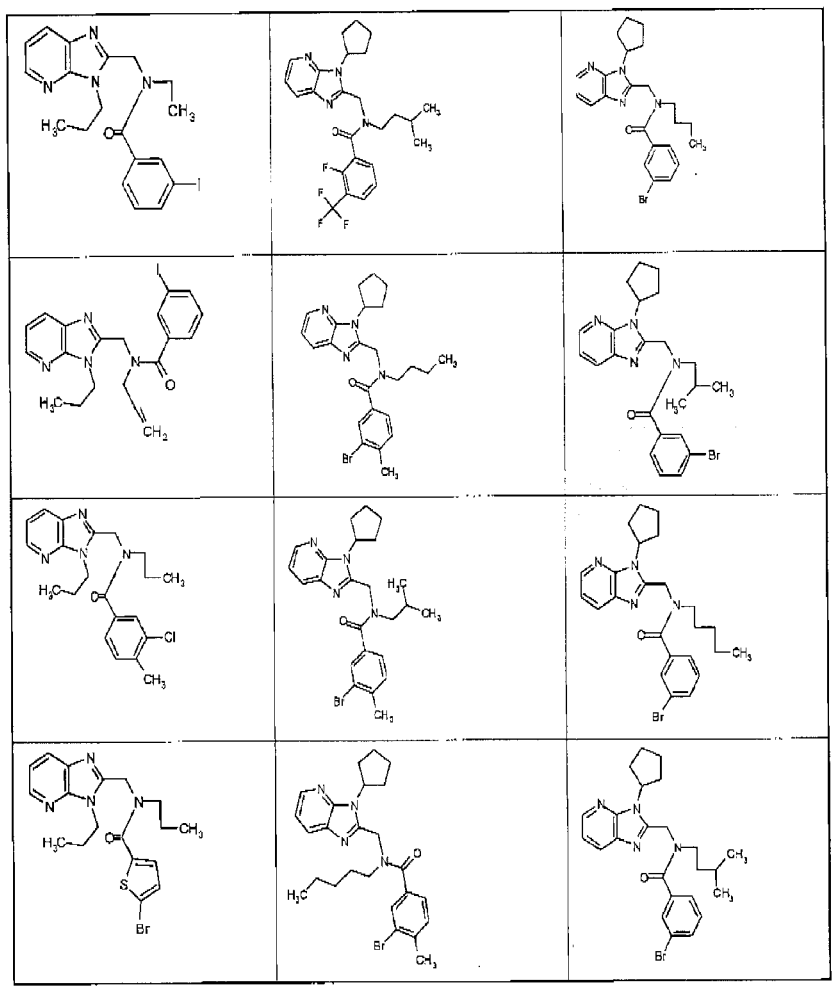

Appendix 1
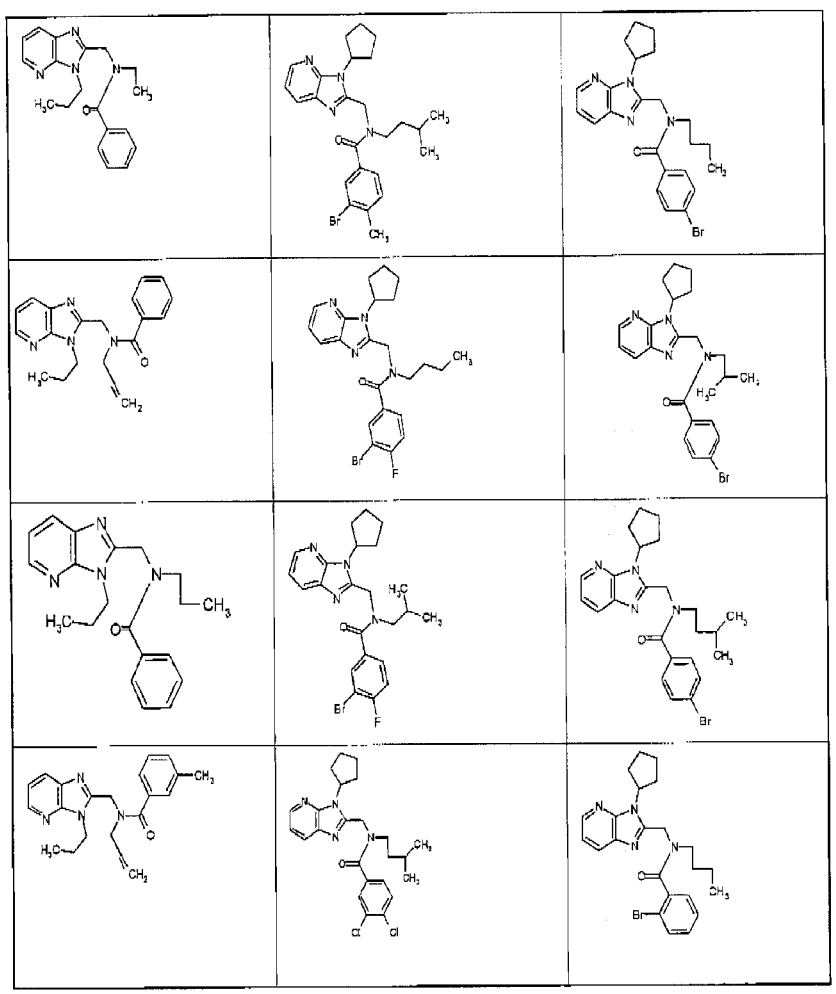

Appendix 1
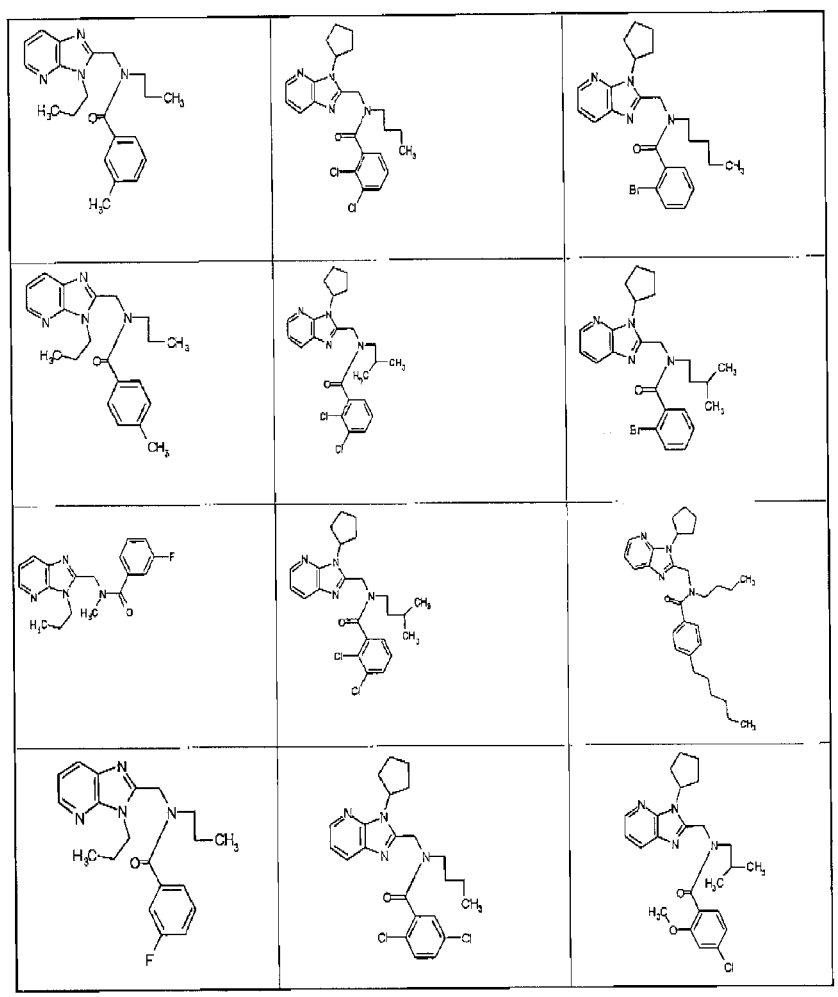

Appendix 1
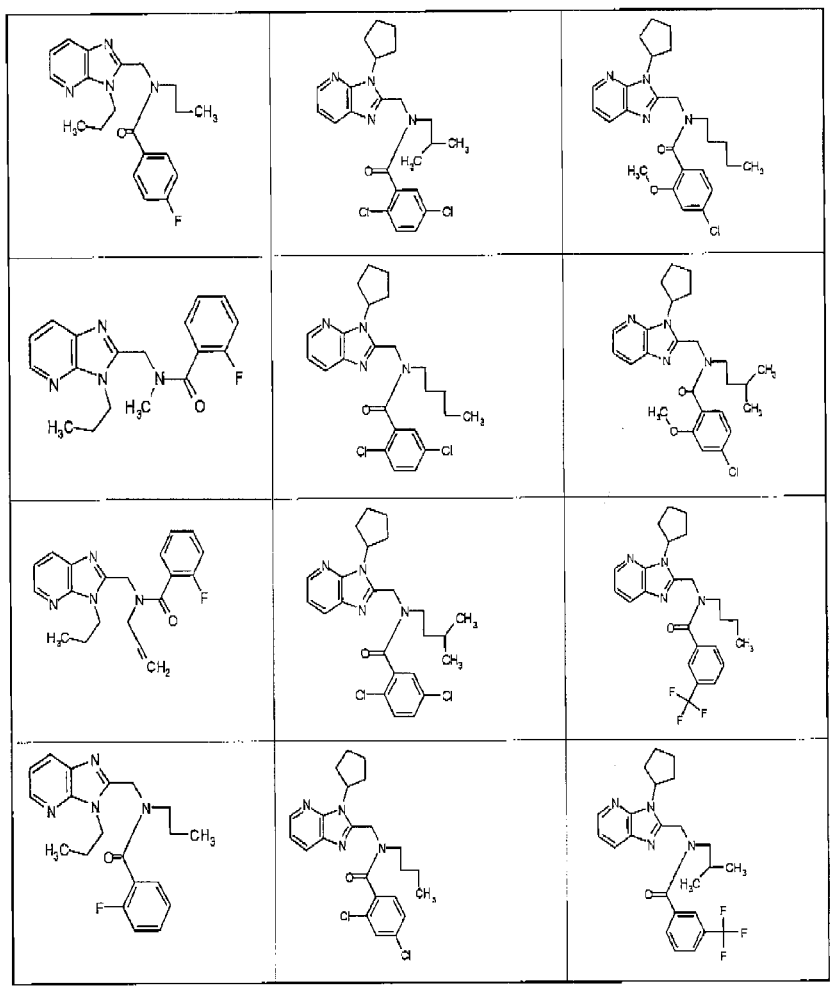

Appendix 1
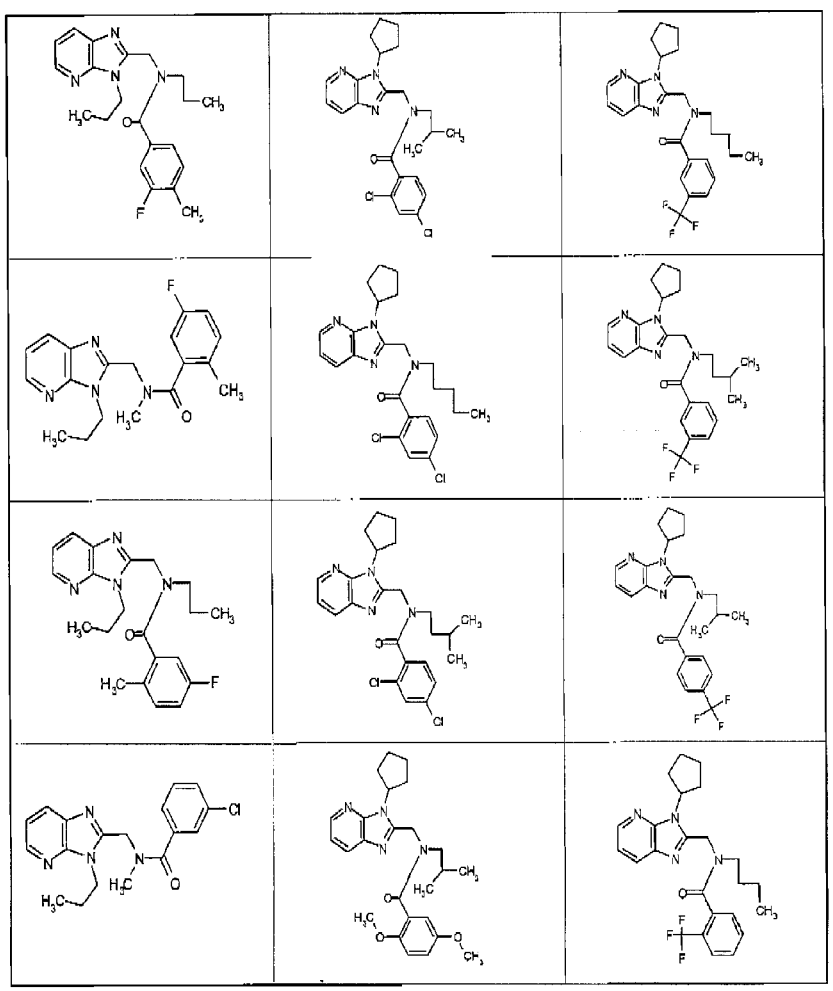

Appendix 1
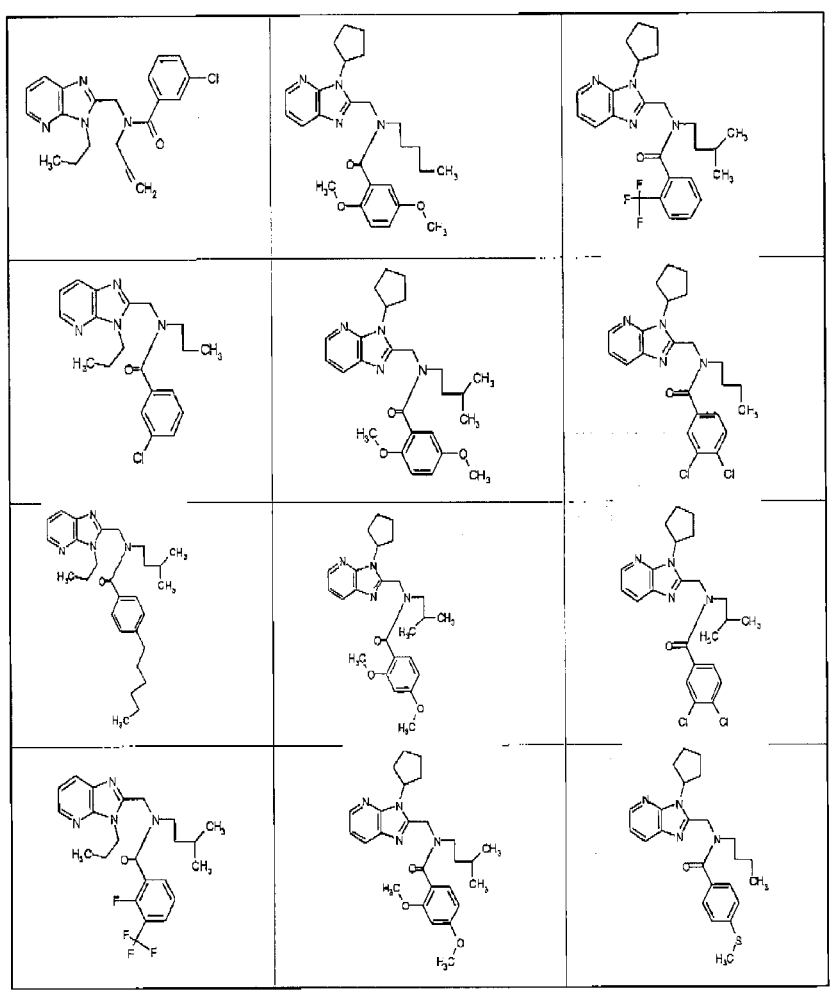

Appendix 1
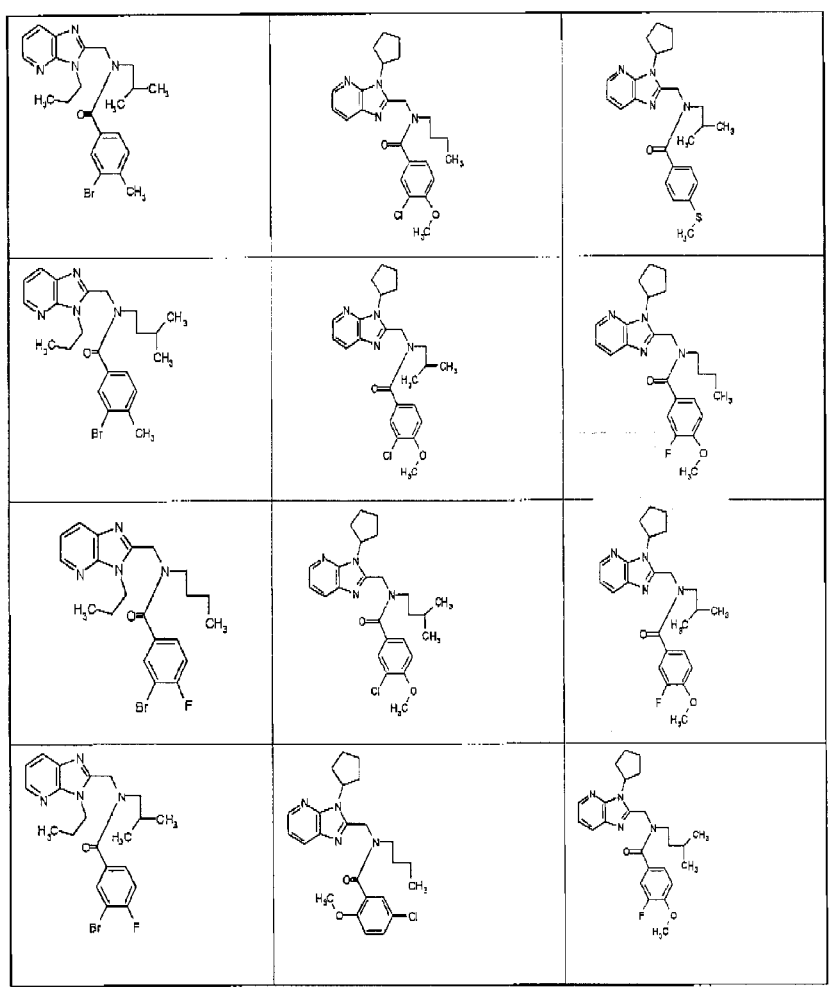

Appendix 1
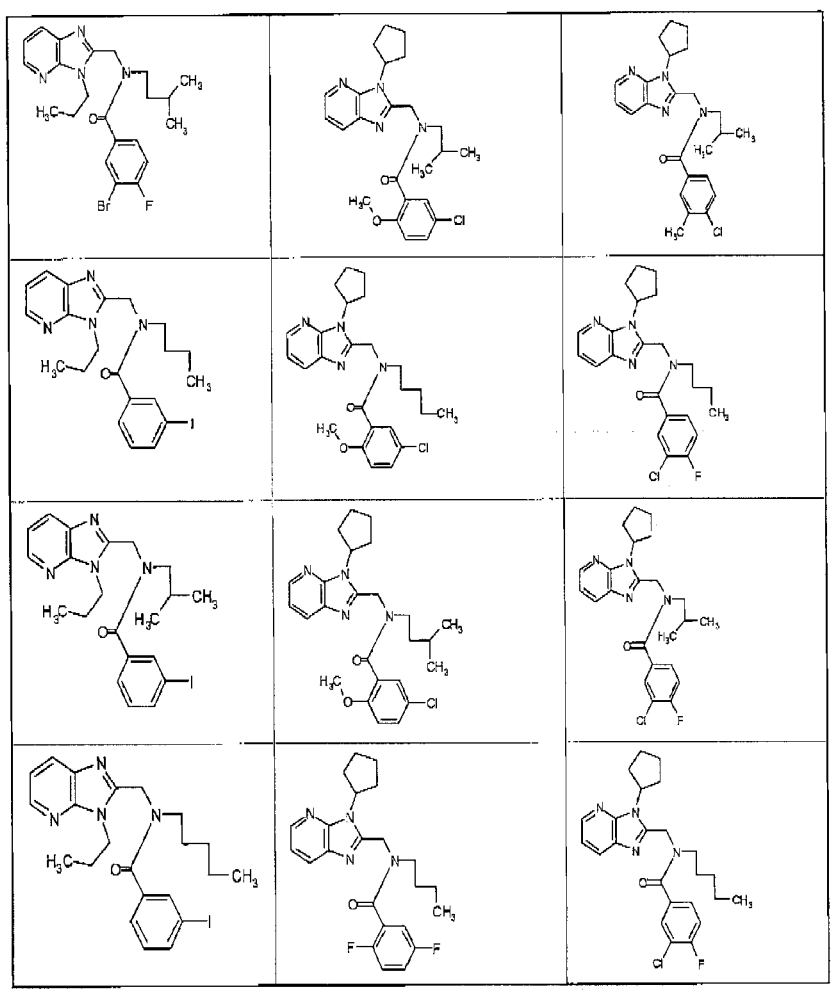

Appendix 1

Appendix 1
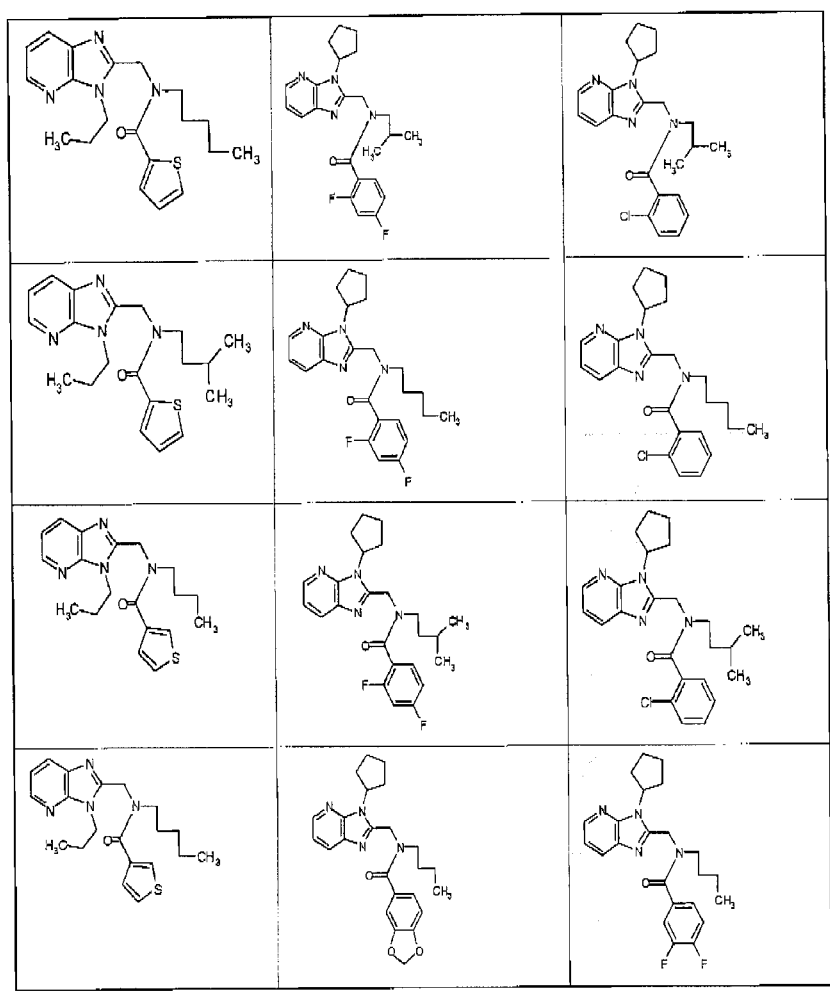

Appendix 1

Appendix 1

Appendix 1
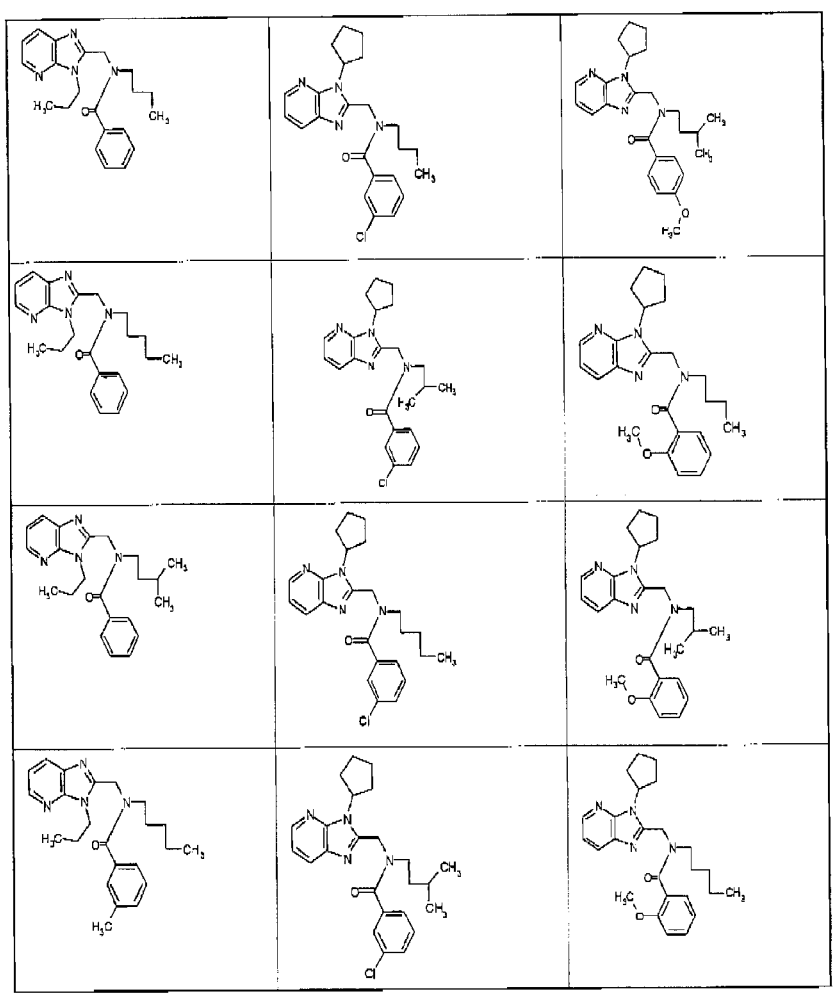

Appendix 1
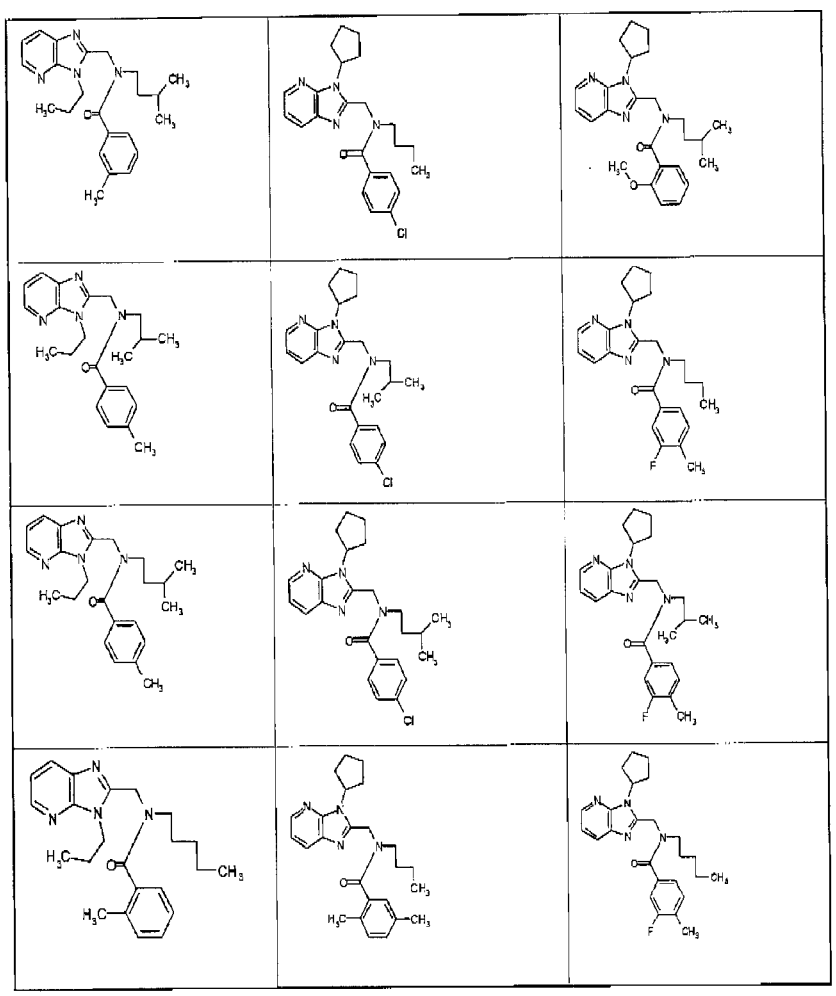

Appendix 1
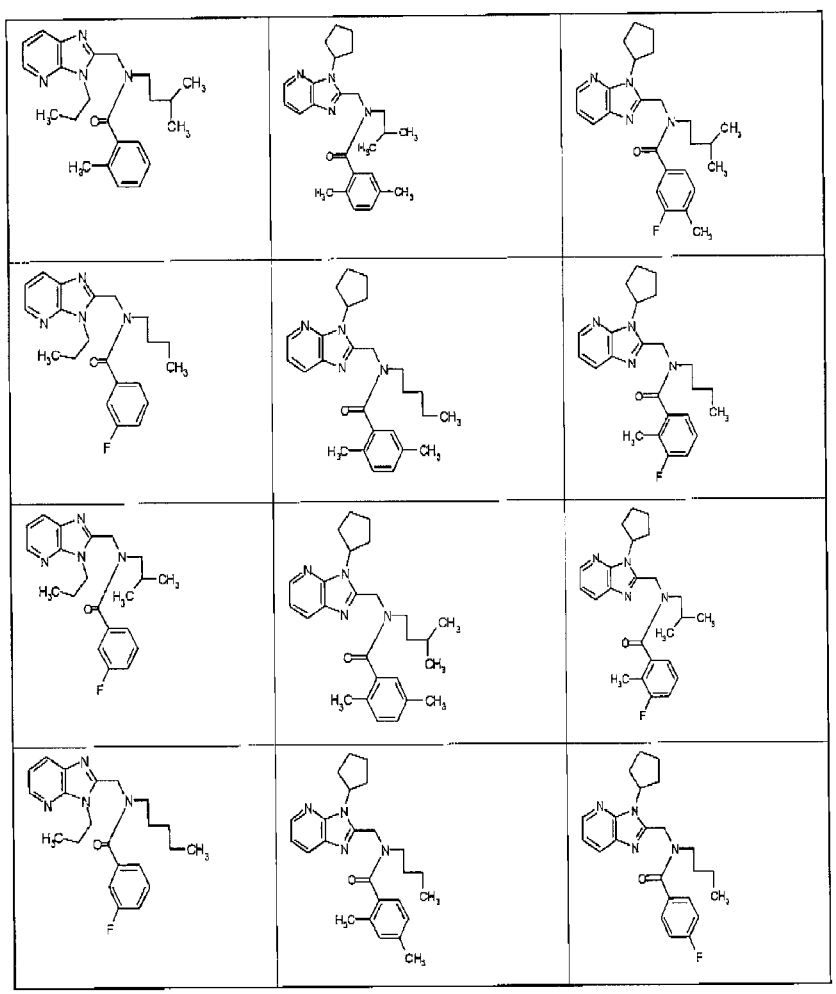

Appendix 1
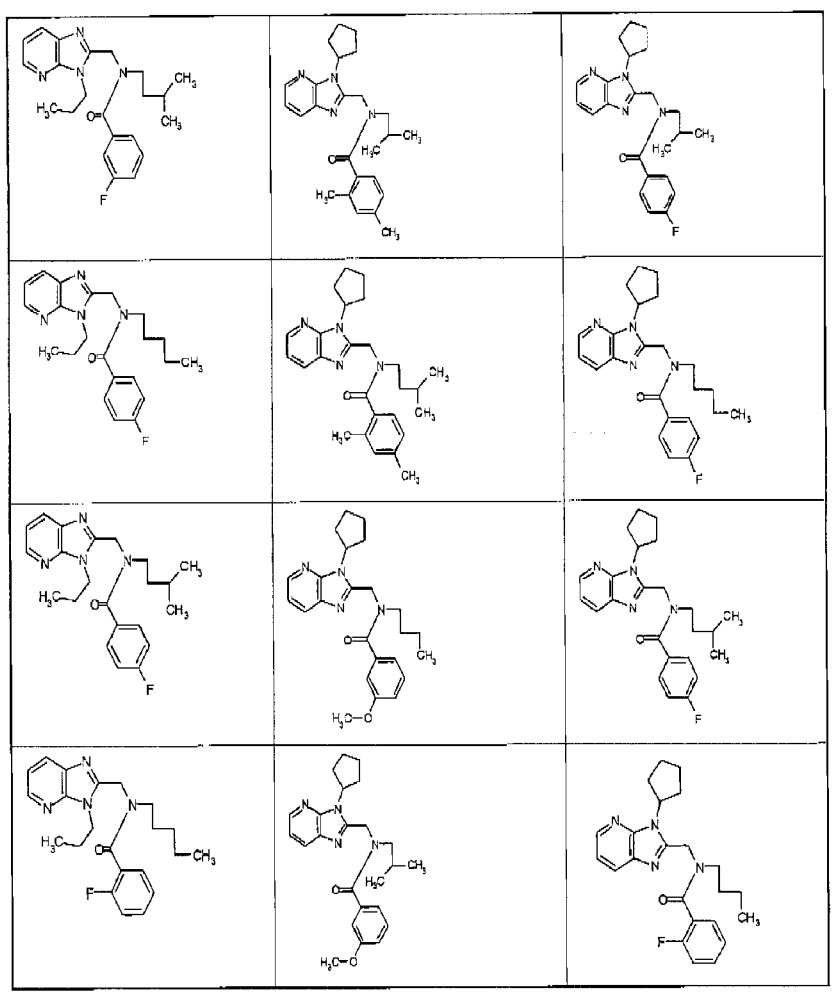

Appendix 1
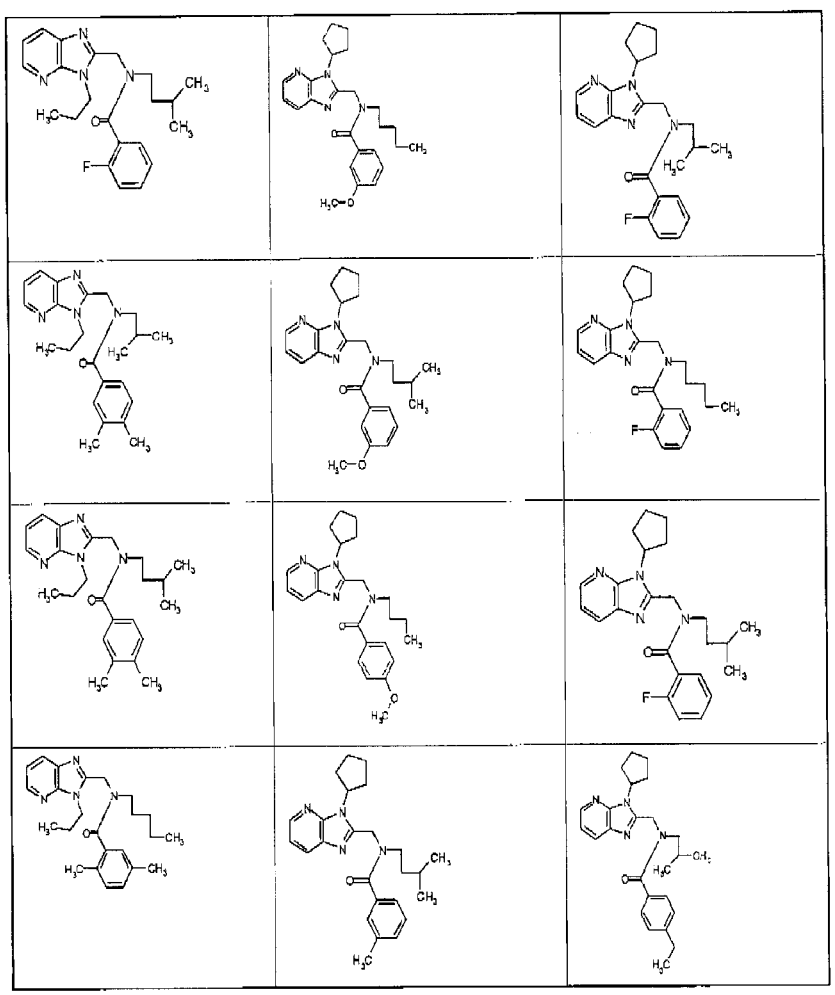

Appendix 1
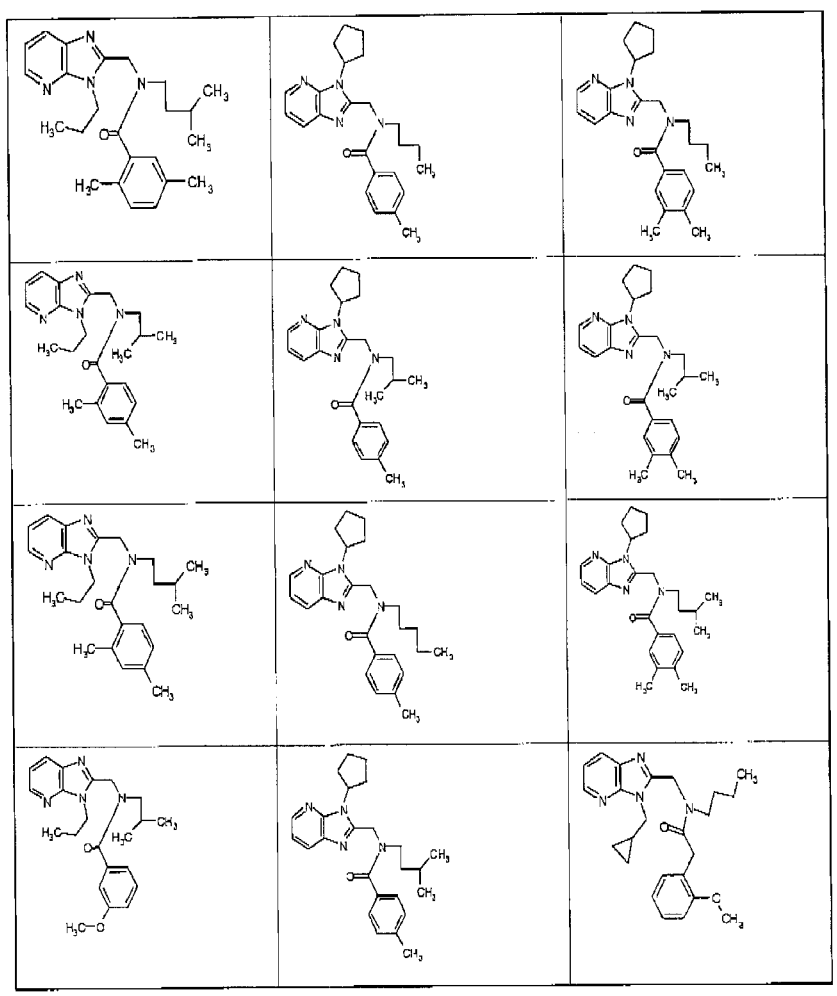

Appendix 1
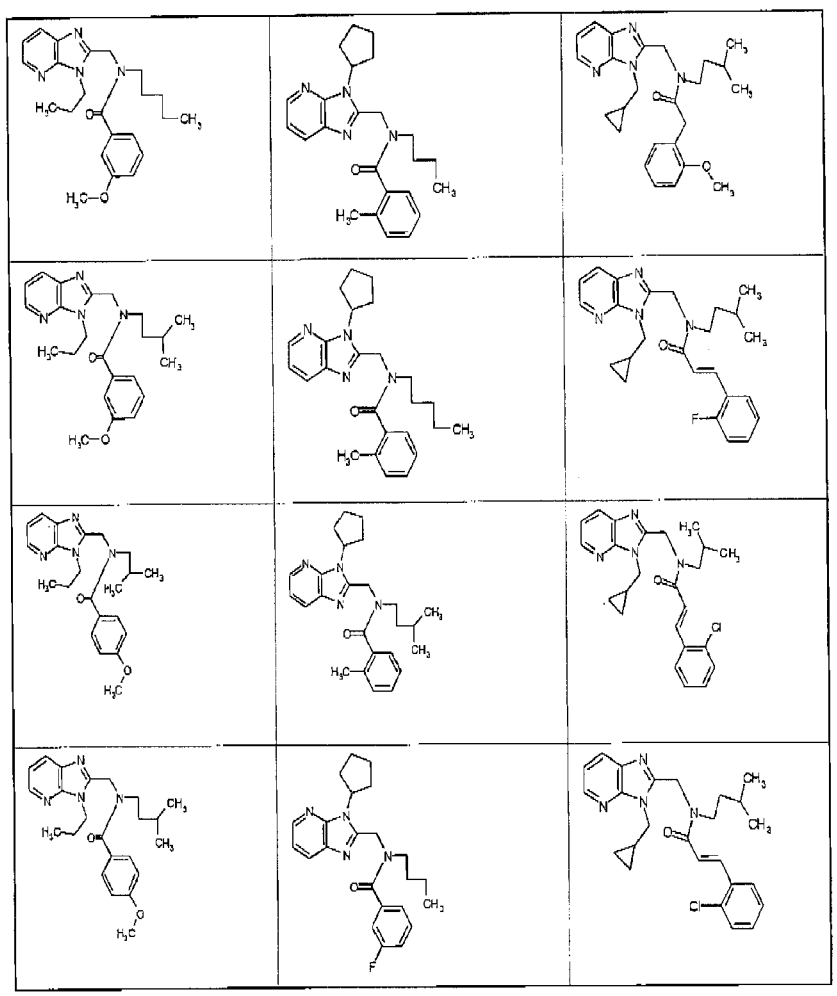

Appendix 1
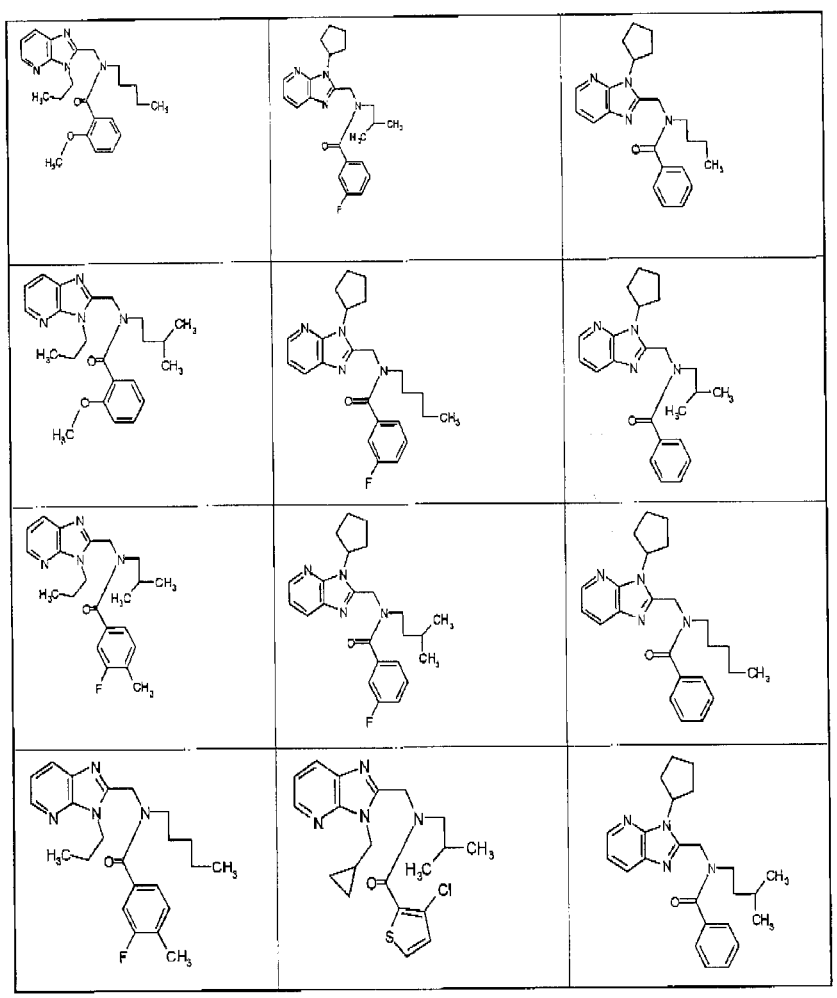

Appendix 1
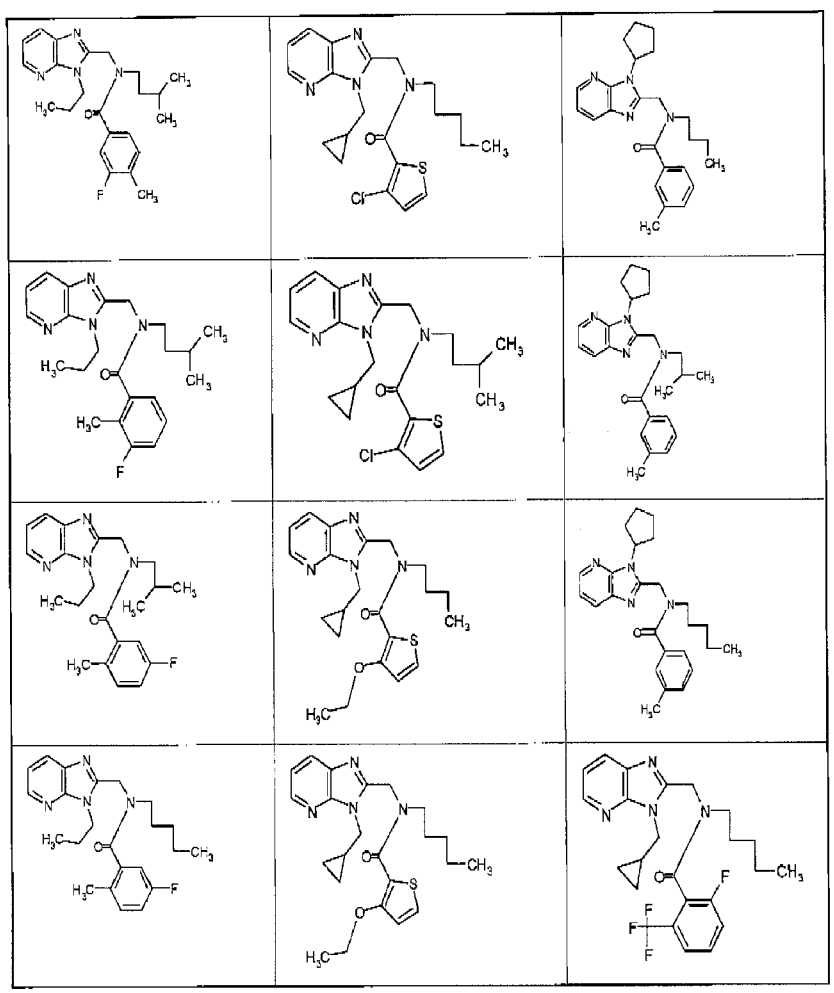

Appendix 1
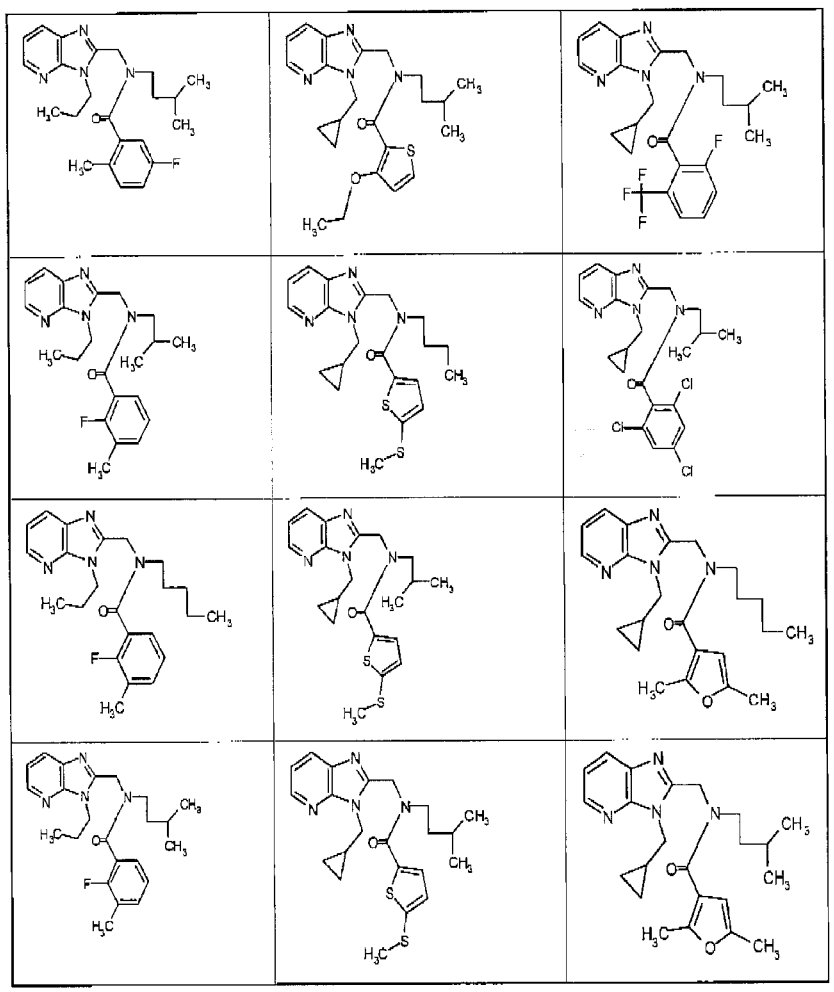

Appendix 1
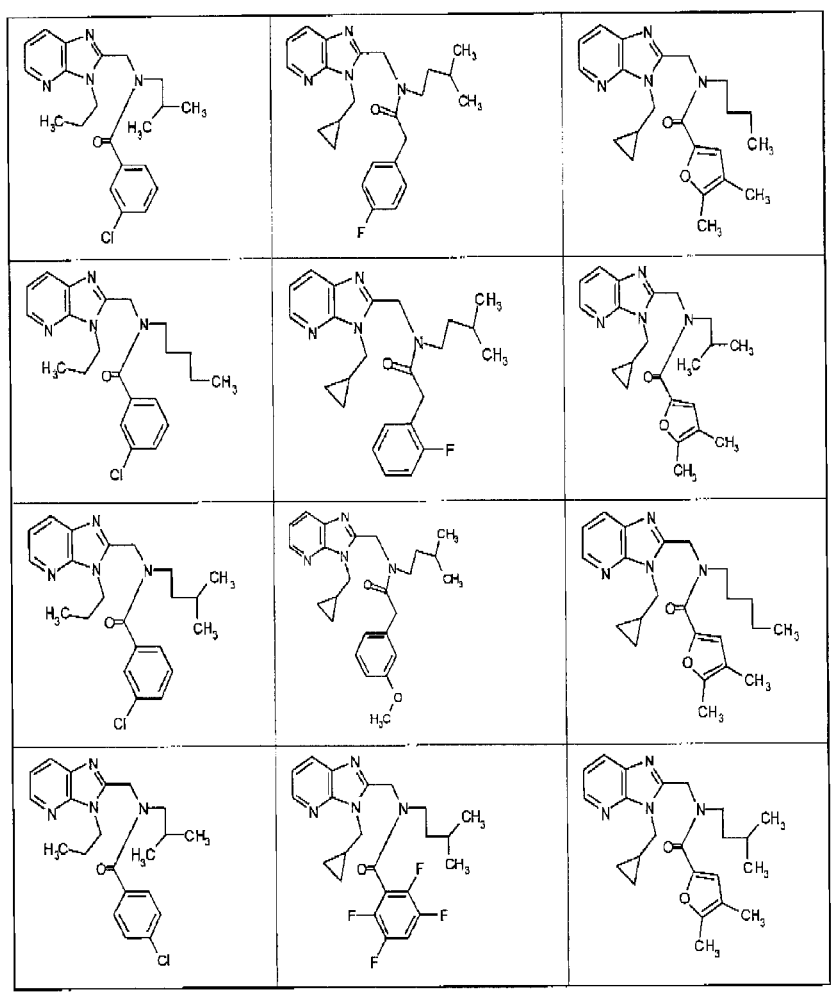

Appendix 1
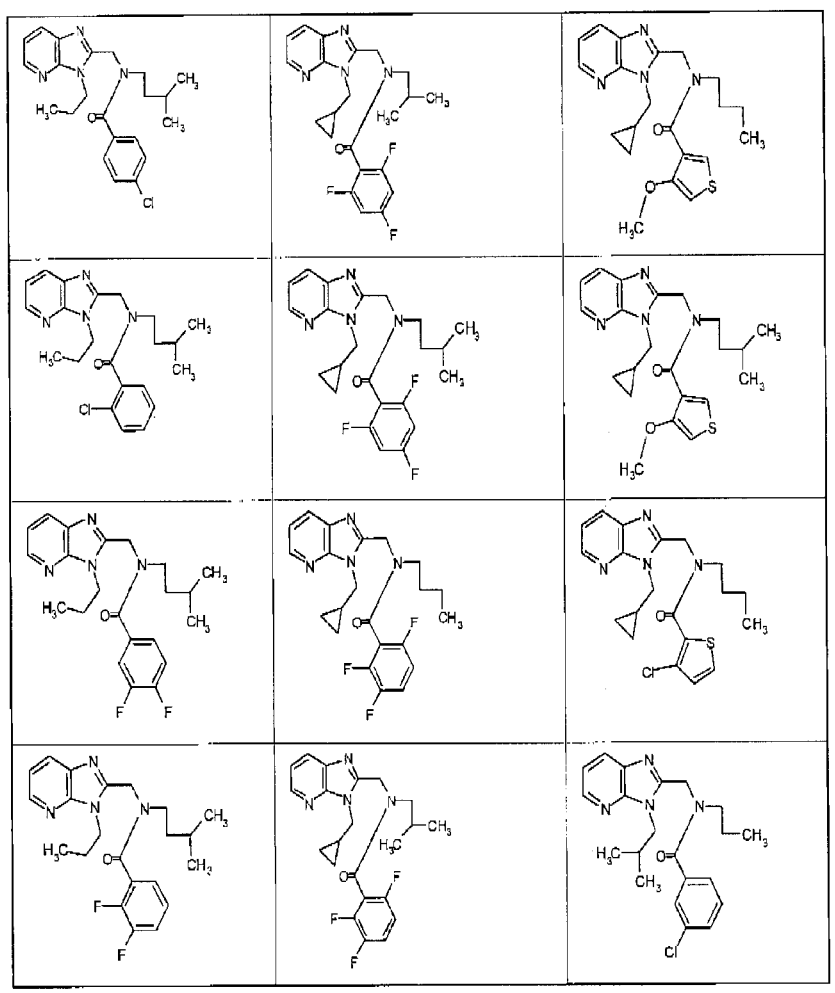

Appendix 1
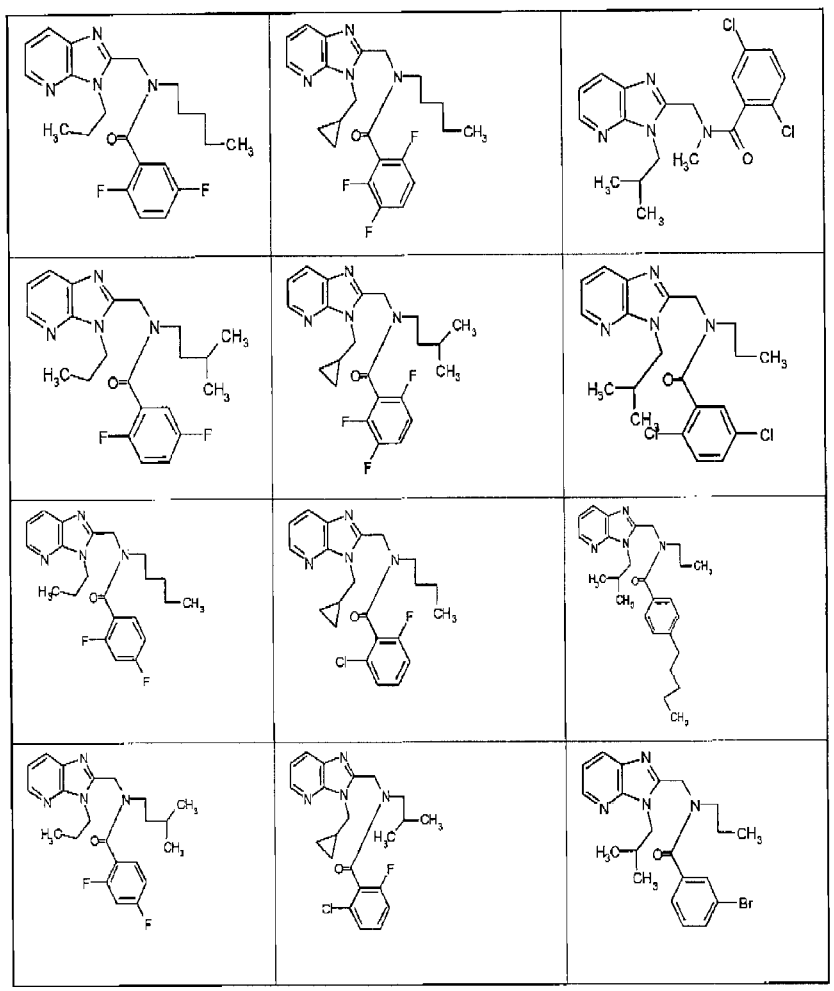

Appendix 1
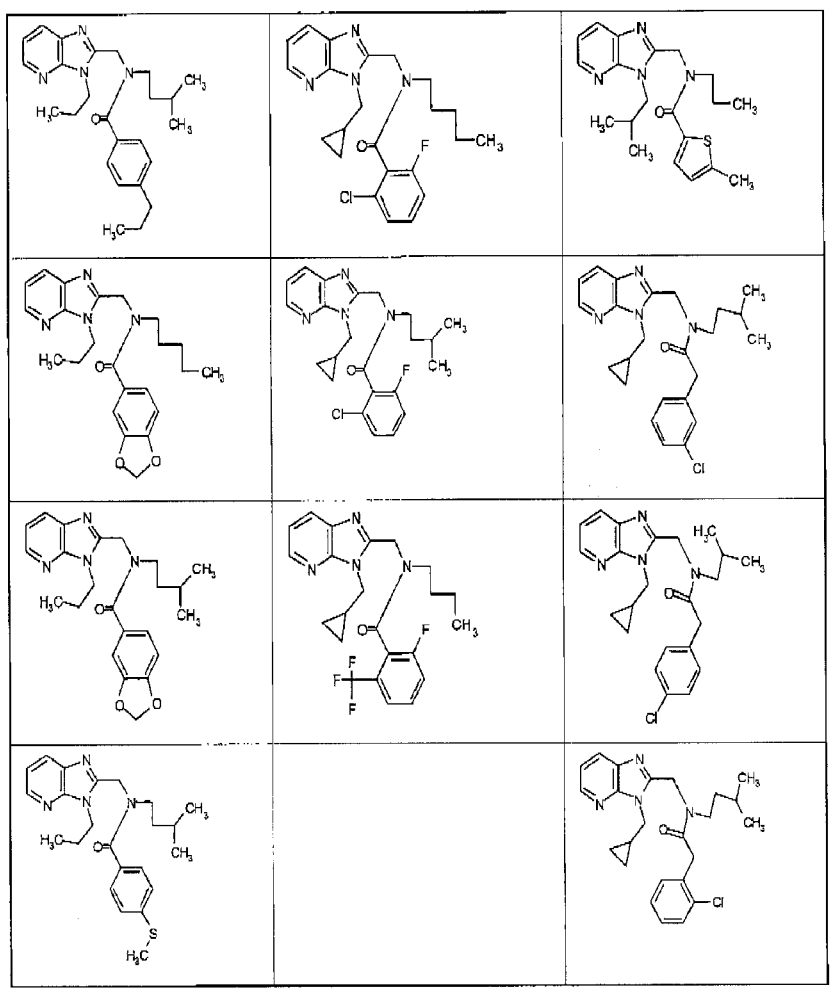

Appendix 1
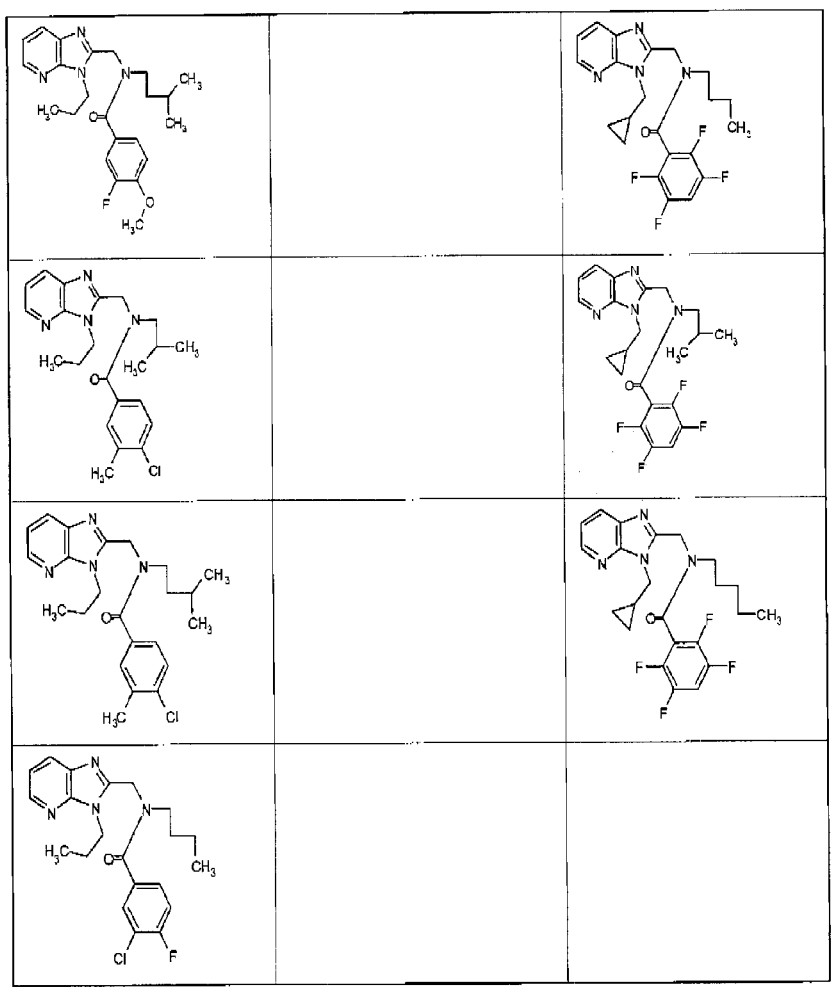

Appendix 1
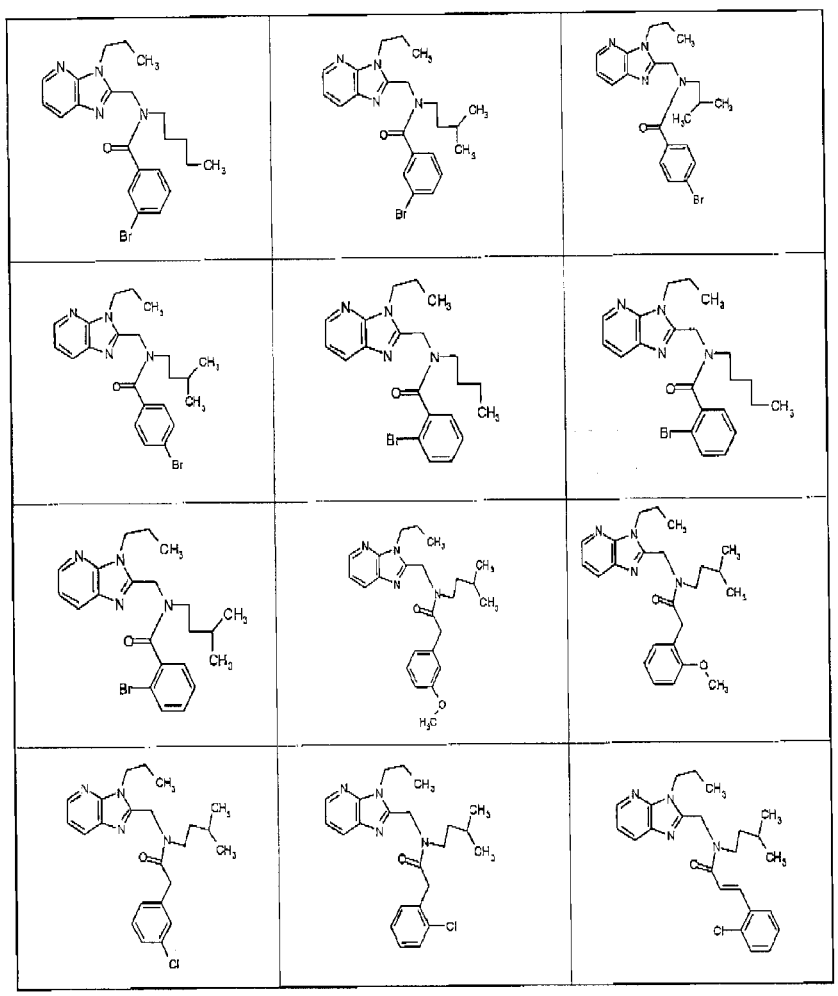

Appendix 1
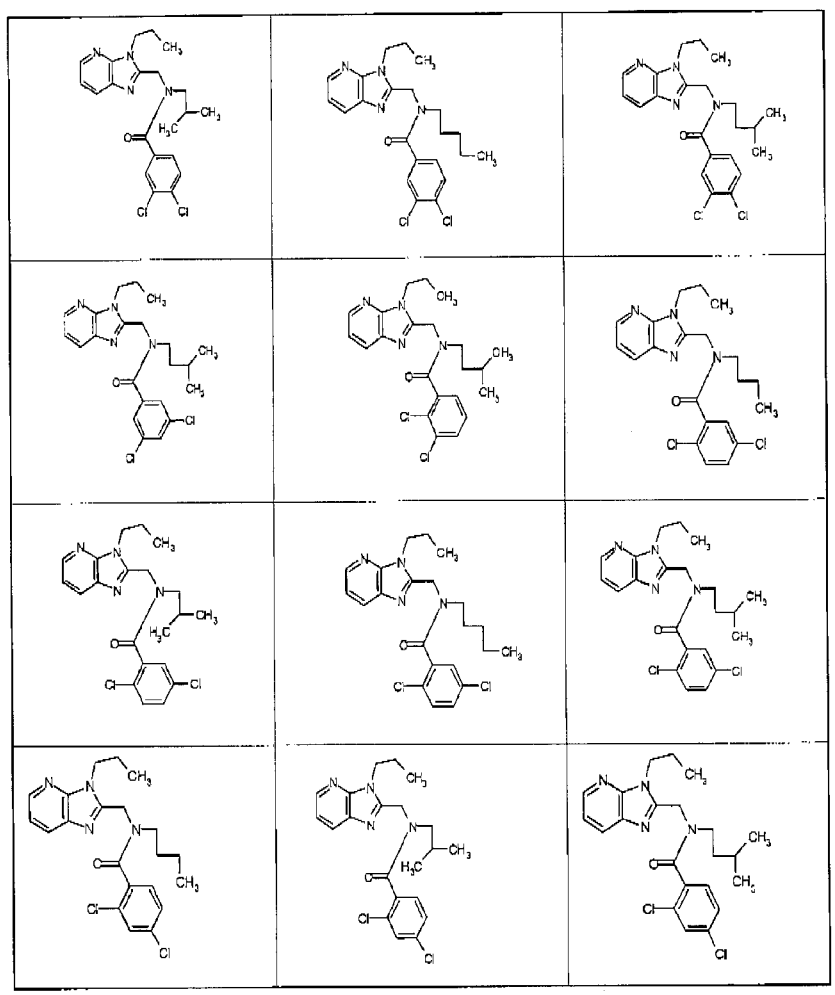

Appendix 1
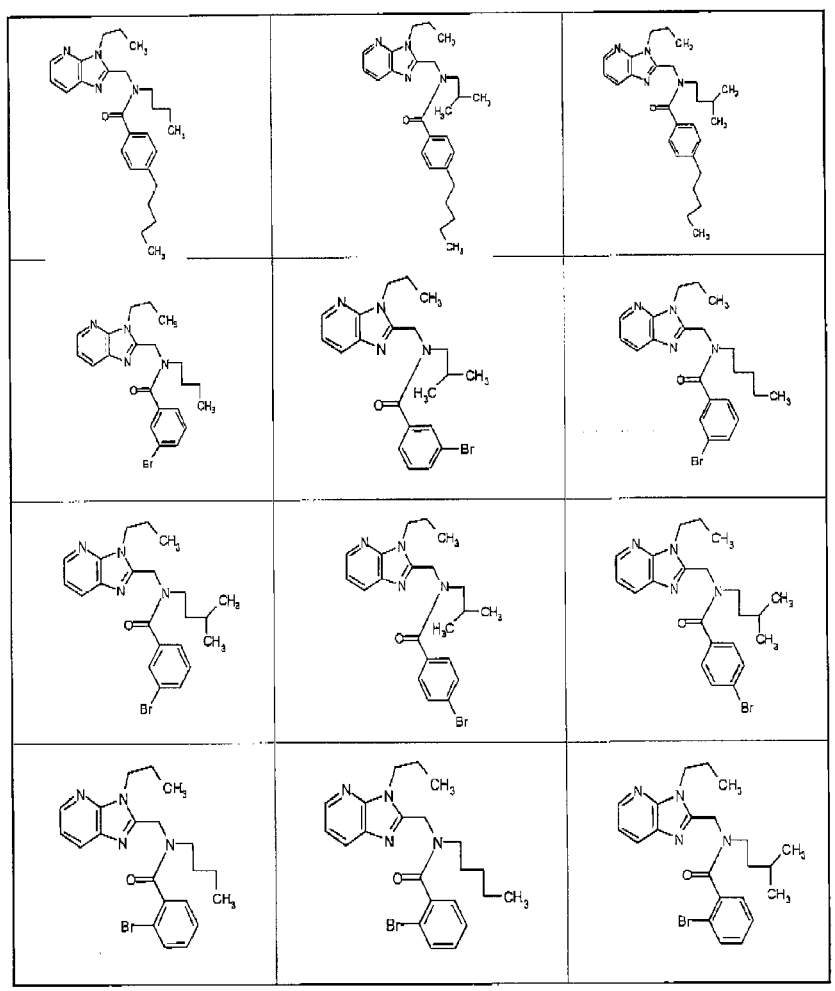

Appendix 1
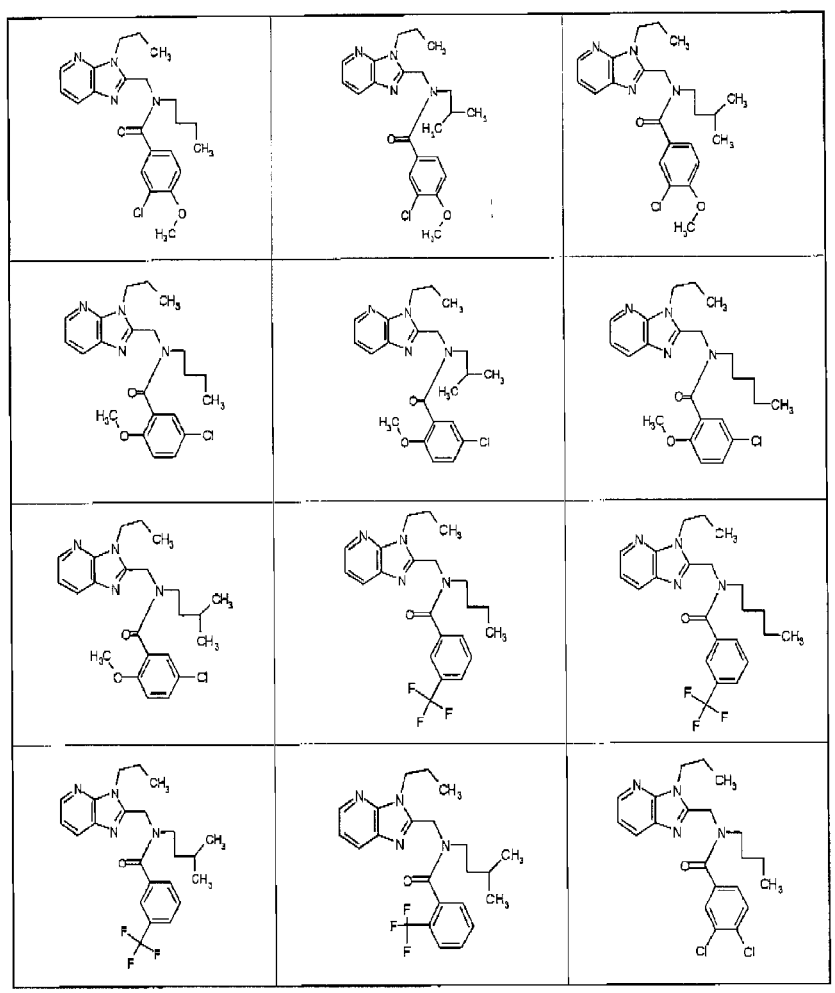

Appendix 1
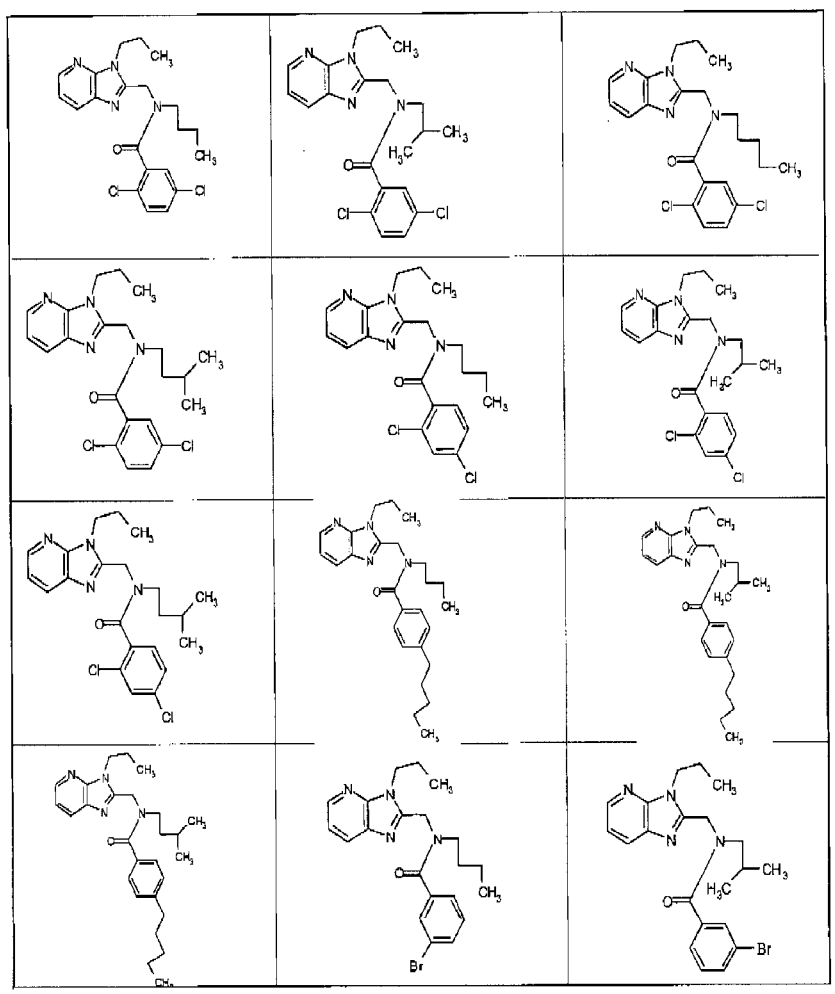

Appendix 1
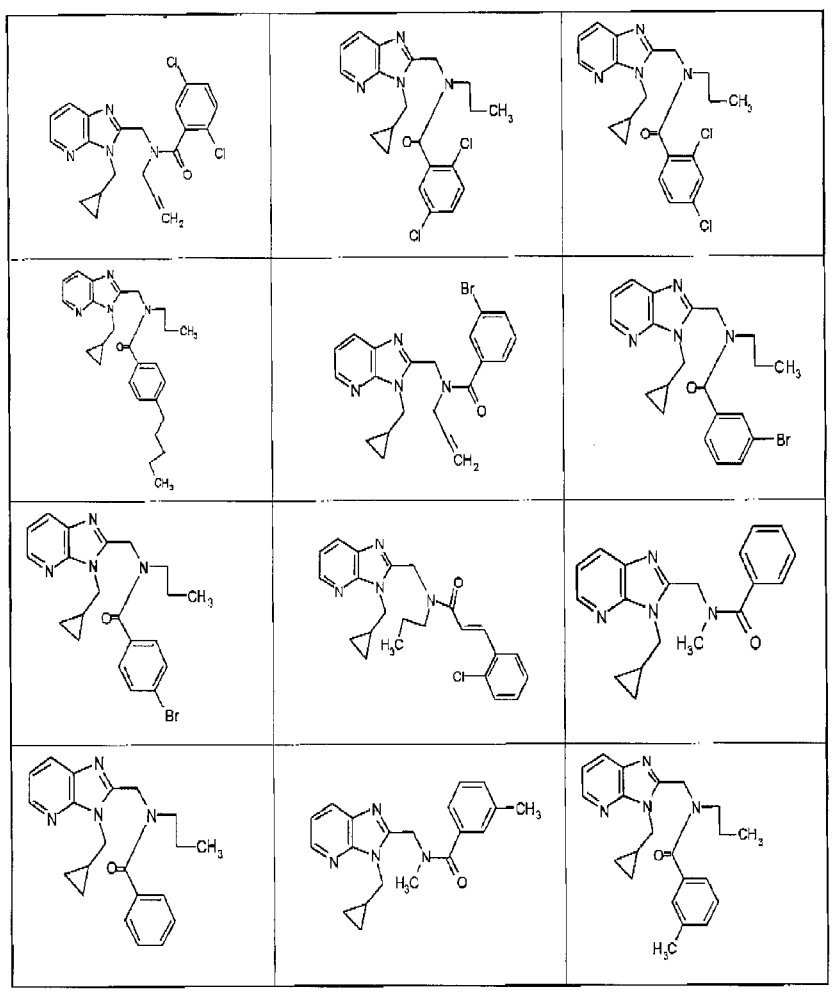

Appendix 1
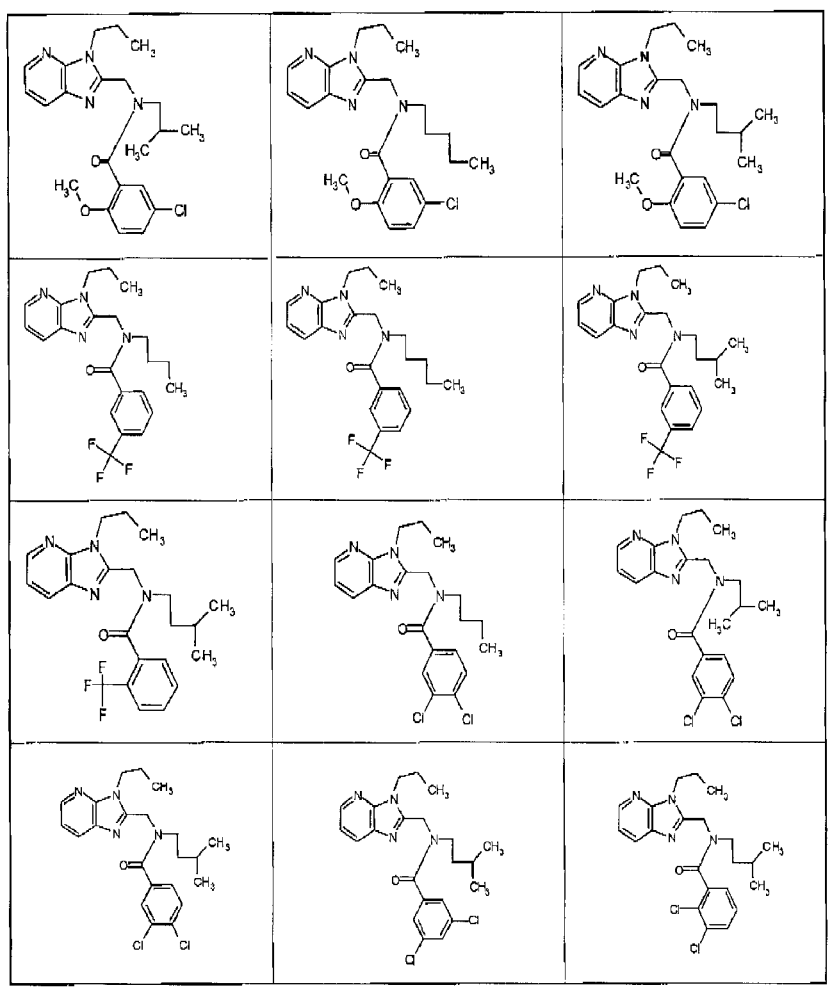

Appendix 1
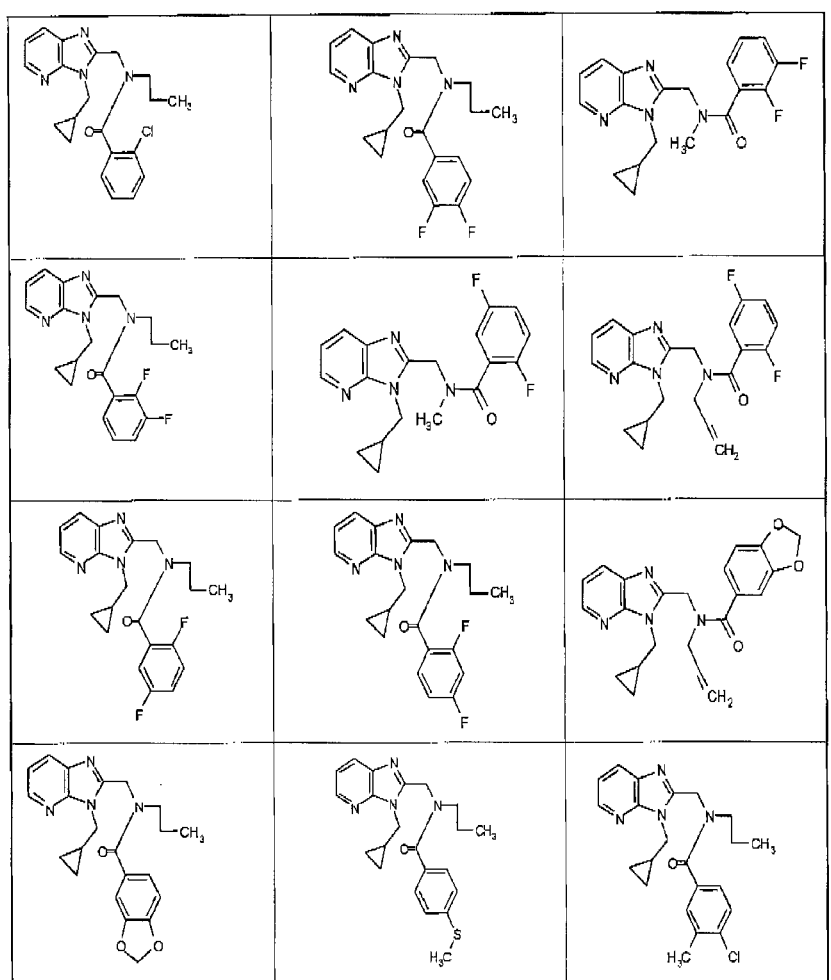

Appendix 1

Appendix 1
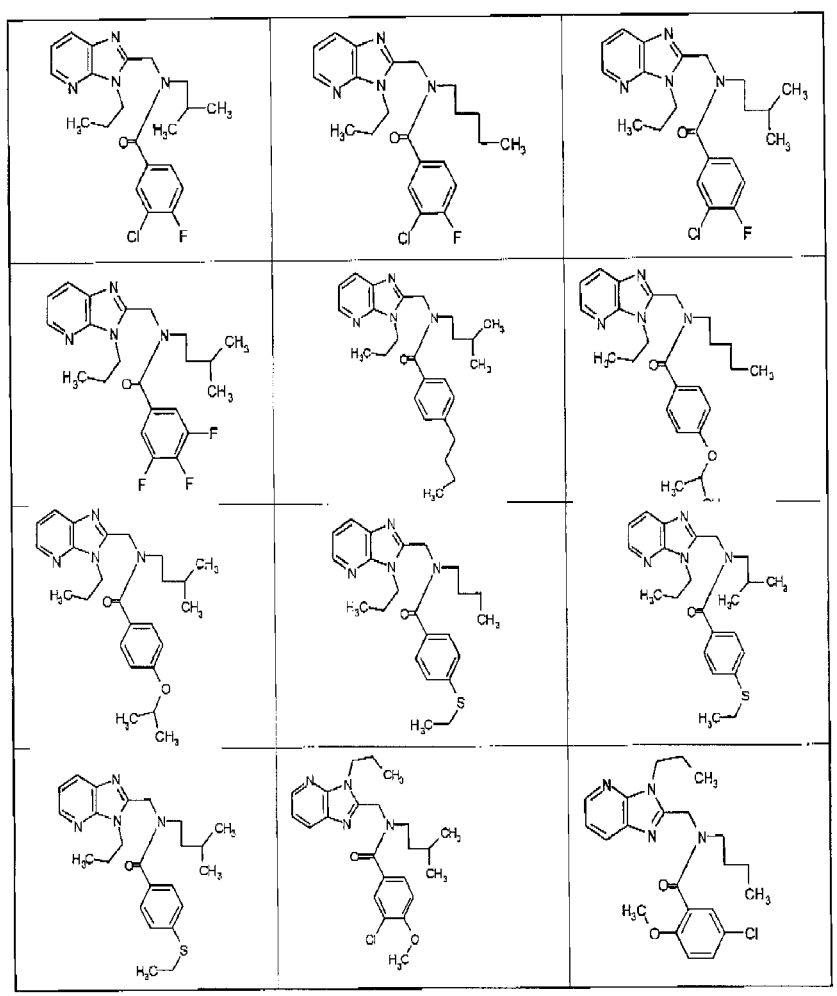

Appendix 1
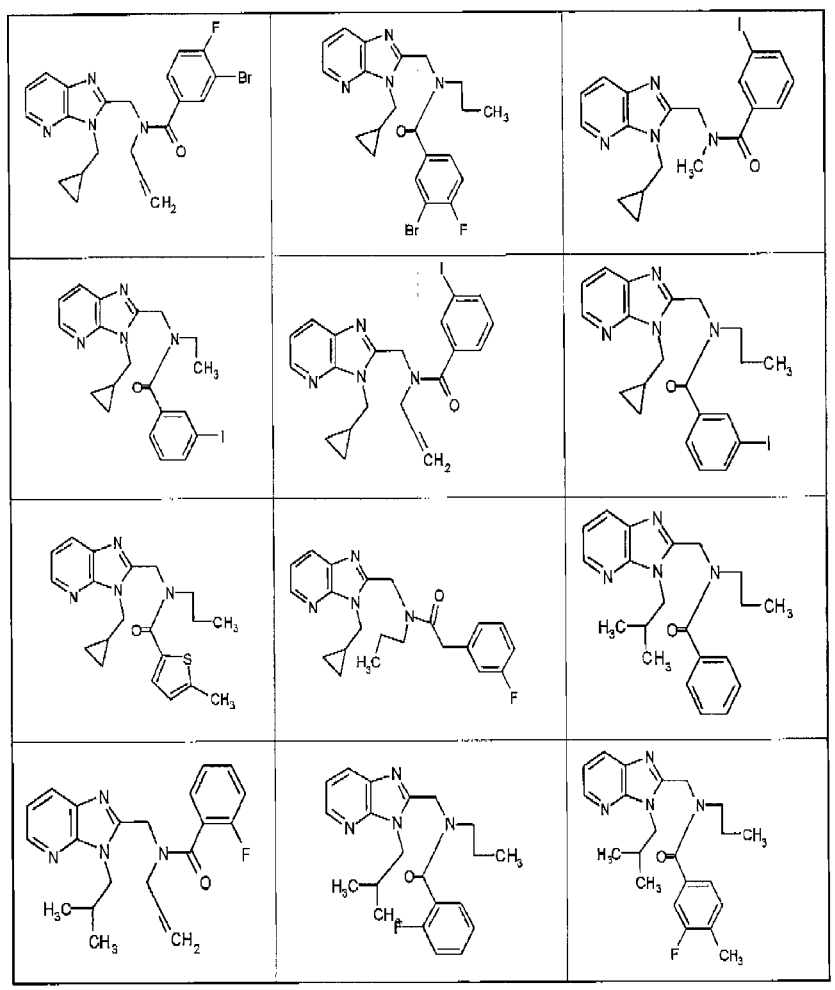

Appendix 1
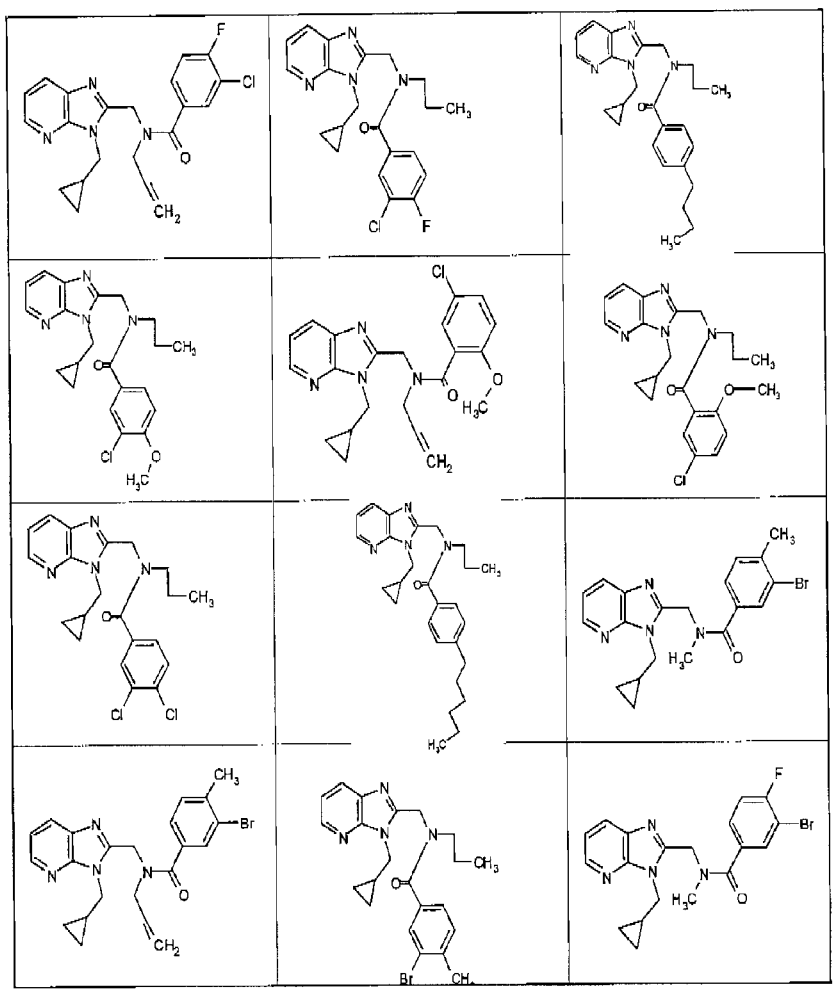

Appendix 2
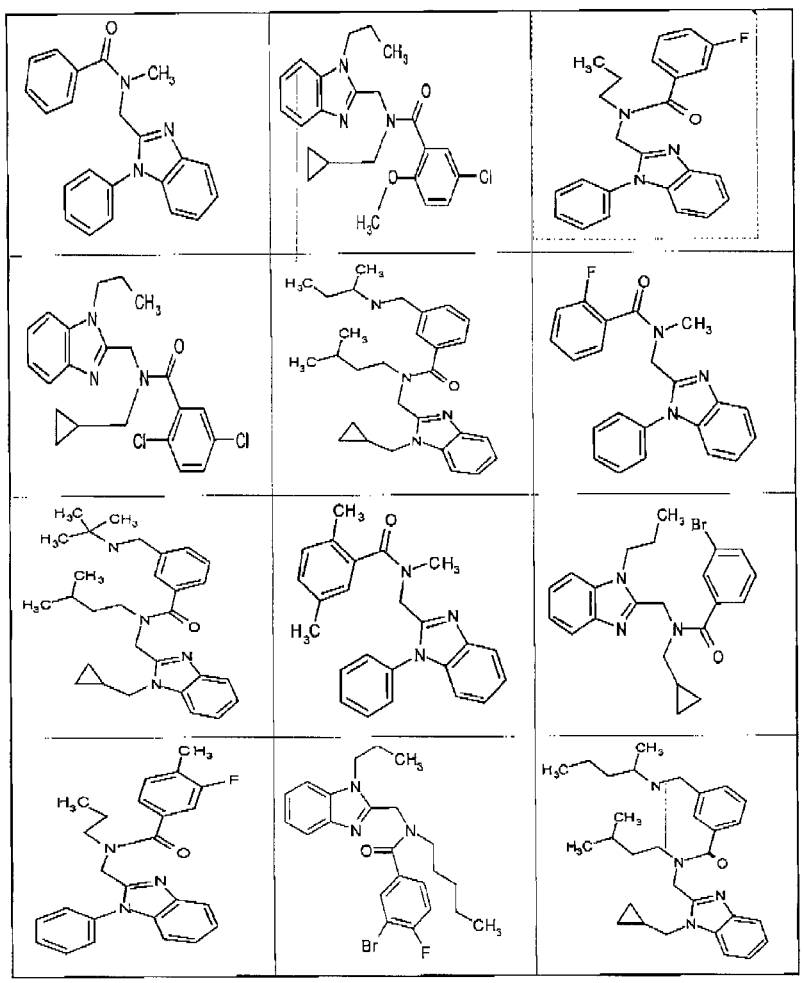

Appendix 2
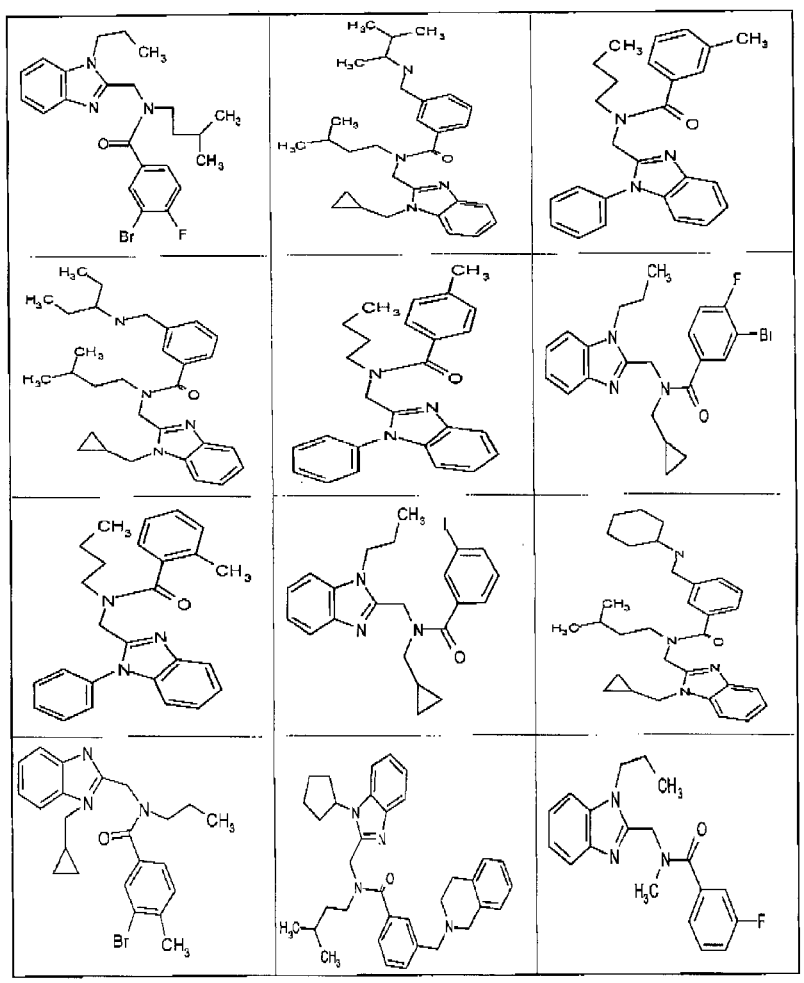

Appendix 2
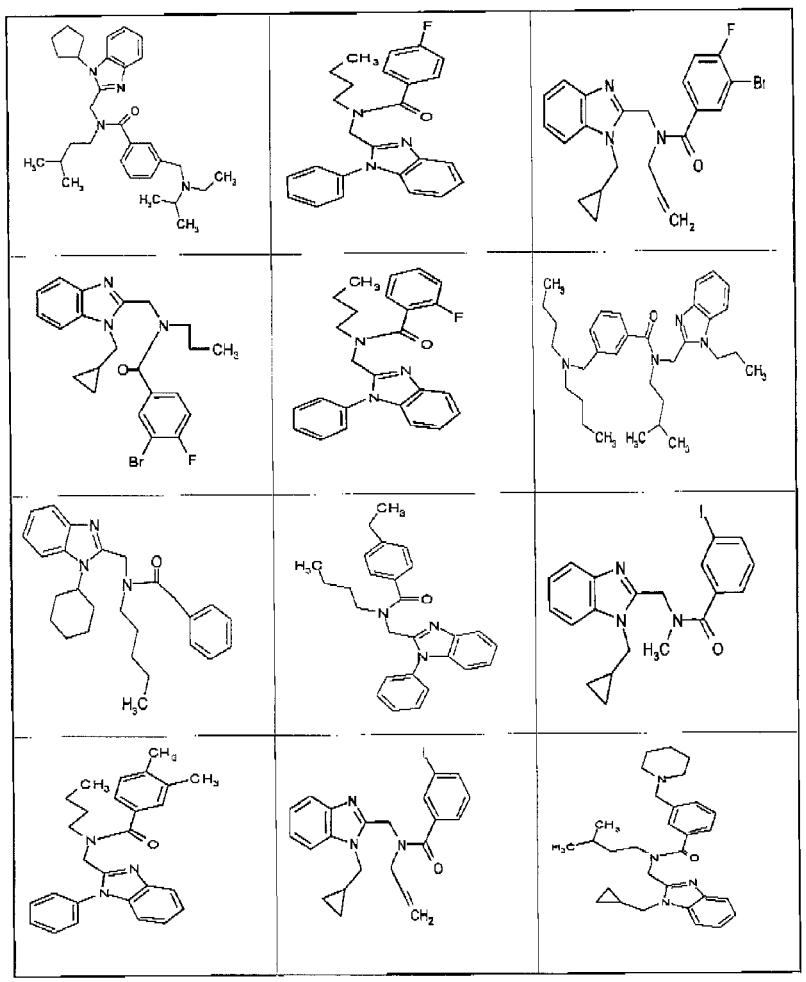

Appendix 2
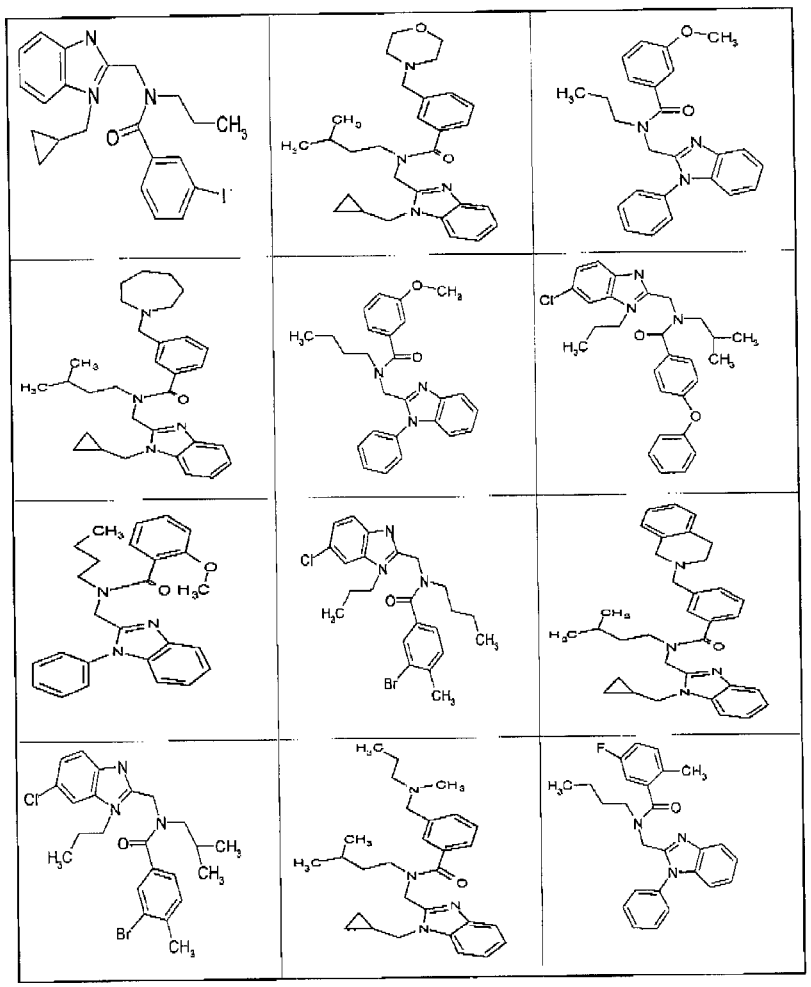

Appendix 2
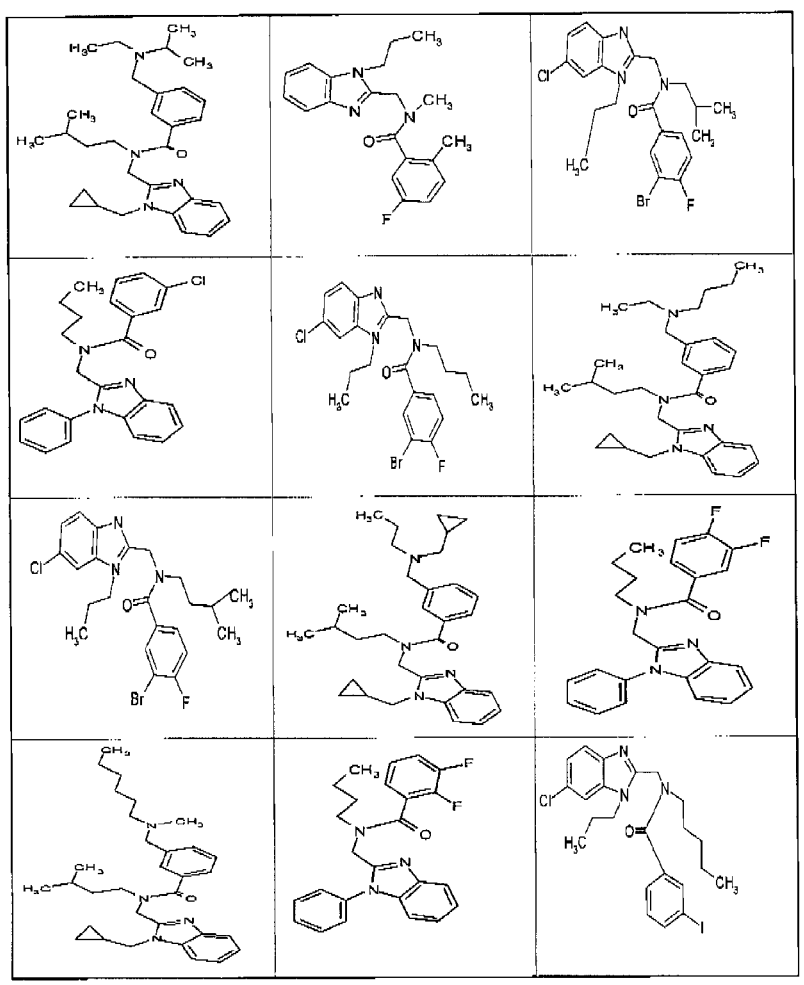

Appendix 2
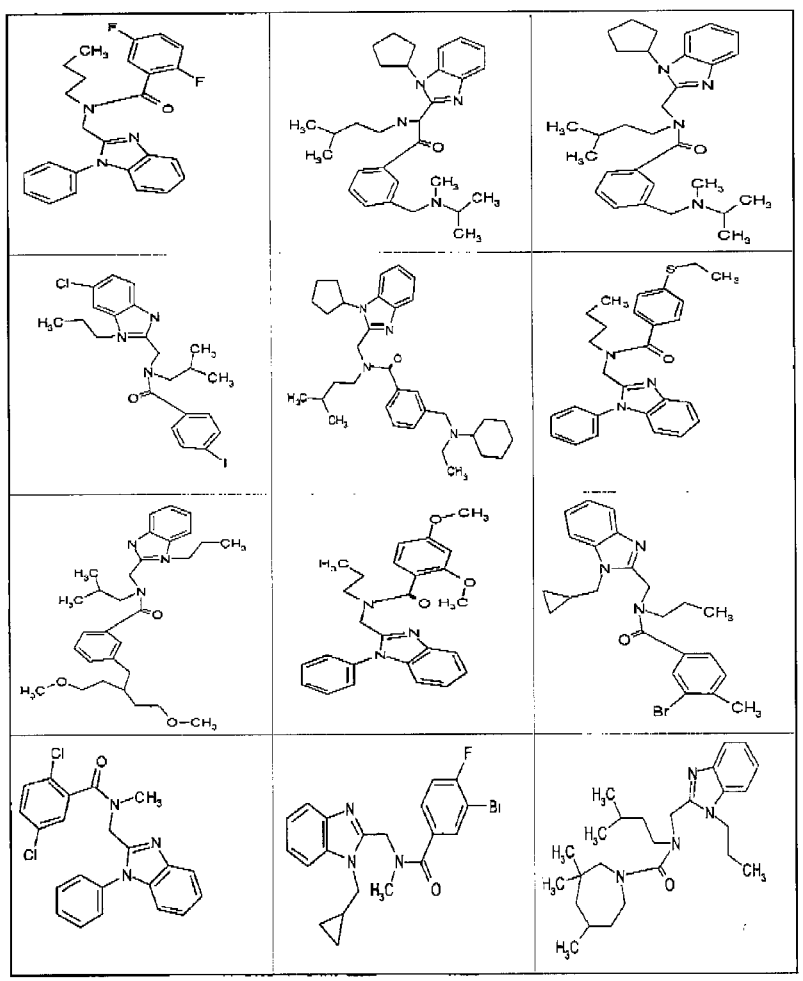

Appendix 2
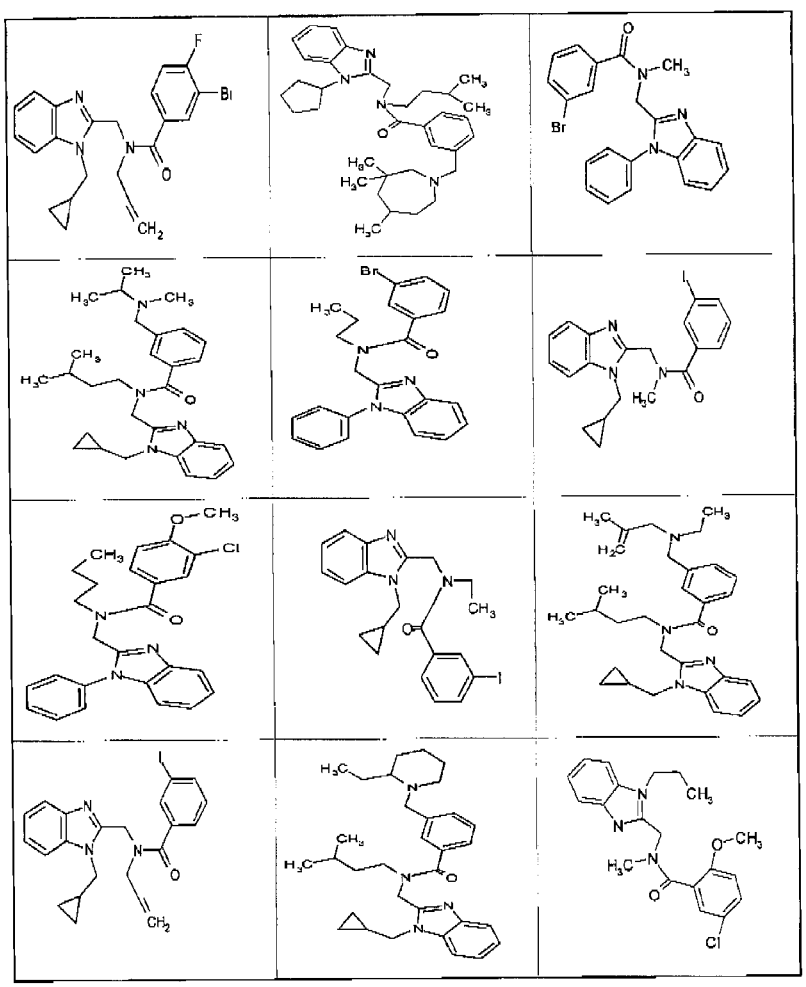

Appendix 2
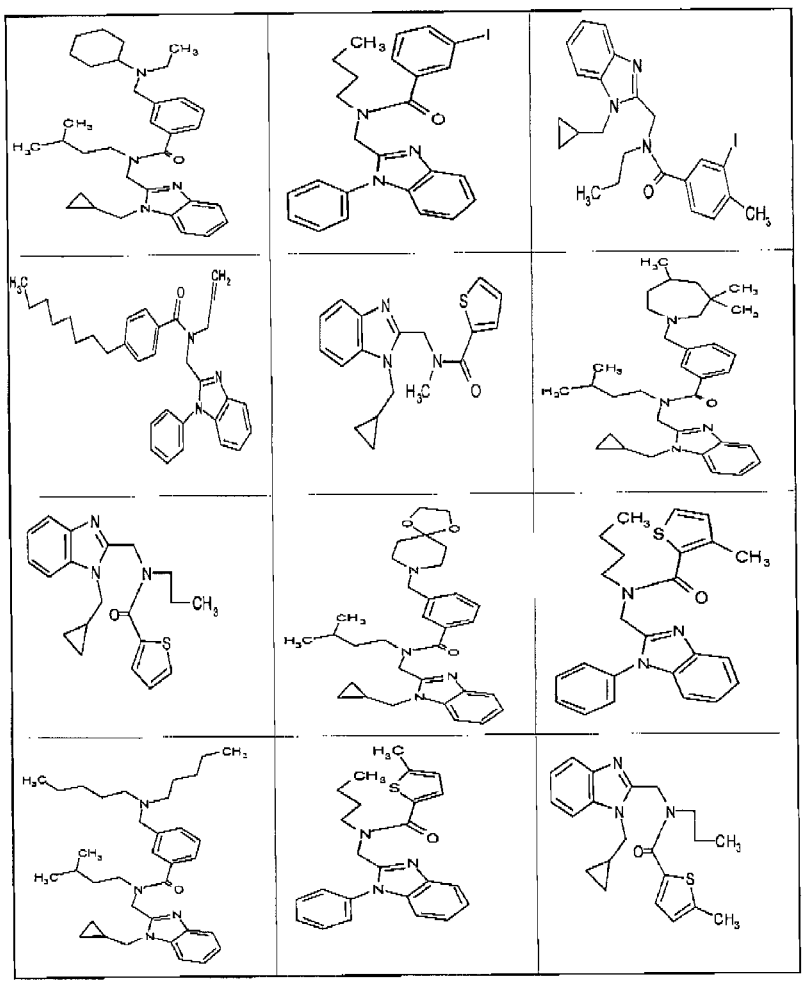

Appendix 2
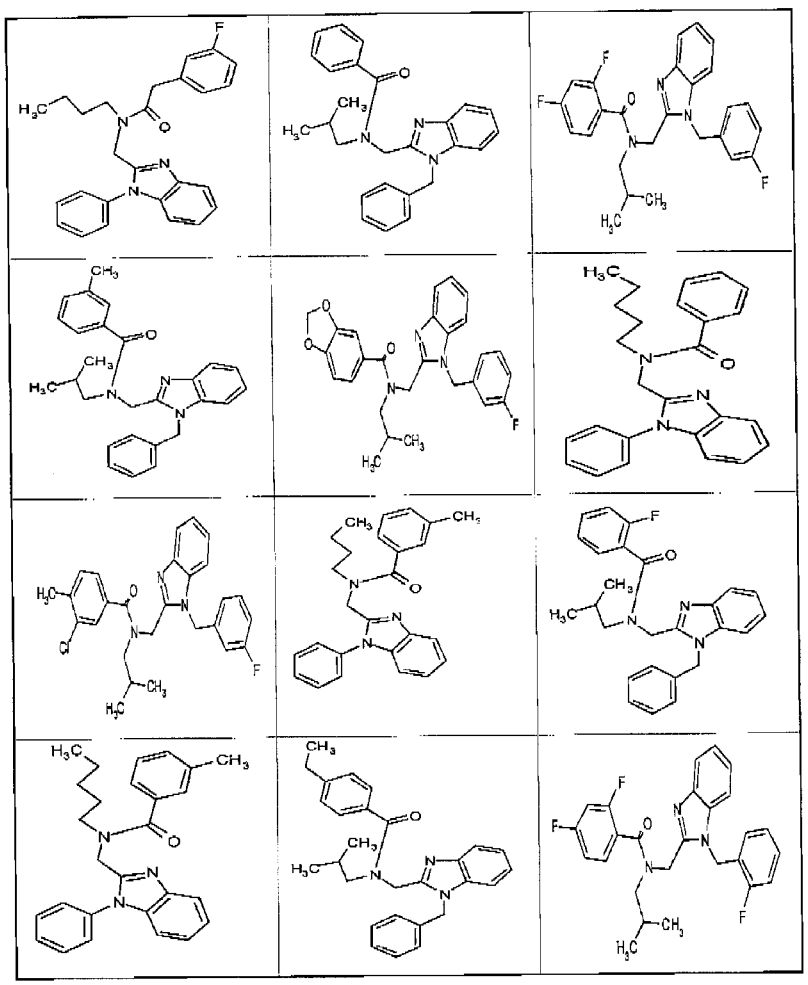

Appendix 2
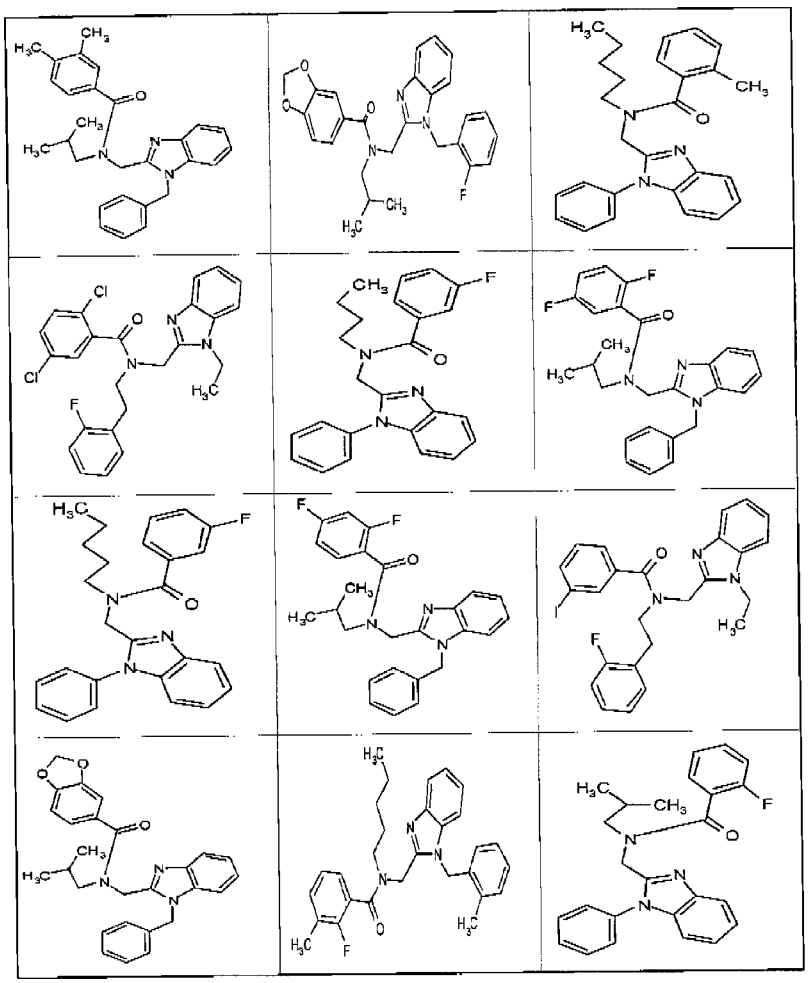

Appendix 2
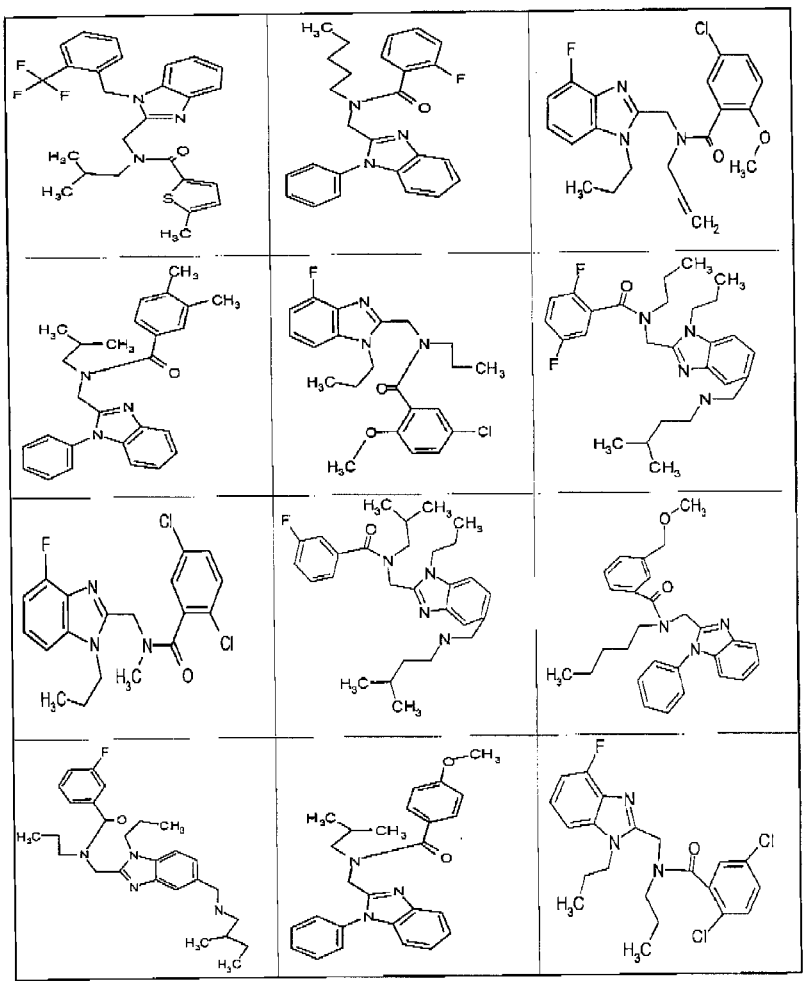

Appendix 2
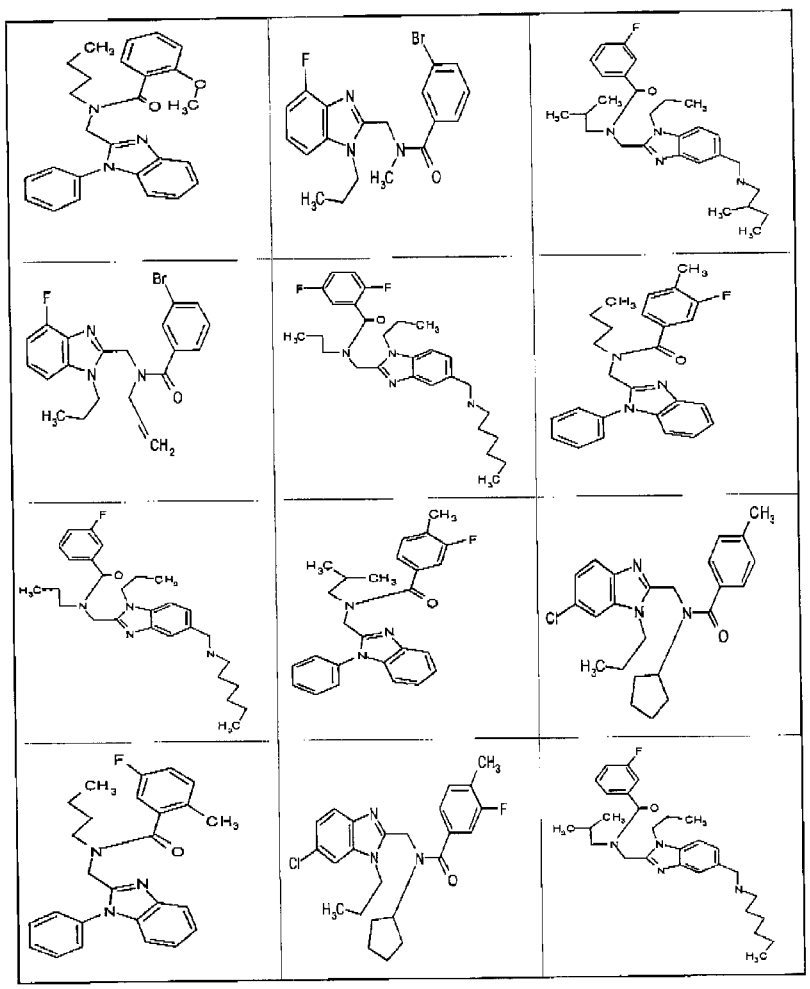

Appendix 2
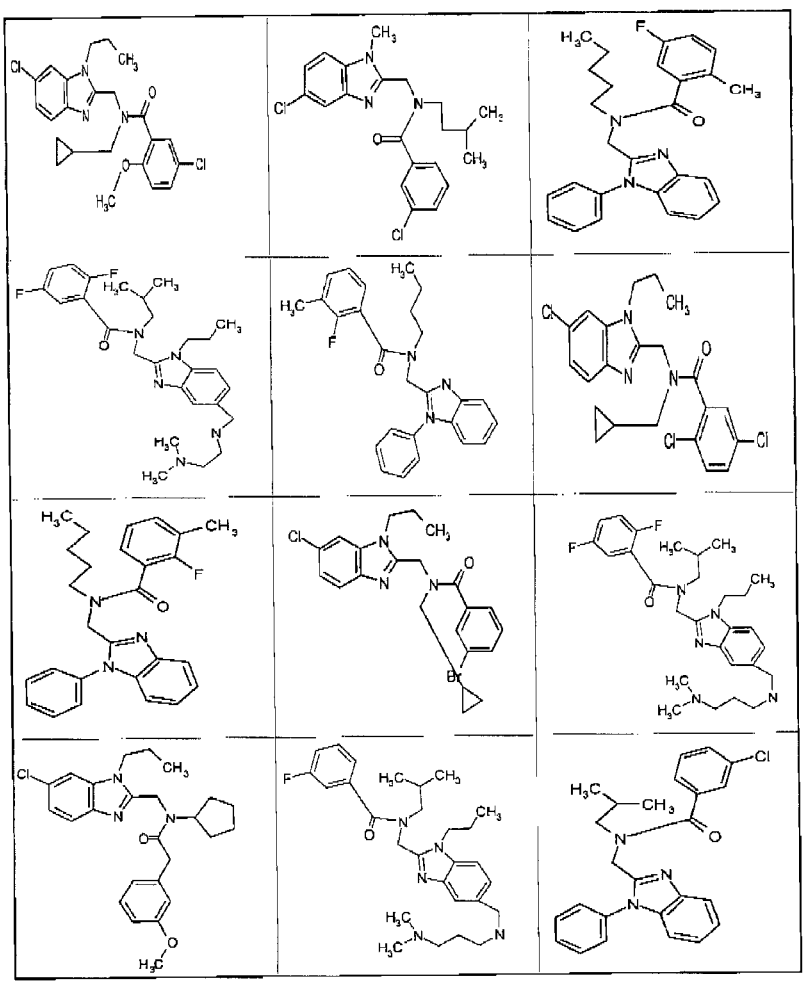

Appendix 2
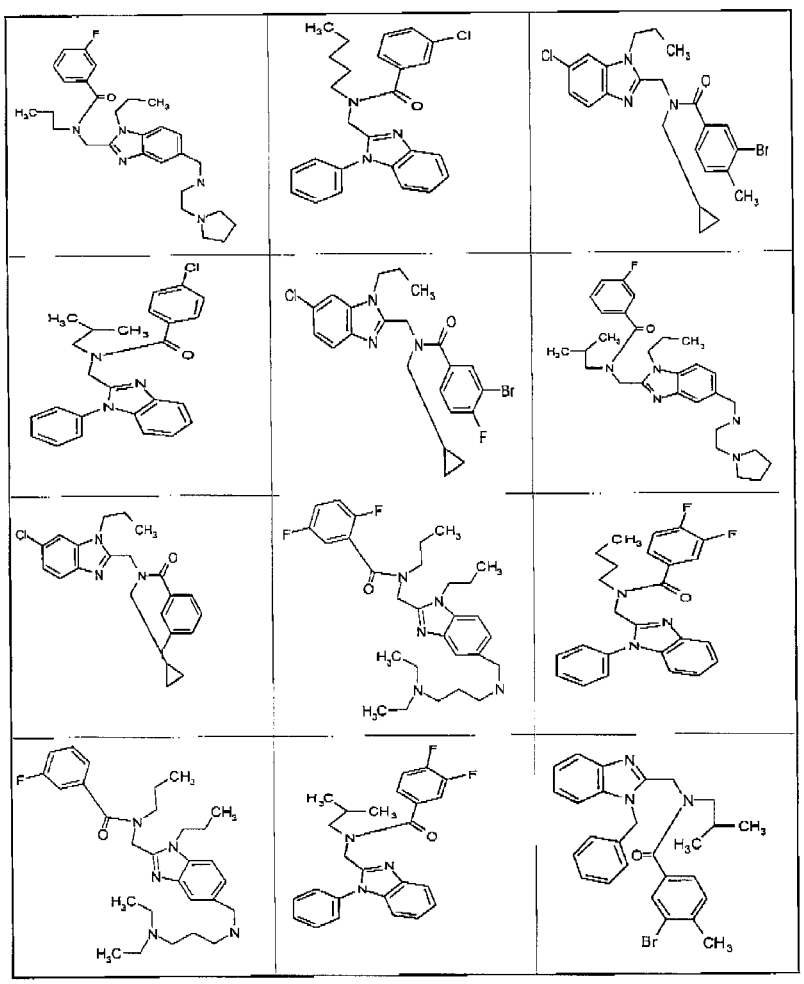

Appendix 2
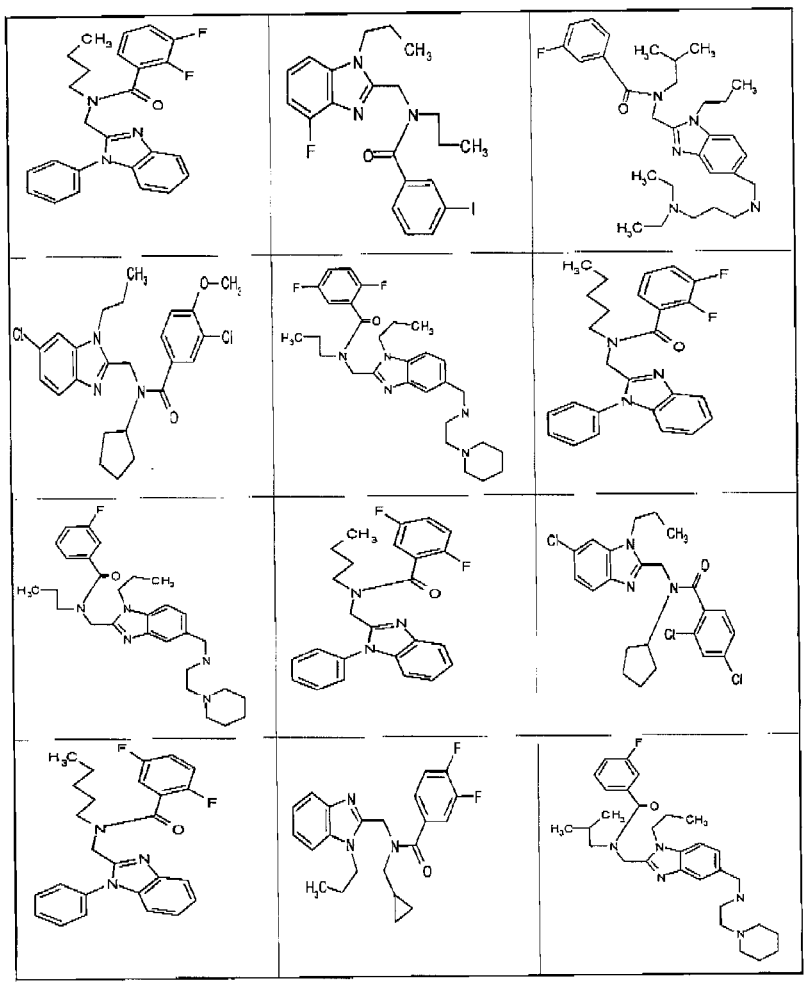

Appendix 2
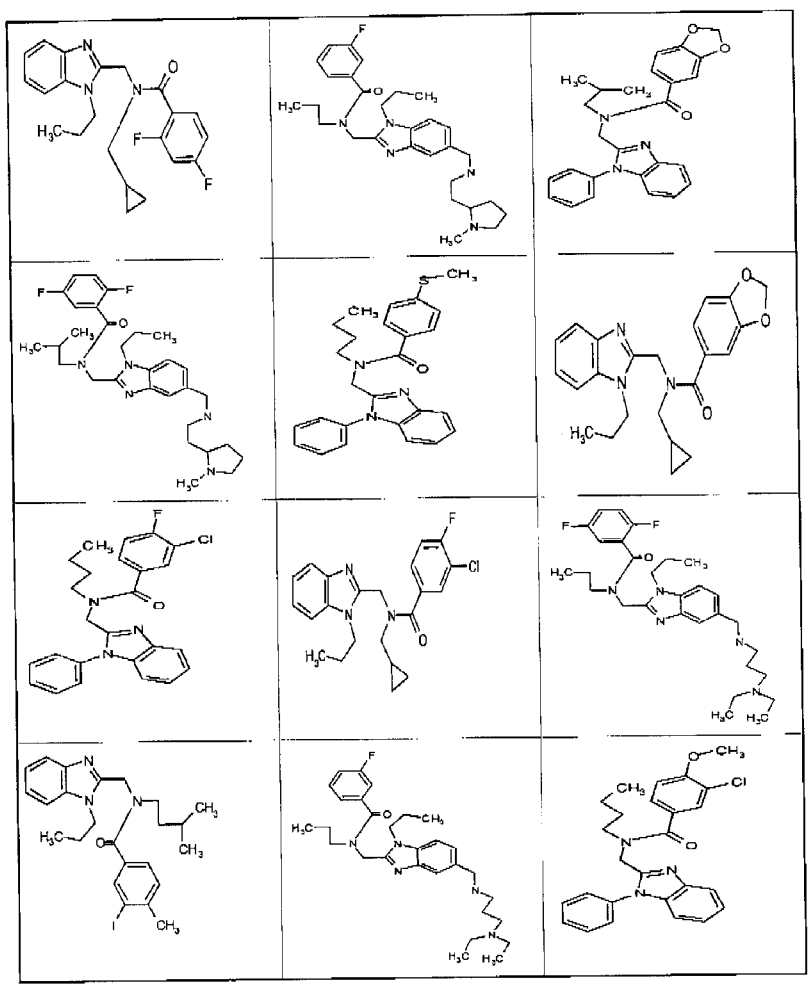

Appendix 2
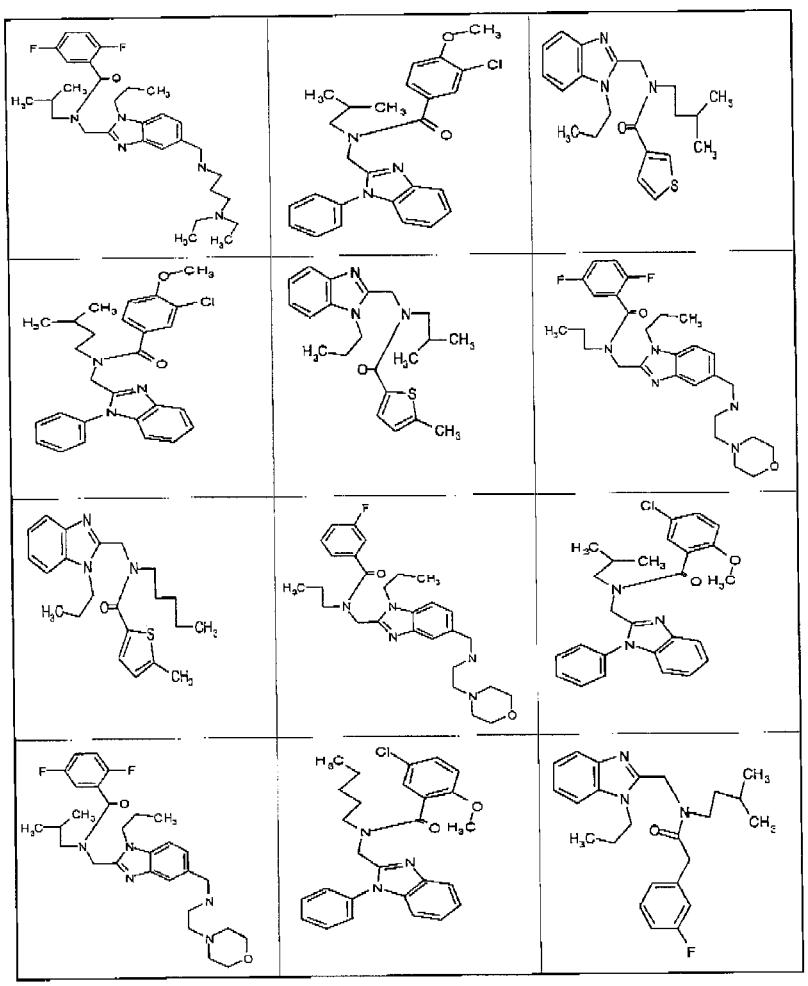

Appendix 2
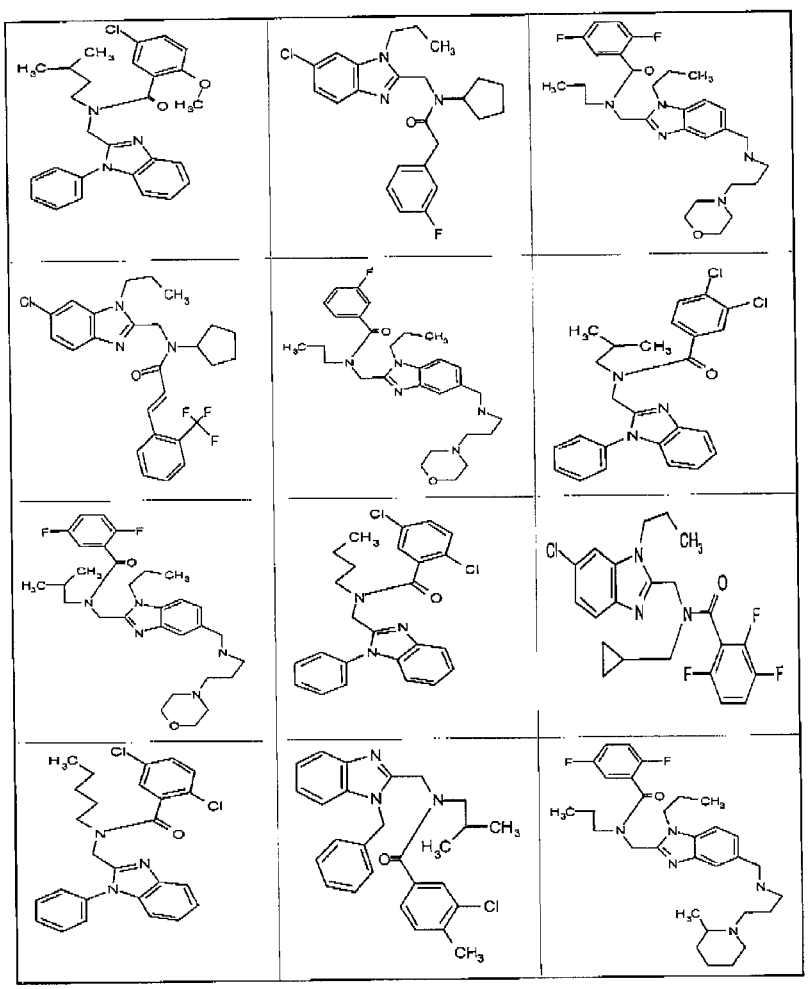

Appendix 2
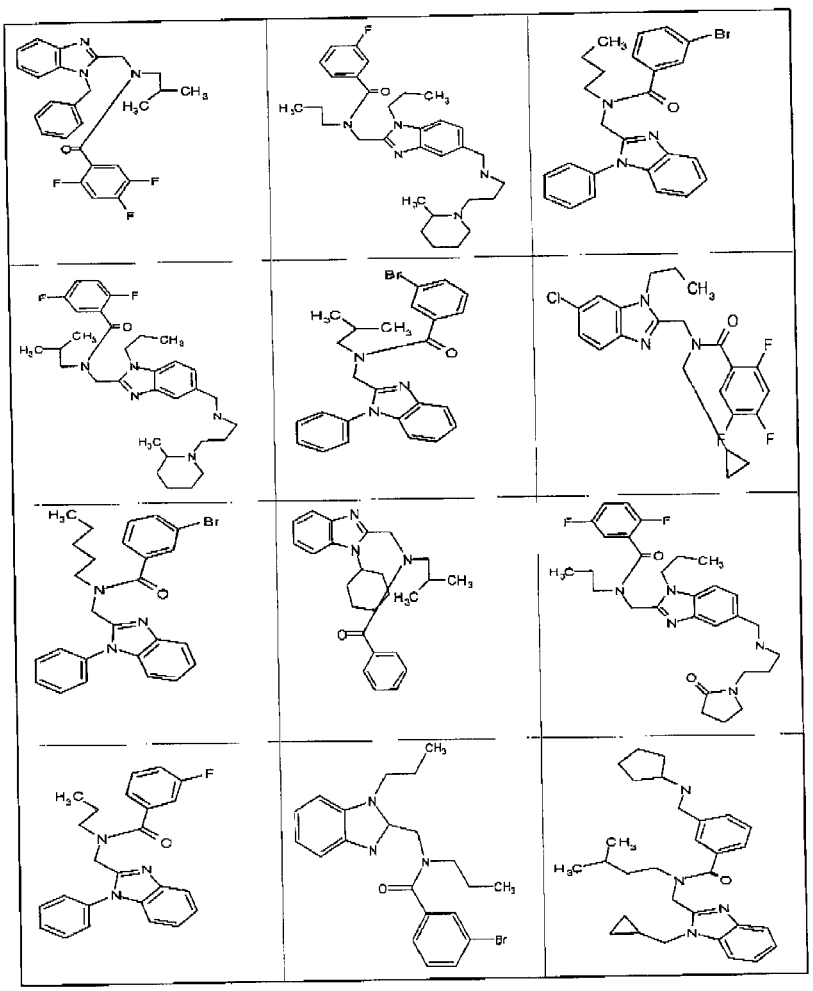

Appendix 2
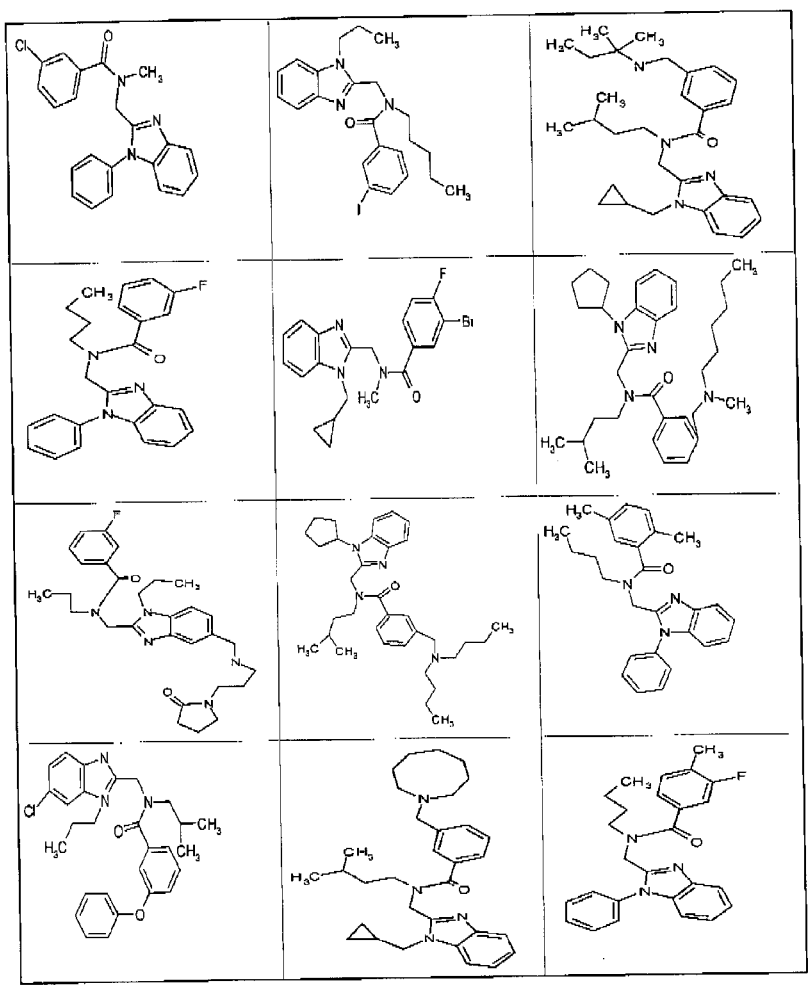

Appendix 2

Appendix 2

Appendix 2
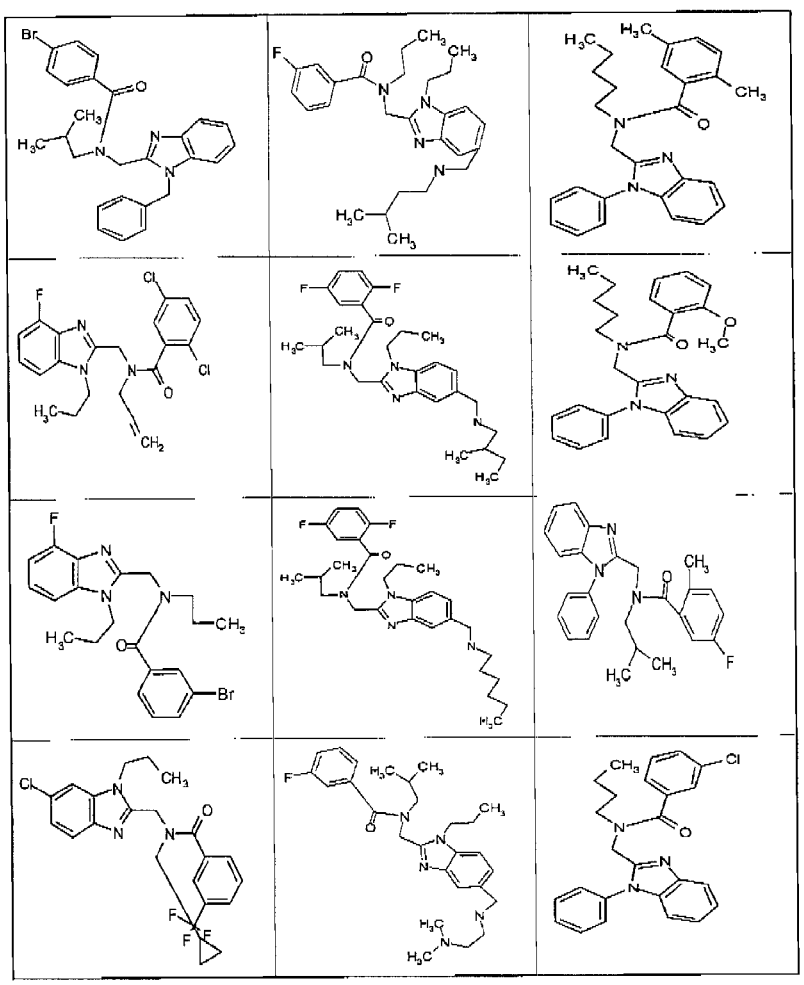

Appendix 2
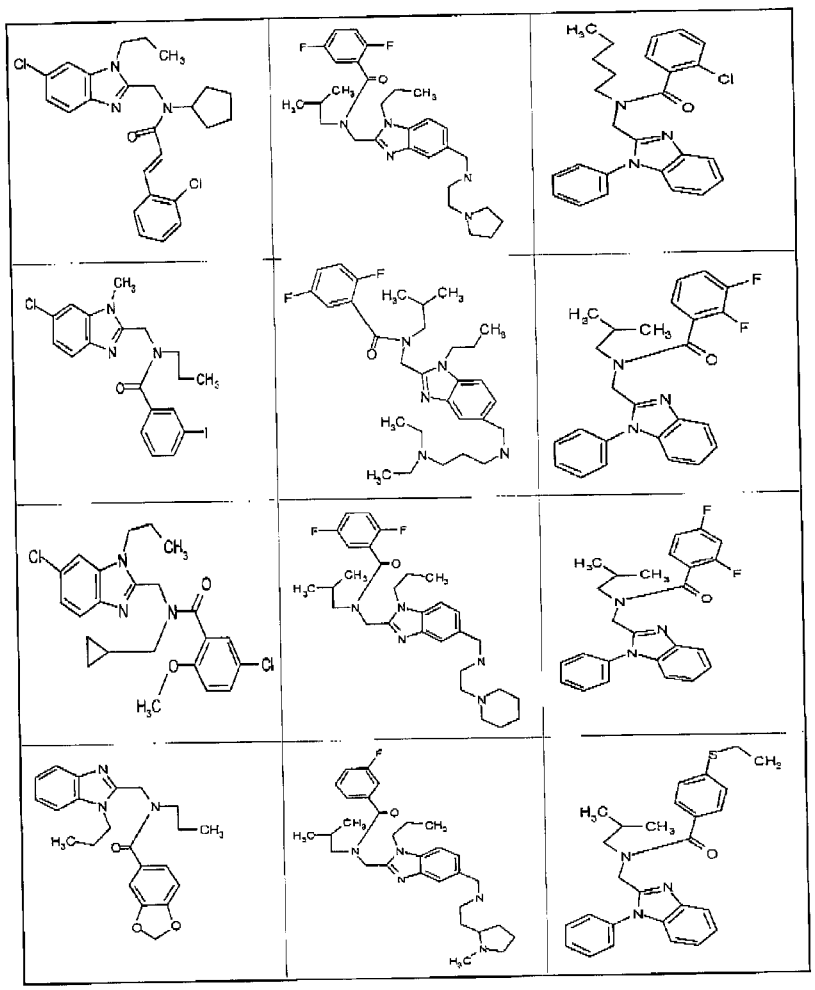

Appendix 2
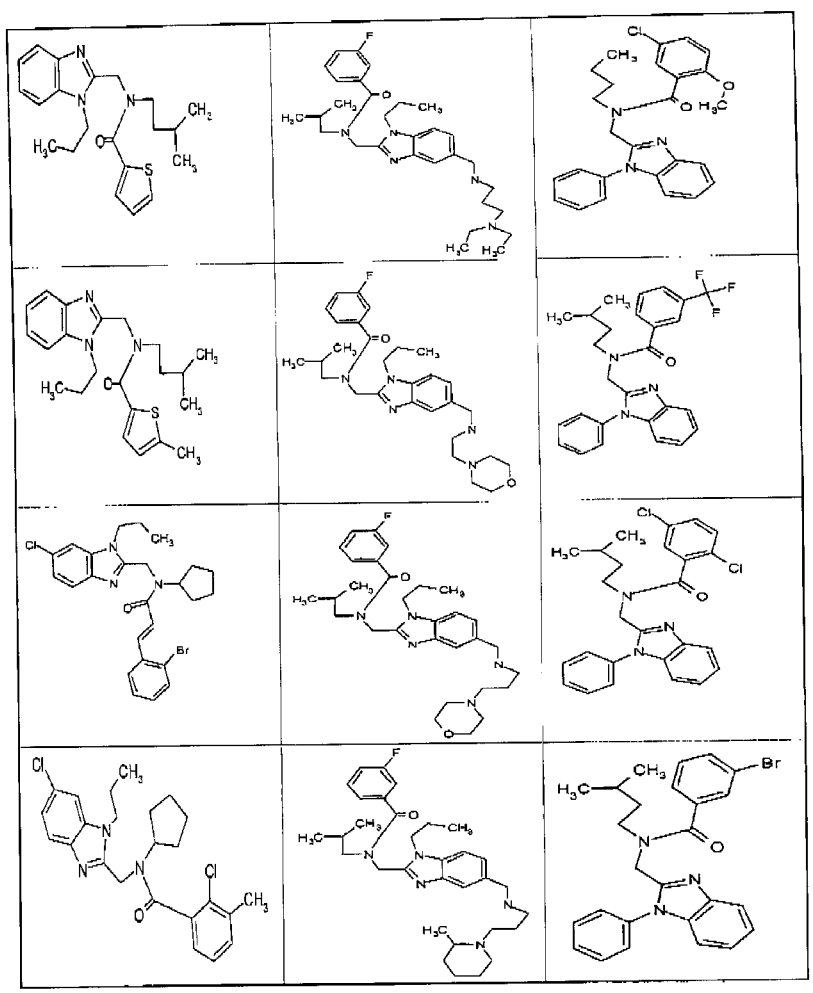

Appendix 2
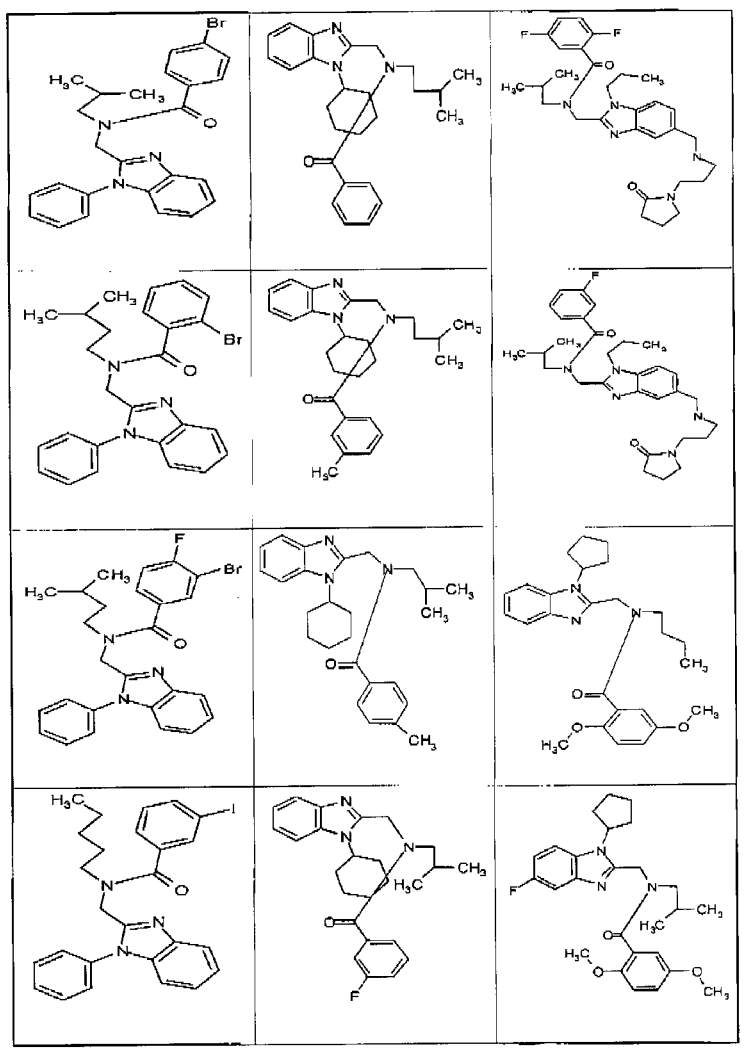

Appendix 2
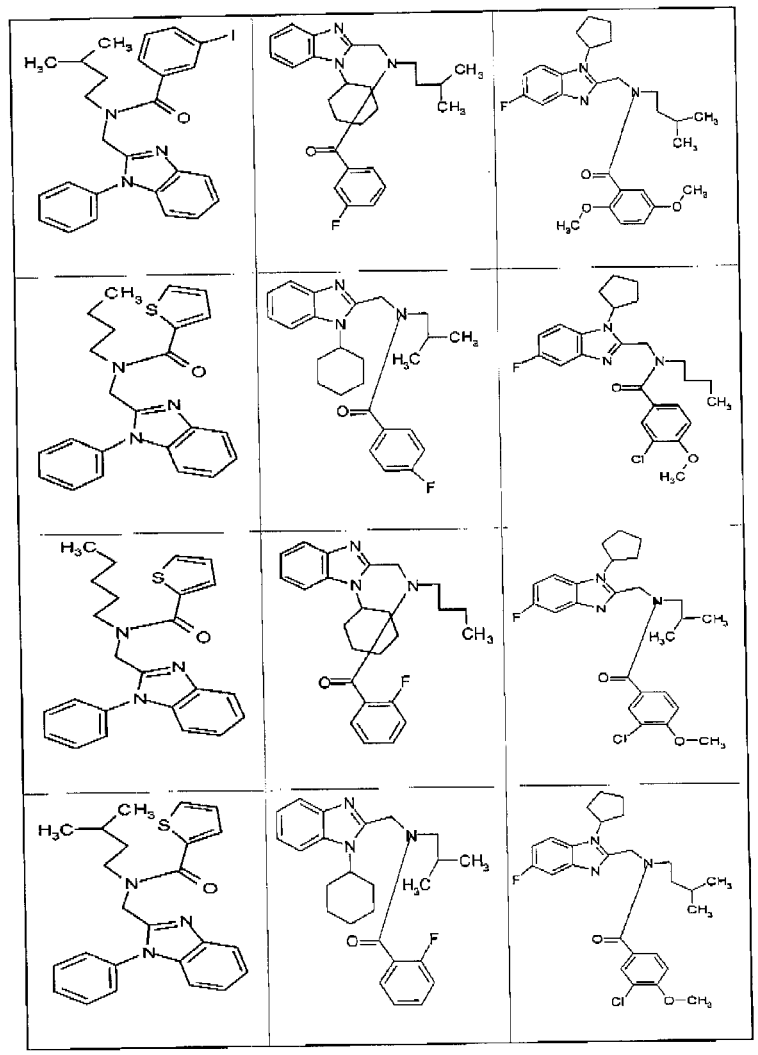

Appendix 2
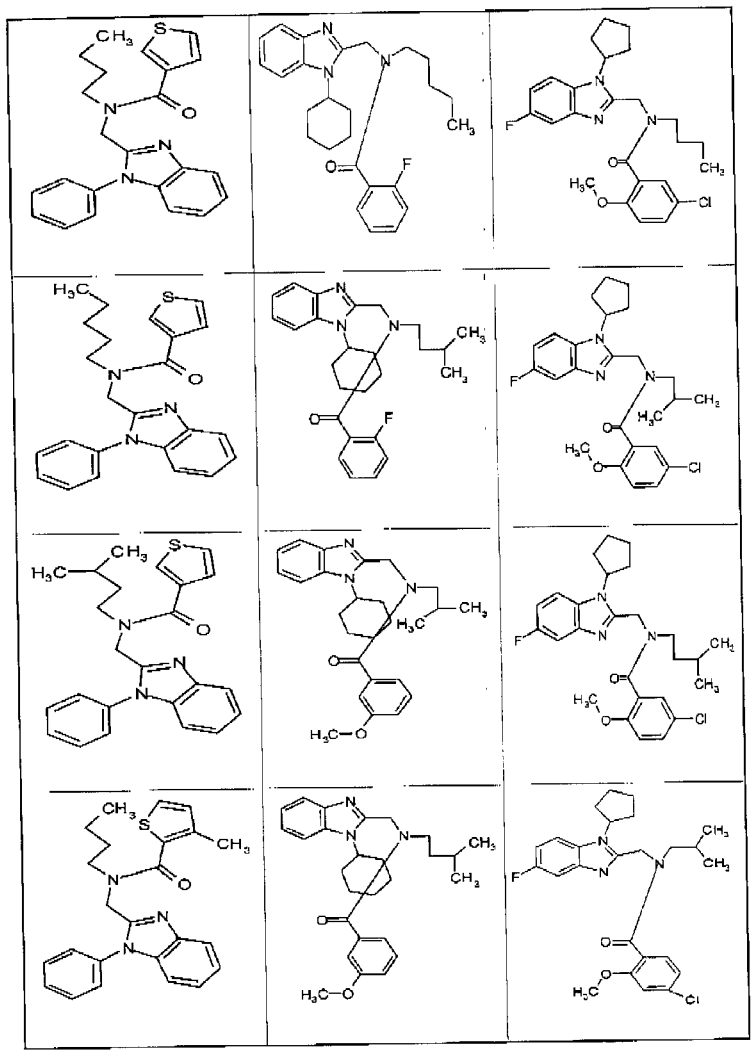

Appendix 2
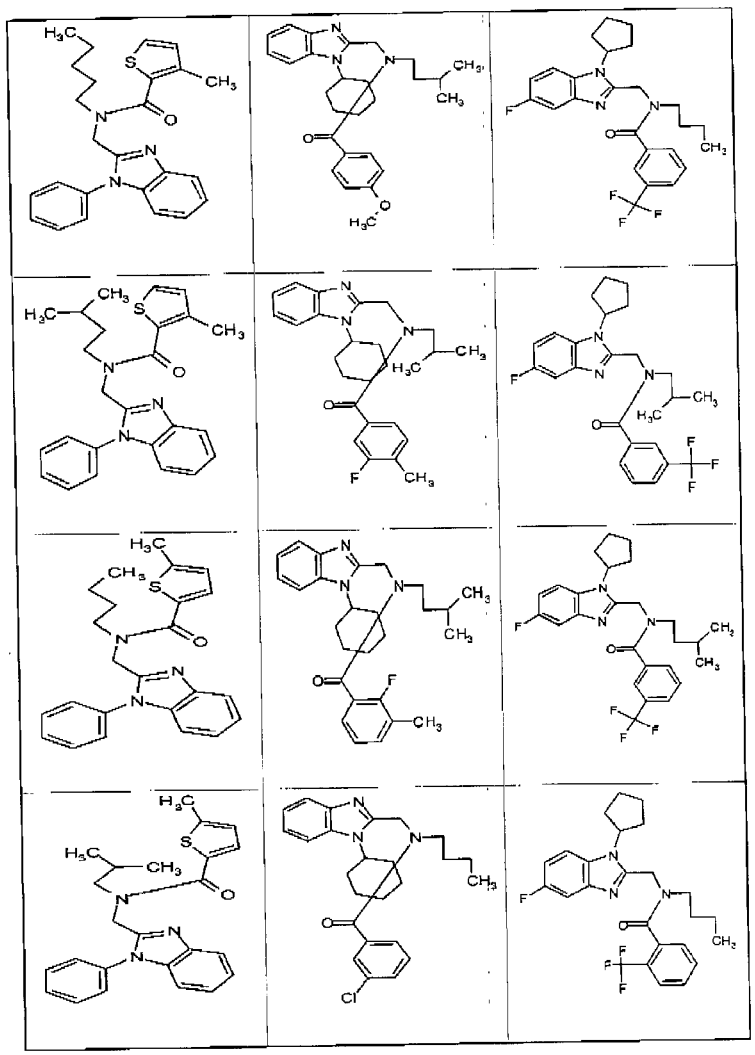

Appendix 2
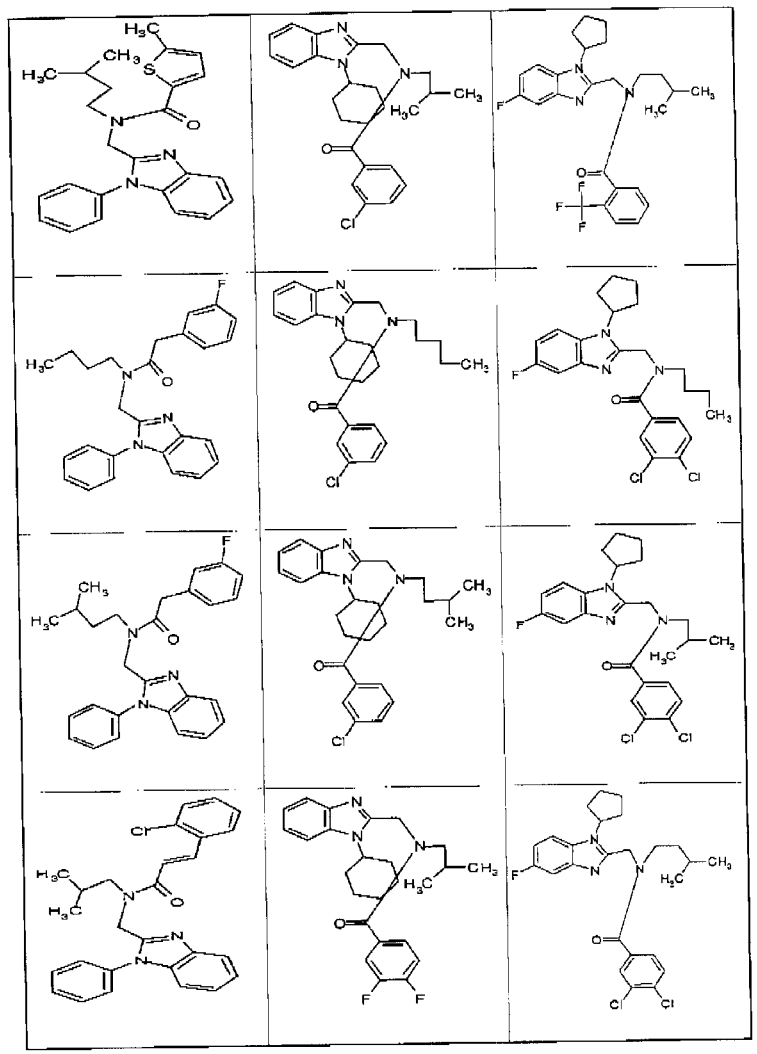

Appendix 2
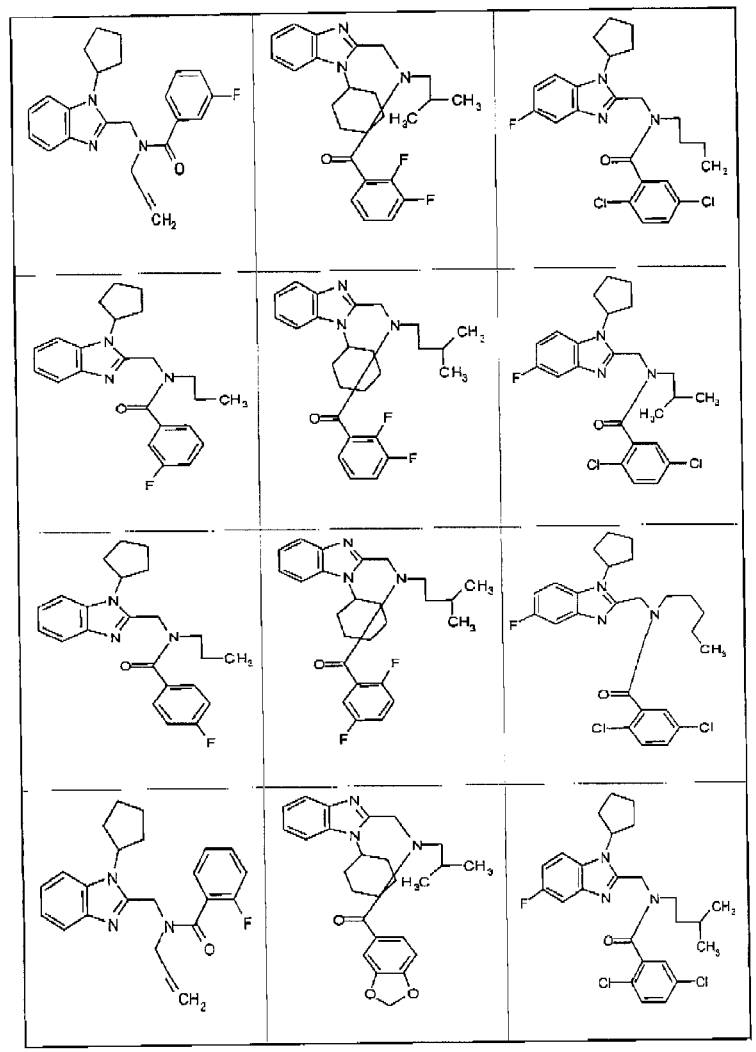

Appendix 2
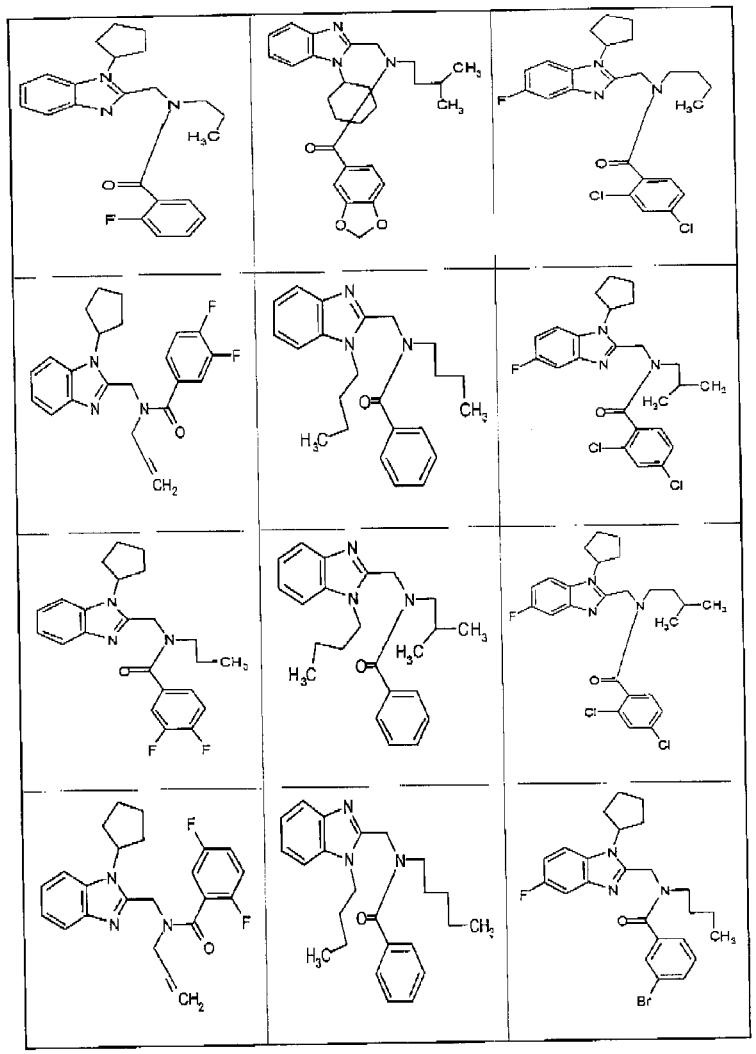

Appendix 2
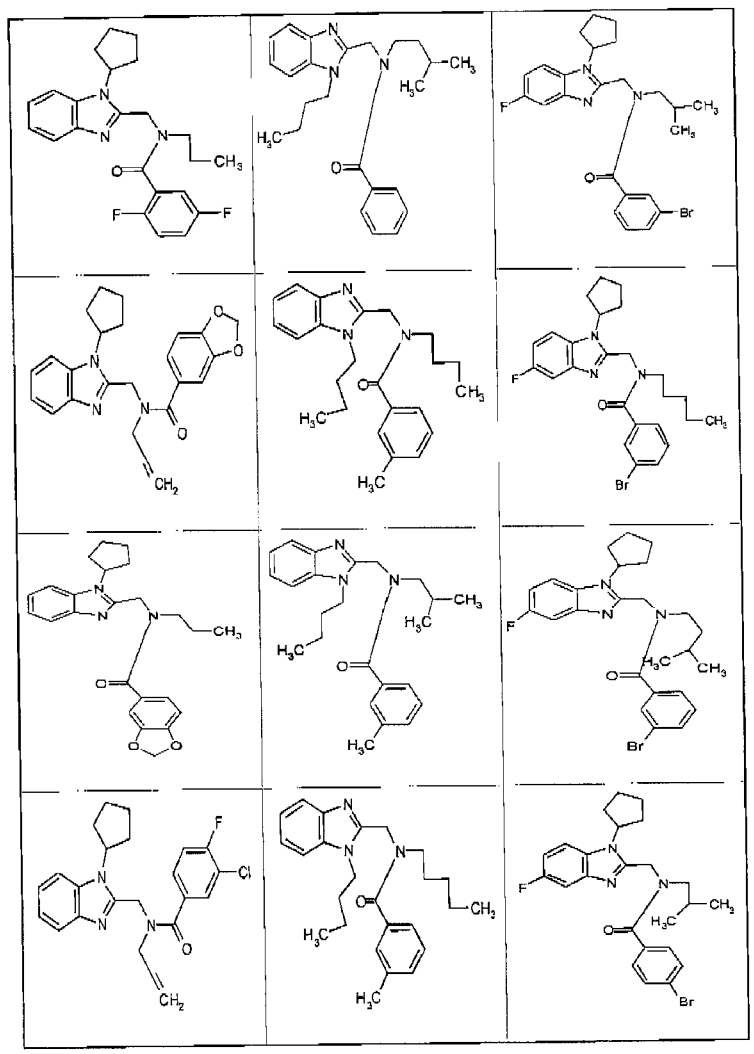

Appendix 2
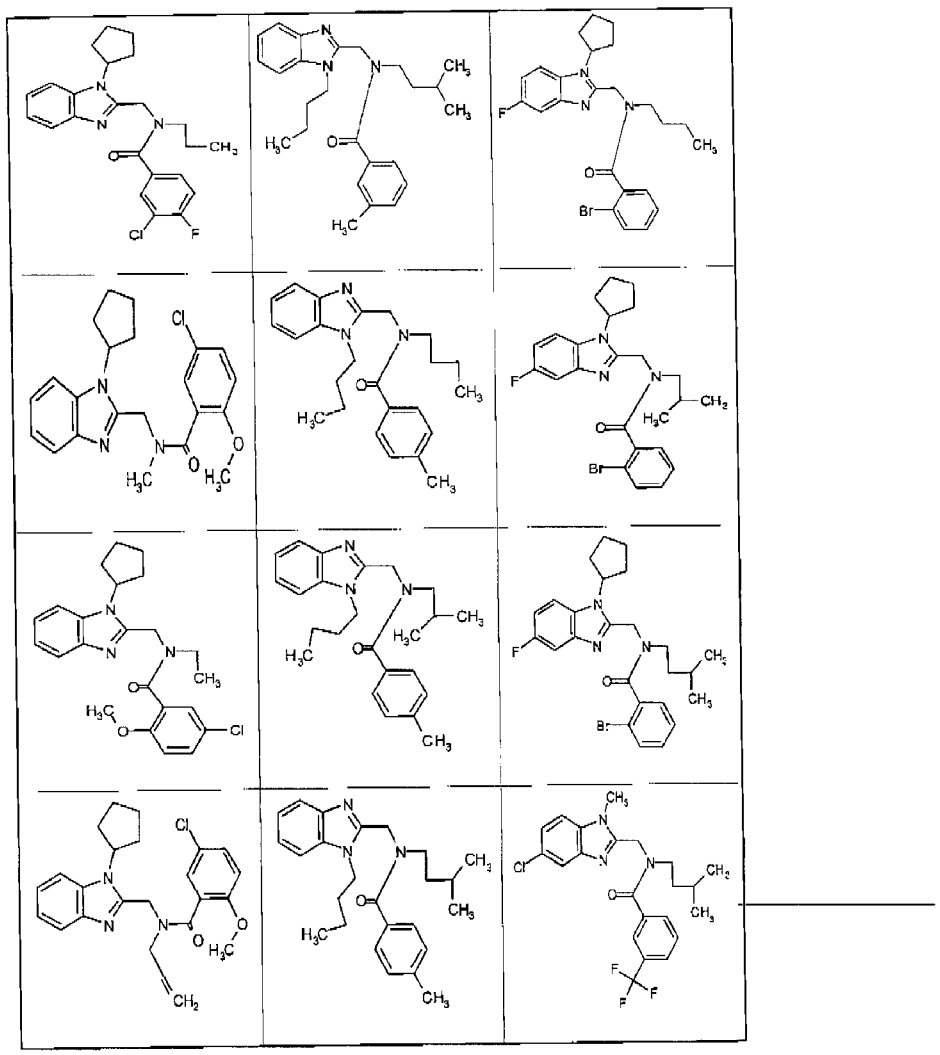

Appendix 2
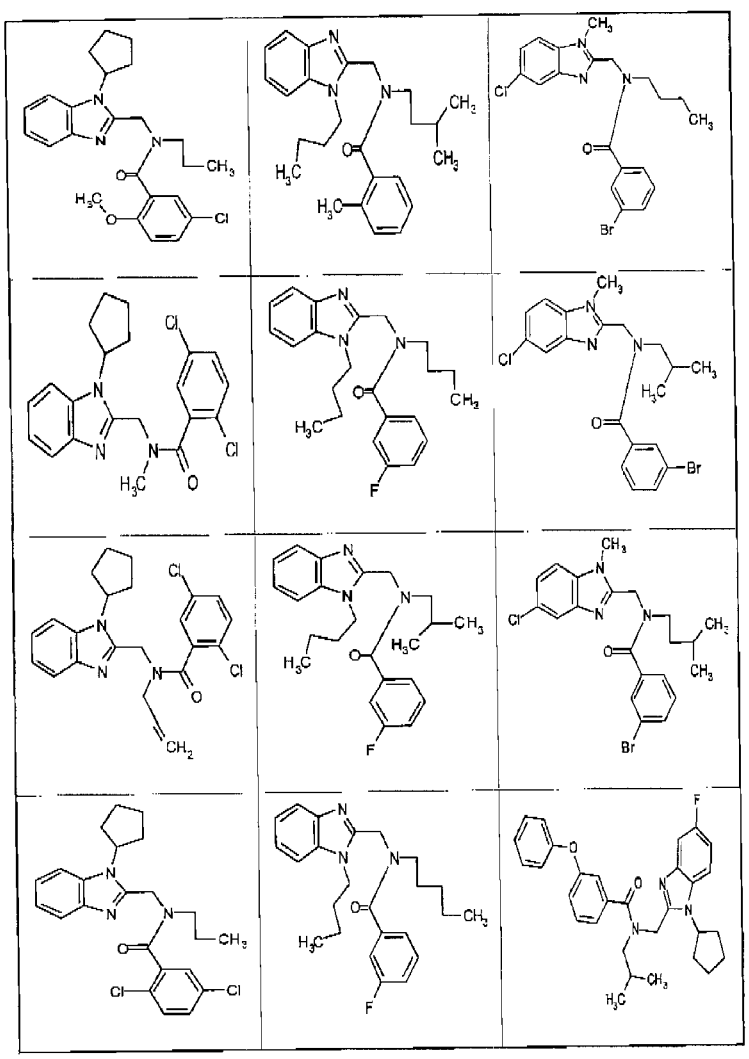

Appendix 2
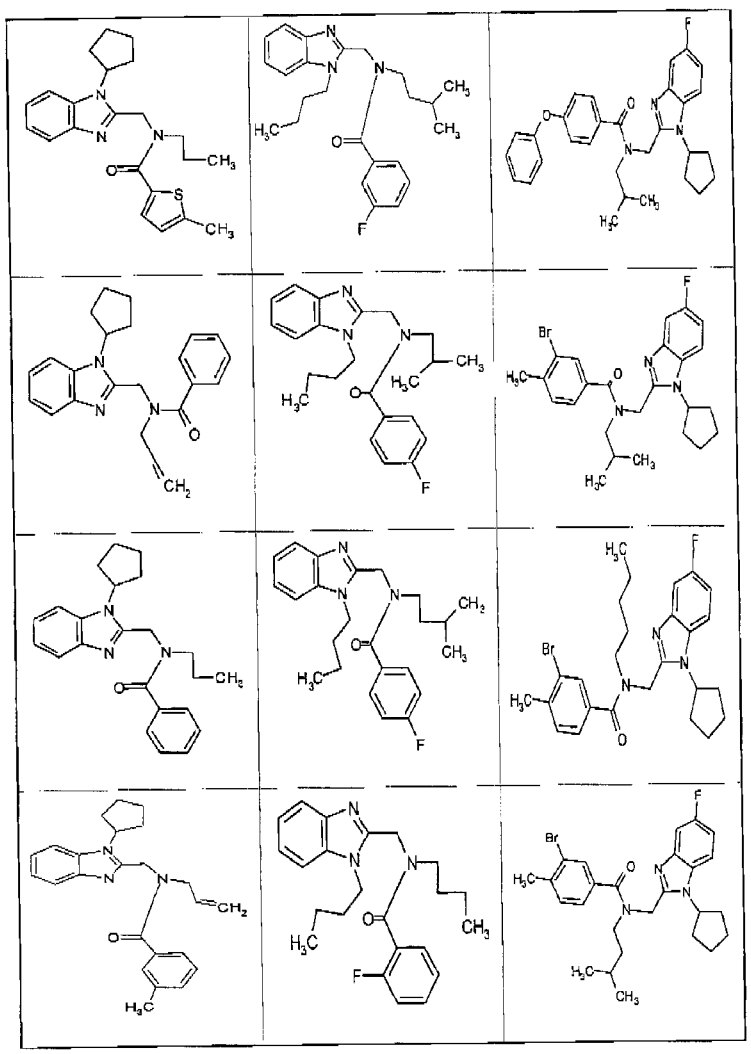

Appendix 2
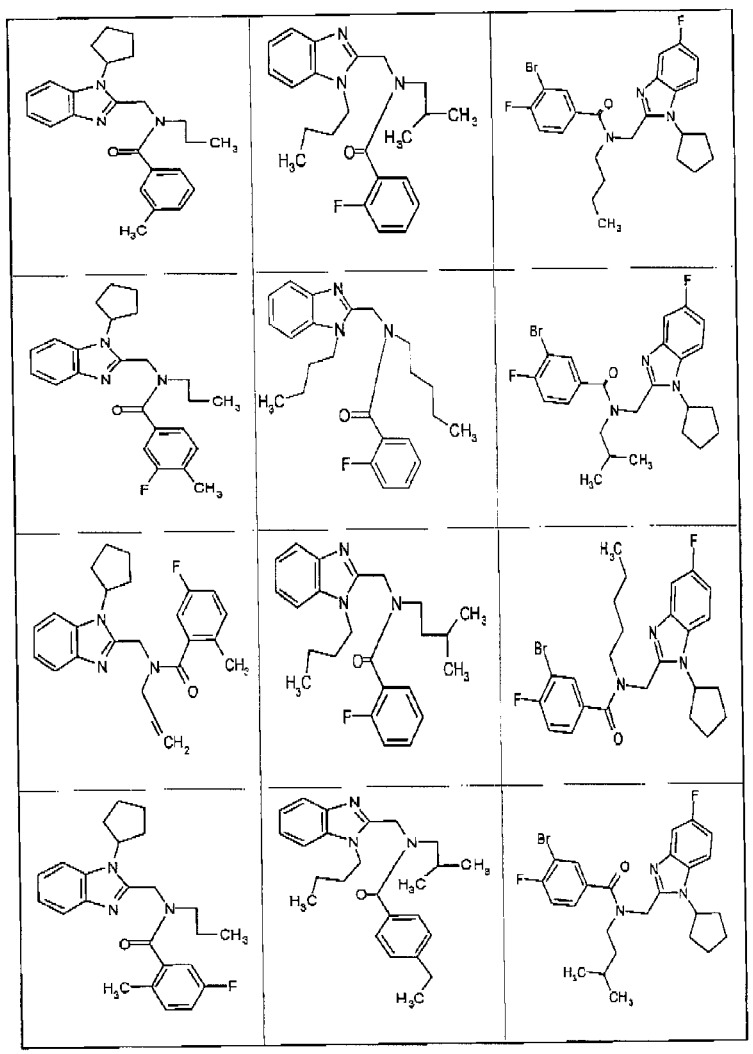

Appendix 2
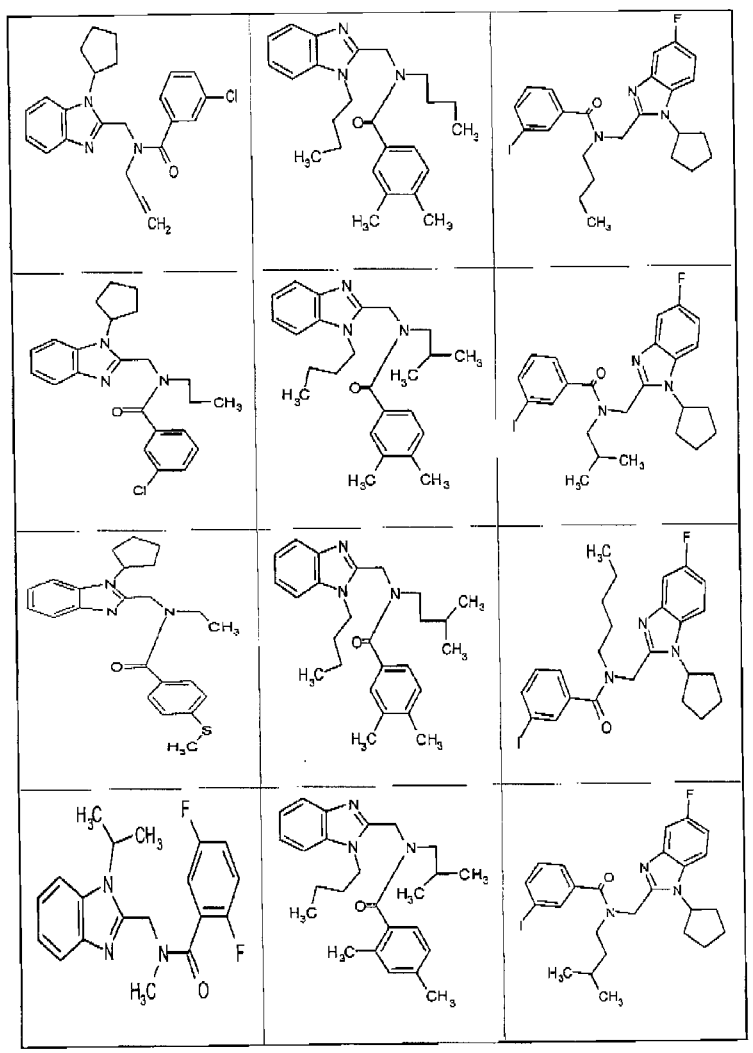

Appendix 2
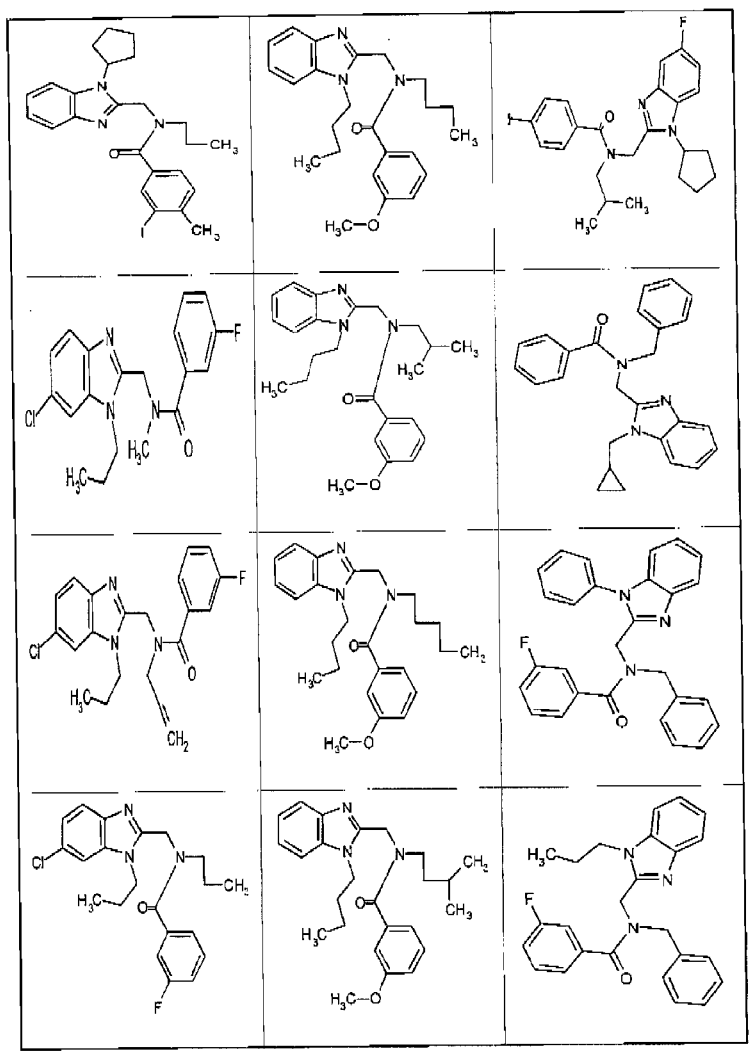

Appendix 2
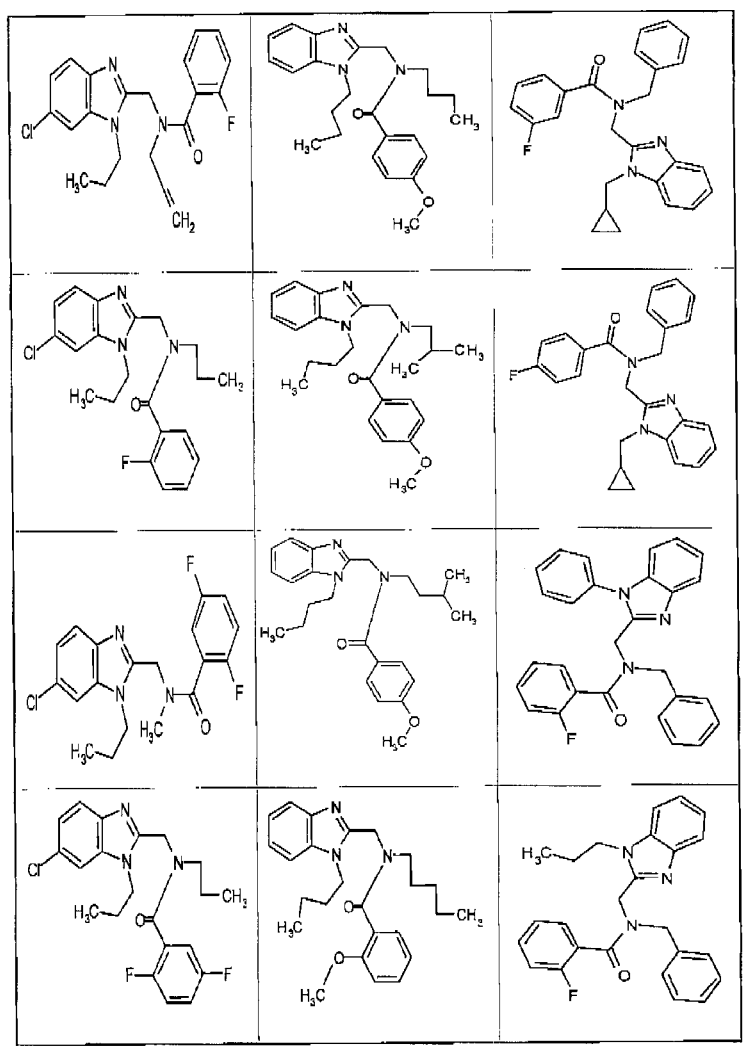

Appendix 2
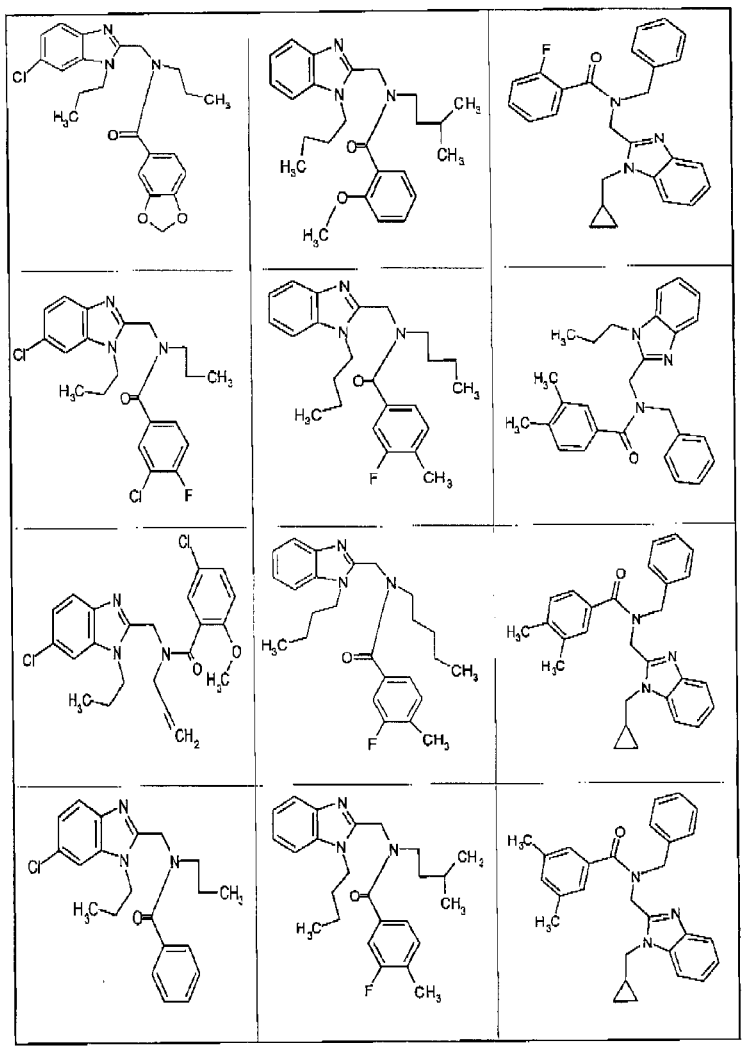

Appendix 2
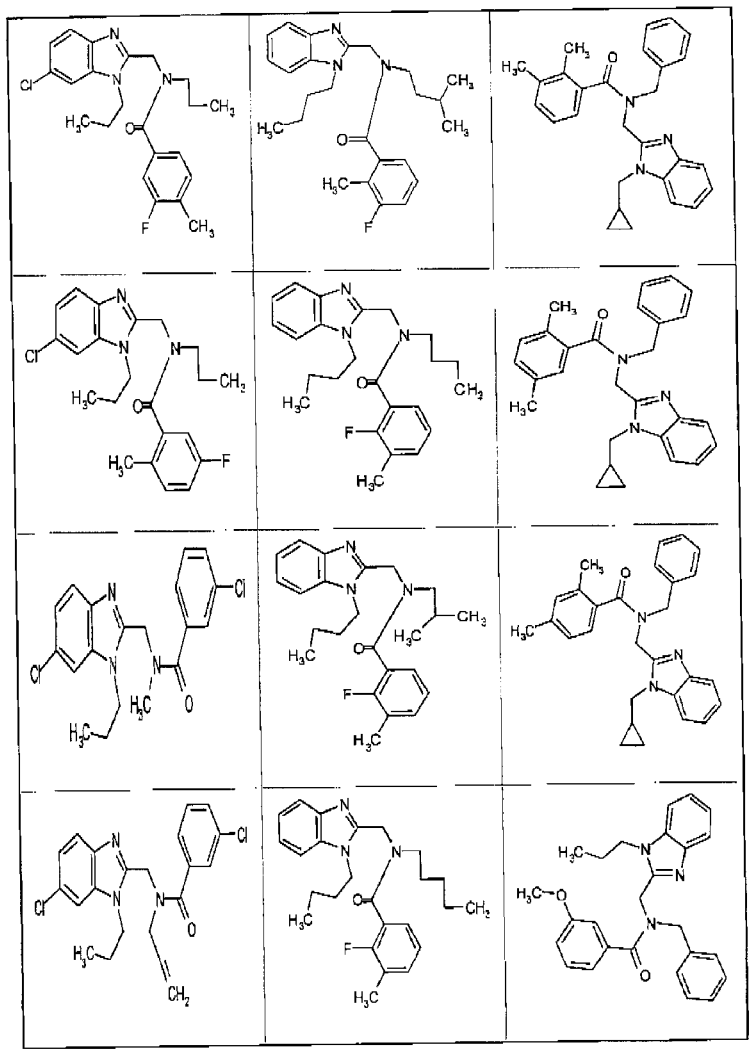

Appendix 2
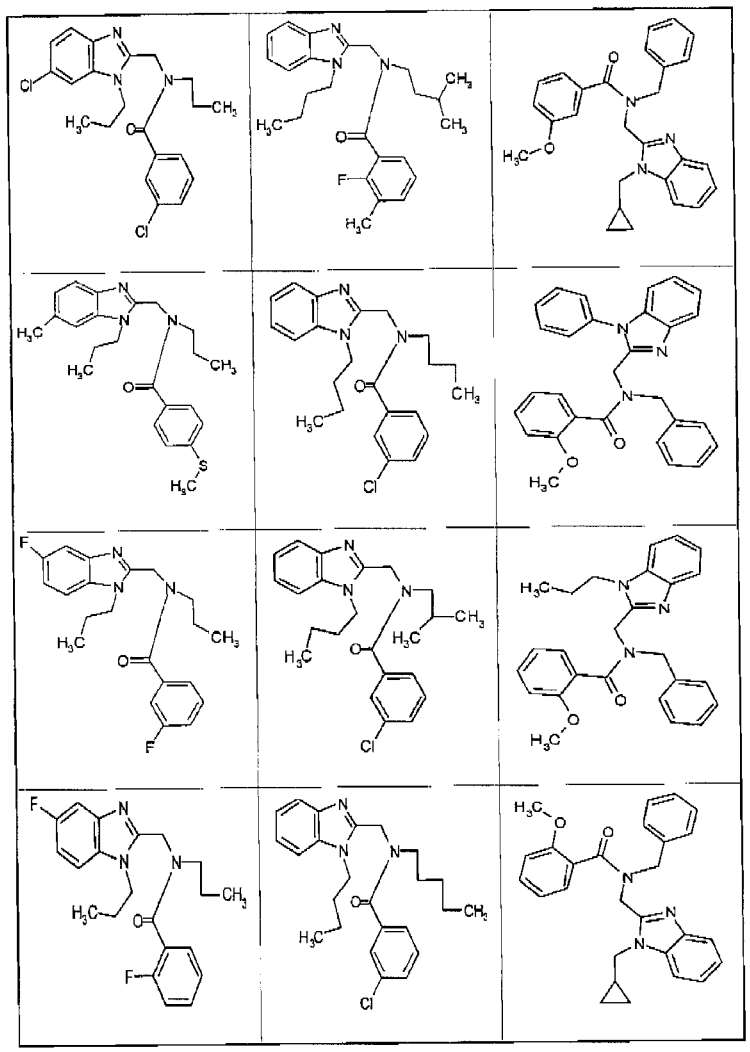

Appendix 2
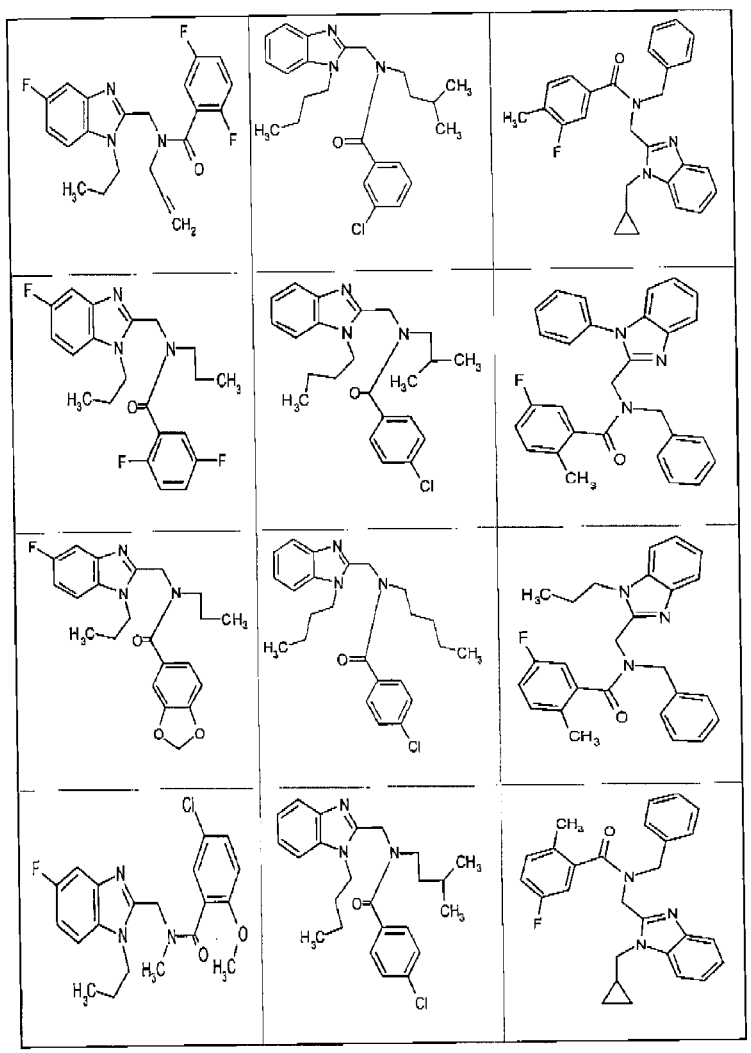

Appendix 2
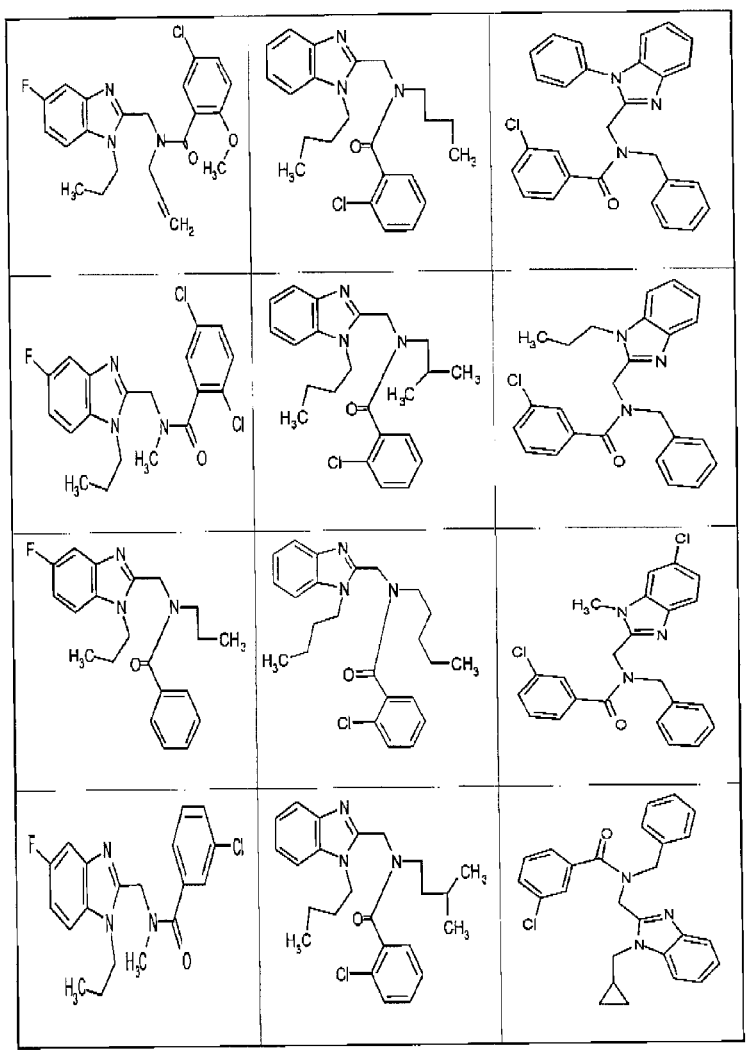

Appendix 2
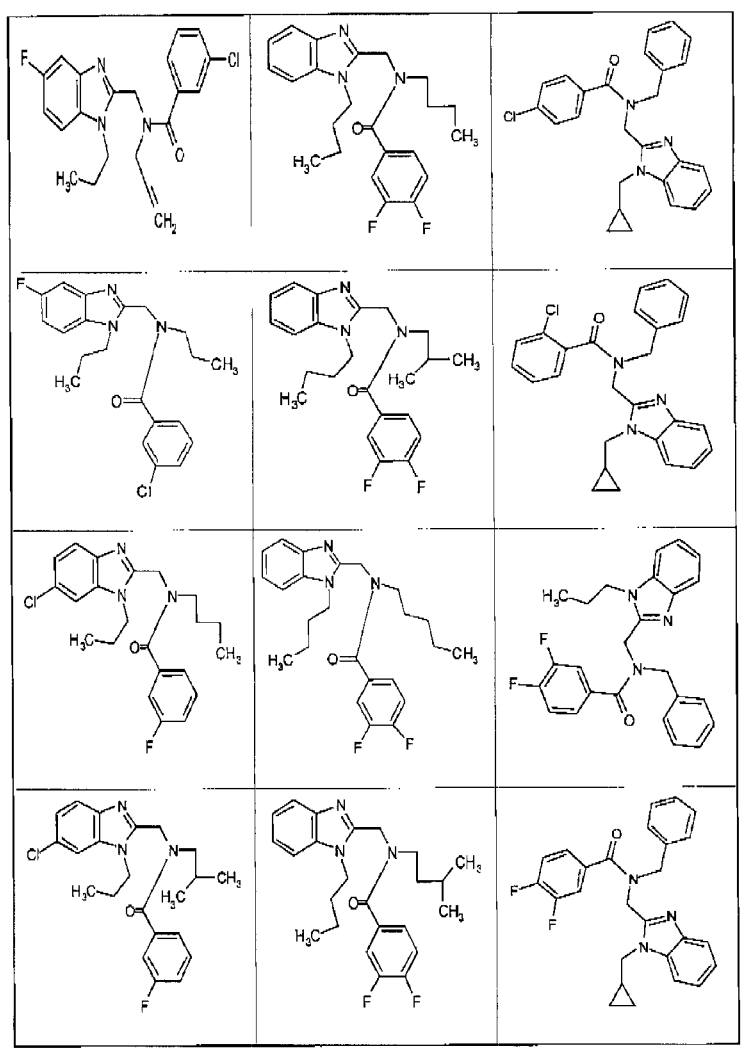

Appendix 2
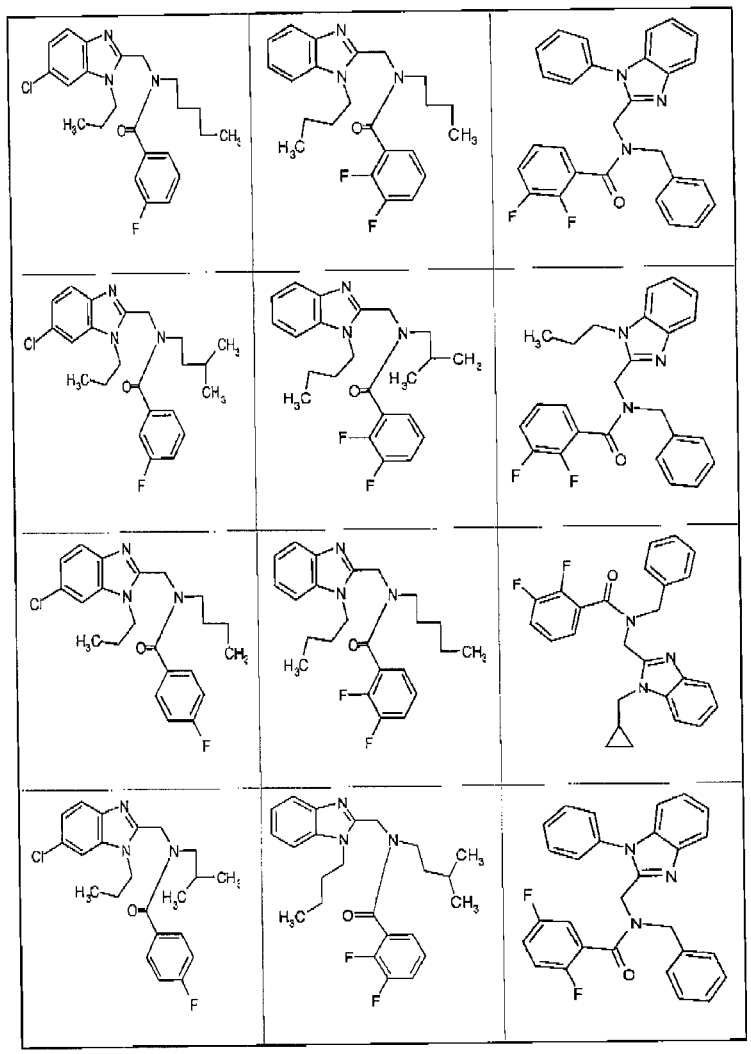

Appendix 2
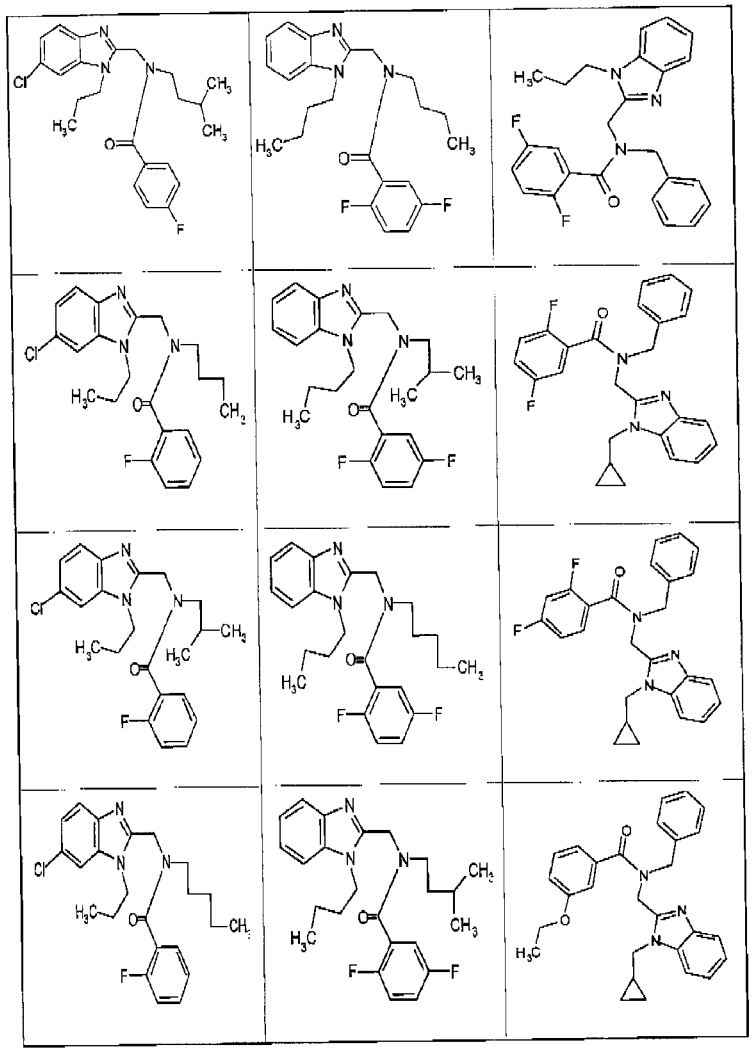

Appendix 2
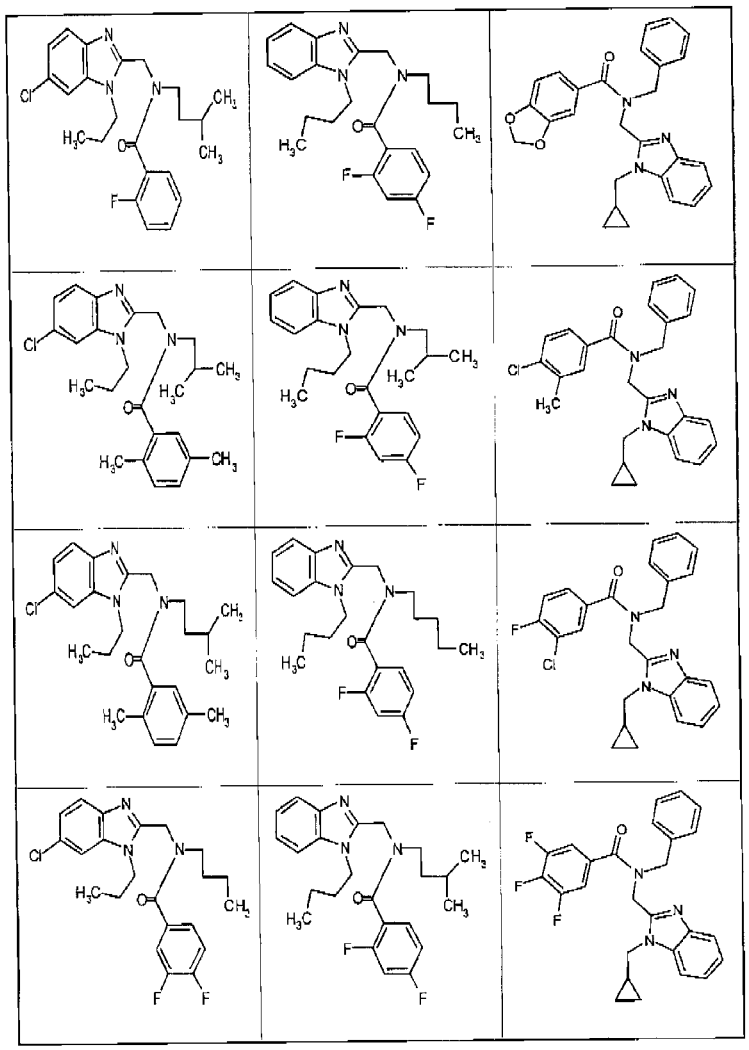

Appendix 2
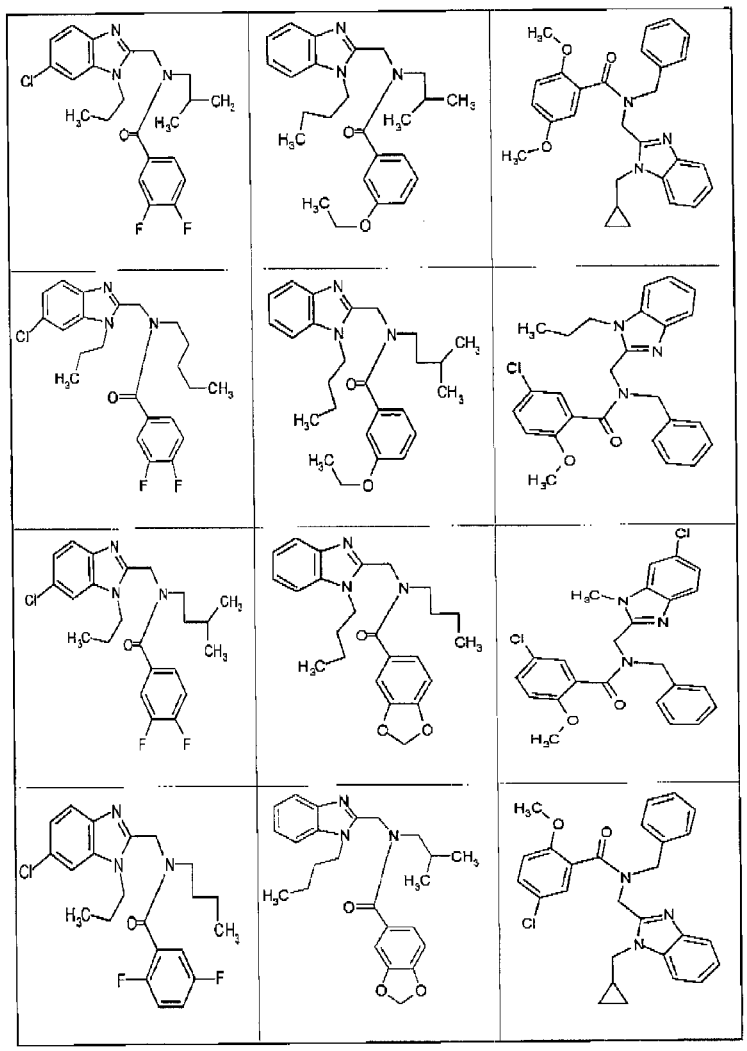

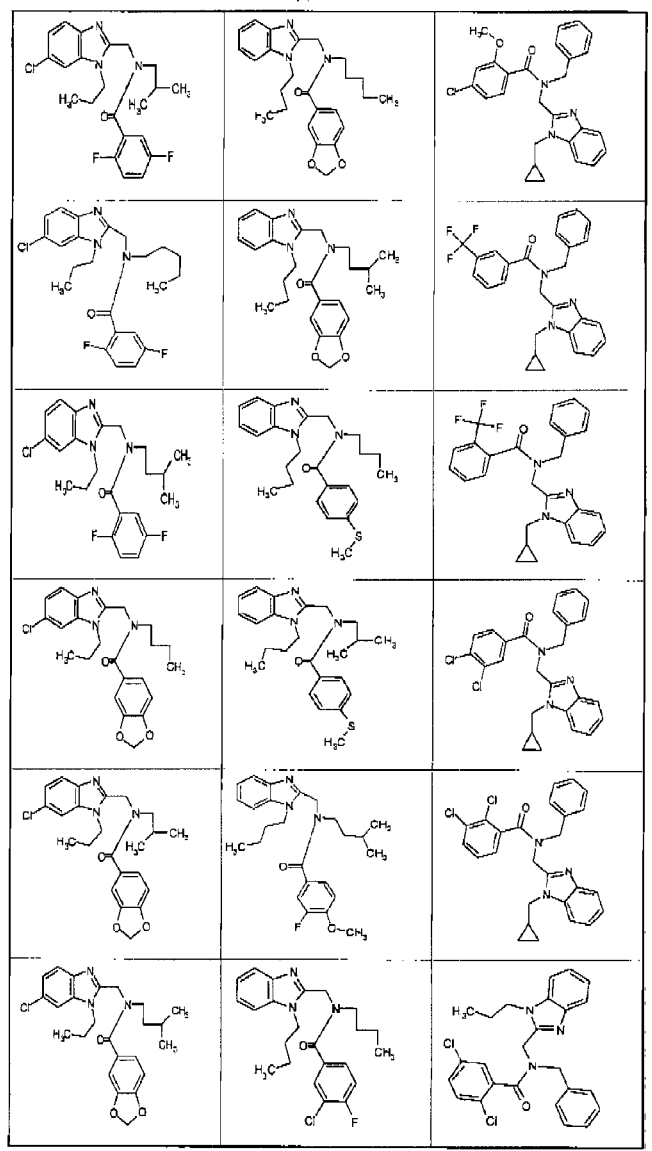
Appendix 2

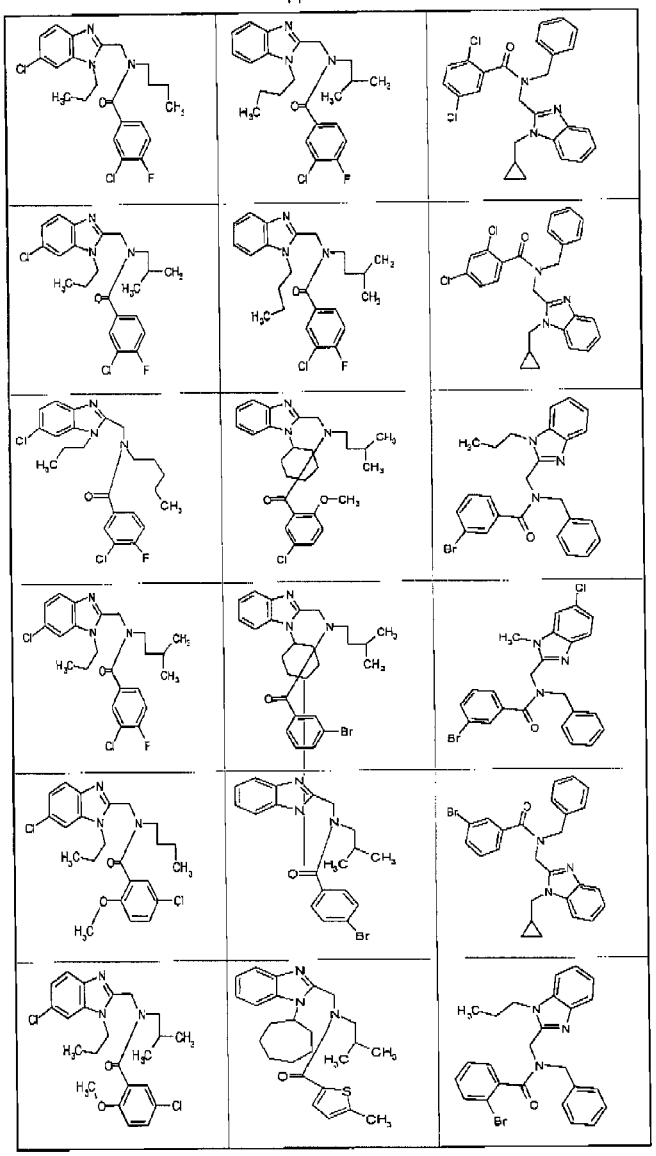
Appendix 2

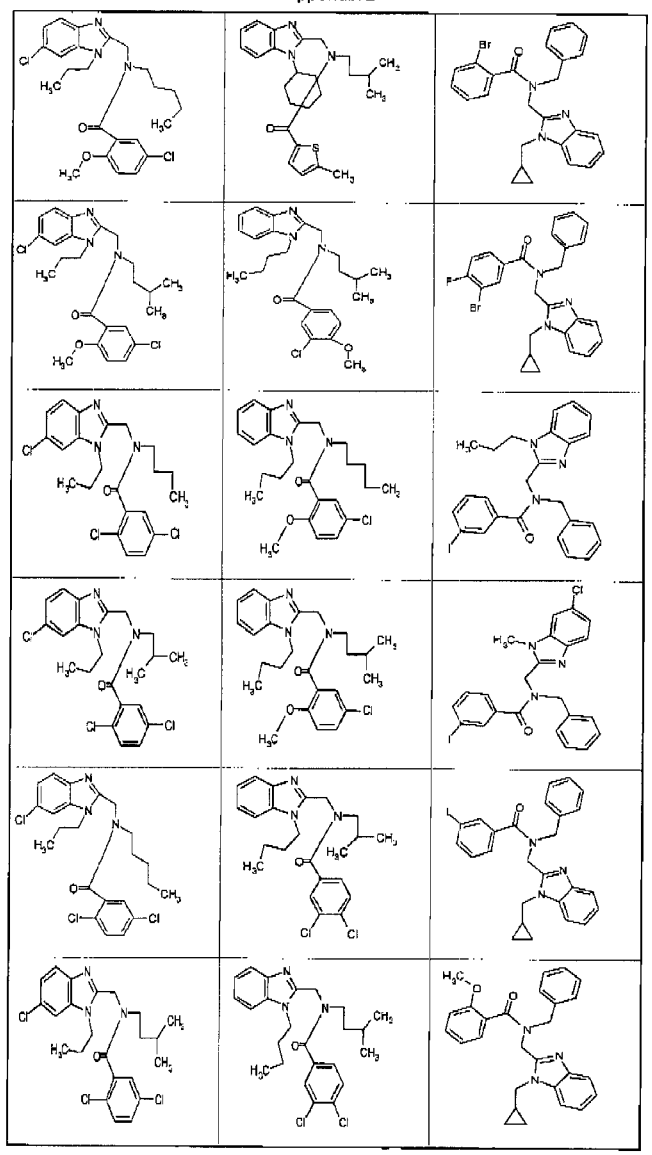
Appendix 2

Appendix 2
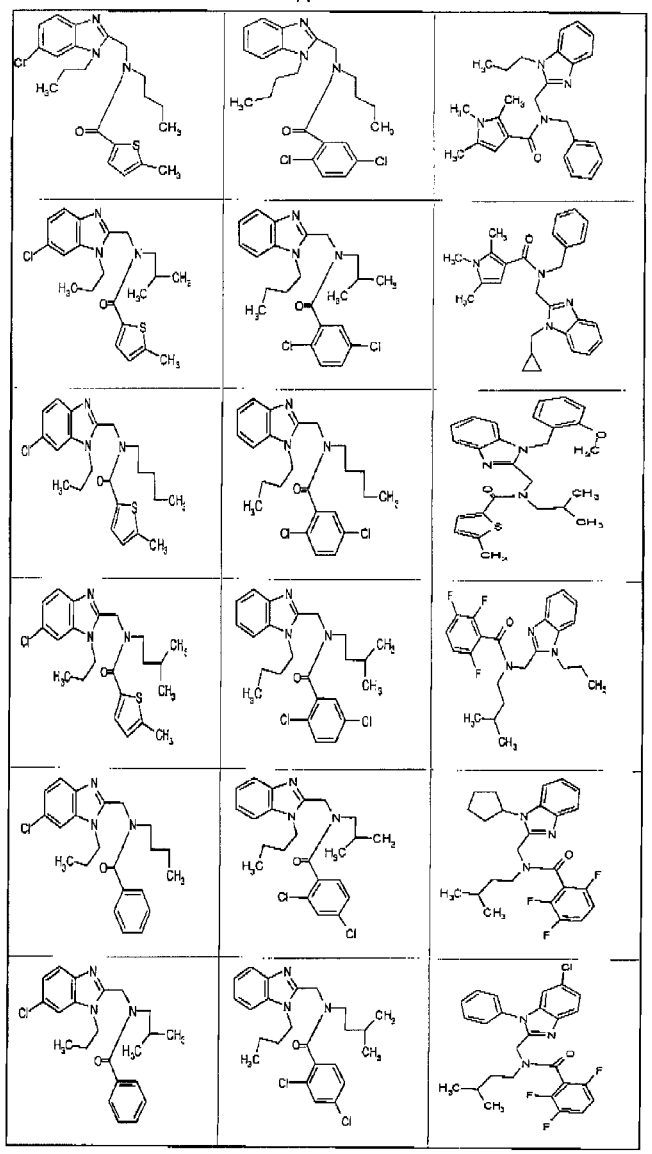

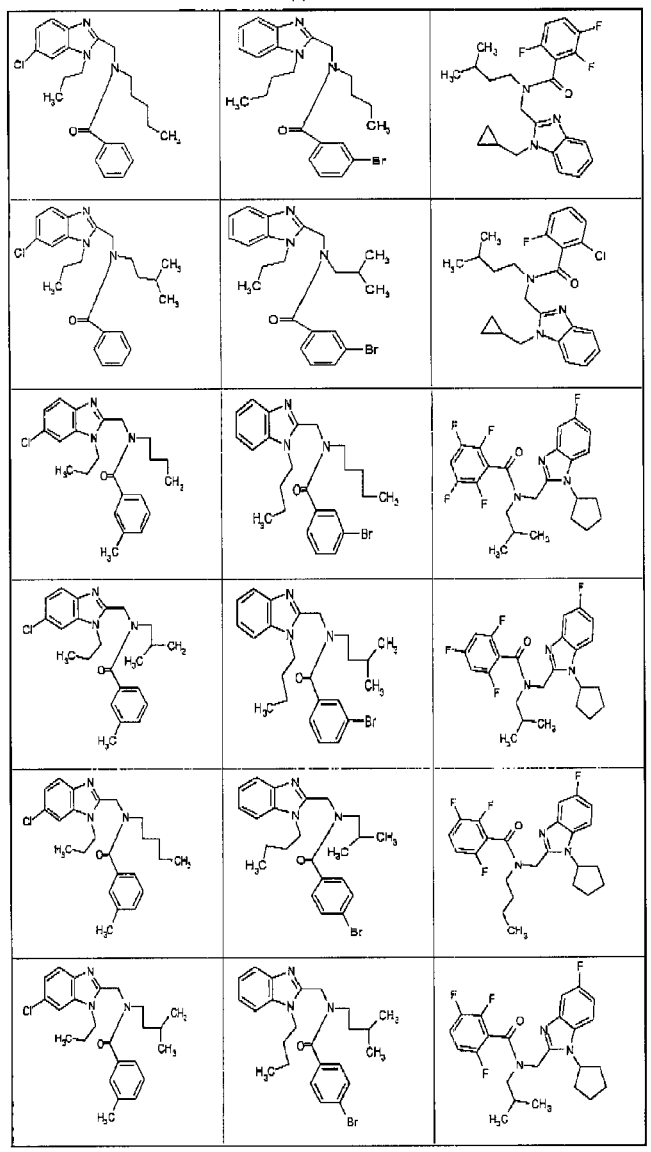

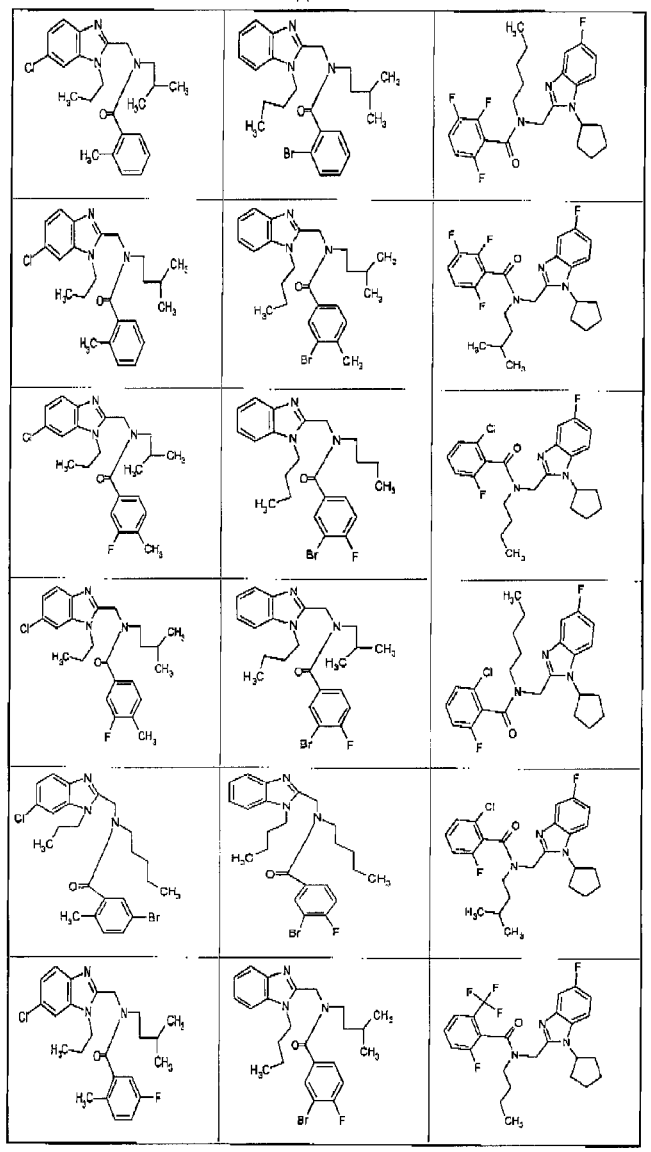

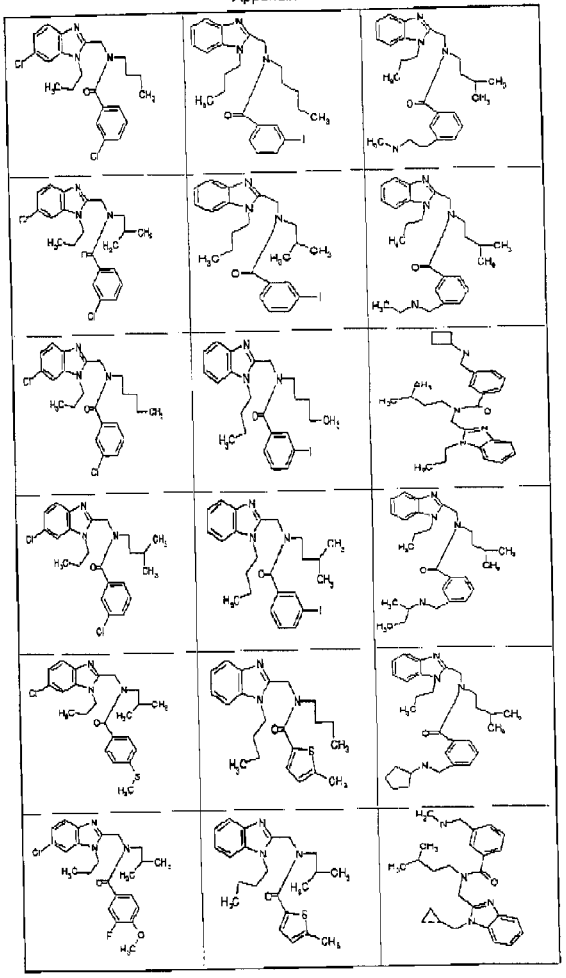

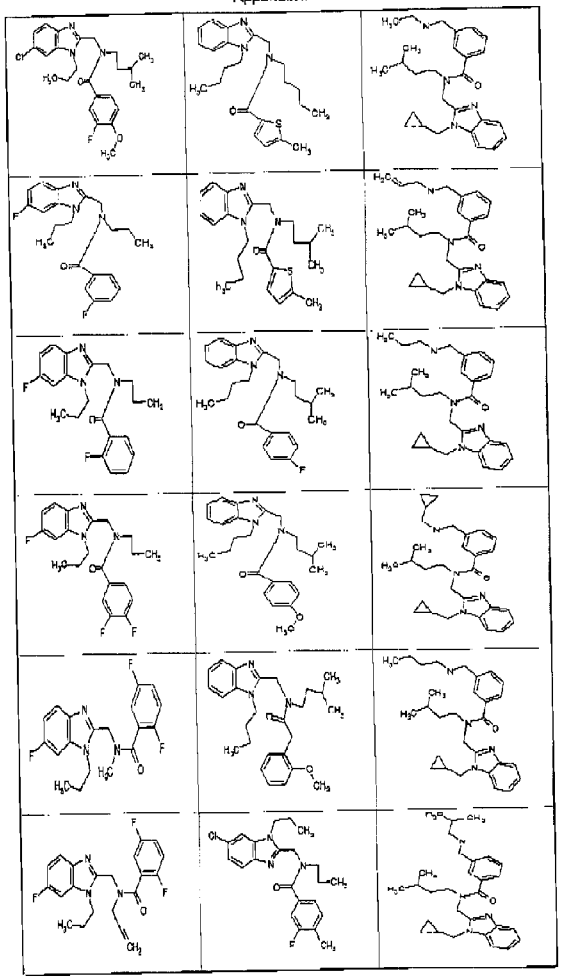

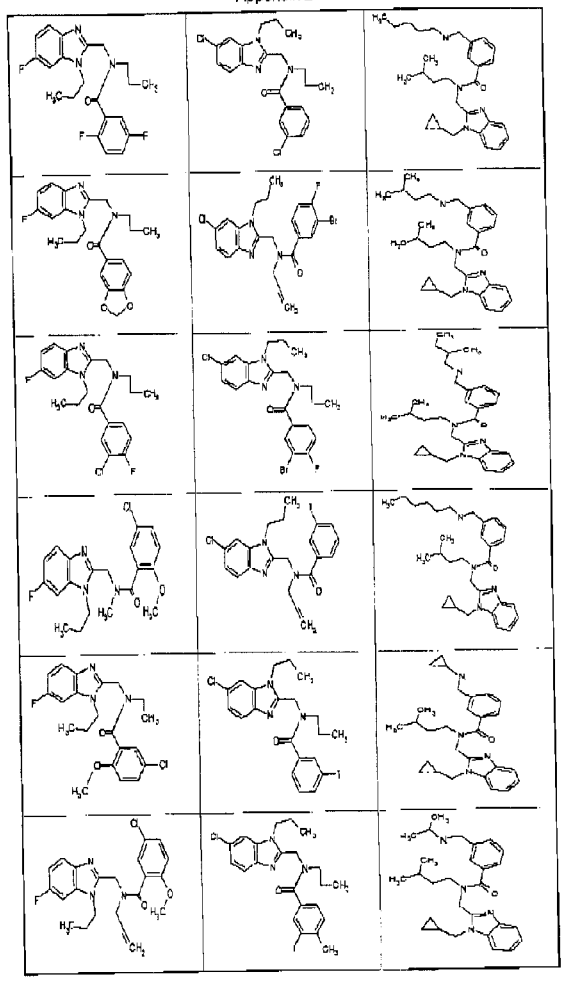

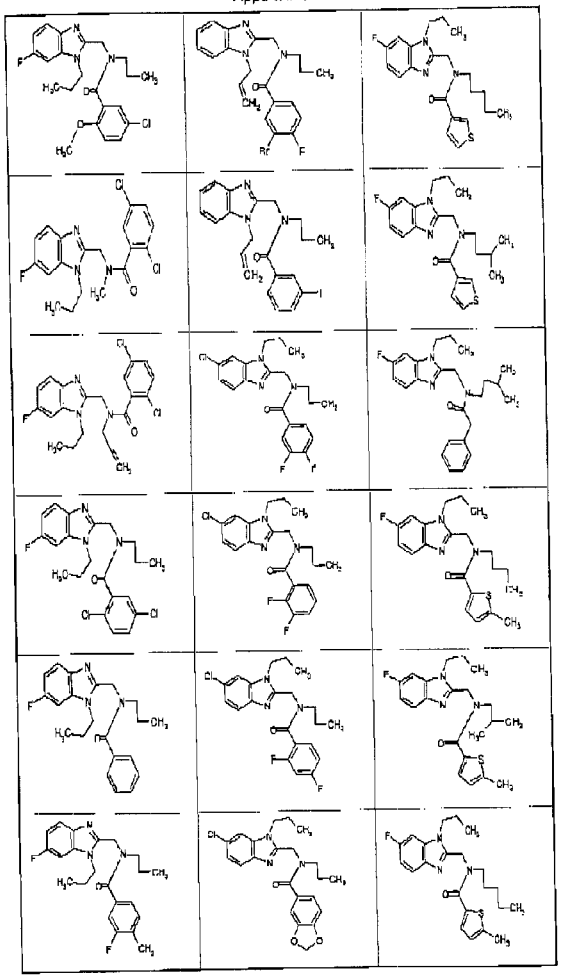
Appendix 2

Appendix 2
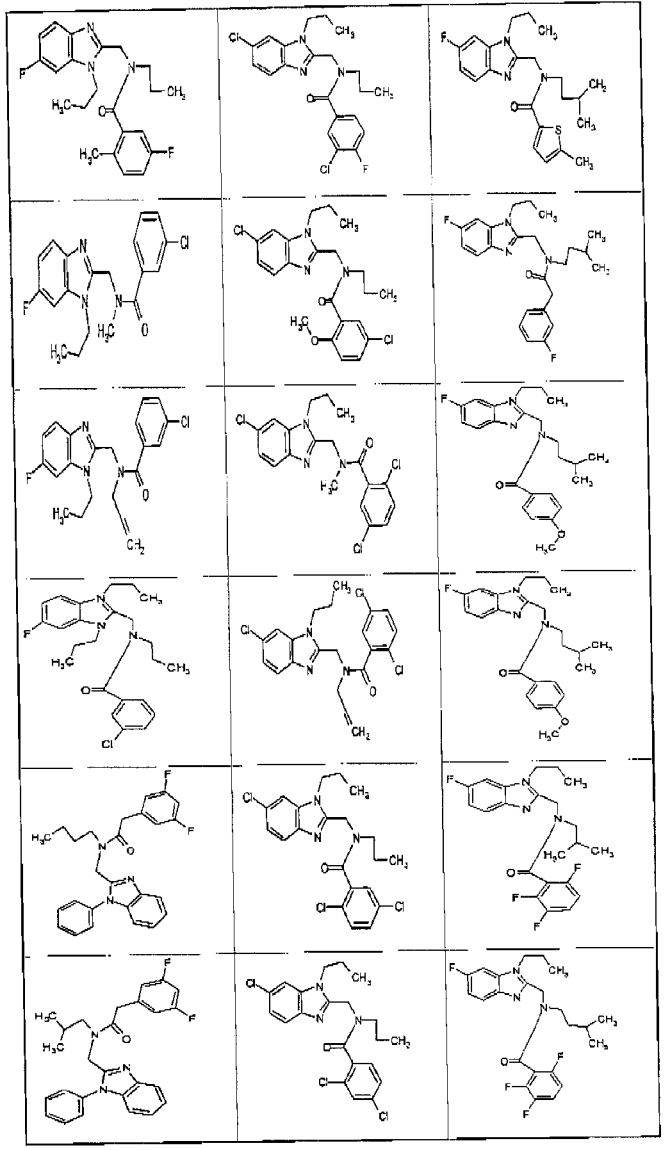

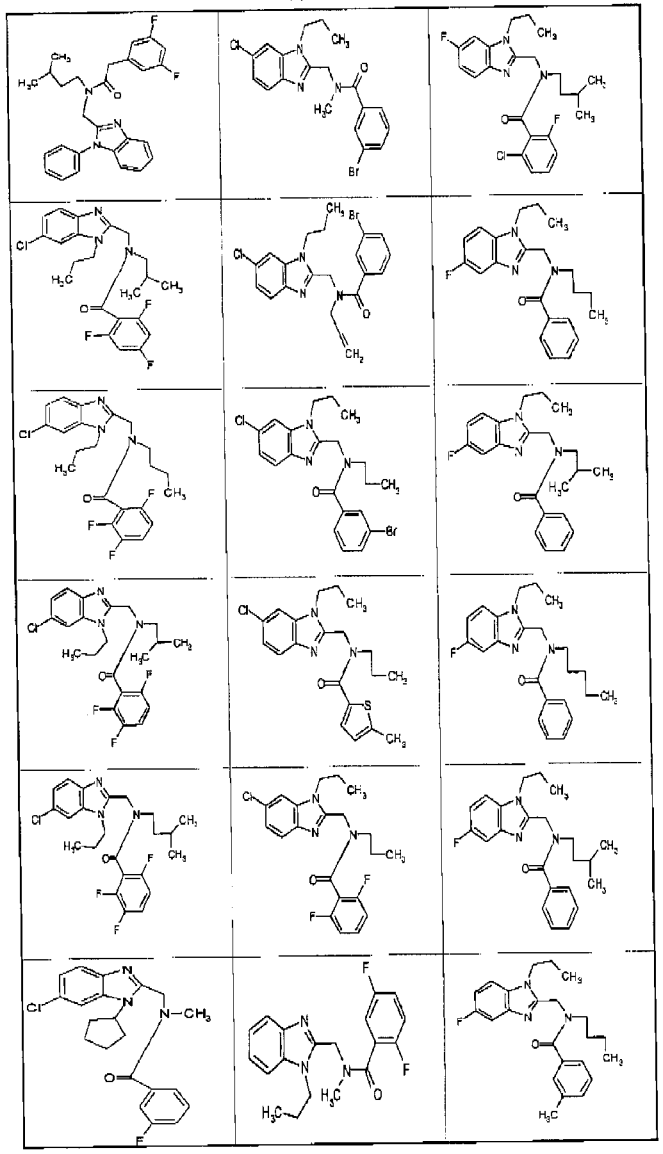
Appendix 2

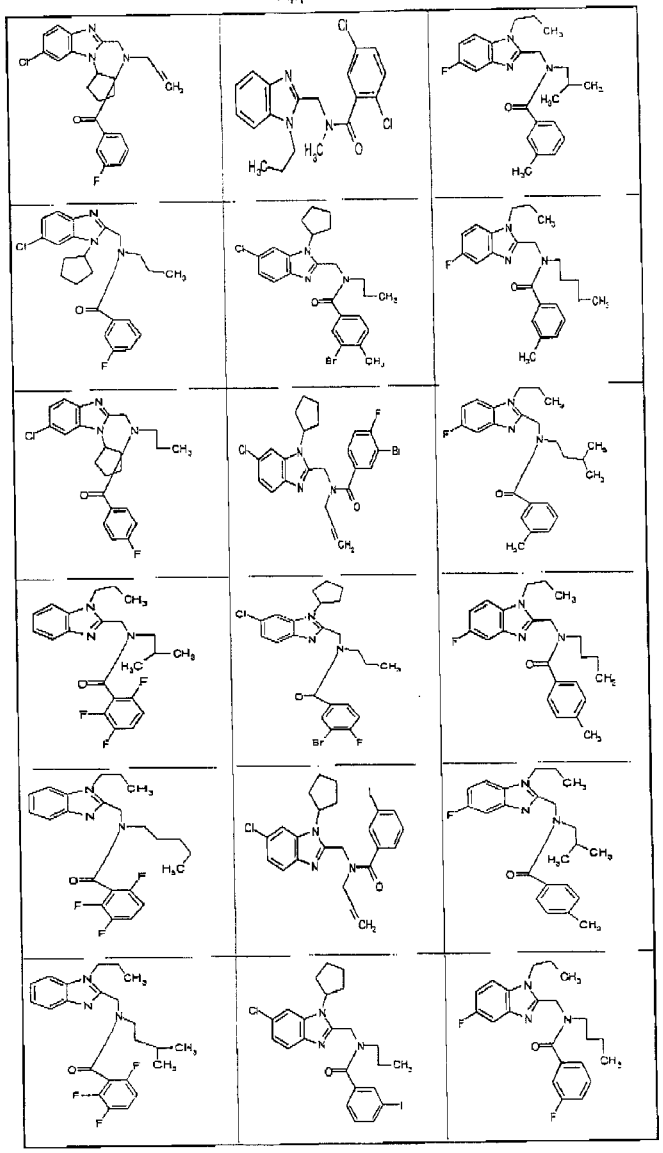
Appendix 2

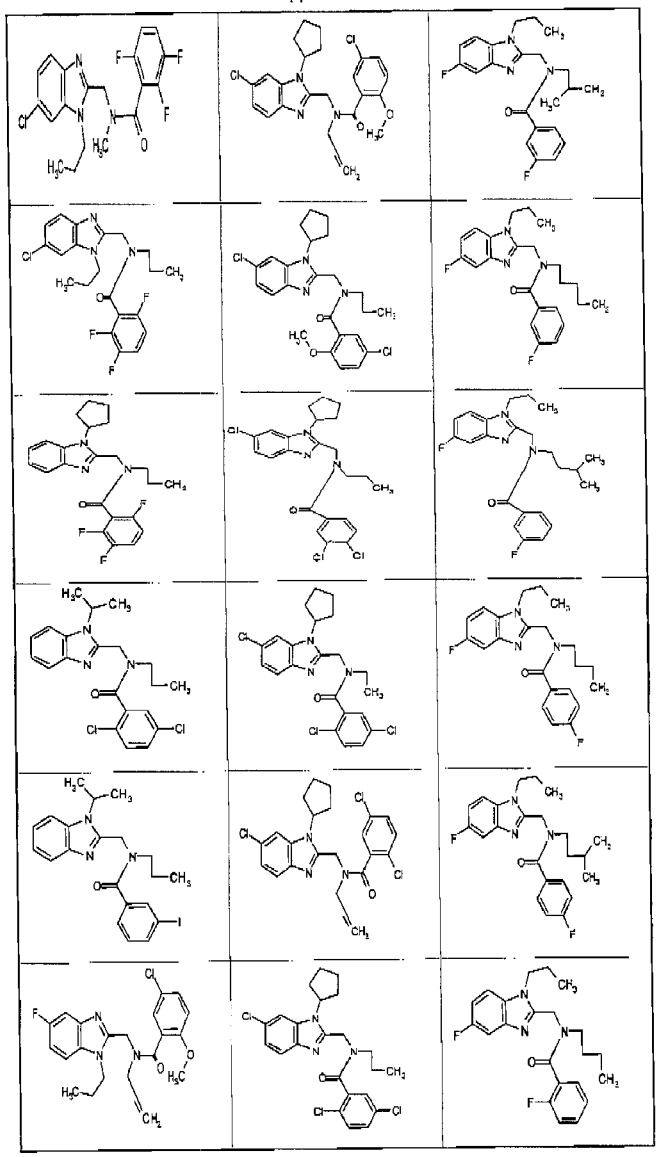
Appendix 2

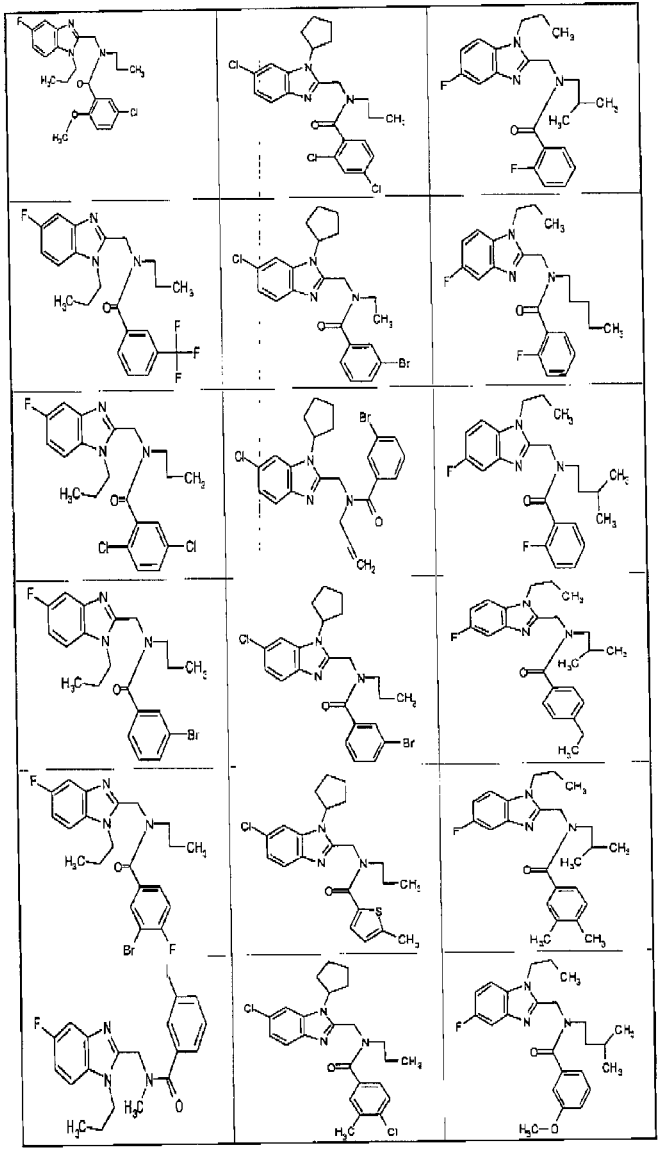

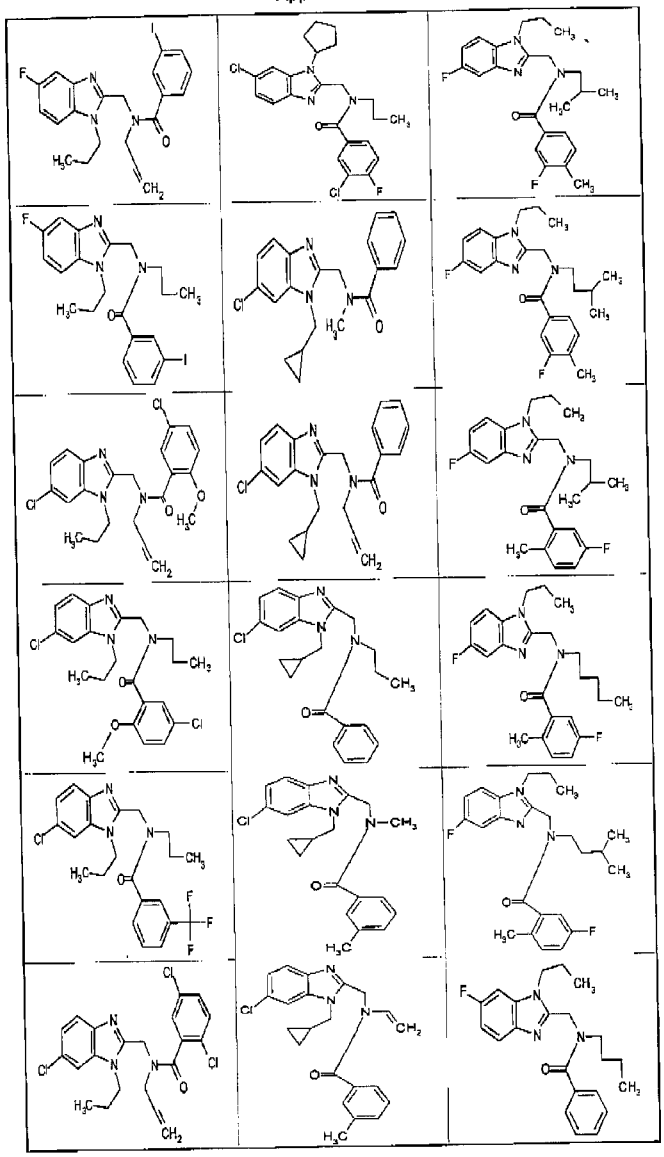
Appendix 2

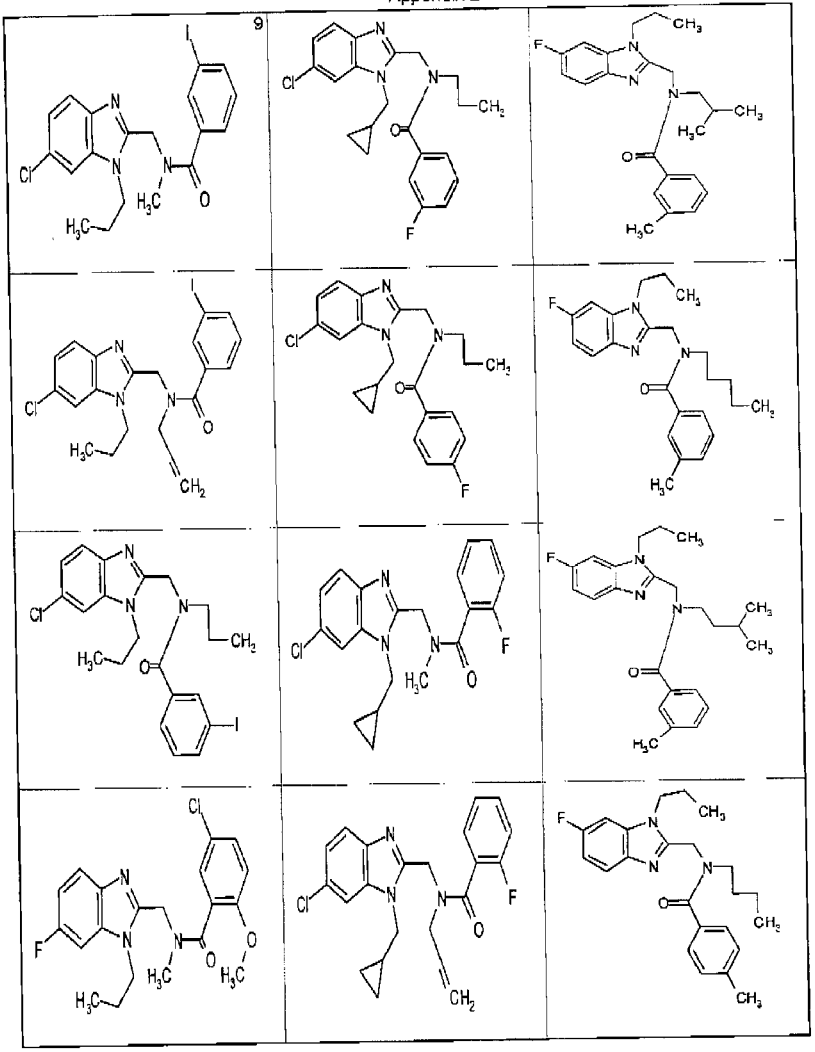

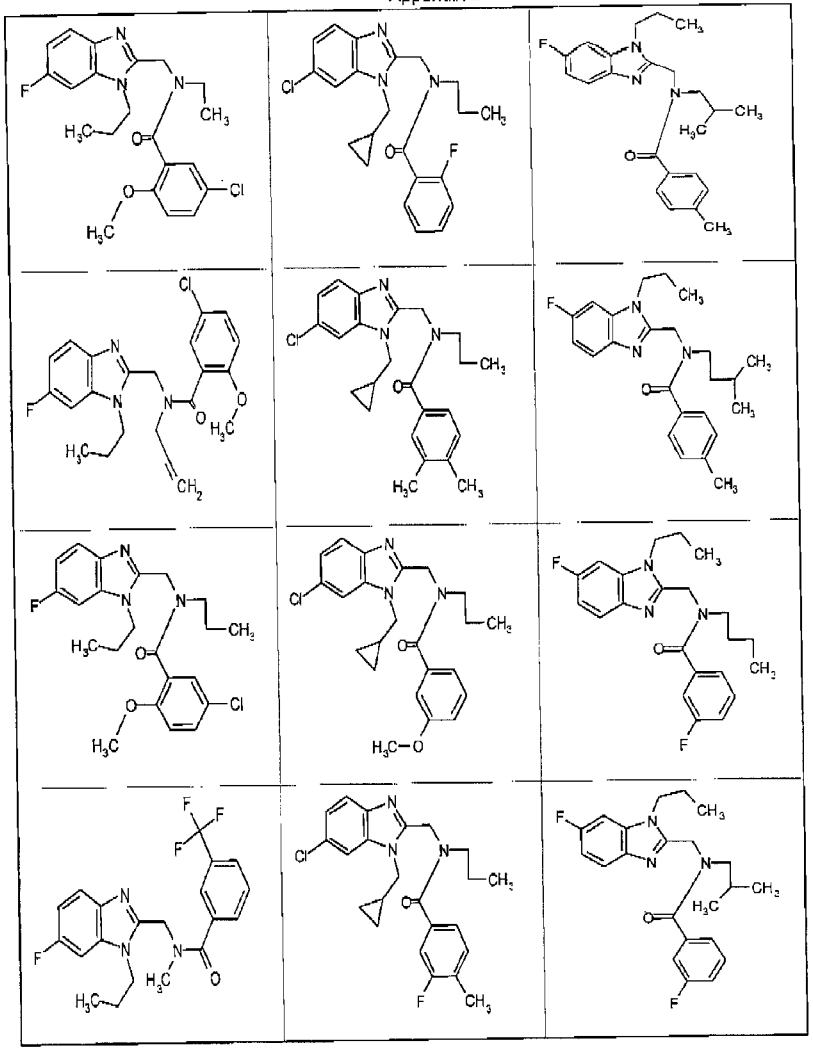

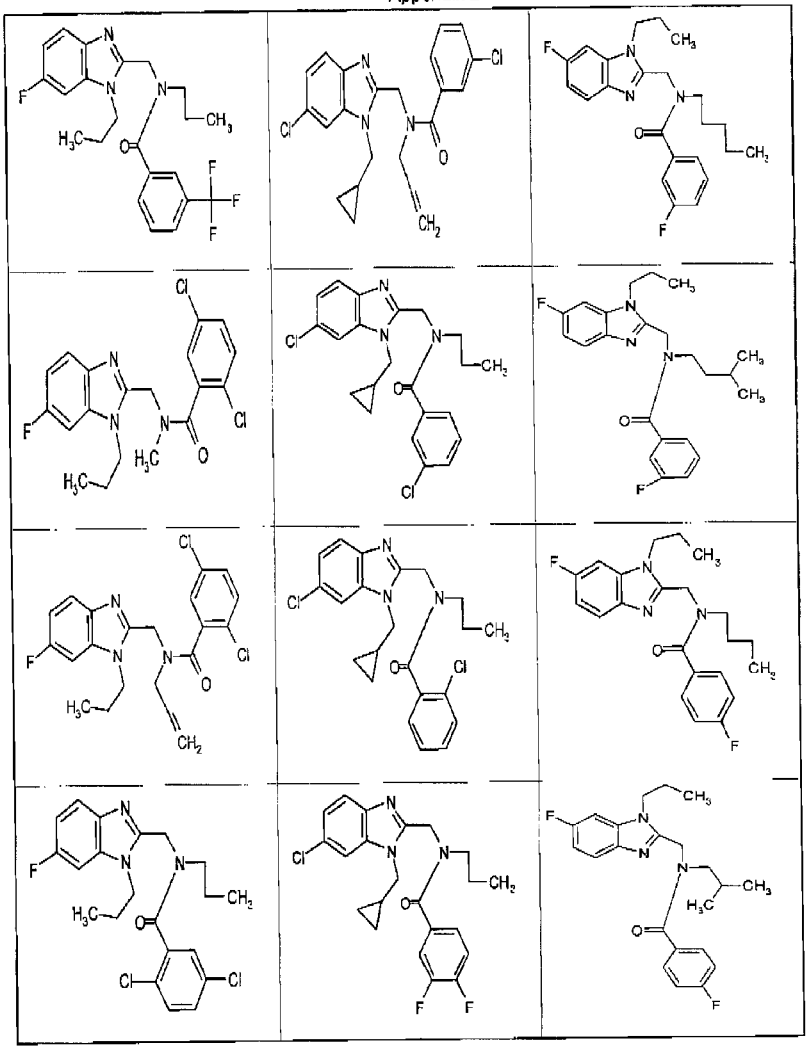

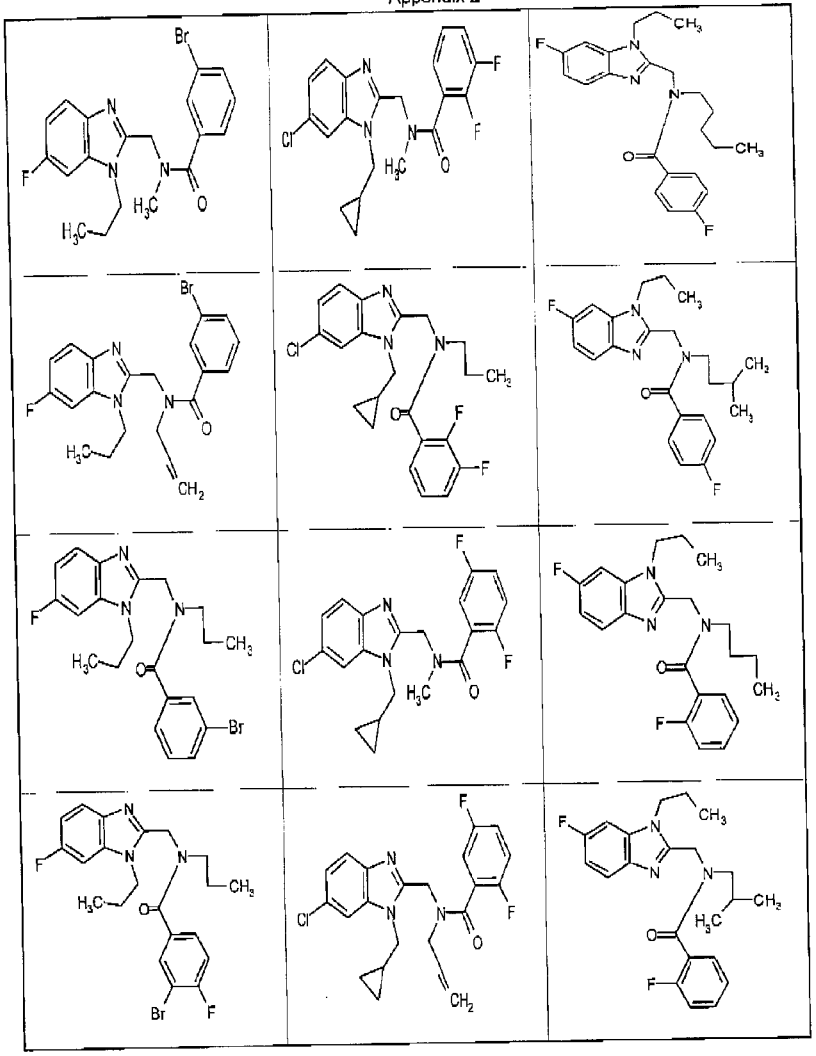
Appendix 2

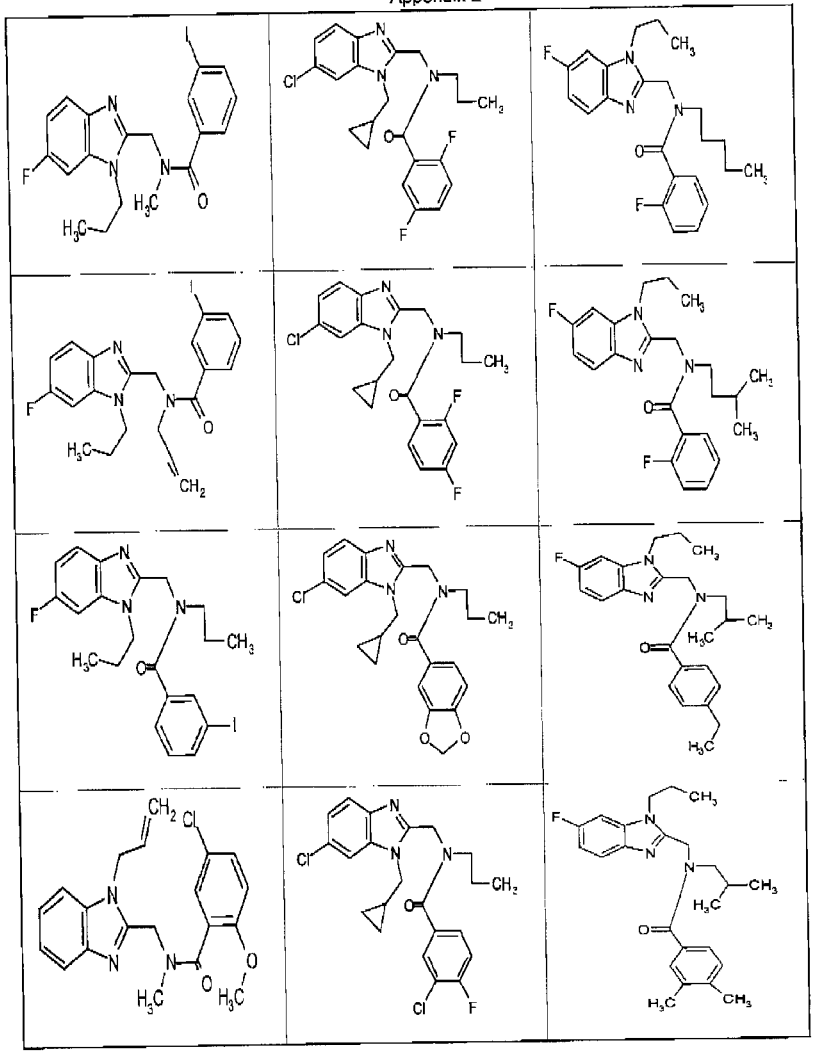
Appendix 2

Appendix 2
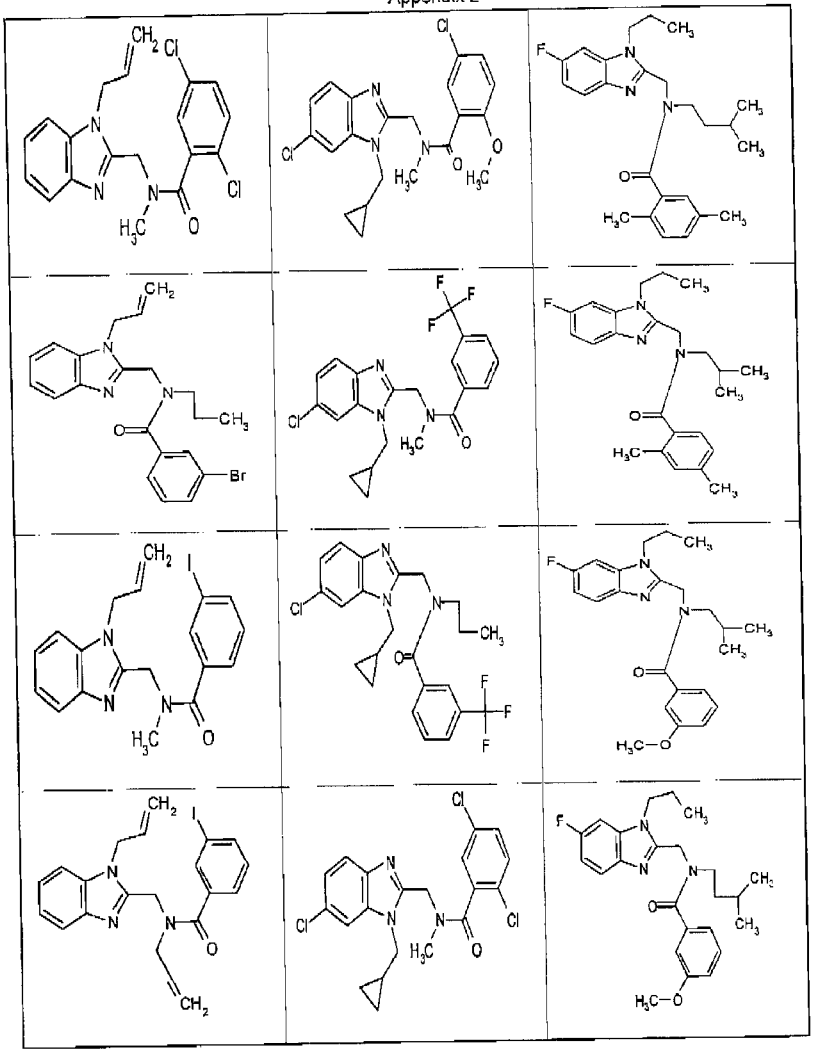

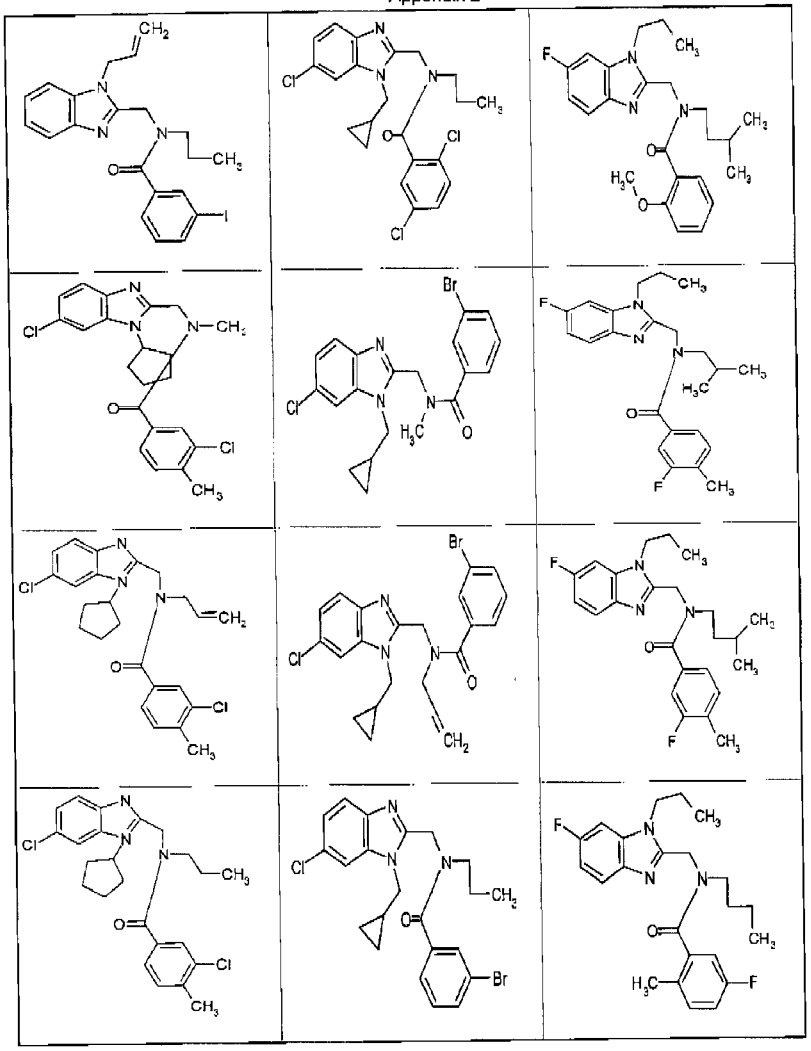
Appendix 2

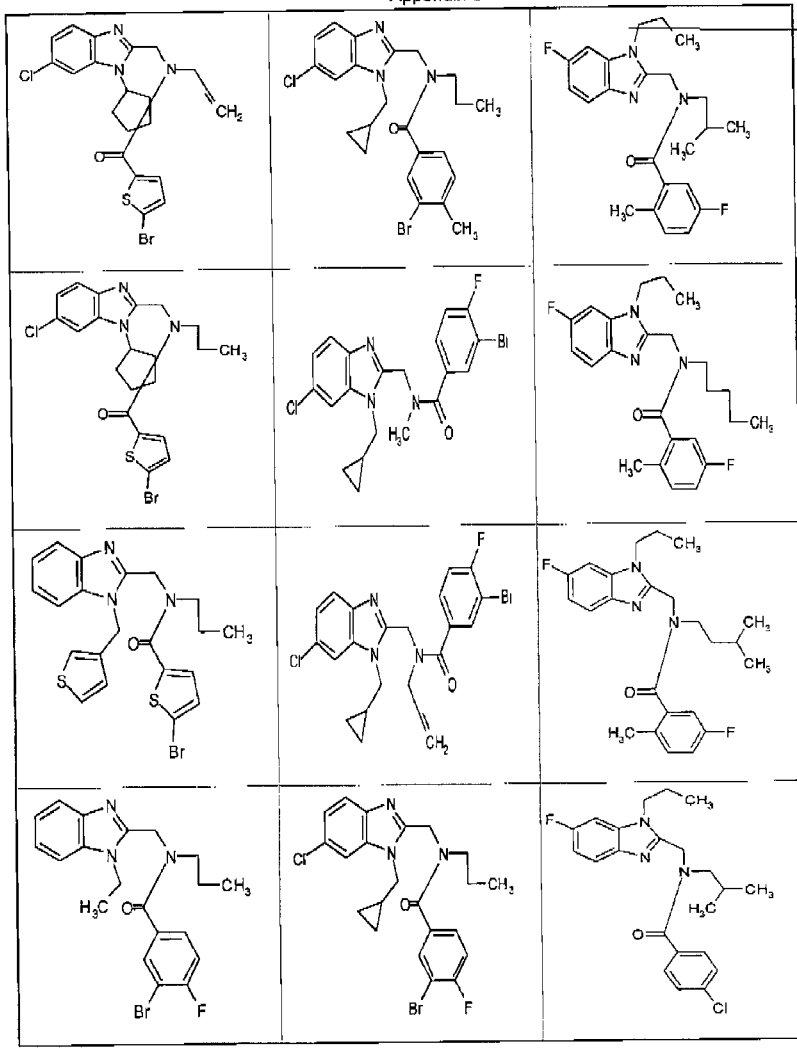

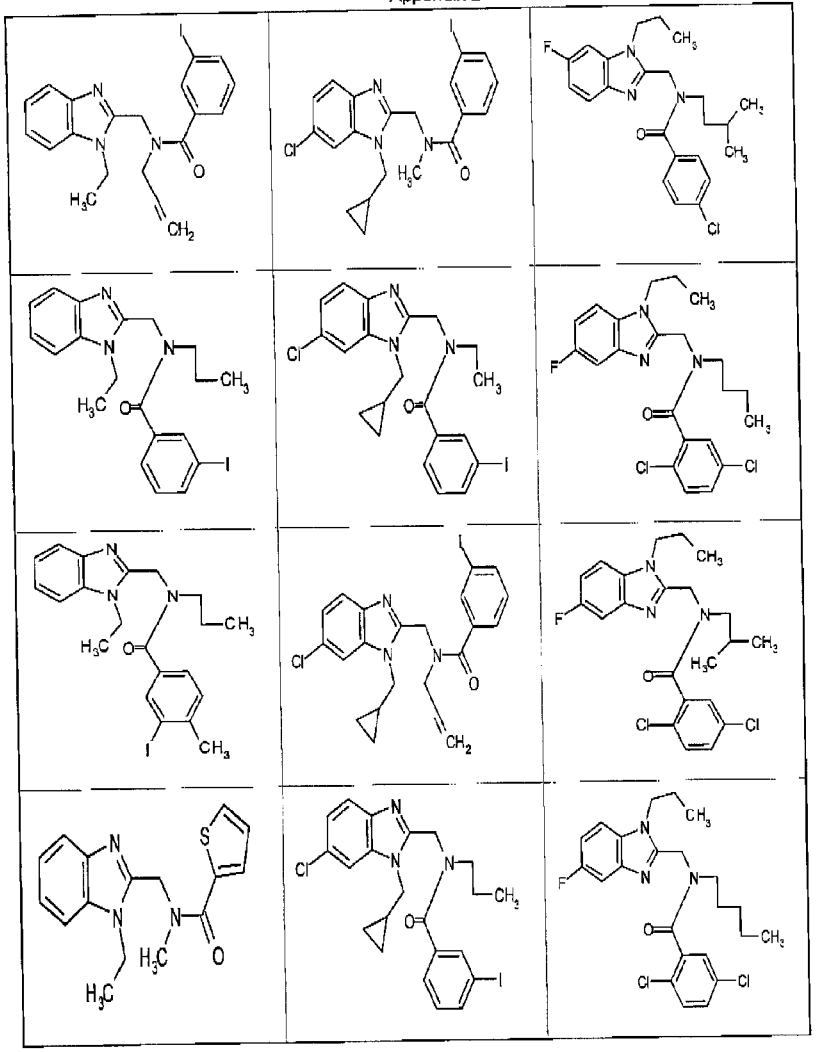
Appendix 2

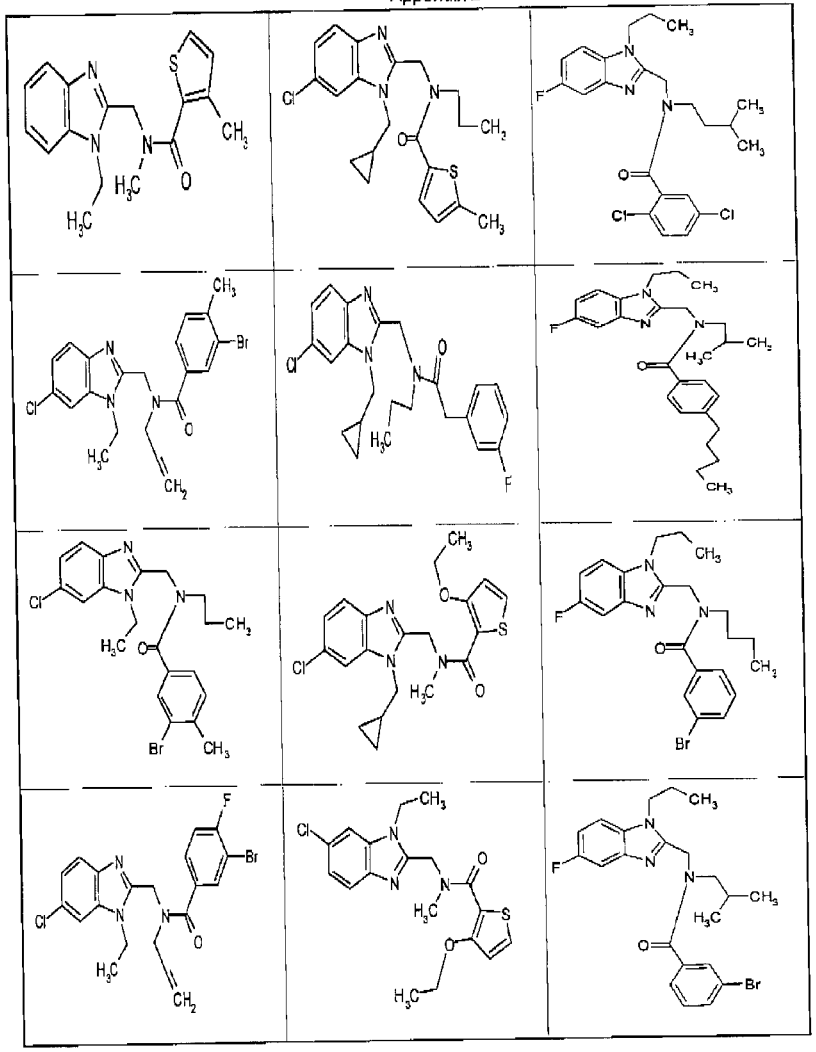
Appendix 2

Appendix 2
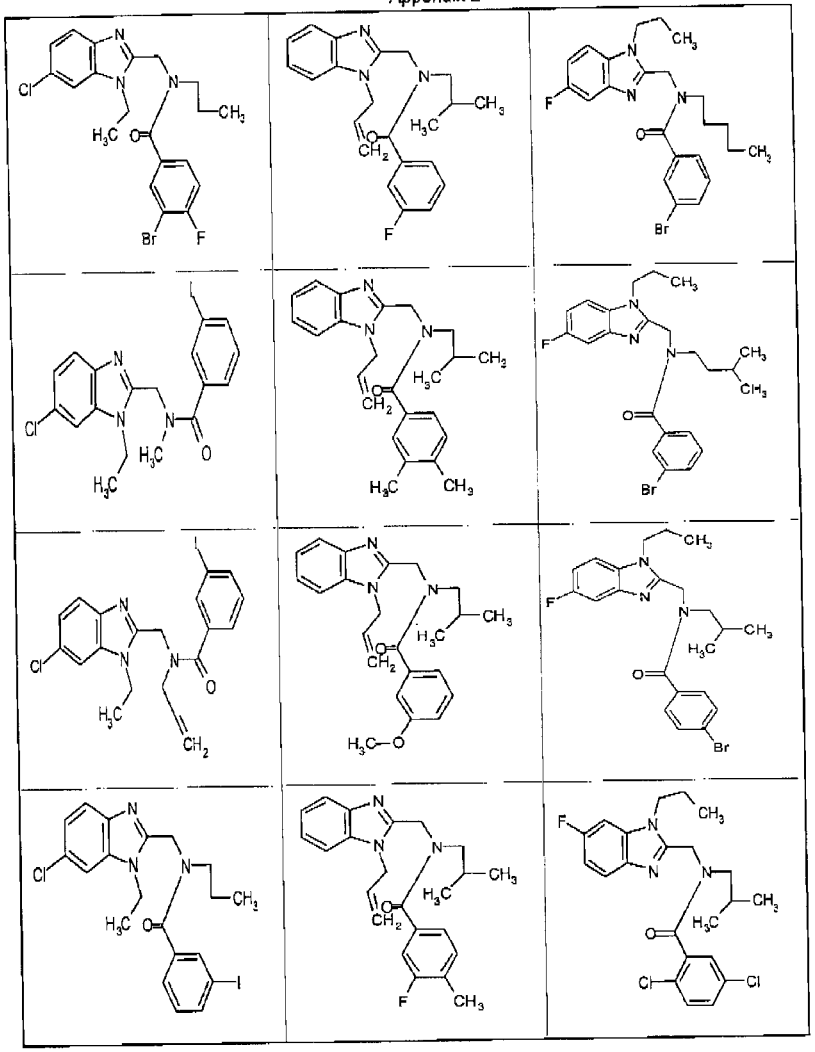

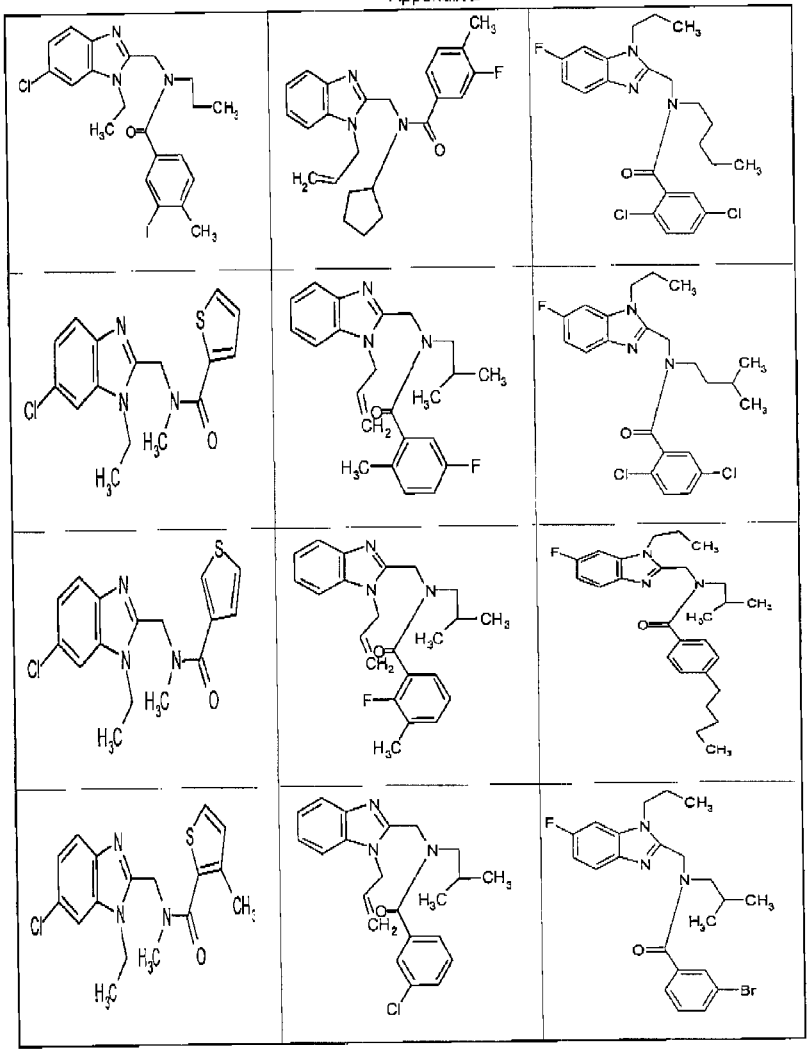
Appendix 2

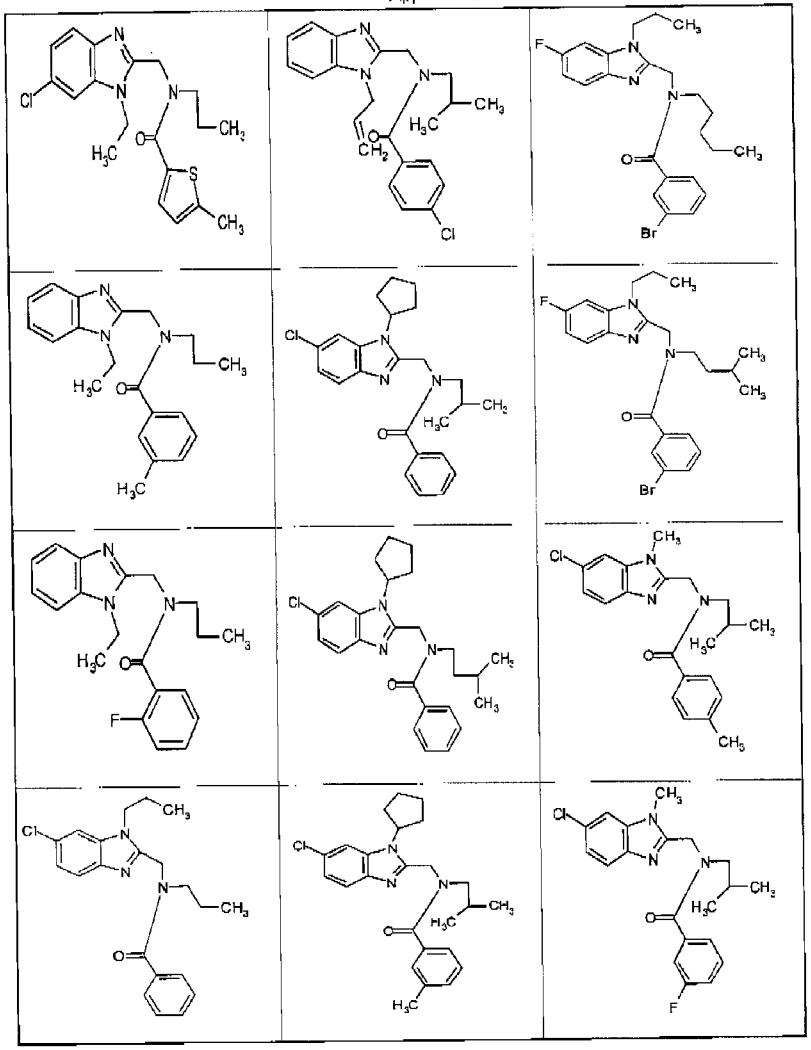

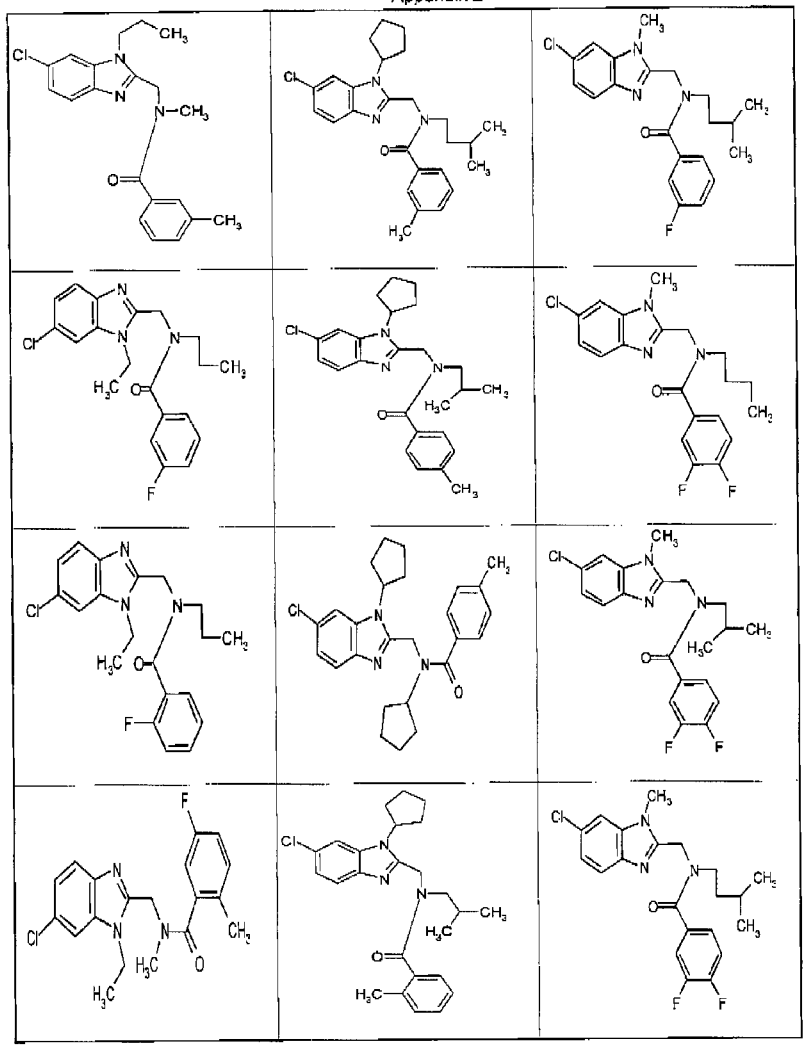
Appendix 2

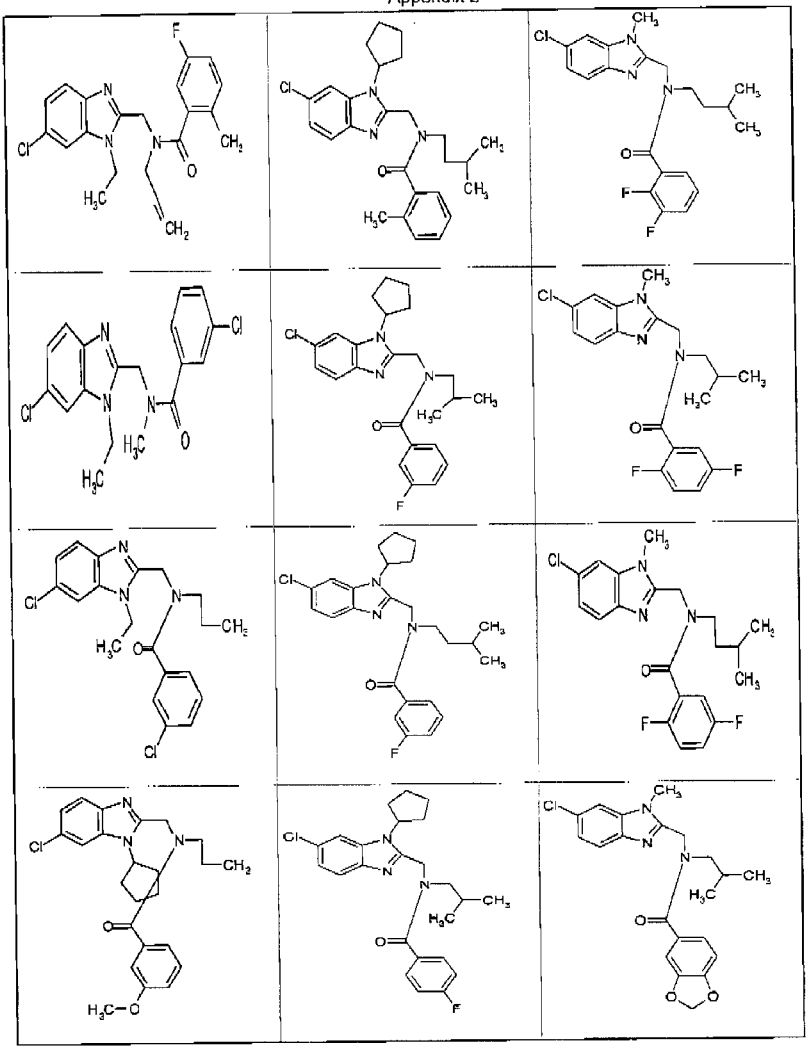
Appendix 2

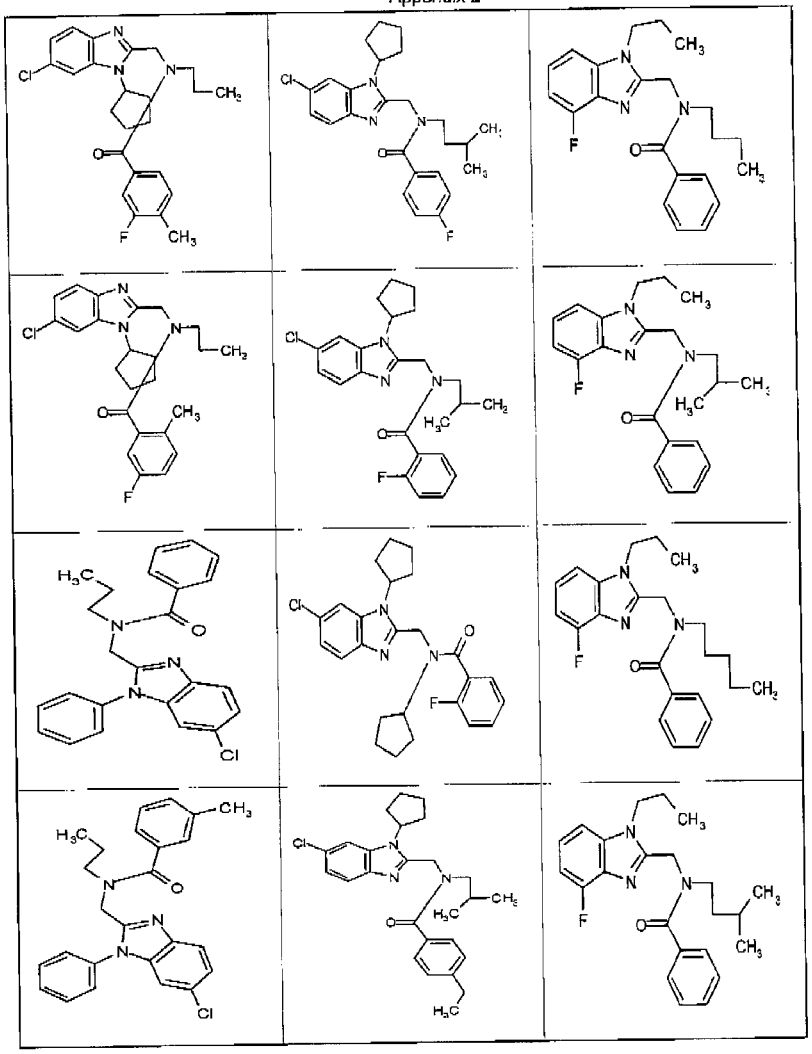

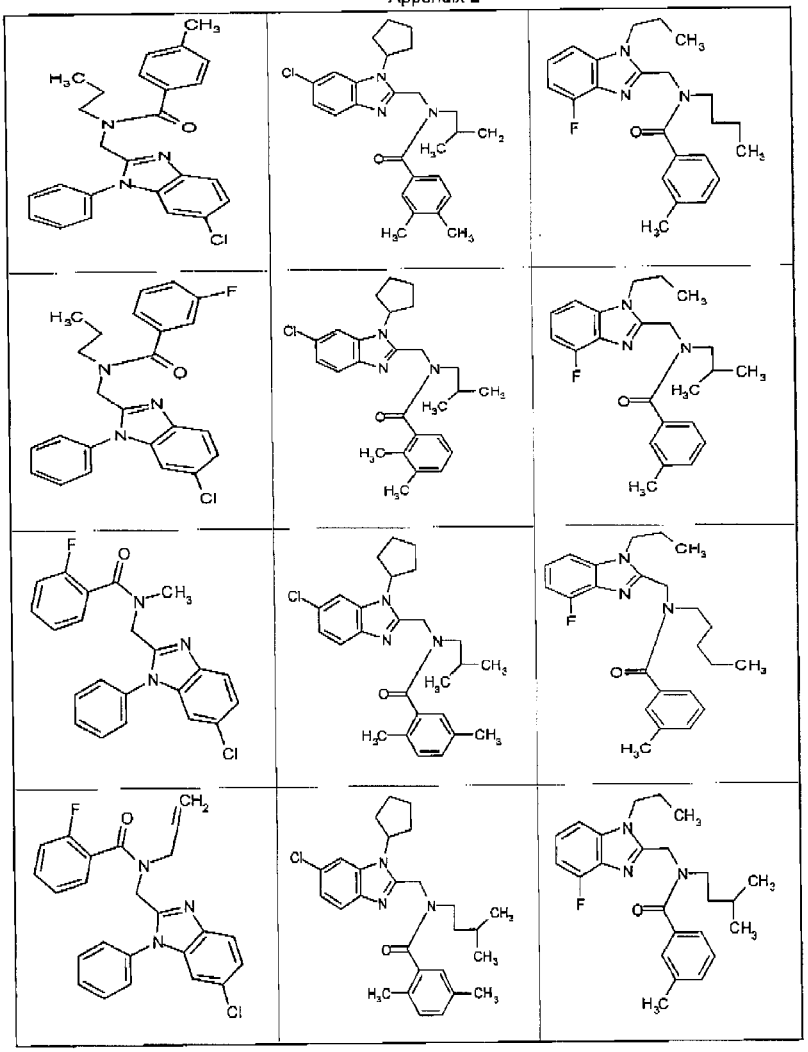
Appendix 2

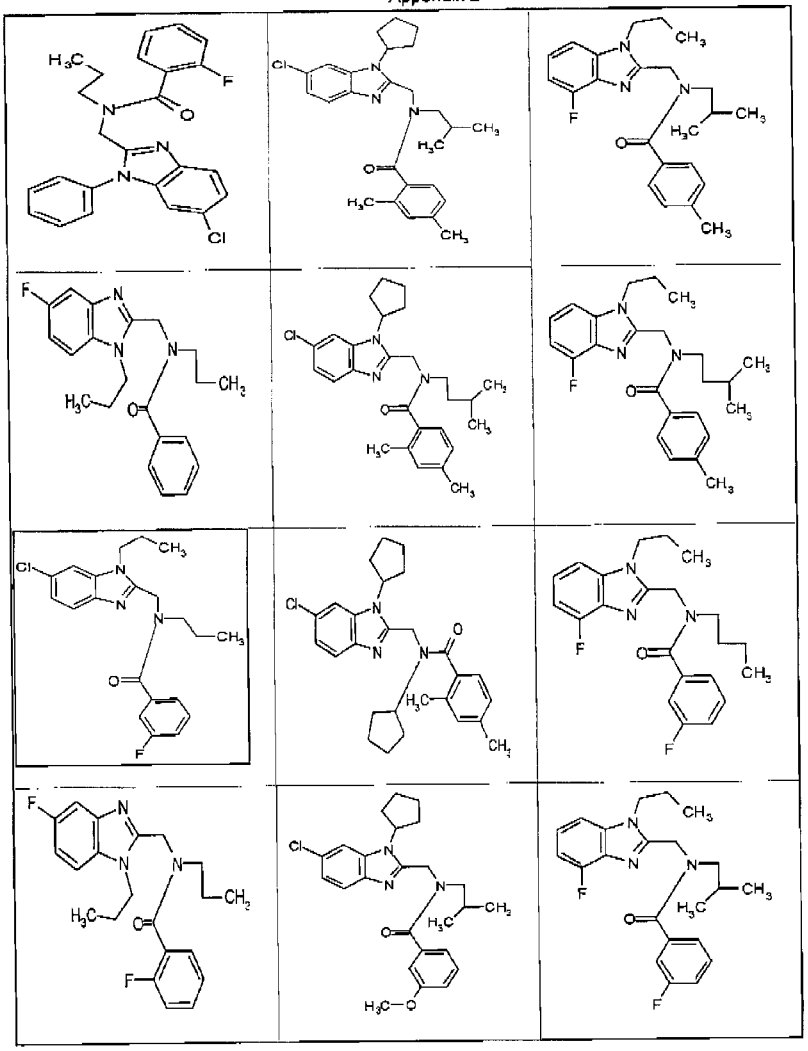

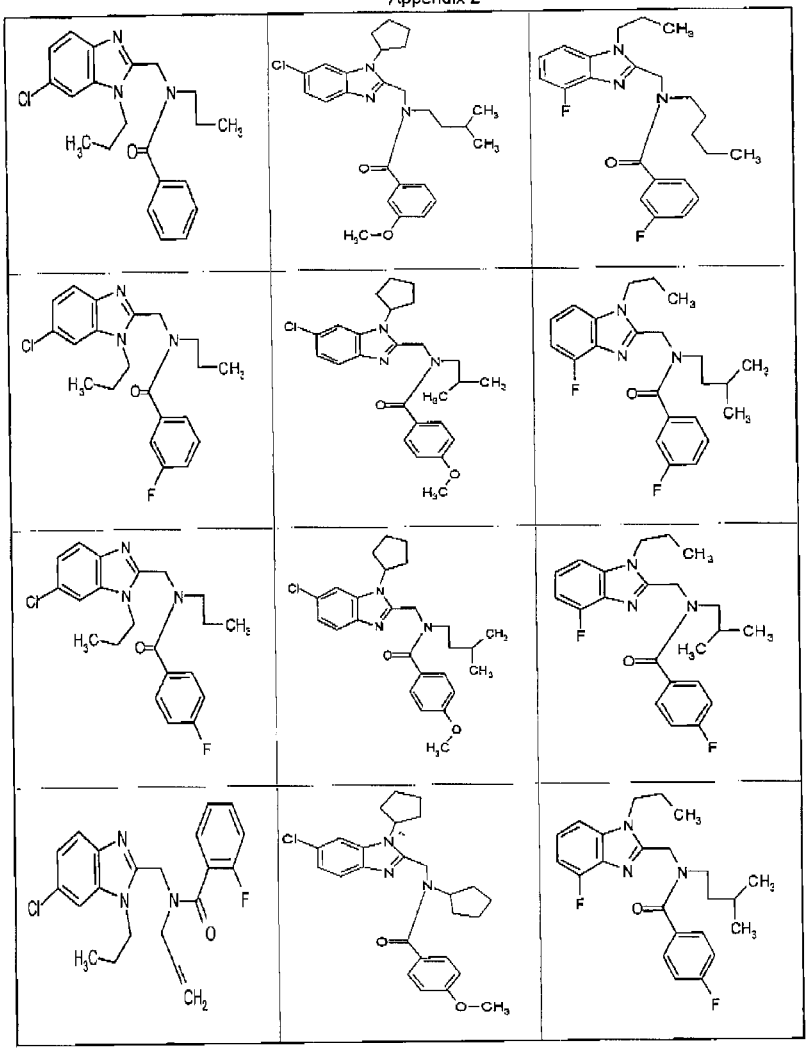
Appendix 2

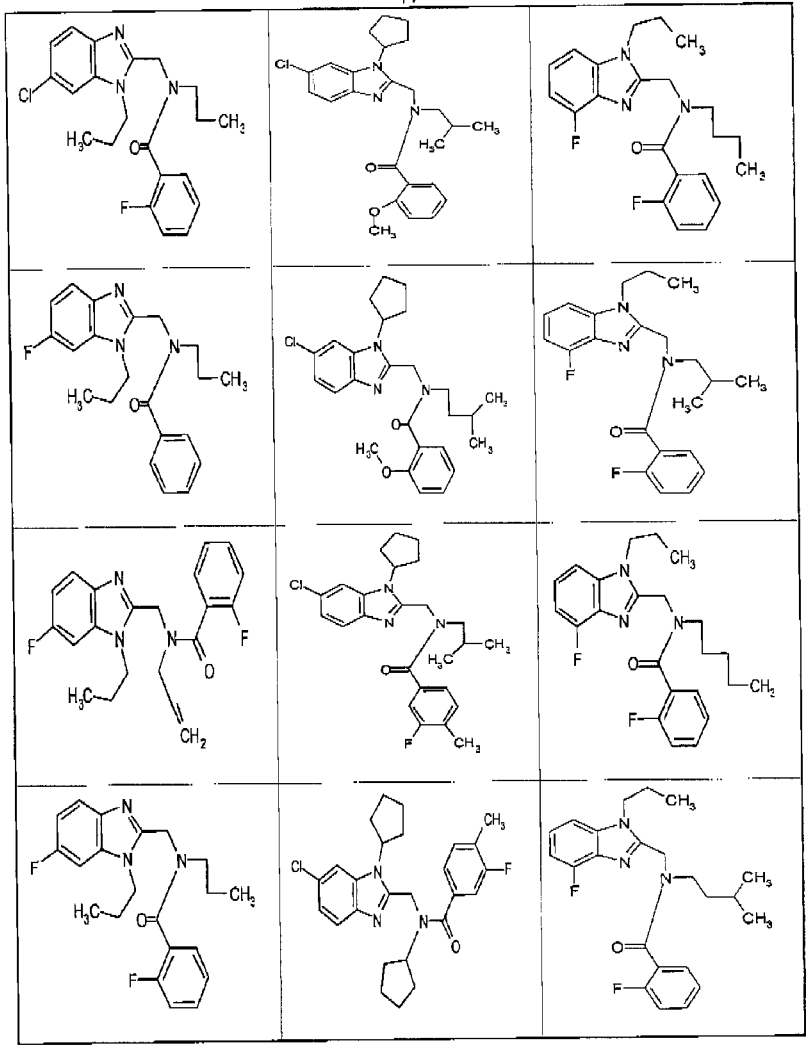
Appendix 2

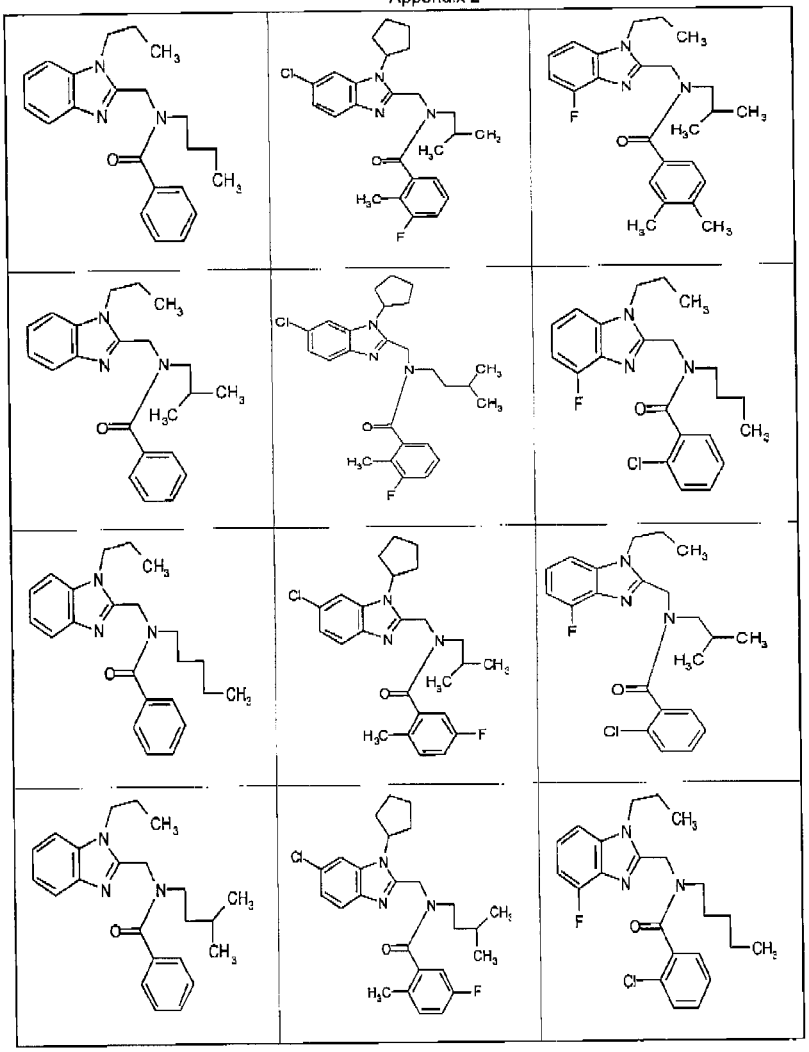
Appendix 2

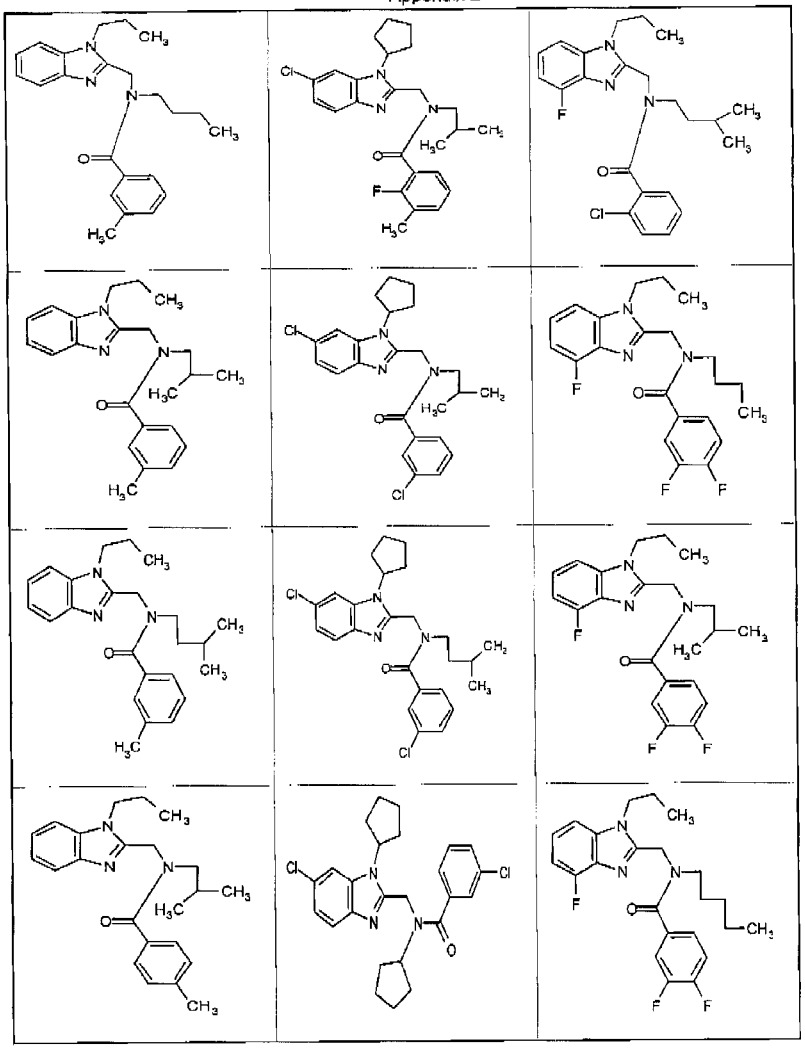

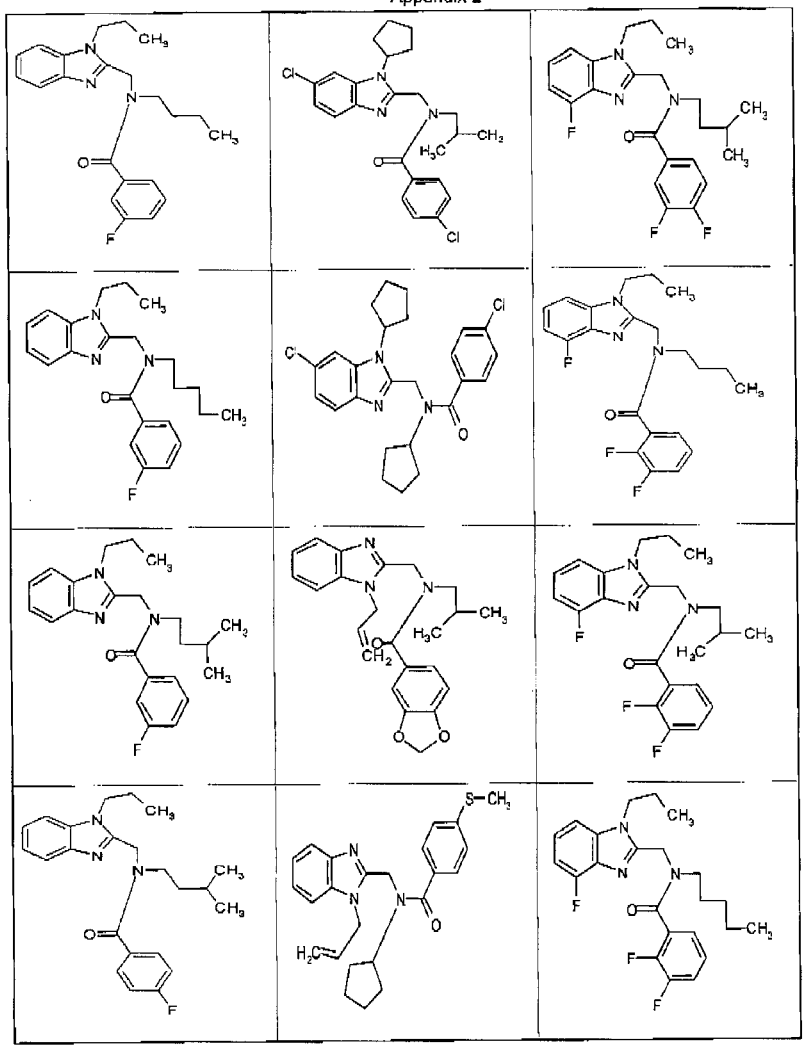

Appendix 2
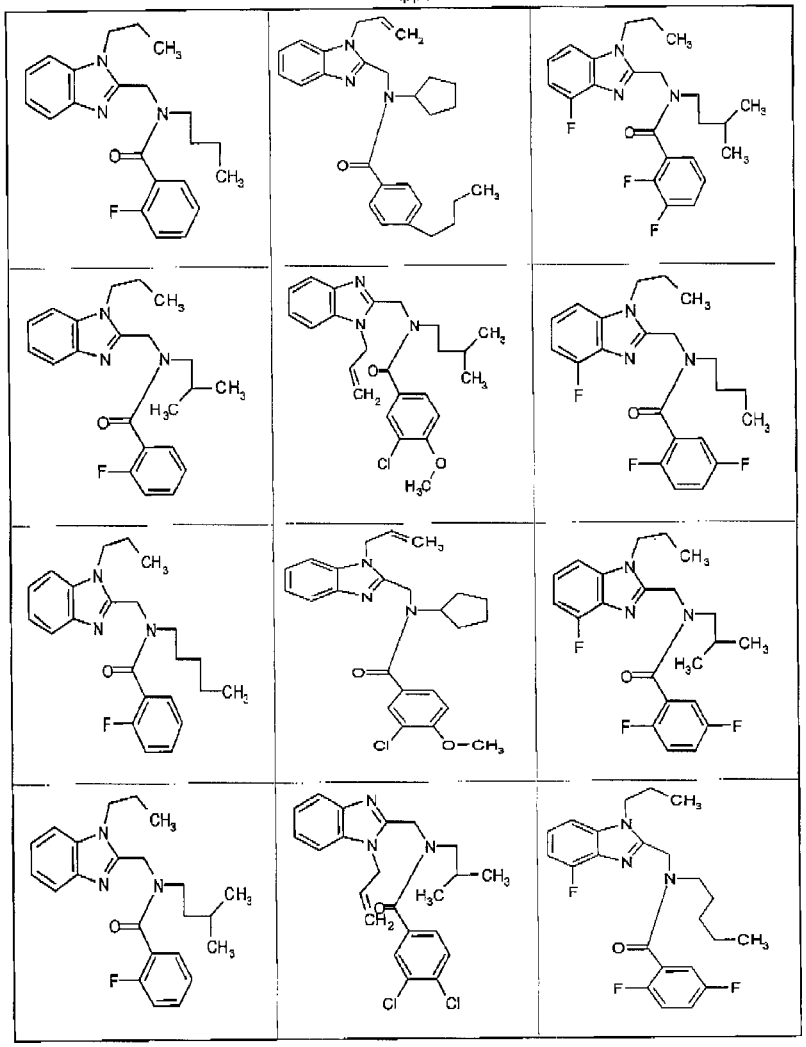

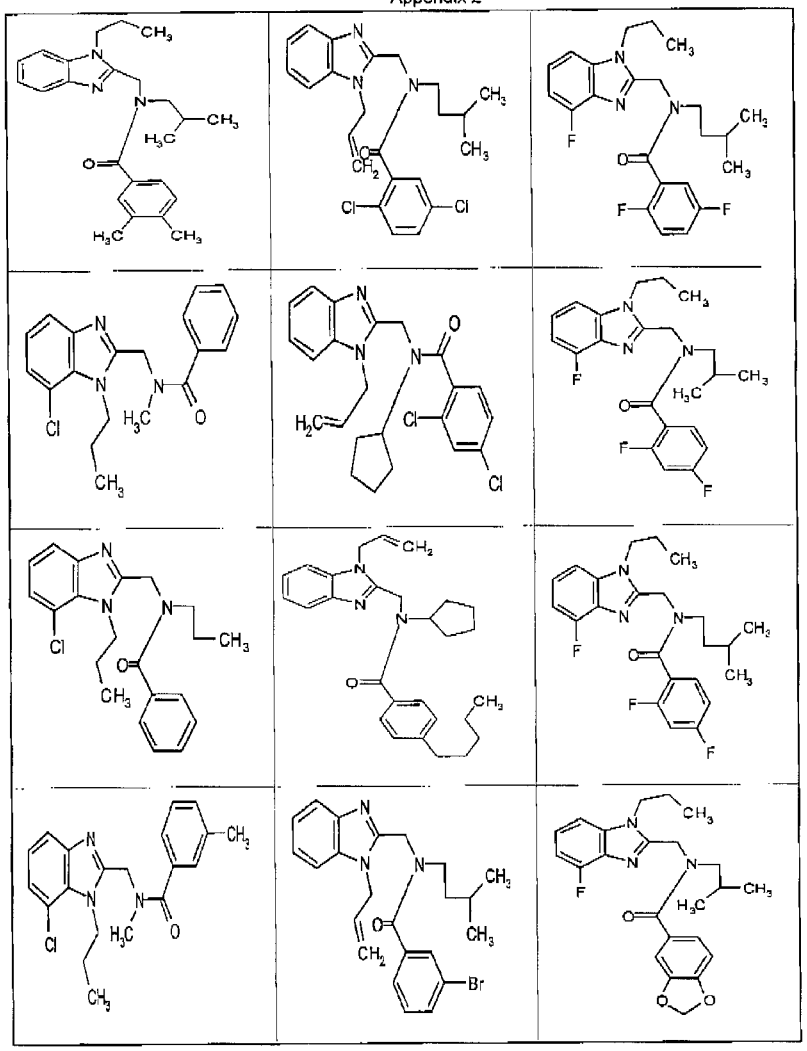
Appendix 2

Appendix 2
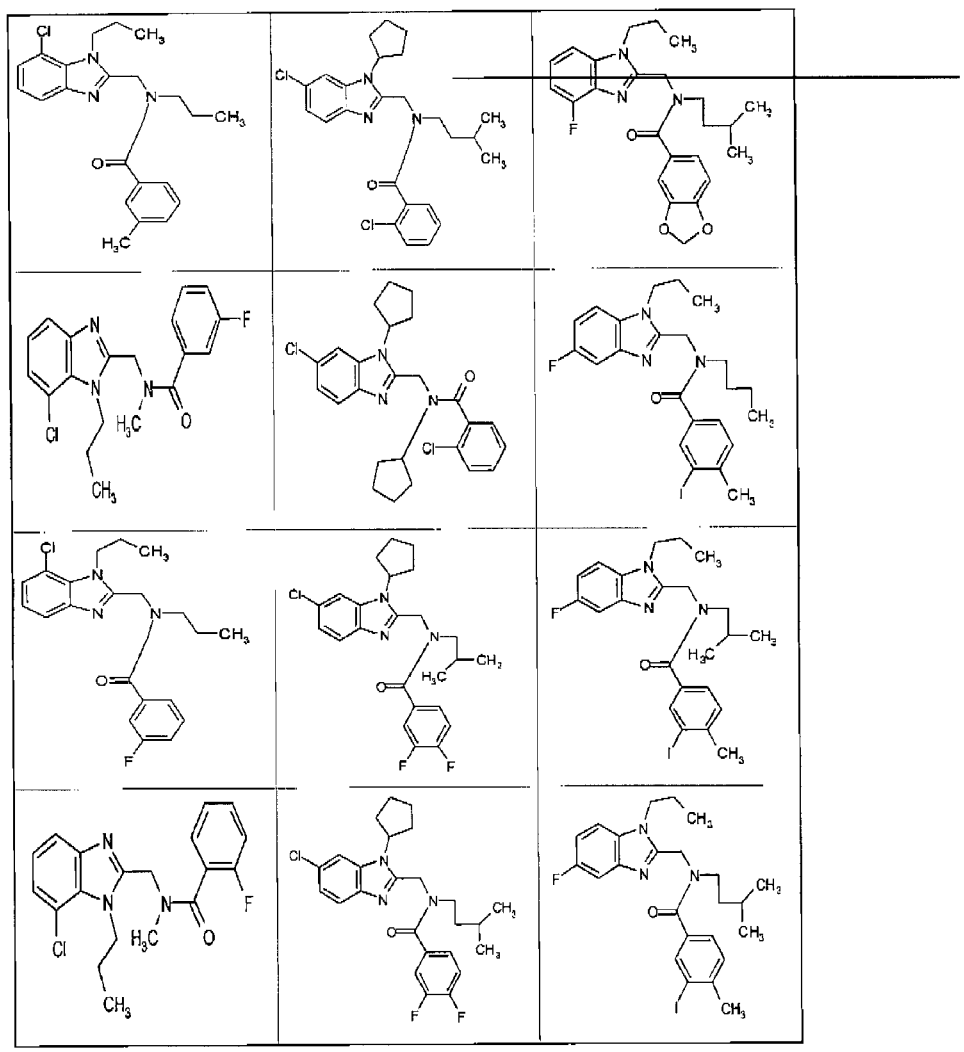

Appendix 2
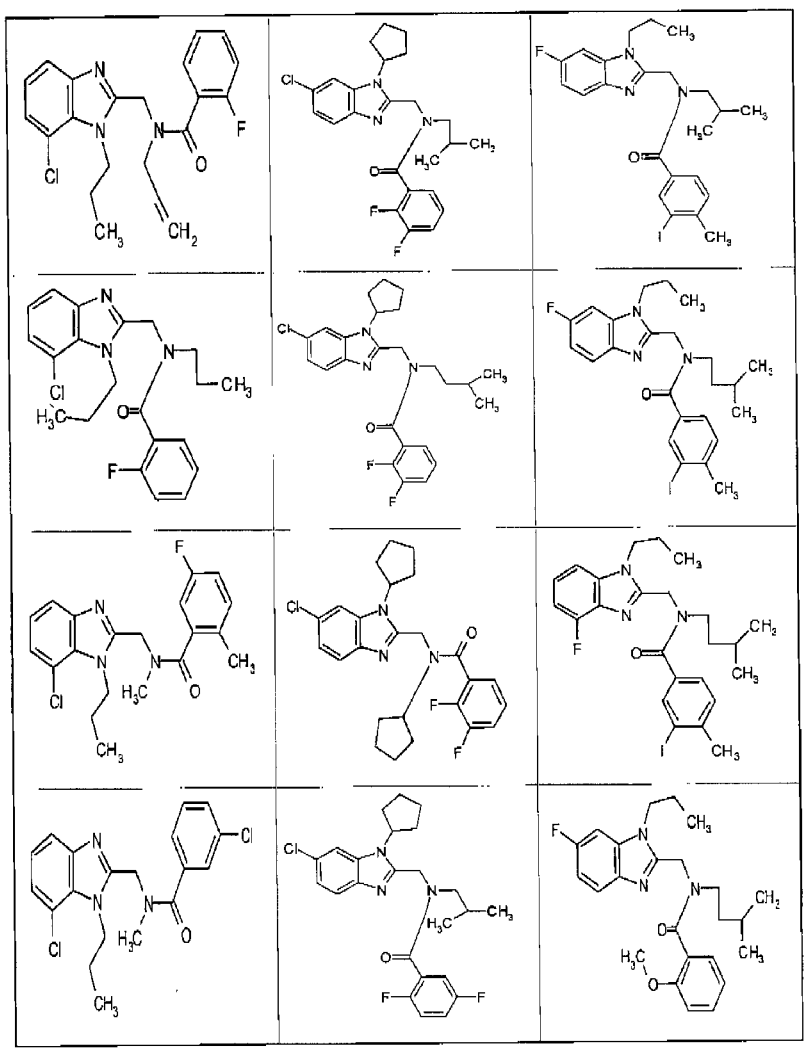

Appendix 2
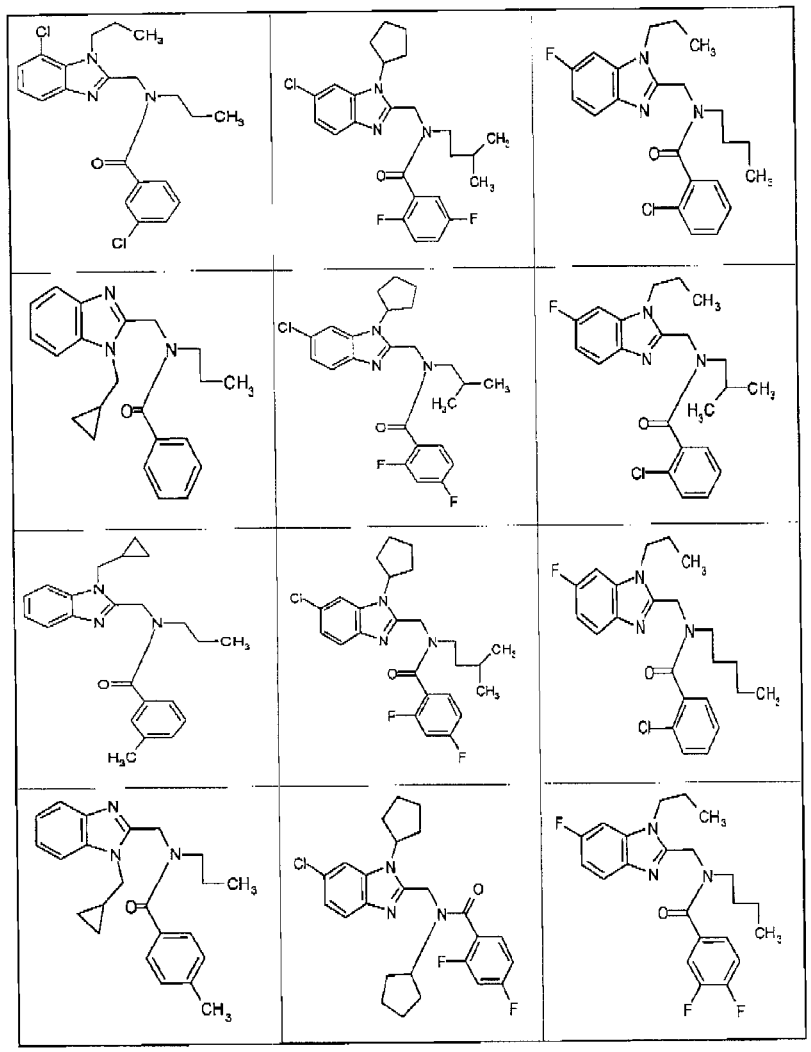
259

Appendix 2
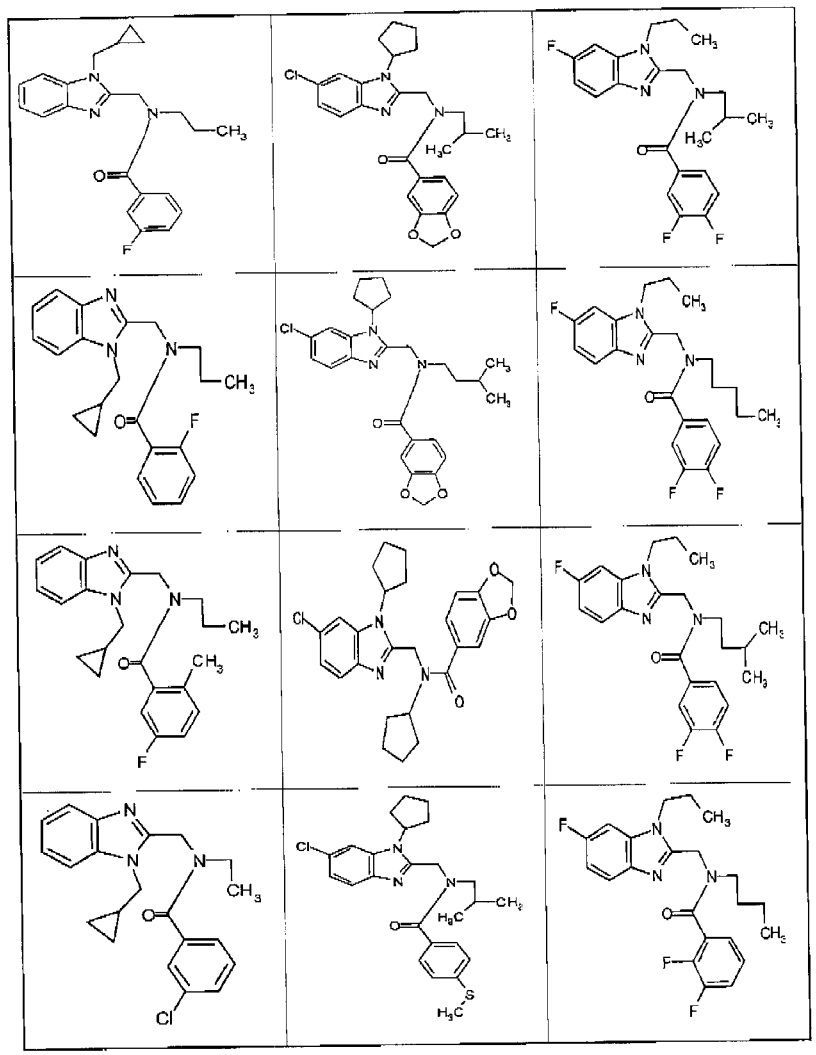

Appendix 2
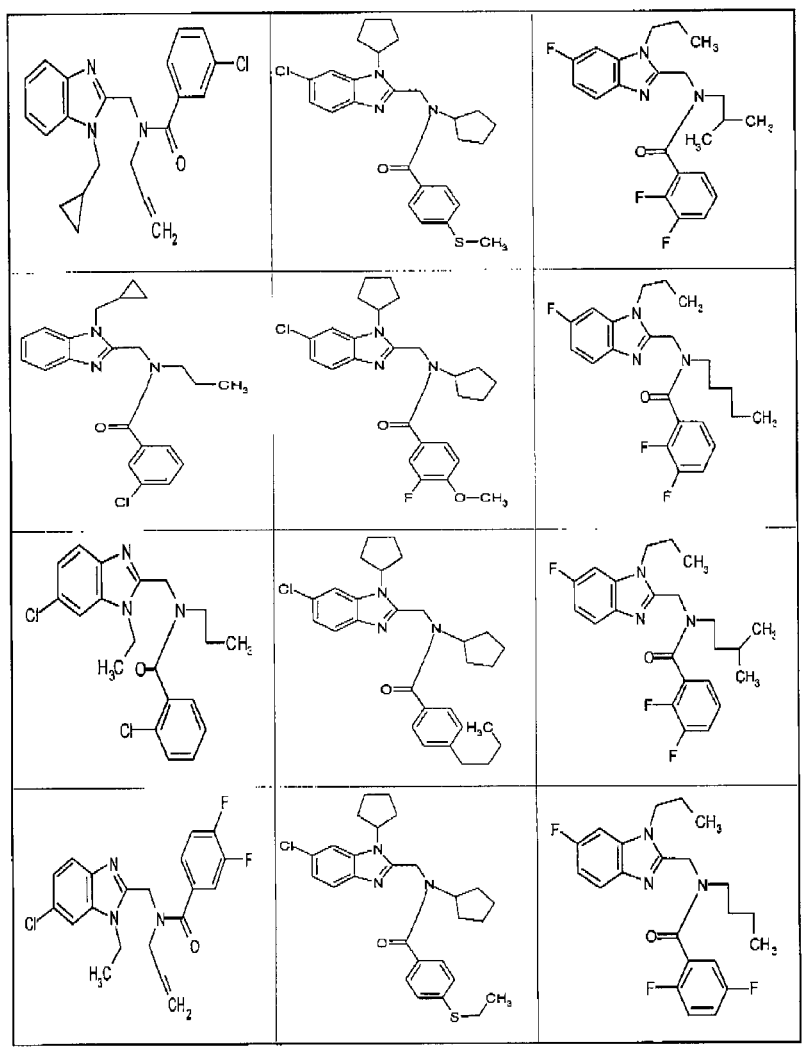

Appendix 2
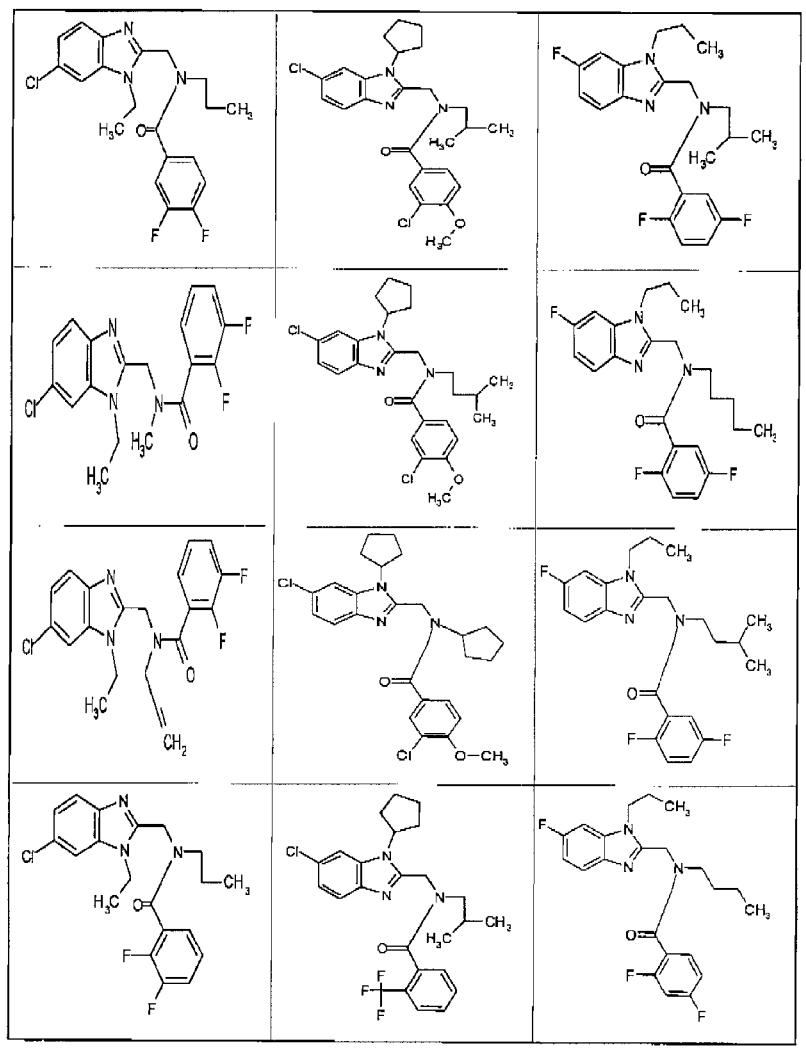

Appendix 2
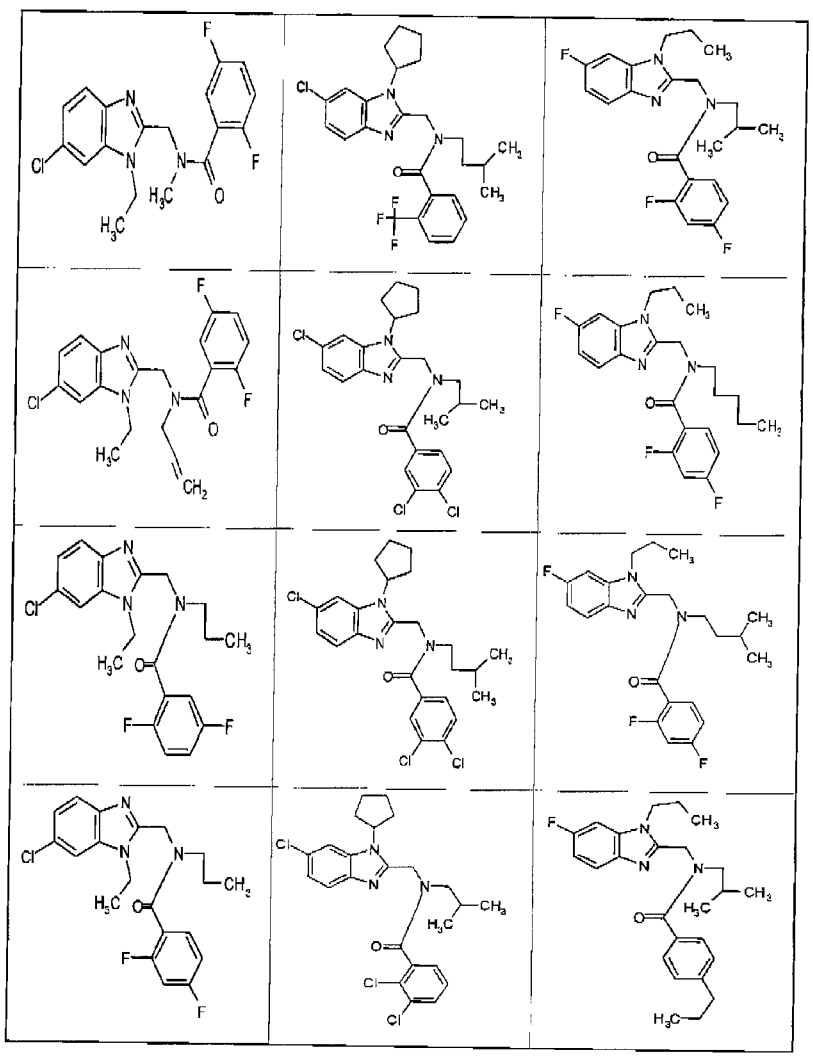

Appendix 2
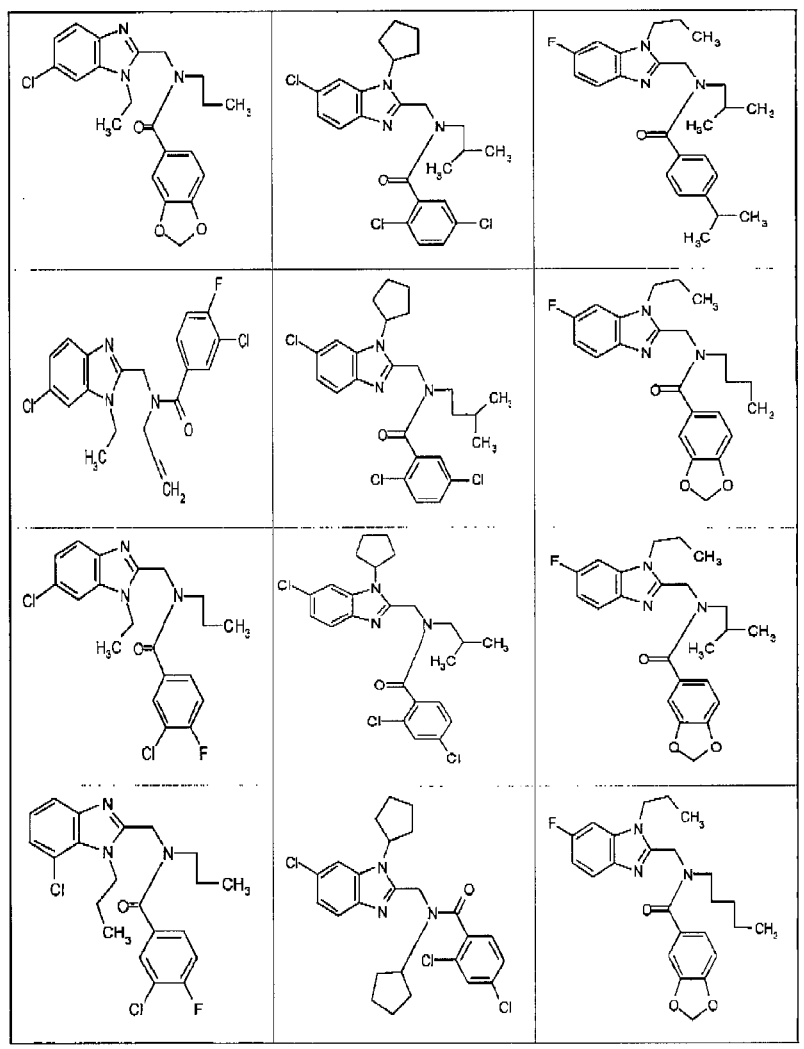

Appendix 2
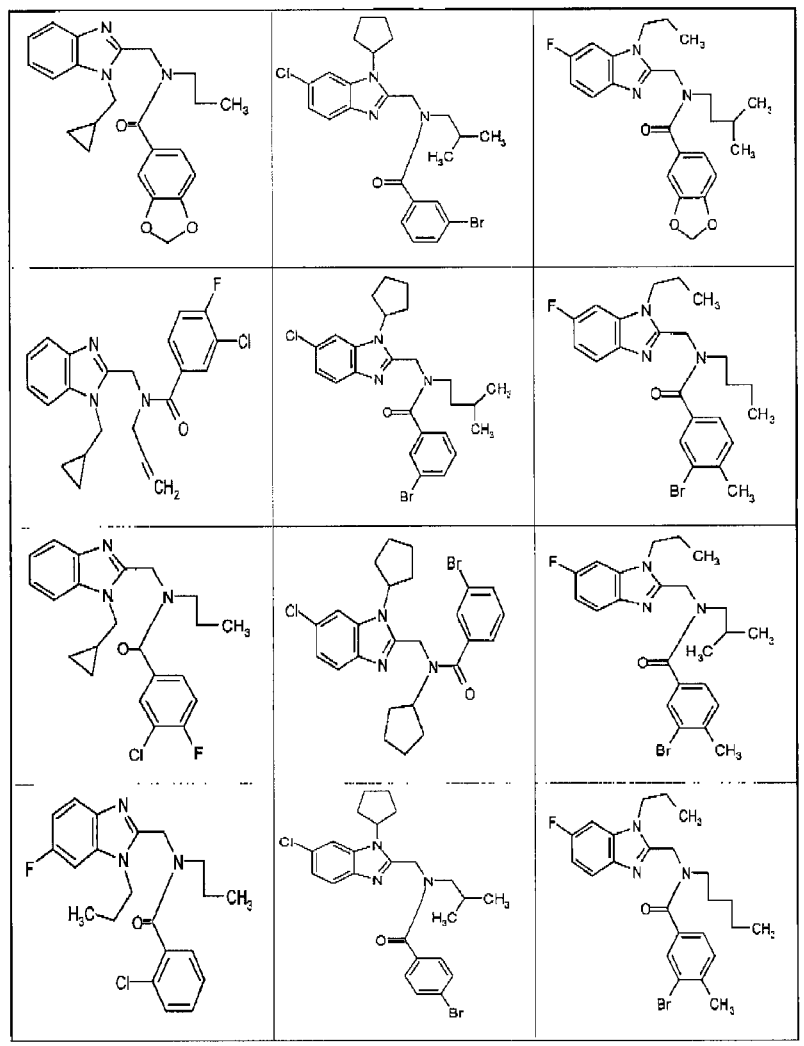

Appendix 2
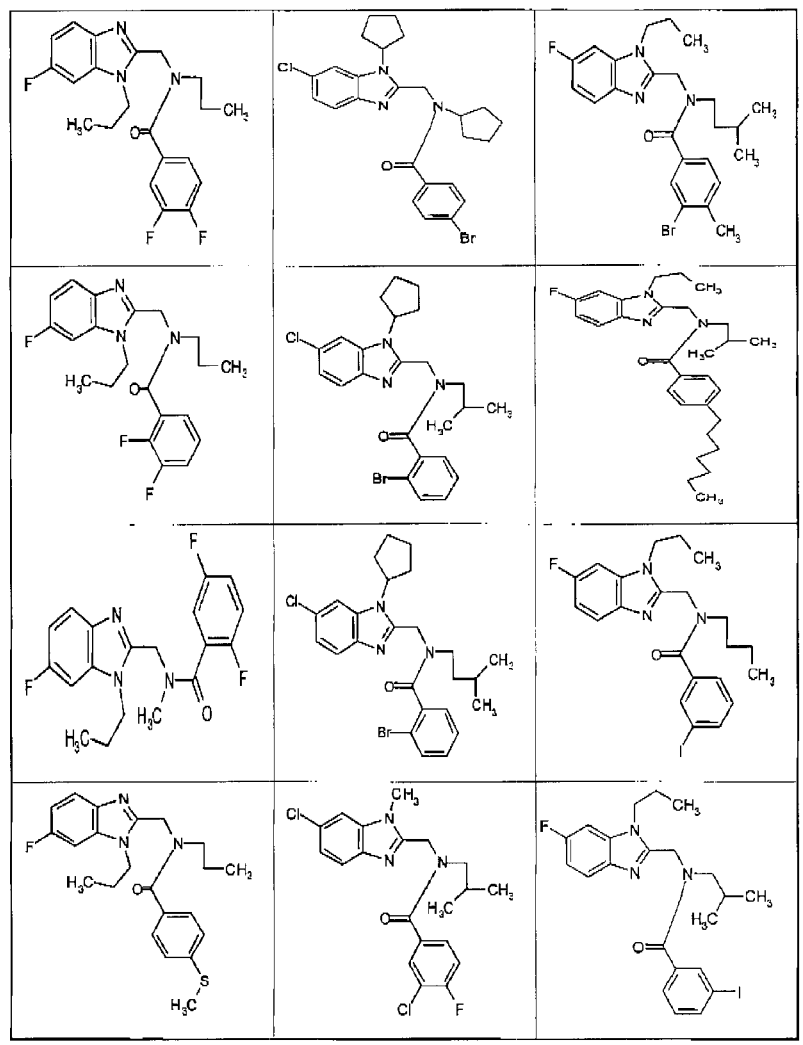

Appendix 2
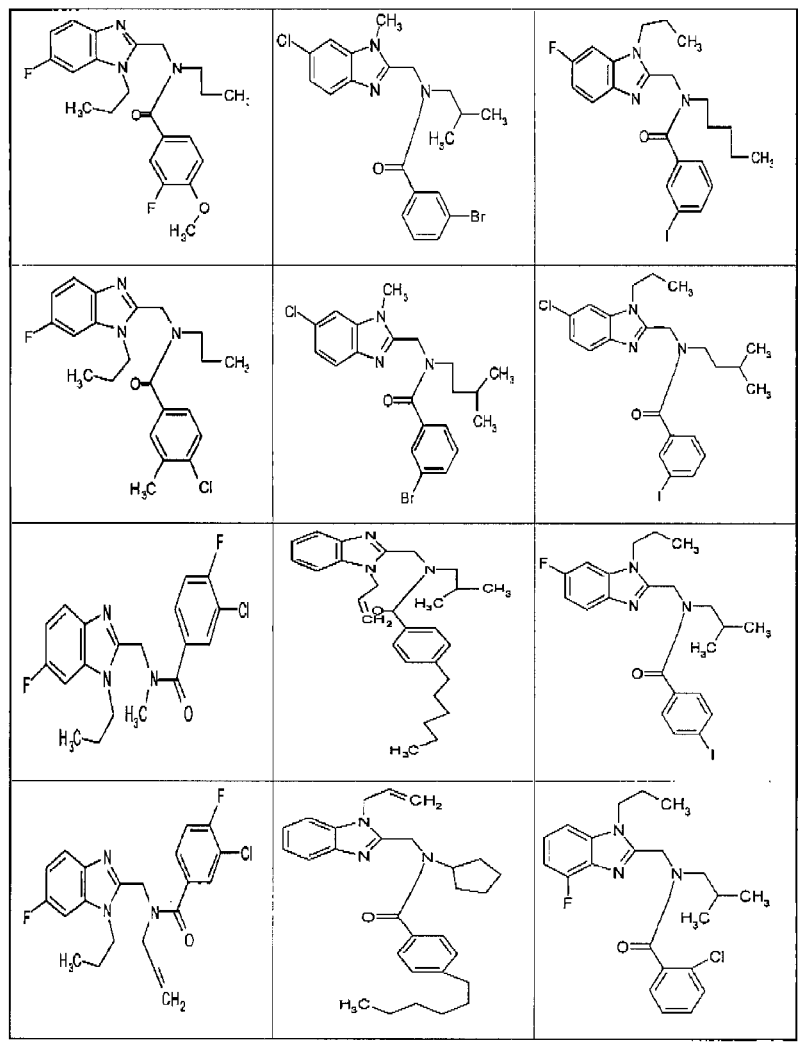

Appendix 2
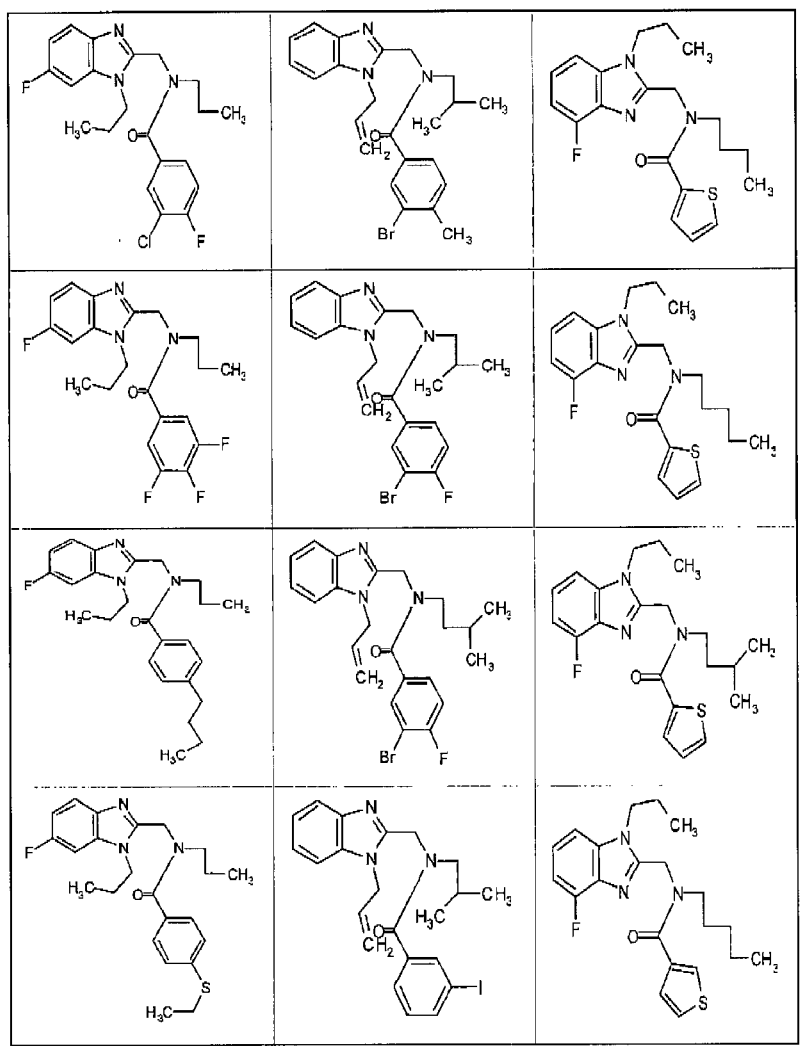

Appendix 2
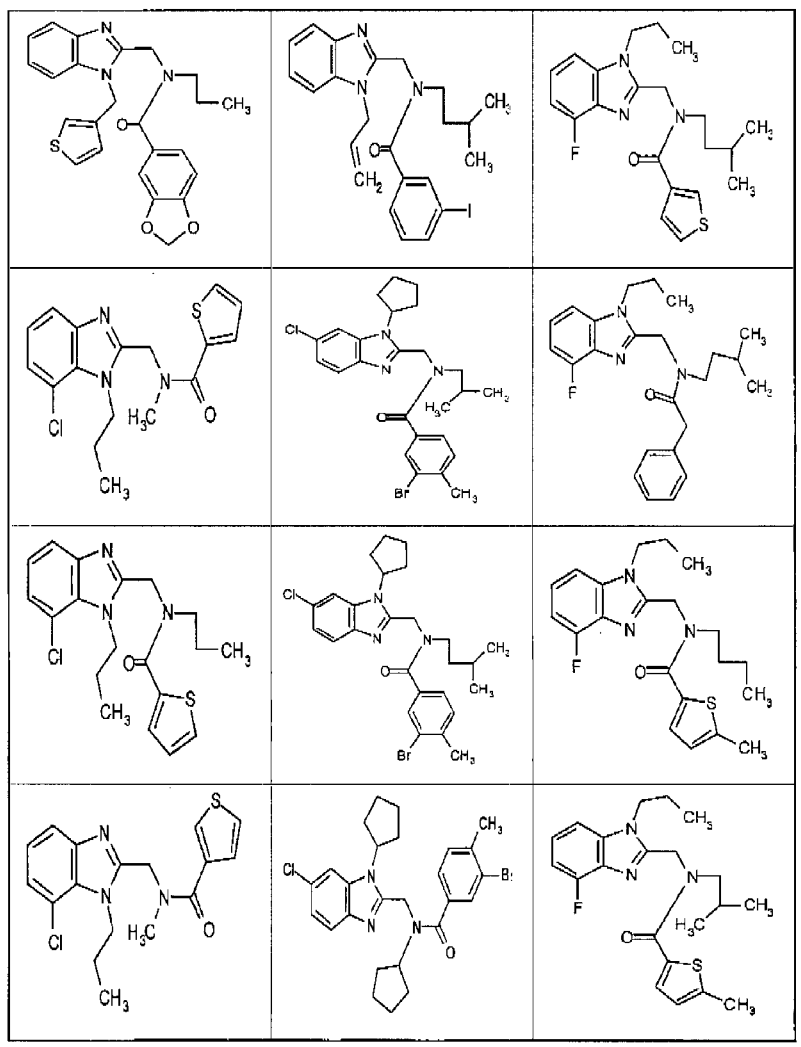

Appendix 2
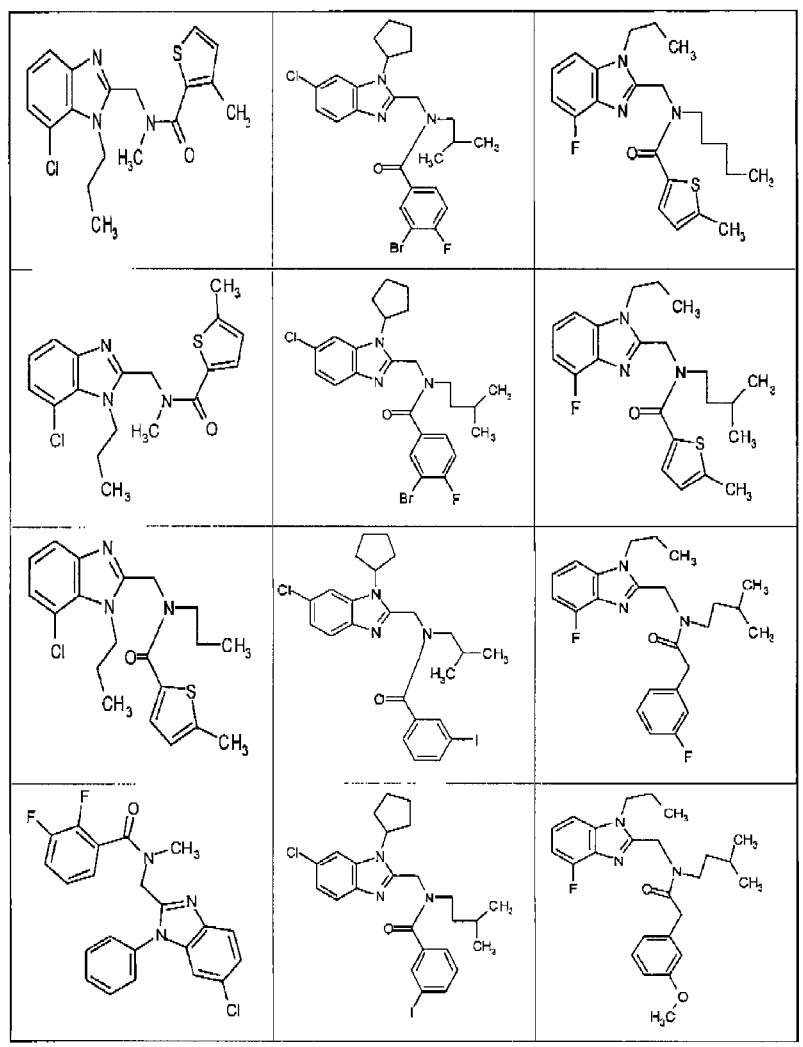

Appendix 2
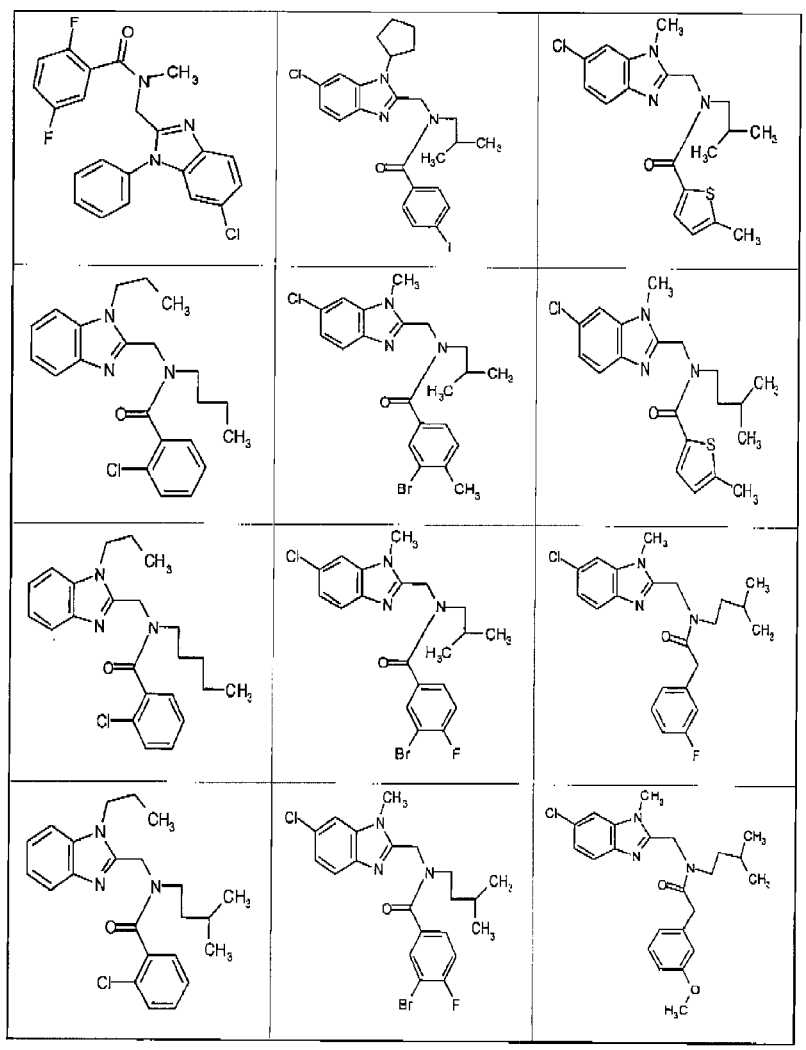

Appendix 2
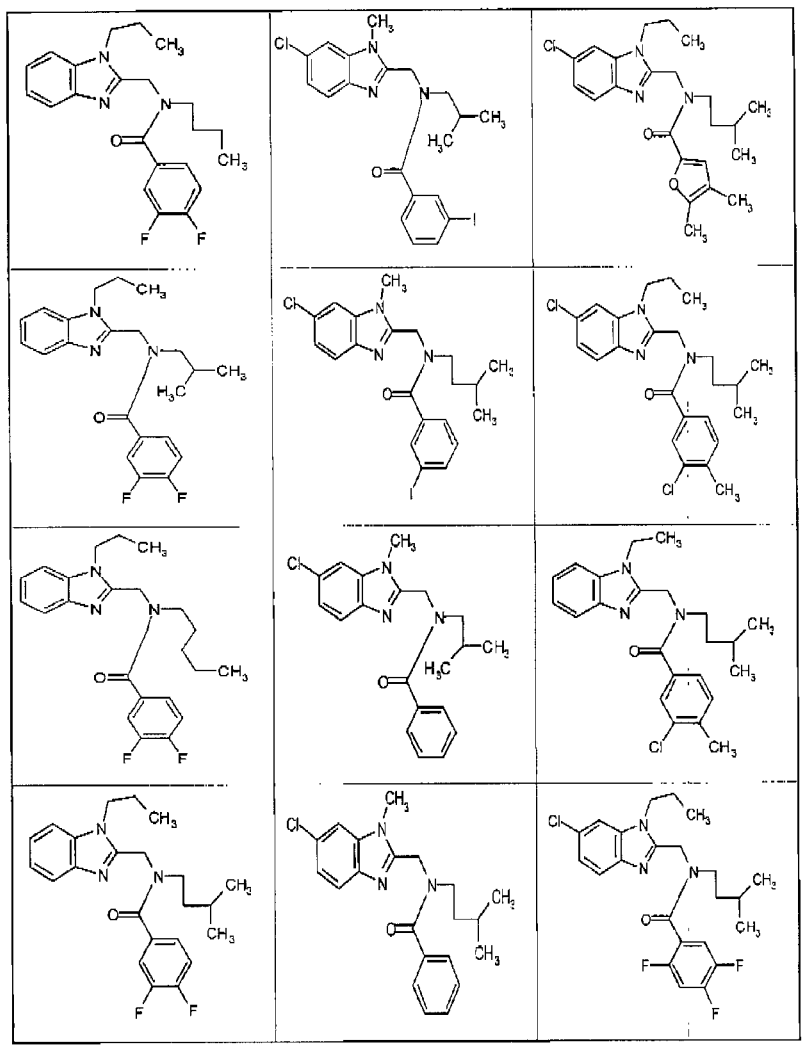

Appendix 2
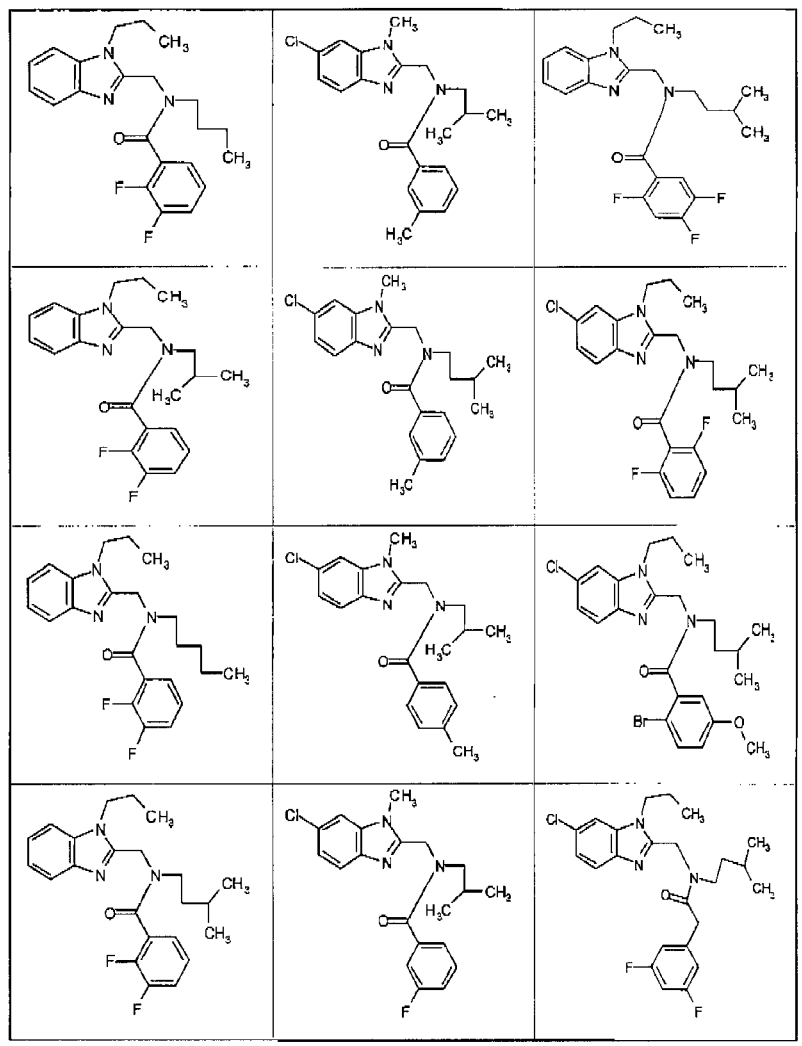

Appendix 2
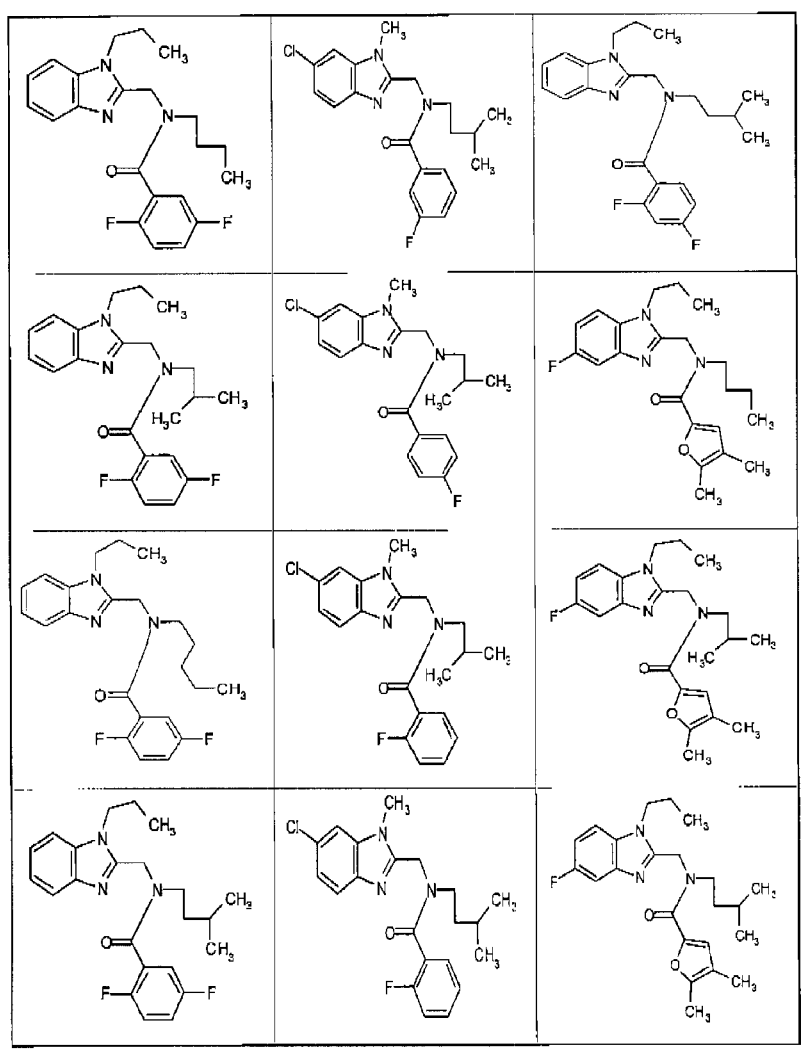

Appendix 2
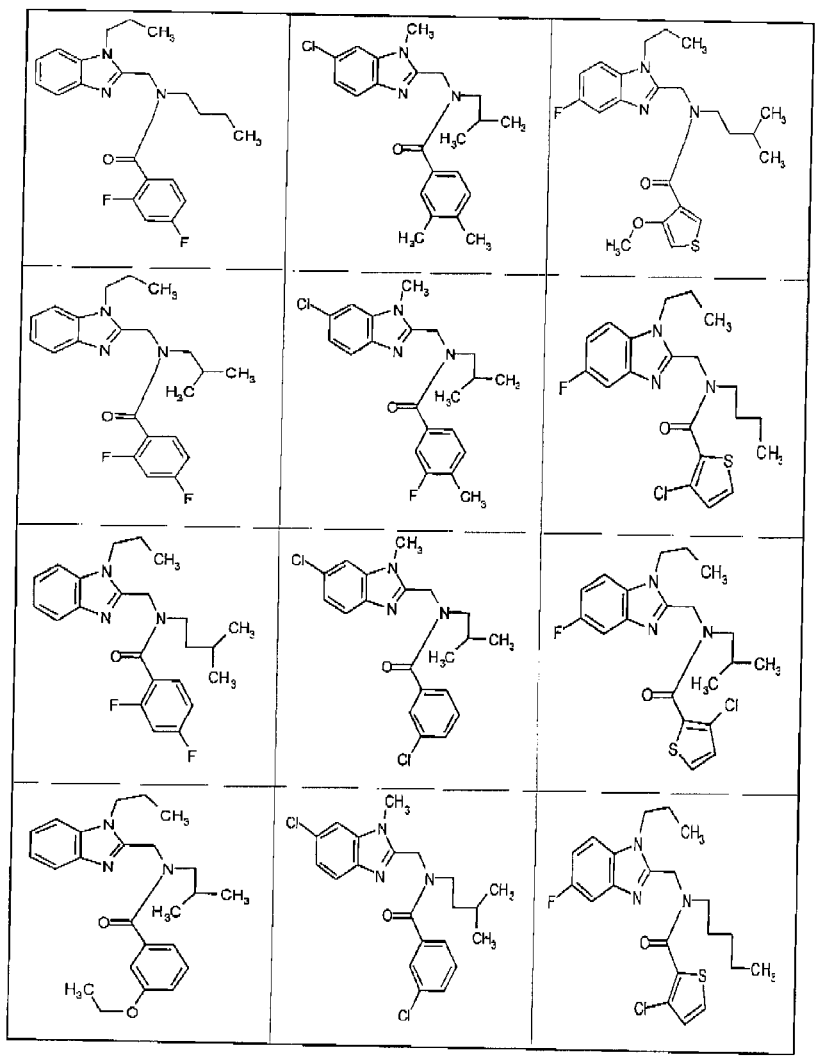

Appendix 2
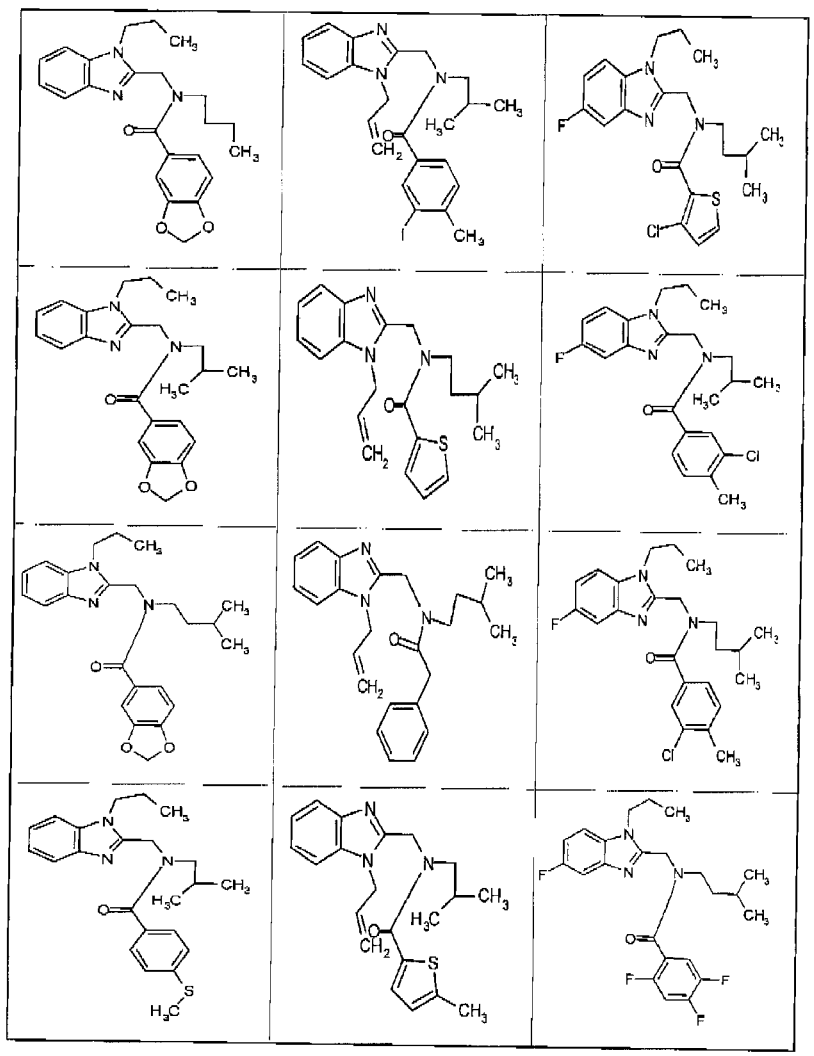

Appendix 2
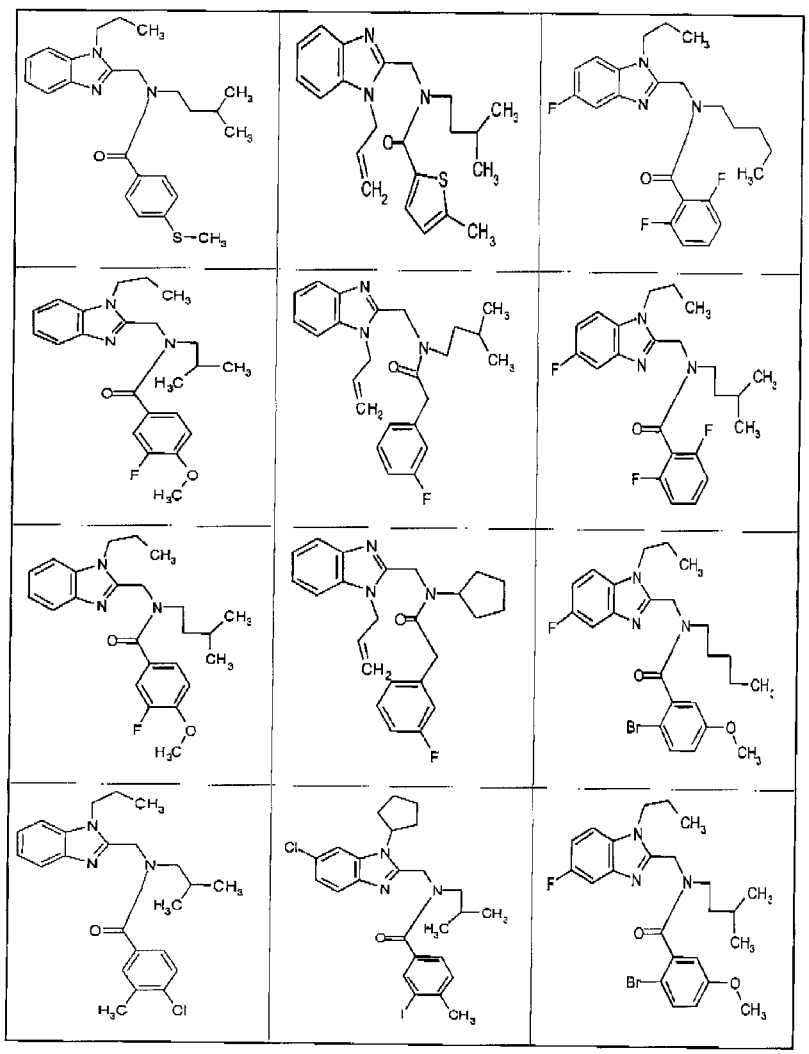

Appendix 2
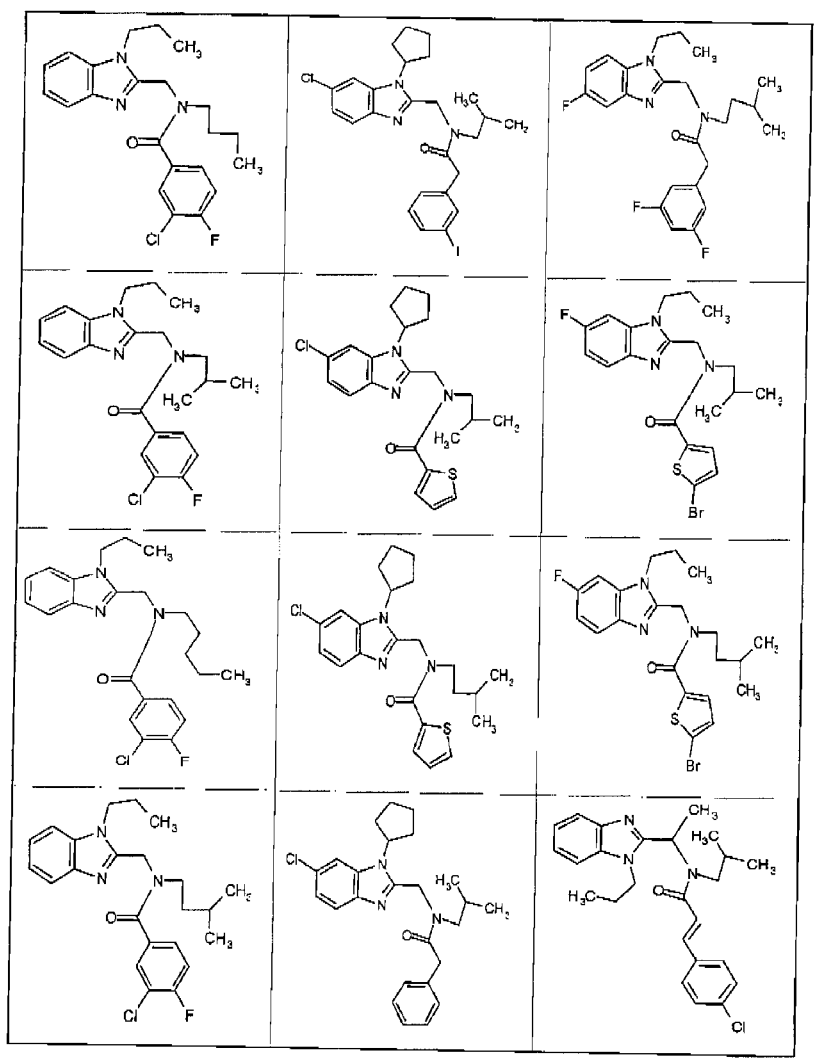

Appendix 2
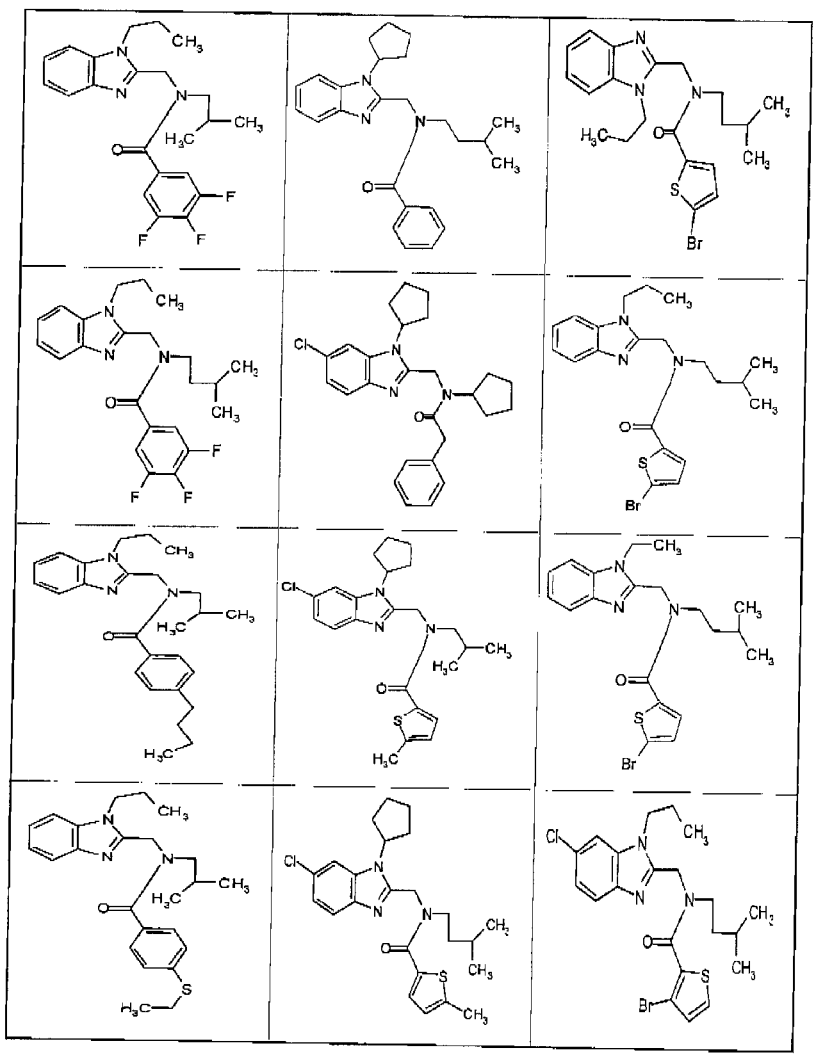

Appendix 2
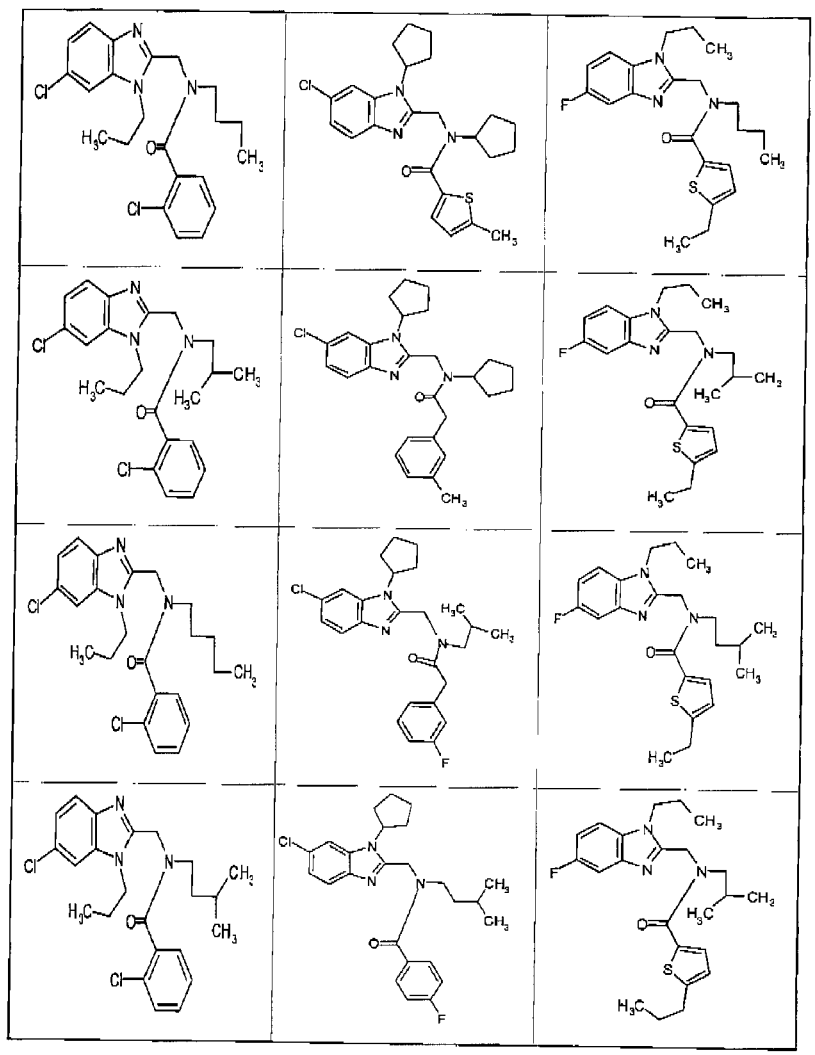

Appendix 2
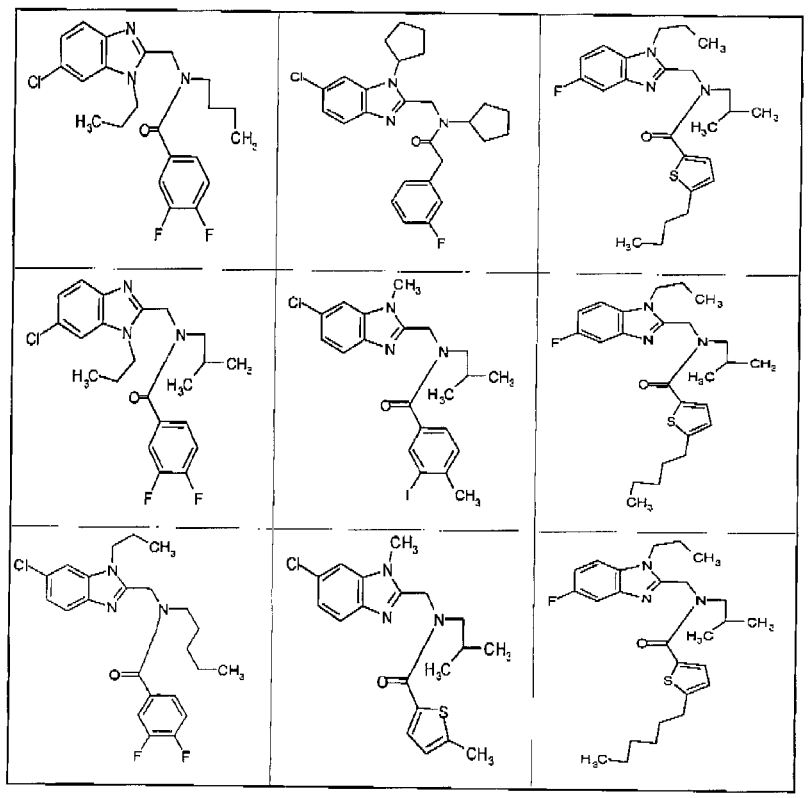

Appendix 2
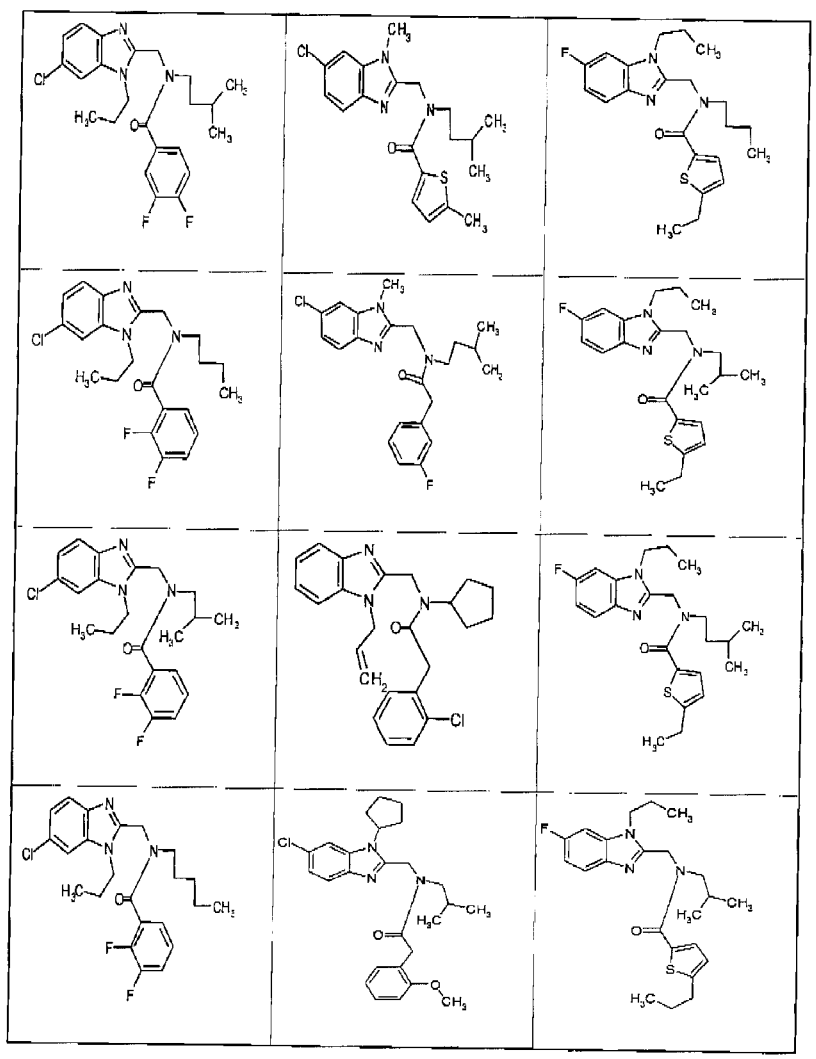

Appendix 2
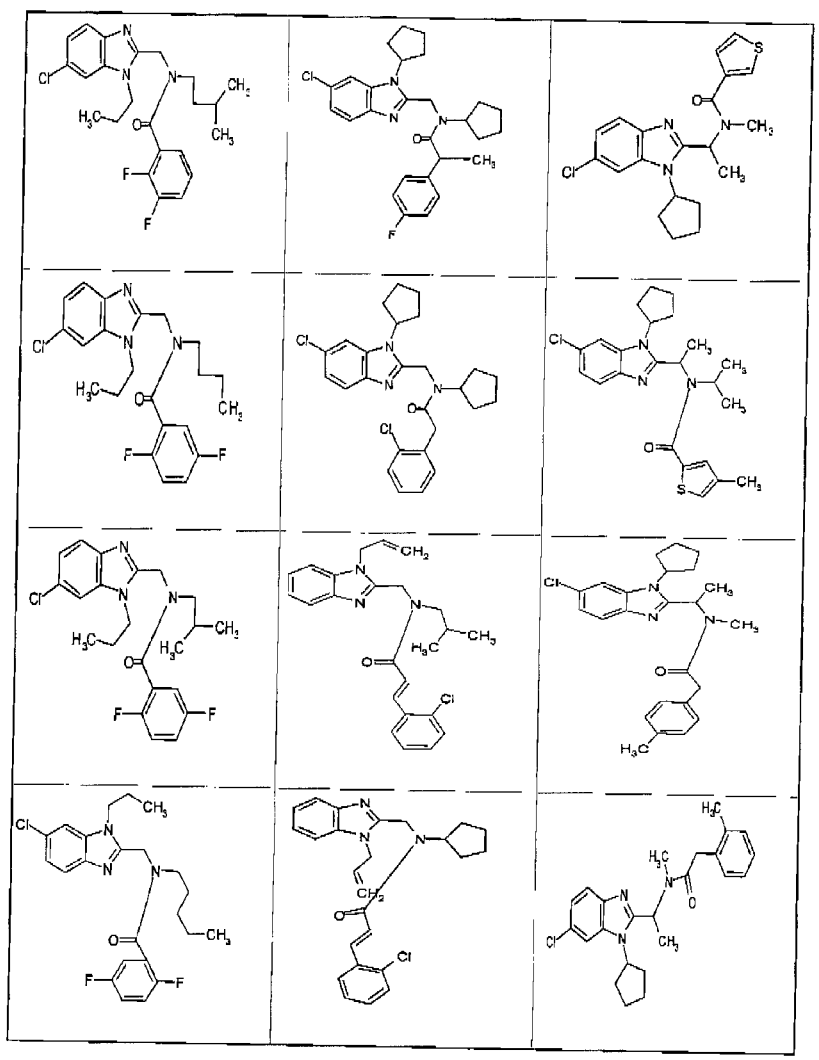

Appendix 2
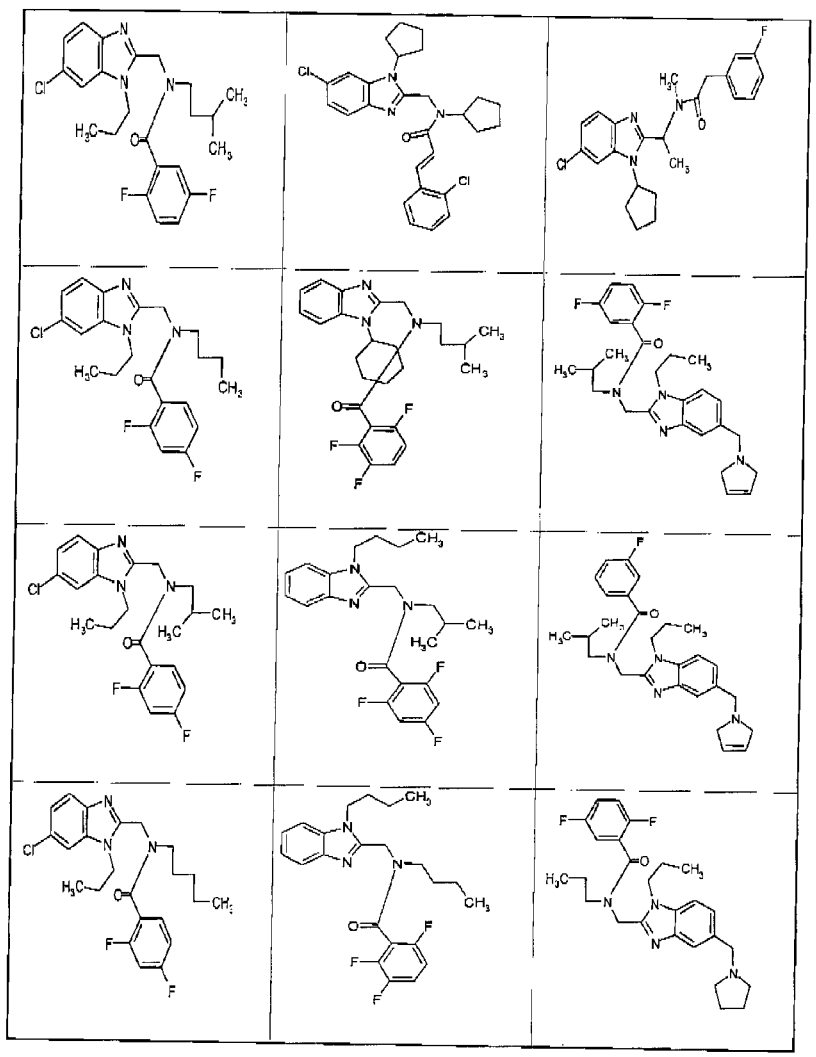

Appendix 2
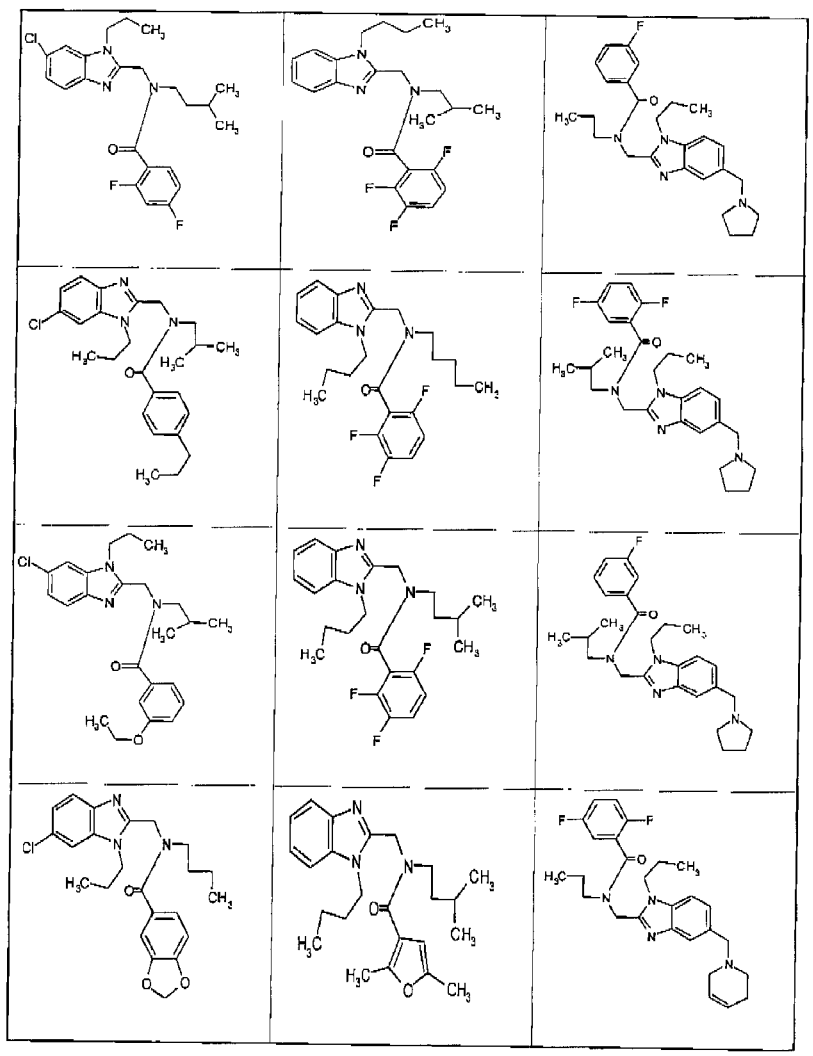

Appendix 2
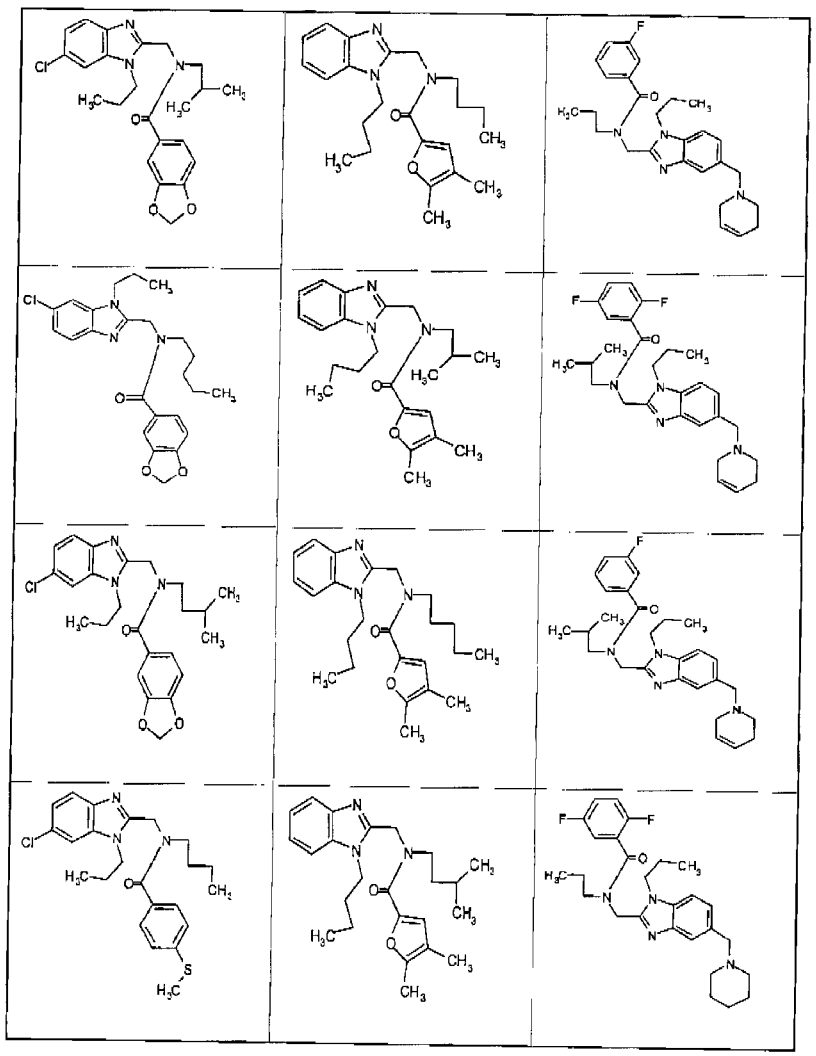

Appendix 2
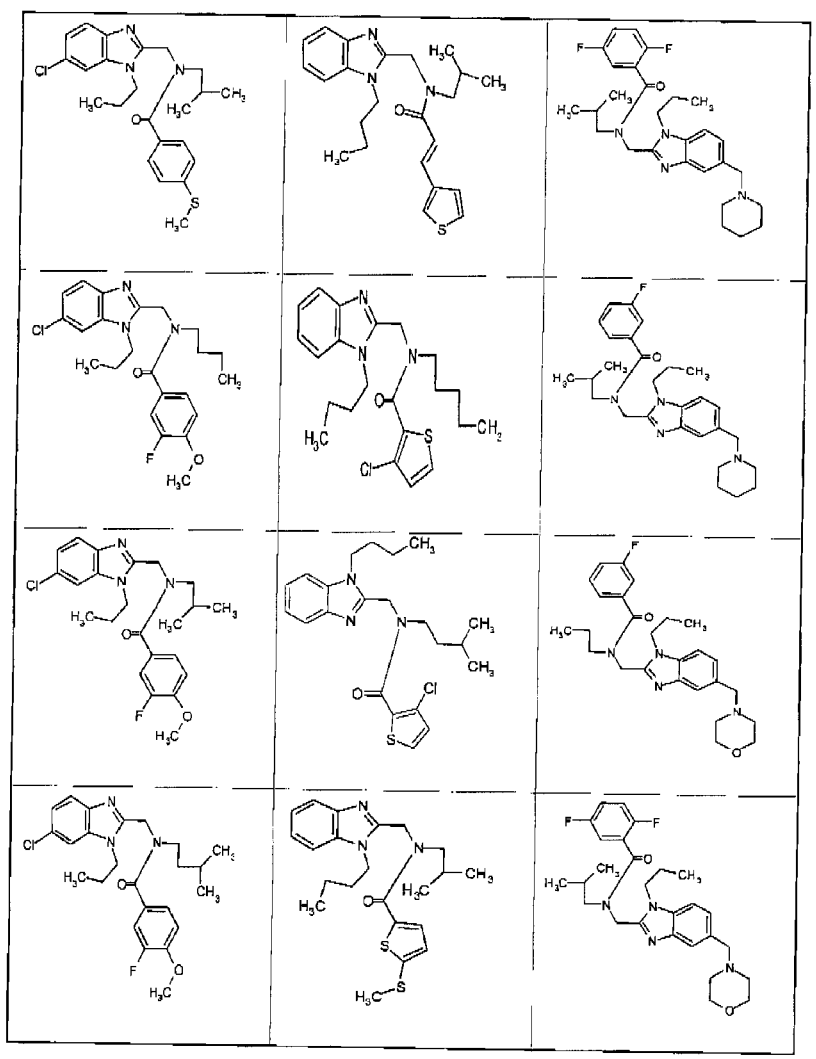

Appendix 2
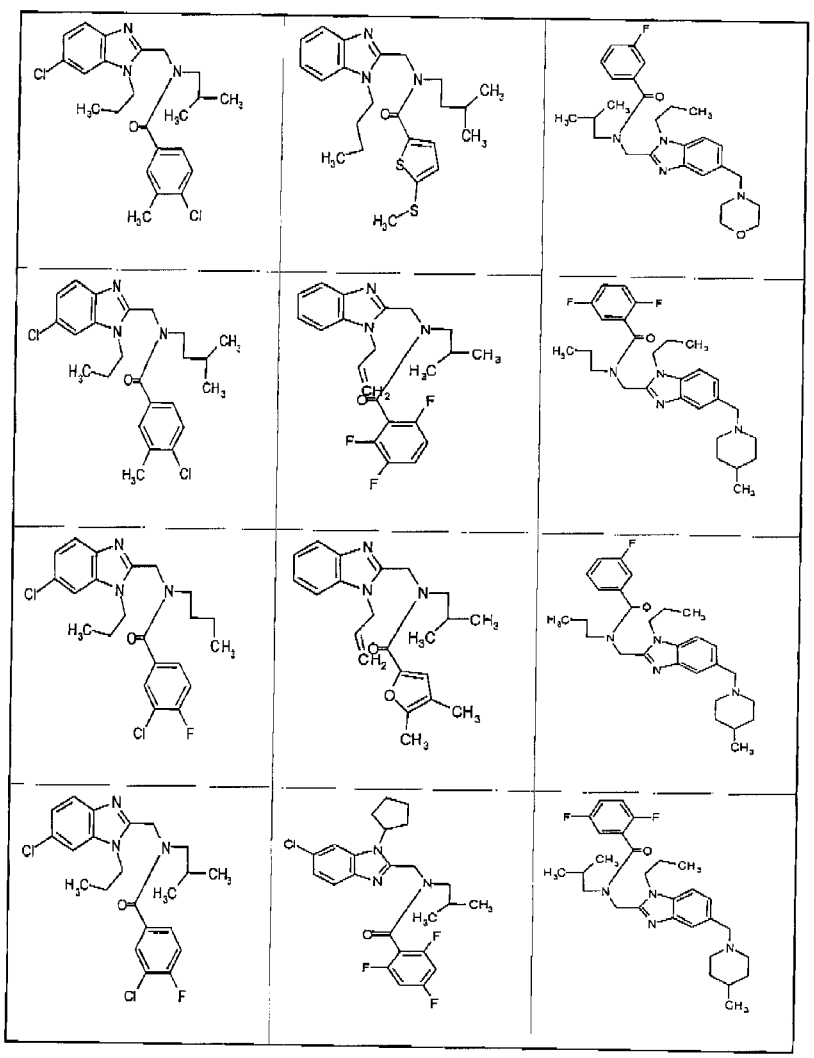

Appendix 2
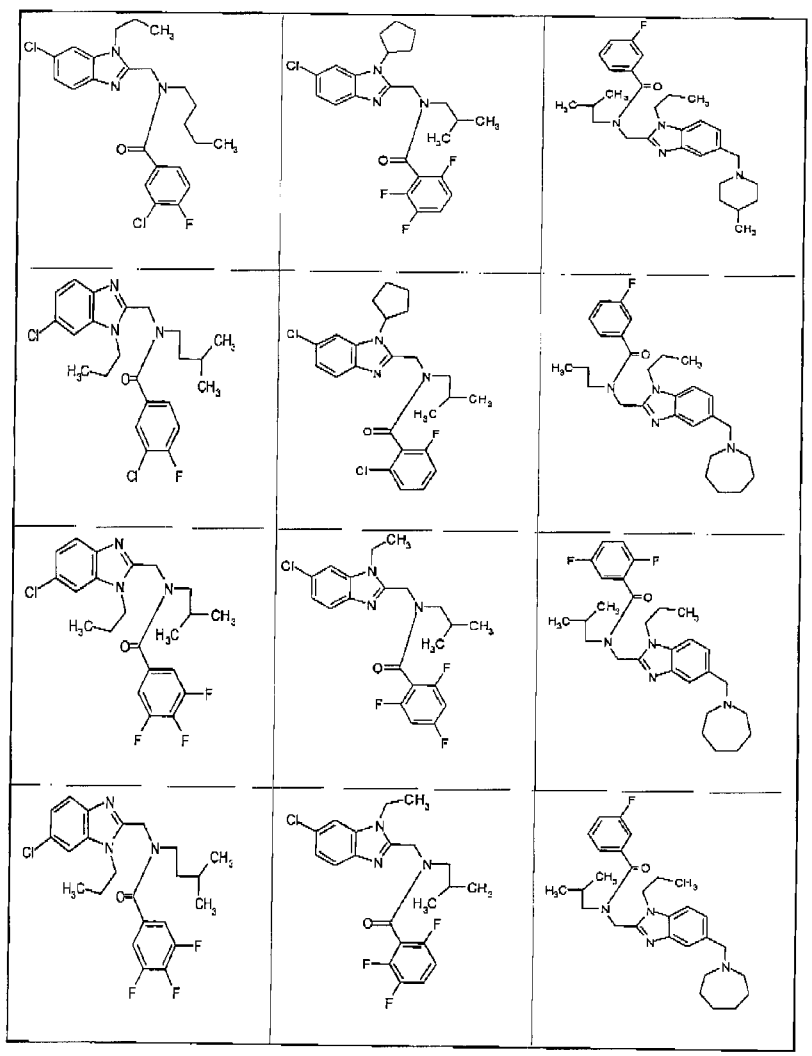

Appendix 2
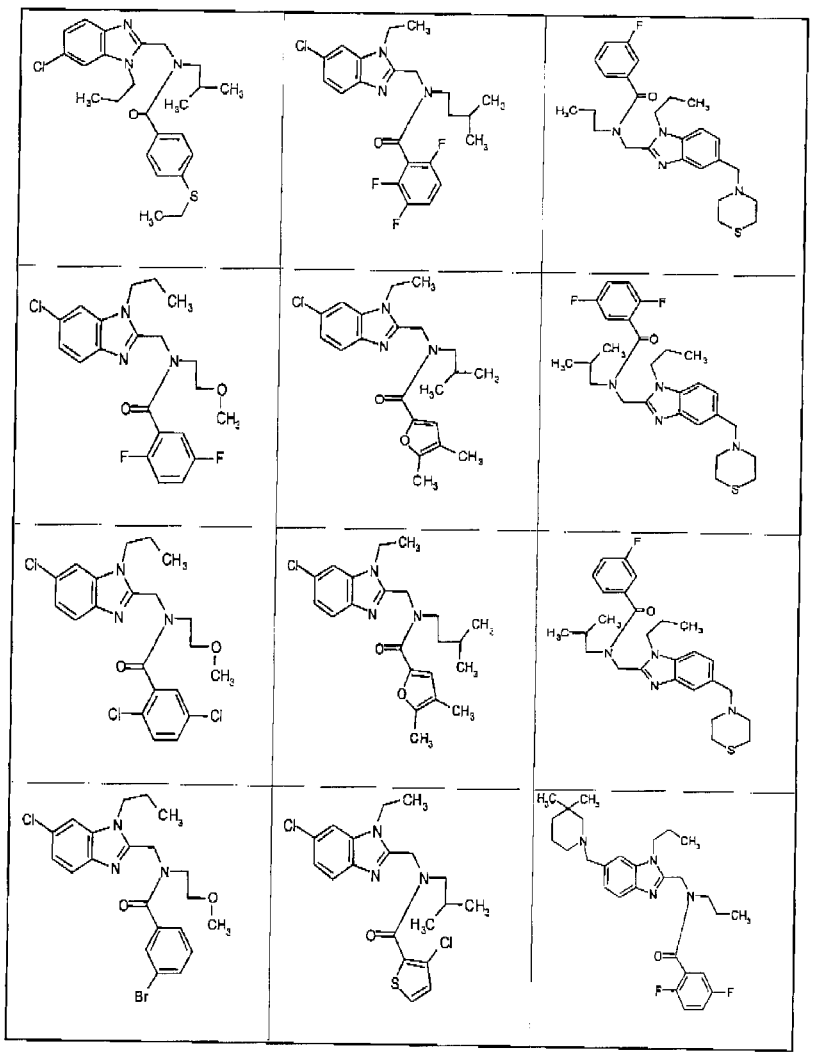

Appendix 2
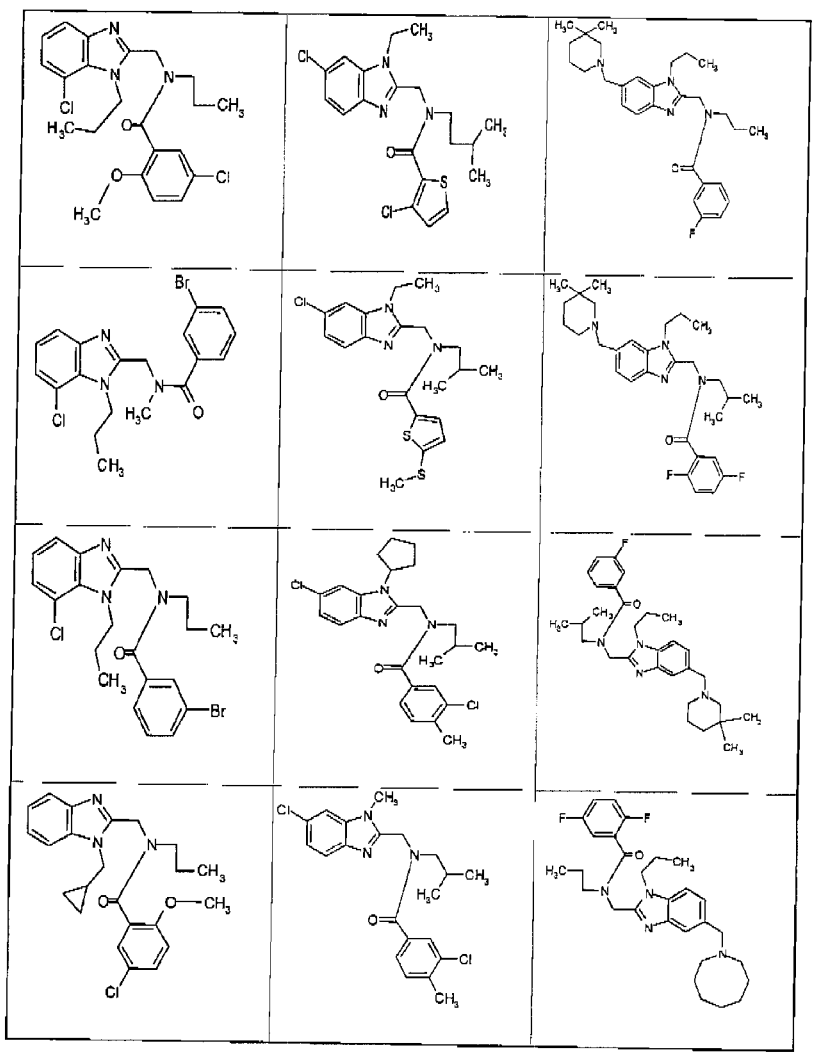

Appendix 2
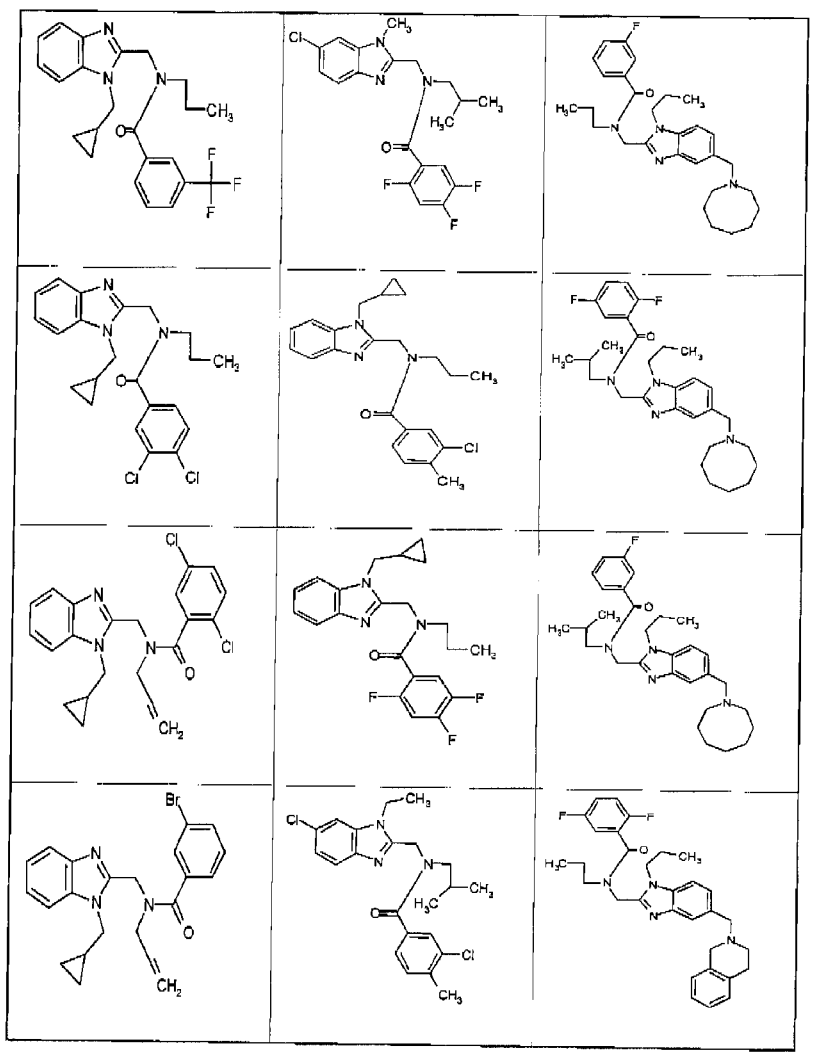

Appendix 2
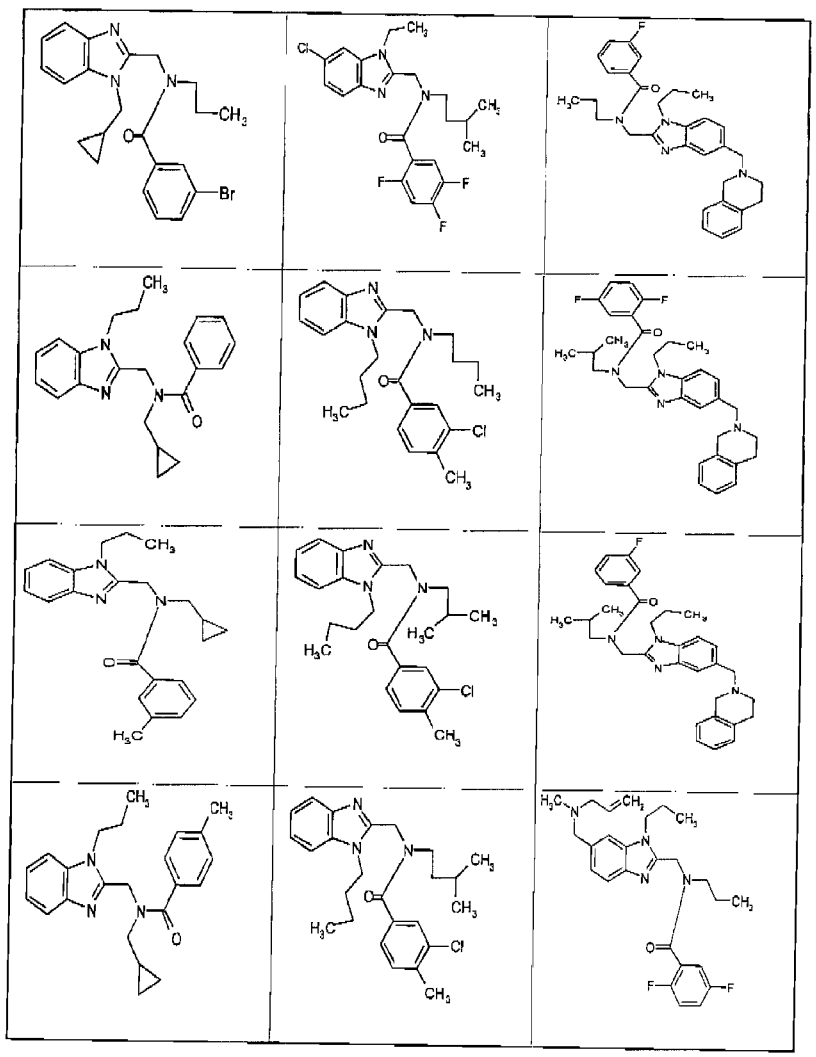

Appendix 2
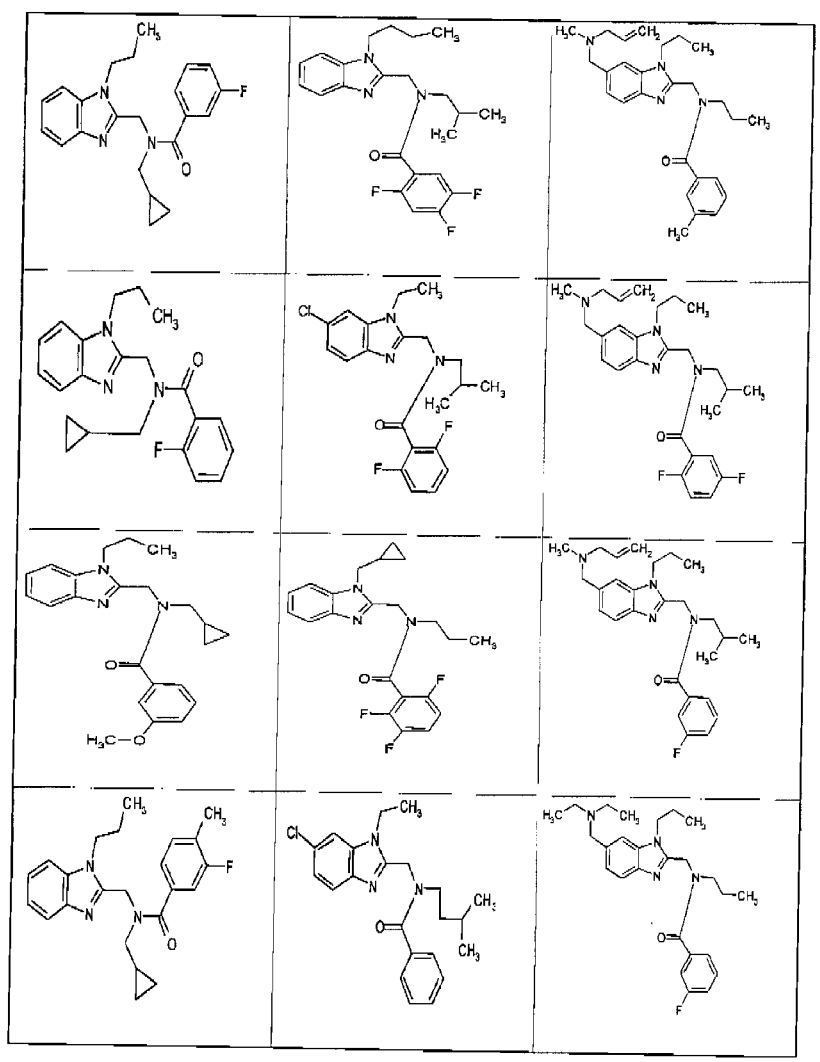

Appendix 2
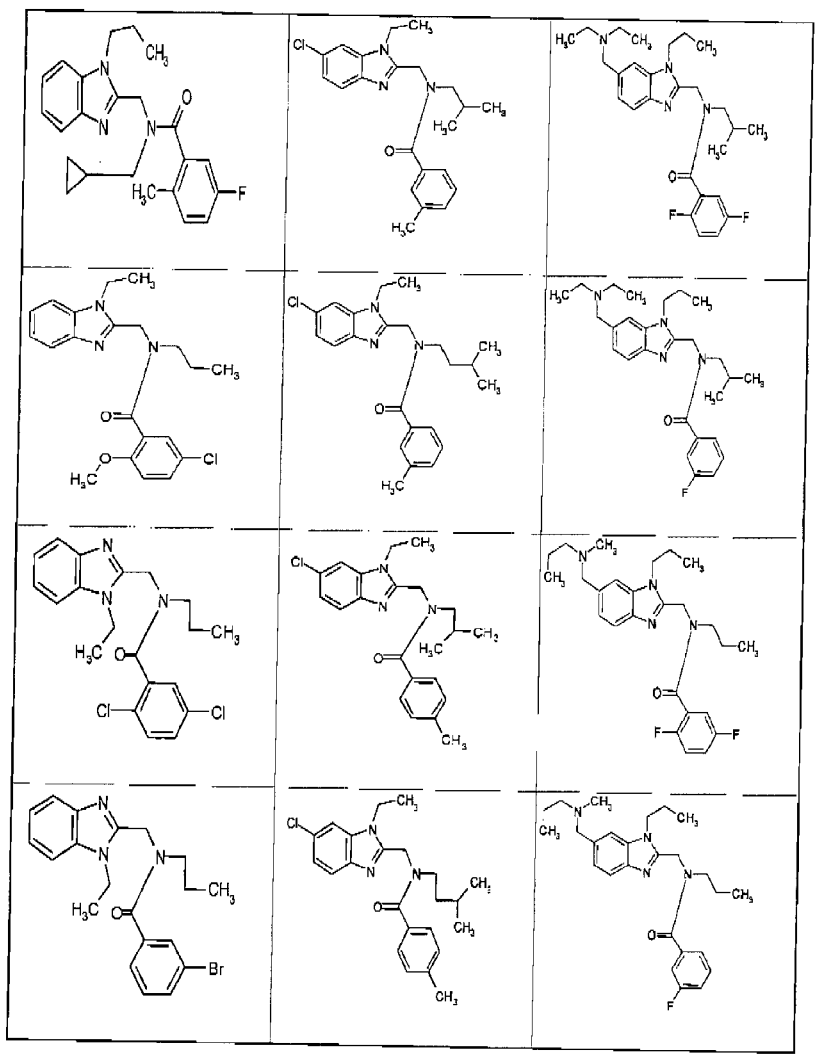

Appendix 2
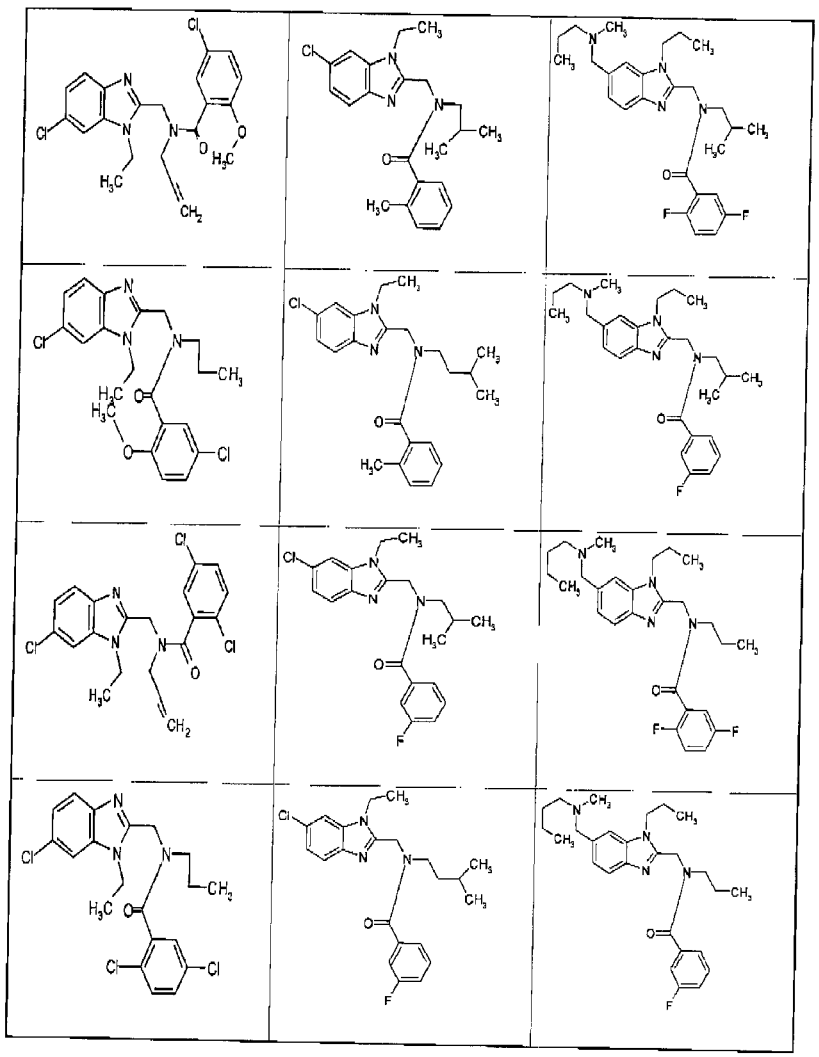

Appendix 2
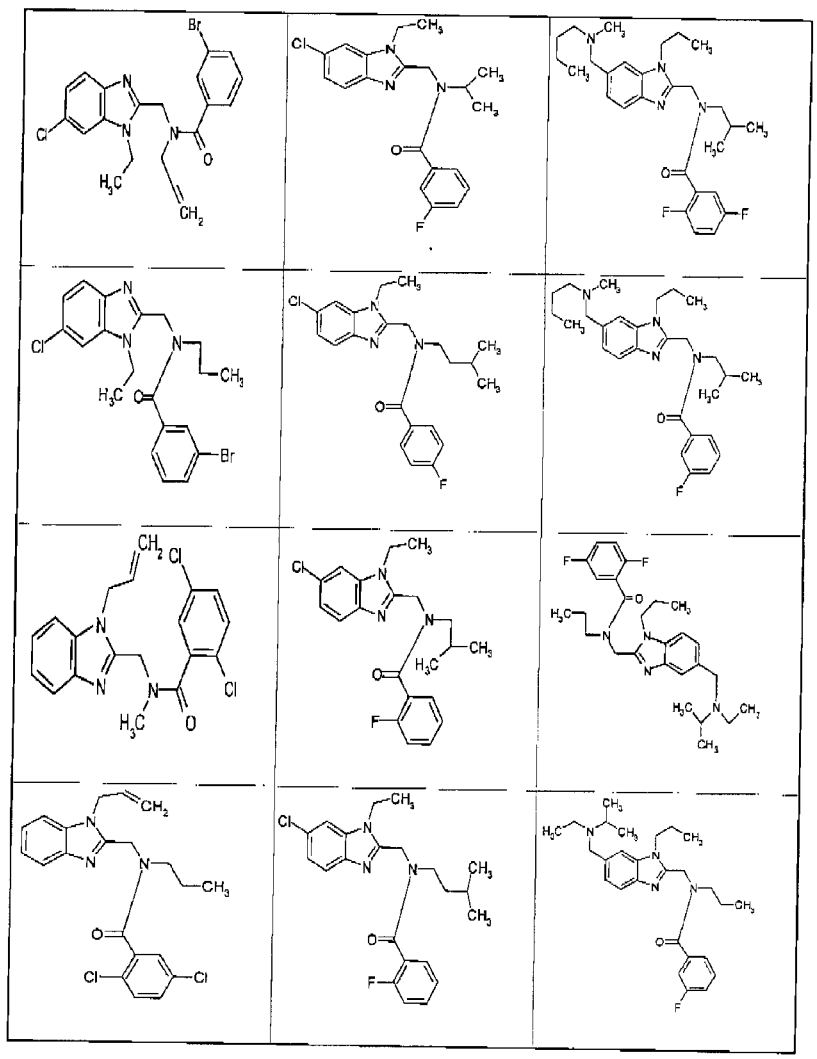

Appendix 2
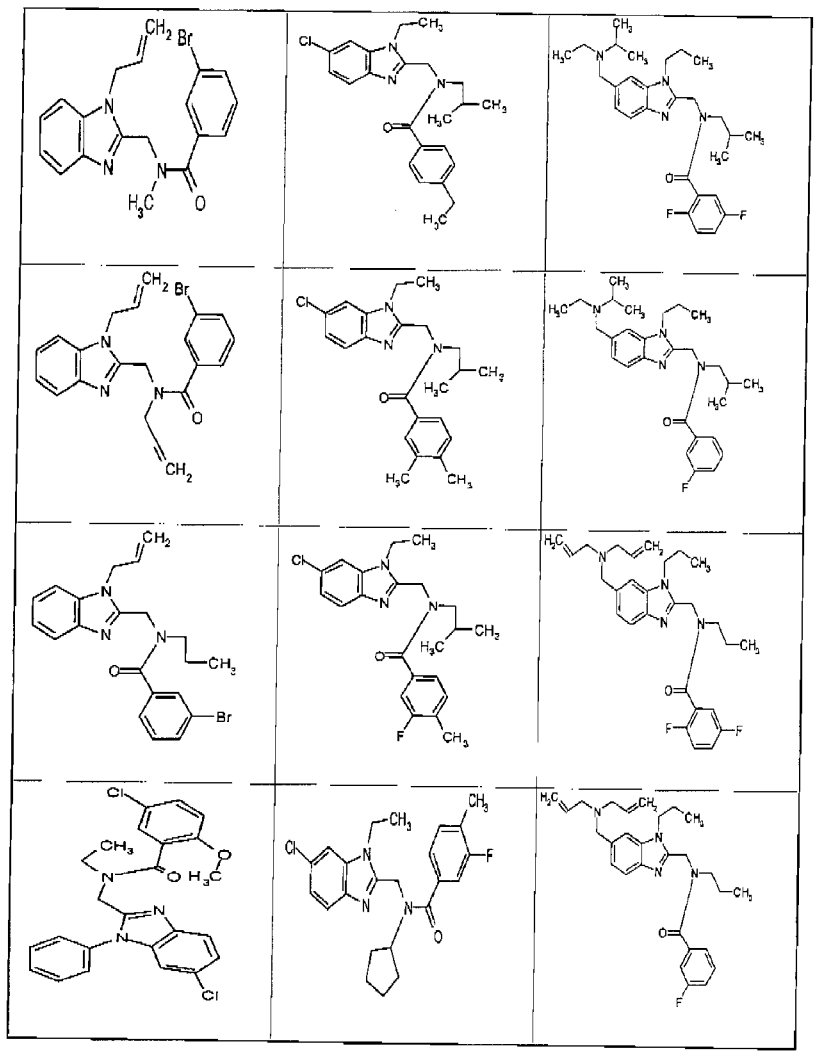

Appendix 2
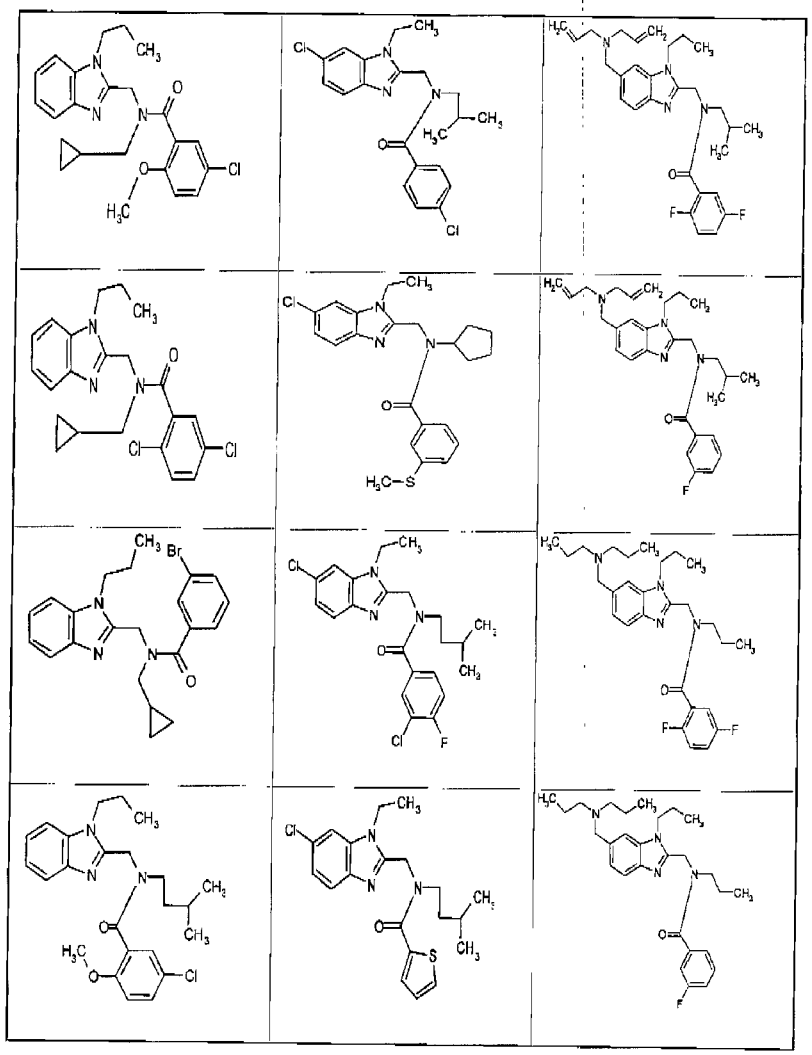

Appendix 2
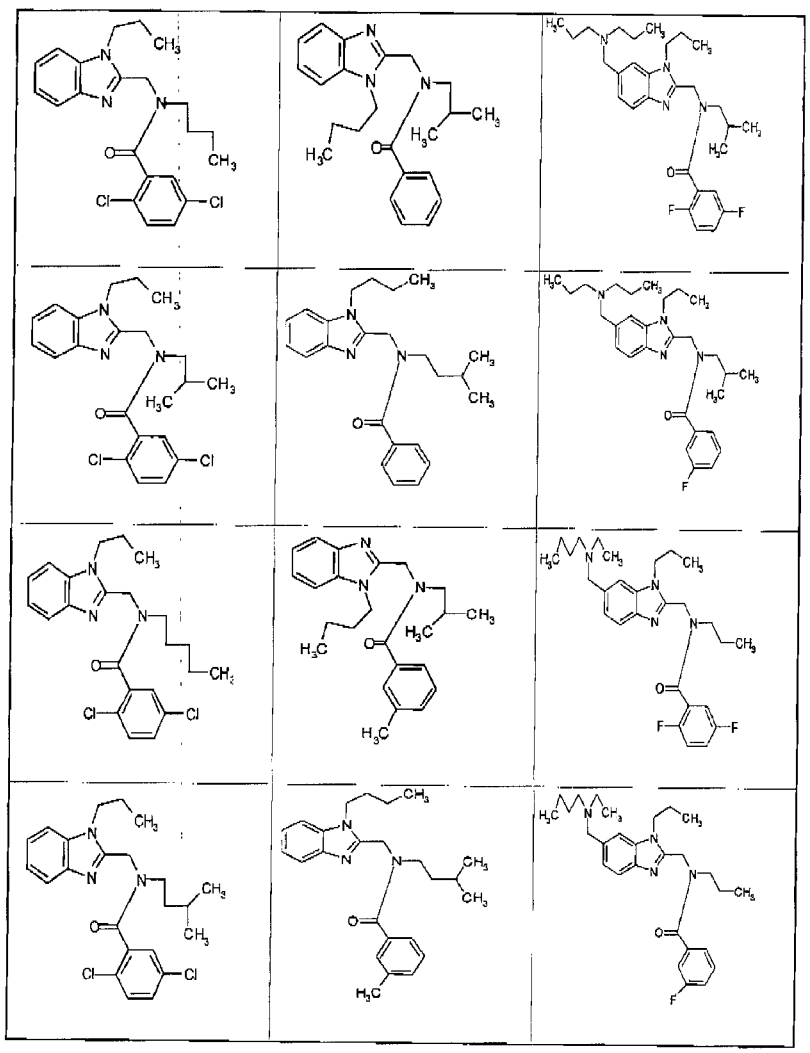
300

Appendix 2
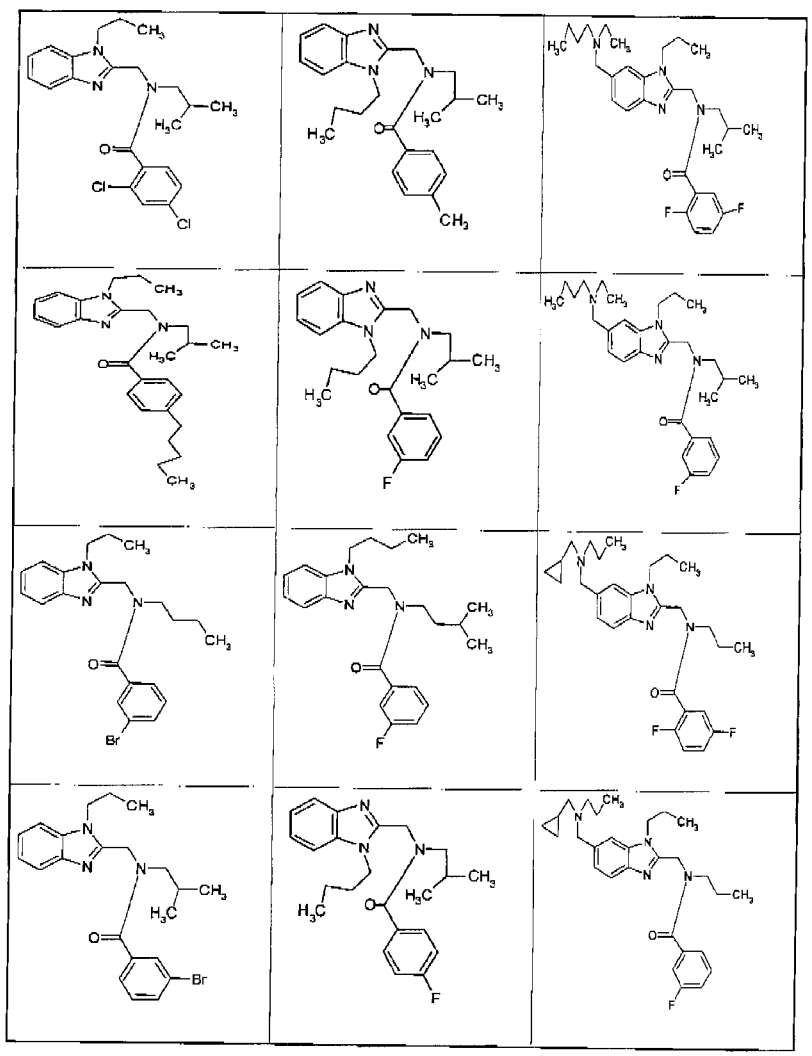

Appendix 2
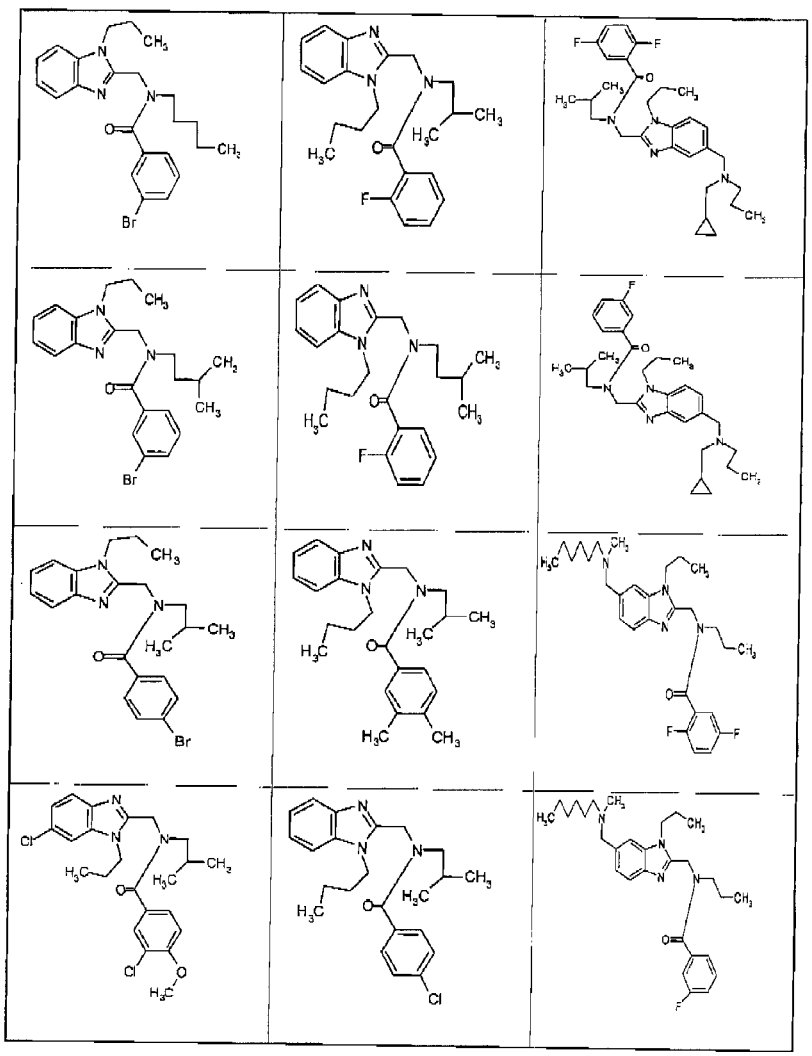

Appendix 2
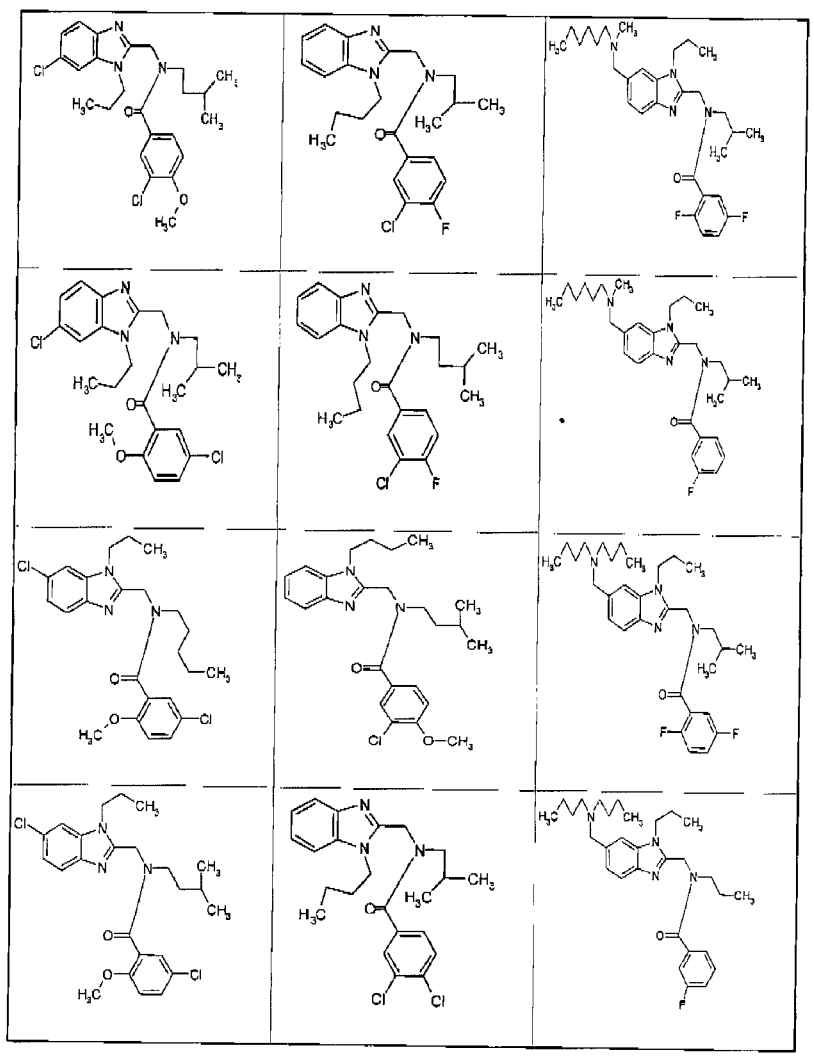

Appendix 2
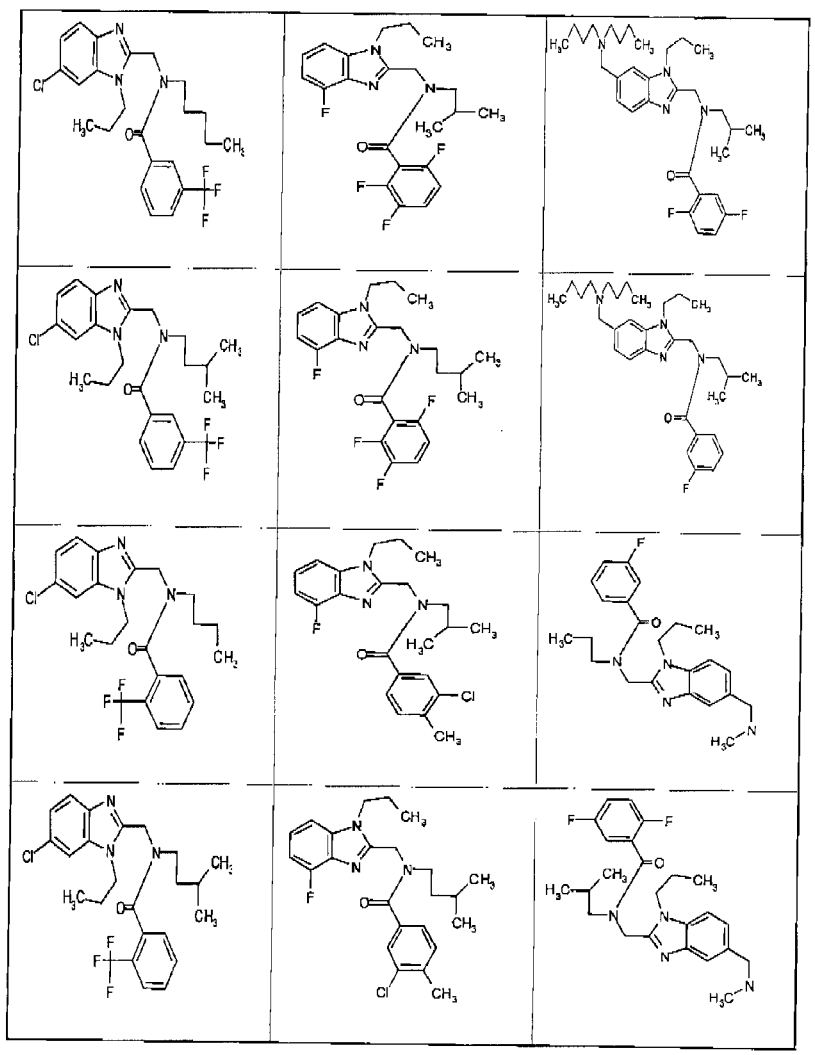

Appendix 2
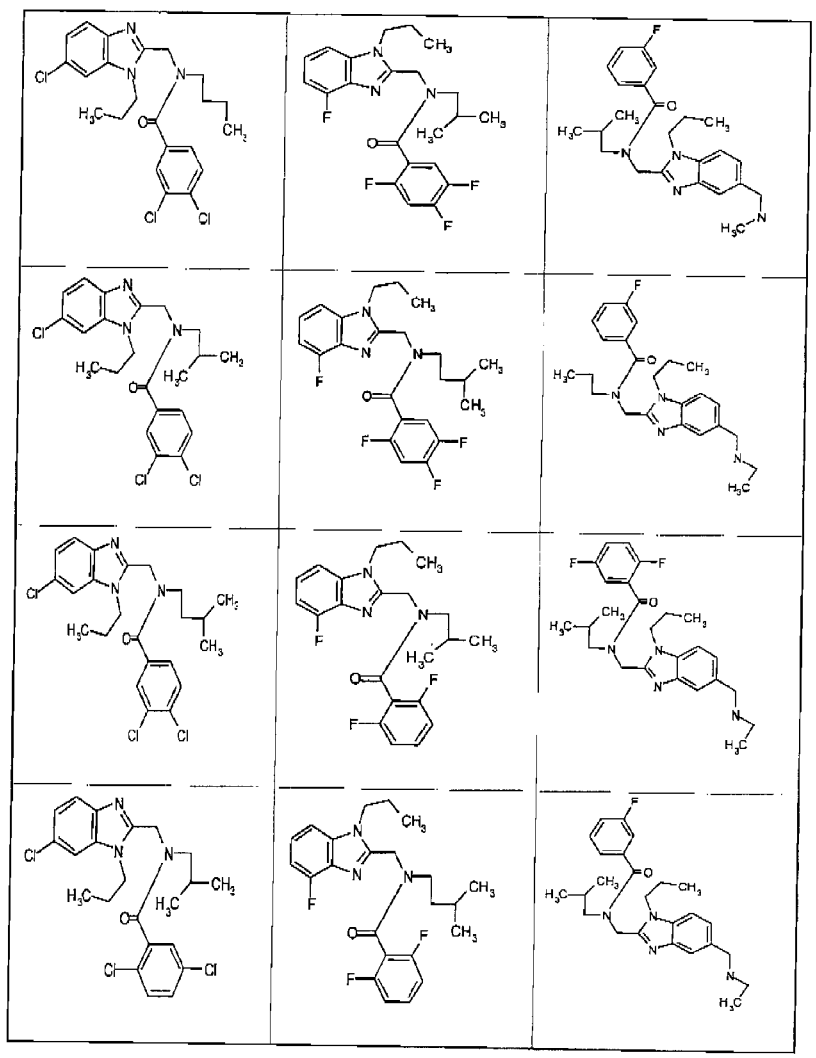

Appendix 2
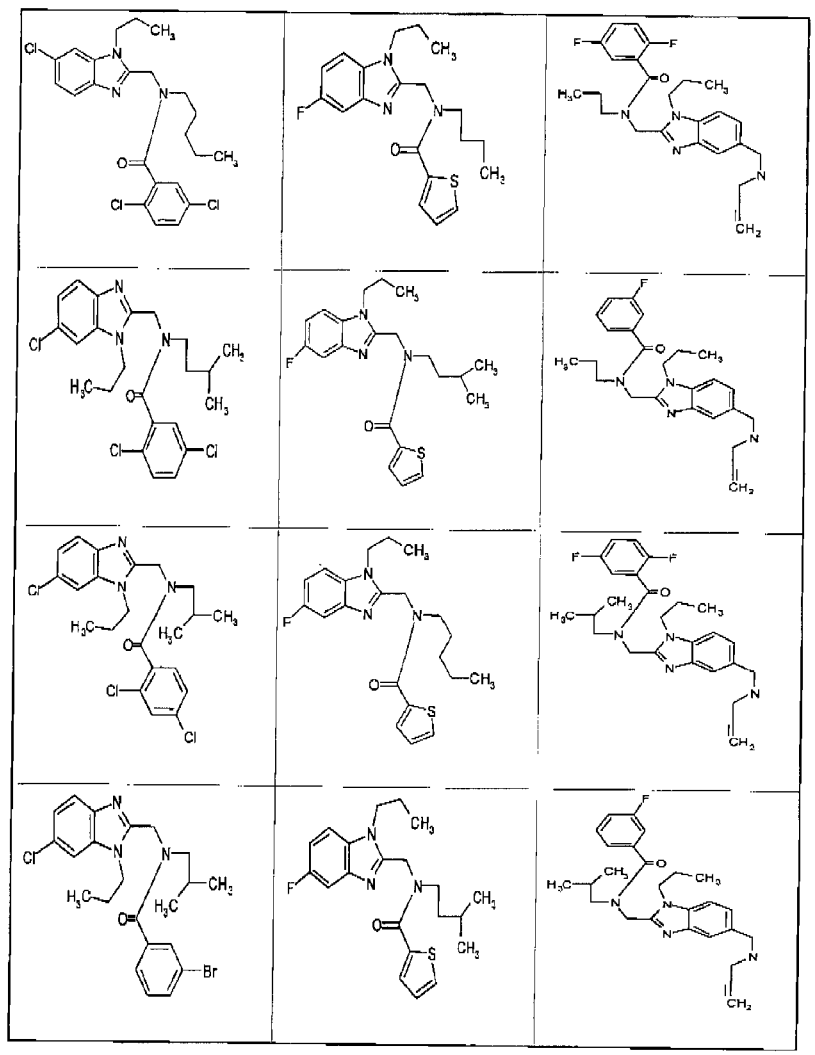

Appendix 2
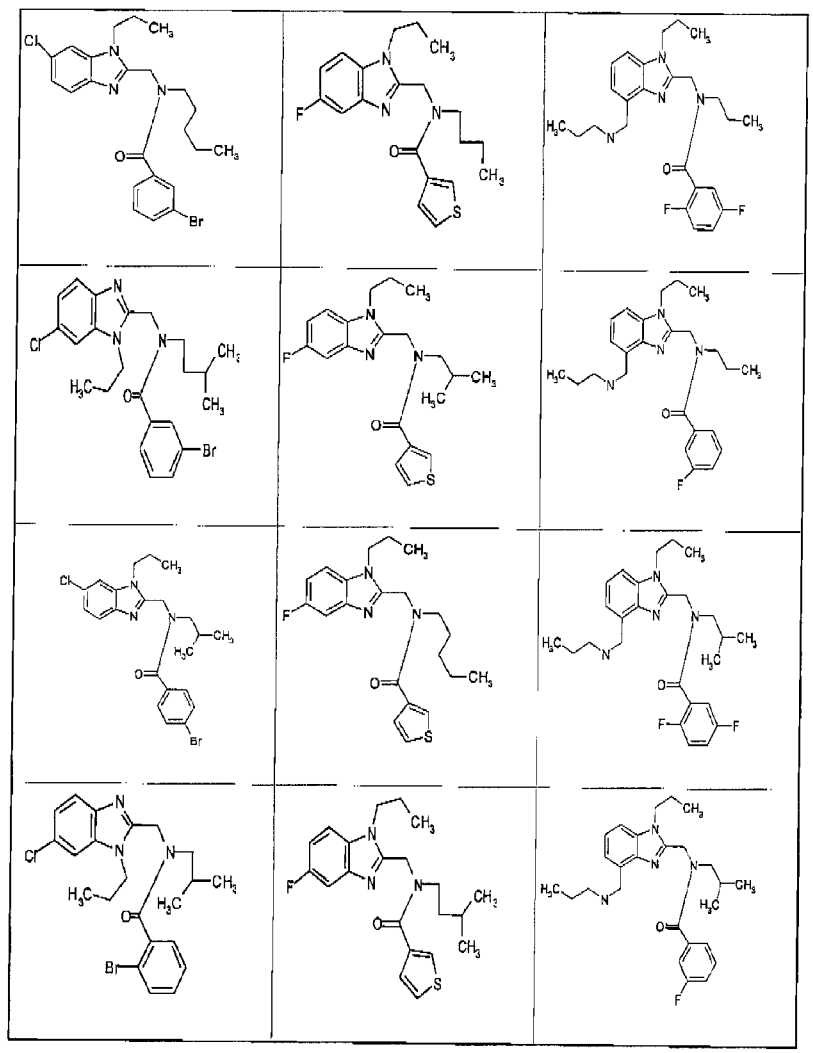

Appendix 2
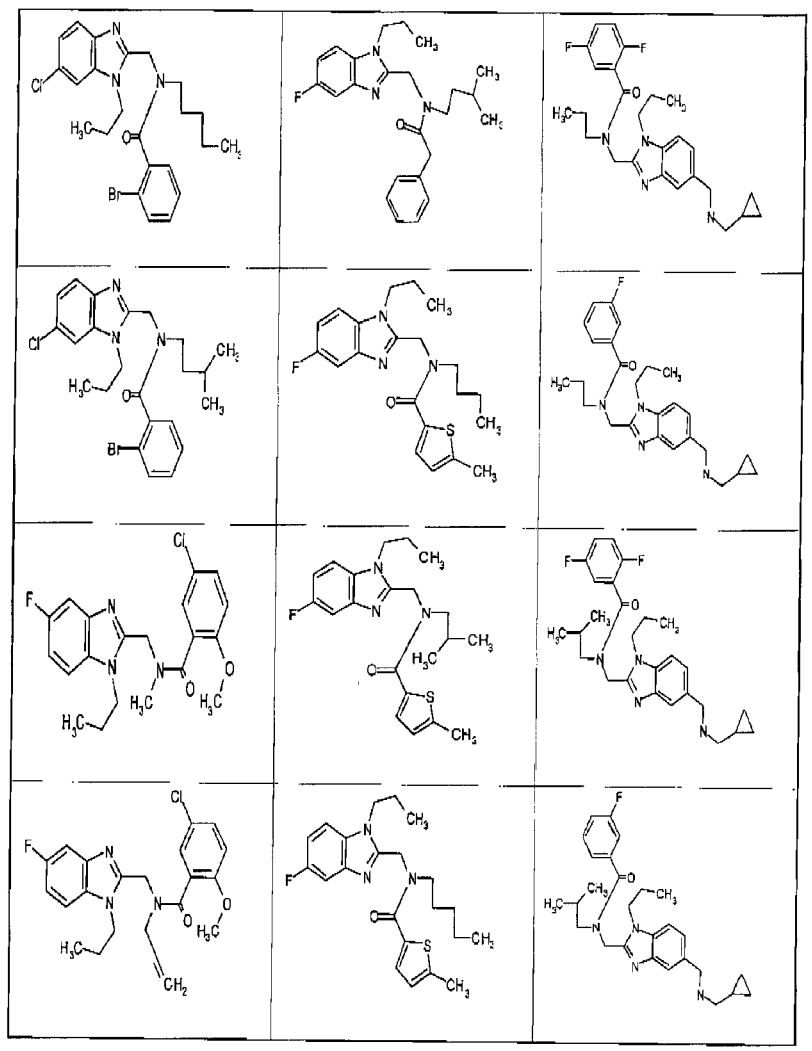

Appendix 2
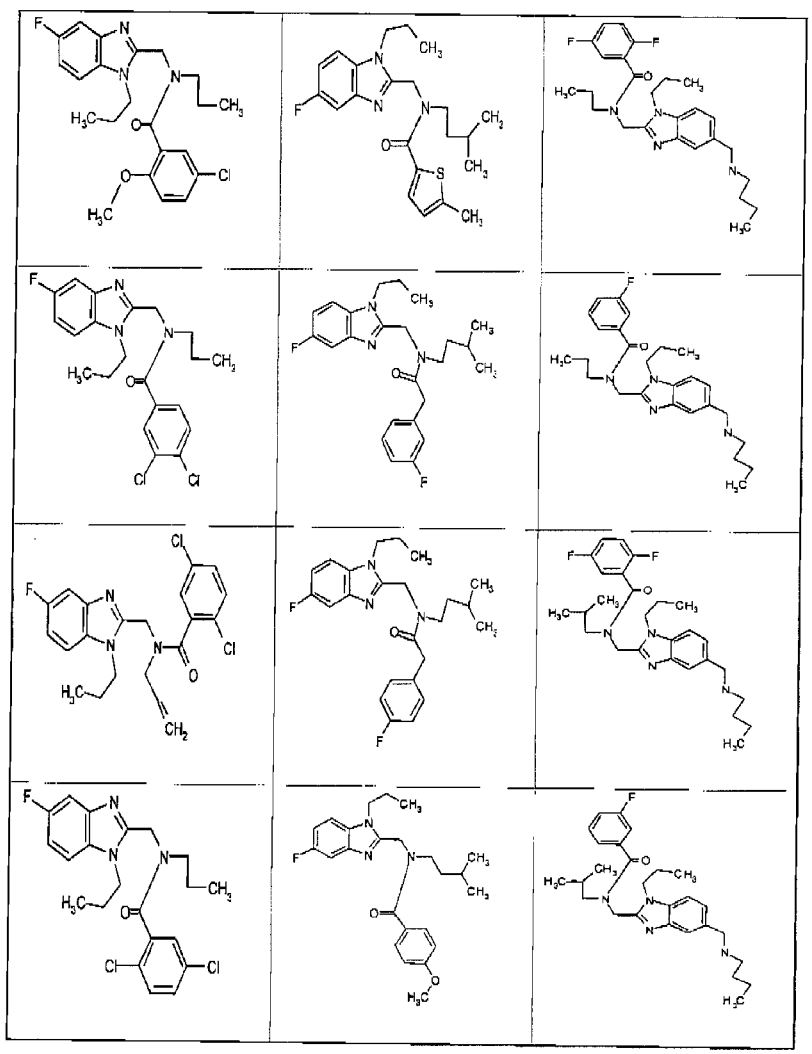

Appendix 2
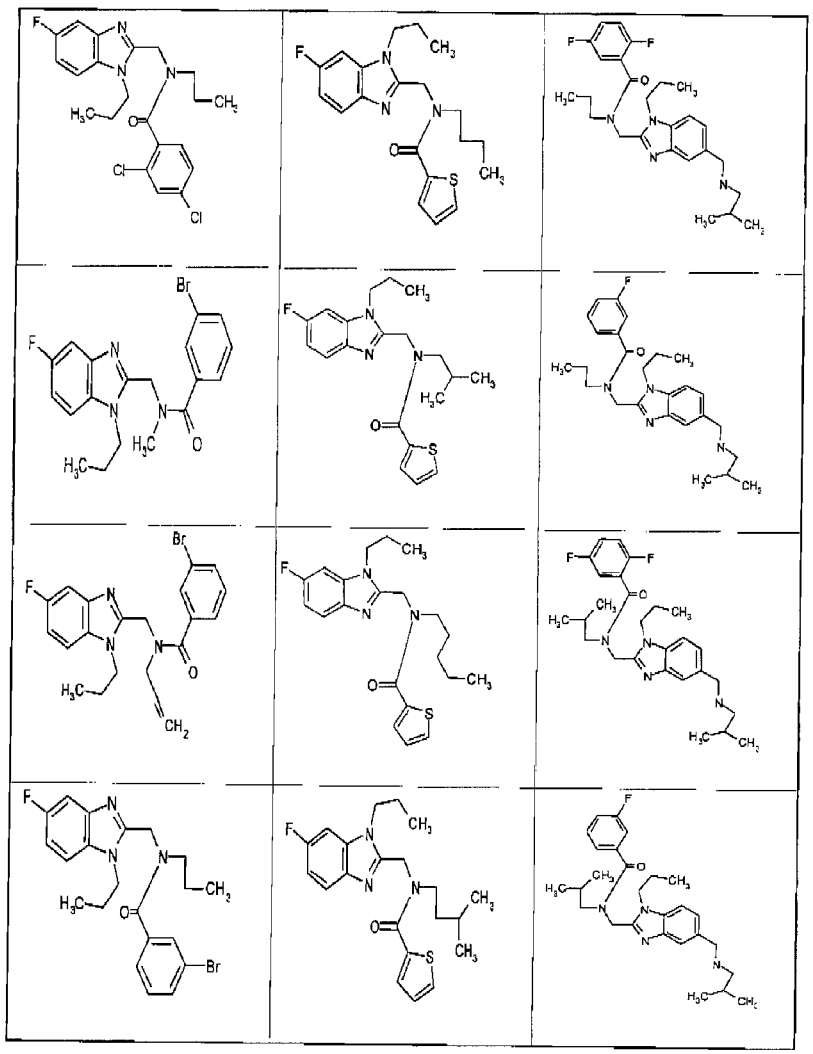

Appendix 2
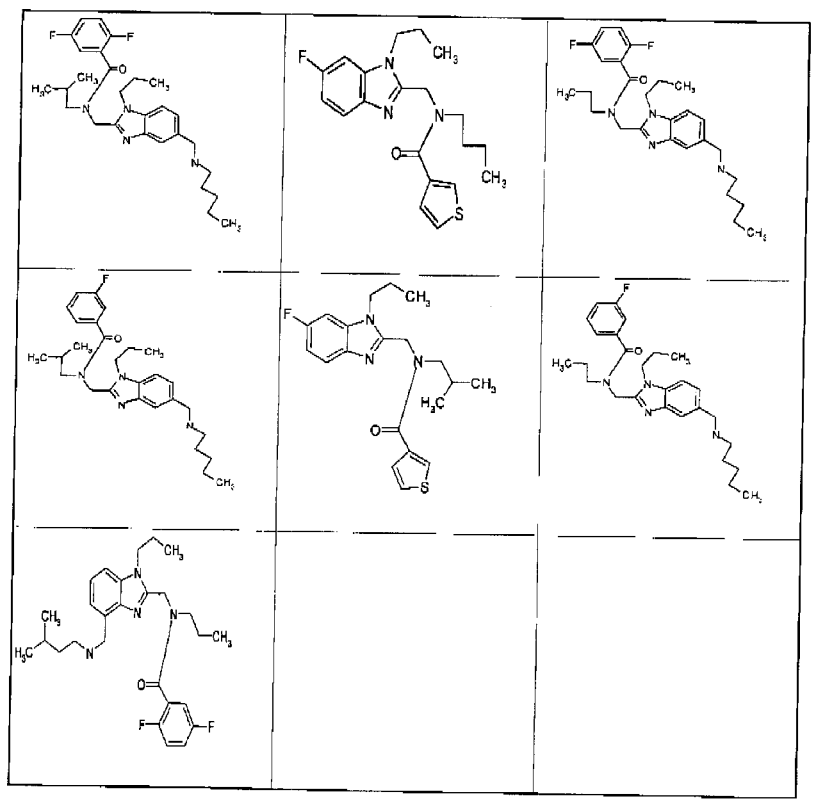

What is claimed is:
1. A compound of the formula

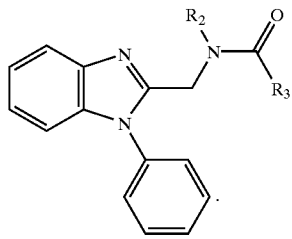

where R₂ and R₃ are defined in the following table:

| R₂ | R₃ |
|---|---|
| Methyl | Phenyl |
| Methyl | 3-Chlorophenyl |
| Butyl | 2,5-Dimethylphenyl |
| Butyl | 5-Fluoro-2-methylphenyl |
| Butyl | 2,3-Dimethylphenyl |
| Propyl | 3-Fluorophenyl |
| Butyl | 3-Methylphenyl |
| Butyl | 4-Fluorophenyl |
| Butyl | 3-Methoxyphenyl |
| Butyl | 2,5-Difluorophenyl |
| Methyl | 2-Fluorophenyl |
| Butyl | 4-Methylphenyl |
| Butyl | 2-Fluorophenyl |
| Butyl | 4-Methoxyphenyl |
| Butyl | 3-Chlorophenyl |
| Methyl | 2,5-Dimethylphenyl |
| Butyl | 2-Methylphenyl |
| Butyl | 4-Ethylphenyl |
| Butyl | 2-Methoxyphenyl |
| Butyl | 3-Chlorophenyl |
| Propyl | 3-Fluoro-4-methylphenyl |
| Butyl | 3-Fluorophenyl |
| Butyl | 3,4-Dimethylphenyl |
| Butyl | 3-Fluoro-4-methylphenyl |
| Butyl | 3,4-Difluorophenyl |
| Propyl | 2,4-Dimethoxyphenyl |
| Methyl | 2,5-Dichlorophenyl |
| Butyl | 5-Chloro-2-methoxyphenyl |
| Butyl | 3-Methyl-2-thienyl |
| Butyl | 3-Methylphenyl |
| Pentyl | 3-Fluorophenyl |
| Pentyl | 2,5-Dimethylphenyl |
| Propyl | 2,5-Dichlorophenyl |
| Butyl | 3-Methyl-2-thienyl |
| Pentyl | 3-Methylphenyl |
| Butyl | 2-Fluorophenyl |
| Pentyl | 3-Methoxyphenyl |
| Methyl | 3-Bromophenyl |
| Butyl | 3-Iodophenyl |
| Butyl | 4-Fluorophenyl |
| 2-Methylpropyl | 4-Methylphenyl |
| 2-Methylpropyl | 2-Fluorophenyl |
| 2-Methylpropyl | 4-Methoxyphenyl |
| Propyl | 3-Bromophenyl |
| Allyl | 4-Octylphenyl |
| Butyl | Phenyl |
| Pentyl | 2-Methylphenyl |
| Pentyl | 2-Fluorophenyl |
| Butyl | 2-Methoxyphenyl |
| Butyl | 3-Chloro-4-methoxyphenyl |
| Propyl | 4-Octylphenyl |
| Pentyl | Phenyl |
| Butyl | 3-Fluorophenyl |
| 2-Methylpropyl | 3,4-Dimethylphenyl |
| Pentyl | 2-Methoxyphenyl |
| Butyl | 3-Fluoro-4-methylphenyl |
| Butyl | 2-Fluoro-3-methylphenyl |
| 2-Methylpropyl | 4-Chlorophenyl |
| 2-Methylpropyl | 2,3-Difluorophenyl |
| 2-Methylpropyl | 1,3-Benzodioxol-5-yl |
| 2-Methylpropyl | 3-Chloro-4-methoxyphenyl |
| 2-Methylpropyl | 3-Fluoro-4-methylphenyl |
| Pentyl | 2-Fluoro-3-methylphenyl |
| Pentyl | 2-Chlorophenyl |
| Pentyl | 2,3-Difluorophenyl |
| Butyl | 4-Methylthiophenyl |
| 2-Methylpropyl | 3-Chloro-4-methoxyphenyl |
| Butyl | 5-Fluoro-2-methylphenyl |
| Butyl | 3-Chlorophenyl |
| Butyl | 3,4-Difluorophenyl |
| Butyl | 2,5-Difluorophenyl |
| Butyl | 3-Chloro-4-fluorophenyl |
| Butyl | 5-Chloro-2-methoxyphenyl |
| 2-Methylpropyl | 5-Fluoro-2-methylphenyl |
| 2-Methylpropyl | 3-Chlorophenyl |
| 2-Methylpropyl | 3,4-Difluorophenyl |
| Pentyl | 2,5-Difluorophenyl |
| 2-Methylpropyl | 4-Ethylthiophenyl |
| 2-Methylpropyl | 5-Chloro-2-methoxyphenyl |
| Pentyl | 5-Fluoro-2-methylphenyl |
| Pentyl | 3-Chlorophenyl |
| Butyl | 2,3-Difluorophenyl |
| 2-Methylpropyl | 2,4-Difluorophenyl |
| Butyl | 3-Chloro-4-methoxyphenyl |
| Pentyl | 5-Chloro-2-methoxyphenyl |
| 3-Methylbutyl | 5-Chloro-2-methoxyphenyl |
| 3-Methylbutyl | 2,5-Dichlorophenyl |
| 2-Methylpropyl | 4-Bromophenyl |
| Butyl | 2-Thienyl |
| 3-Methylbutyl | 3-Thienyl |
| 2-Methylpropyl | 3-Methyl-2-thienyl |
| 3-Methylbutyl | 3-Trifluoromethylphenyl |
| Butyl | 3-Bromophenyl |
| 3-Methylbutyl | 2-Bromophenyl |
| Pentyl | 2-Thienyl |
| Butyl | 5-Methyl-2-thienyl |
| 3-Methylbutyl | 3-Methyl-2-thienyl |
| 2-Methylpropyl | 3,4-Dichlorophenyl |
| 2-Methylpropyl | 3-Bromophenyl |
| 3-Methylbutyl | 3-Bromo-4-fluorophenyl |
| 3-Methylbutyl | 2-Thienyl |
| Pentyl | 5-Methyl-2-thienyl |
| Butyl | 3-Fluorophenyl |
| Butyl | 2,5-Dichlorophenyl |
| Pentyl | 3-Bromophenyl |
| Pentyl | 3-Iodophenyl |
| Butyl | 3-Thienyl |
| 3-Methylbutyl | 5-Methyl-2-thienyl |
| 3-Methylbutyl | 3-Fluorophenyl |
| Pentyl | 2,5-Dichlorophenyl |
| 3-Methylbutyl | 3-Bromophenyl |
| 3-Methylbutyl | 3-Iodophenyl |
| Pentyl | 3-Thienyl |
| Butyl | 3-Methyl-2-thienyl |
| 2-Methylpropyl | 2-Chlorophenyl |
| 2-Methylpropyl | 3,5-Difluorophenyl |
| 3-Methylbutyl | 35-Difluorophenyl |
| Butyl | 3,5-Difluorophenyl |
| Benzyl | 3-Fluorophenyl |
| Benzyl | 2-Fluorophenyl |
| Benzyl | 2-Methoxyphenyl |
| Benzyl | 5-Fluoro-2-methylphenyl |
| Benzyl | 3-Chlorophenyl |
| Benzyl | 2,3-Difluorophenyl |
| Benzyl | 2,5-Difluorophenyl. |

2. A compound of the formula

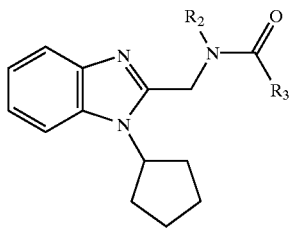

where $R_2$ and $R_3$ are defined in the following table:

| $R_2$ | $R_3$ |
|---|---|
| Allyl | 3-Fluorophenyl |
| Allyl | 3,4-Difluorophenyl |
| Propyl | 1,3-Benzodioxol-5-yl |
| Allyl | 5-Chloro-2-methoxyphenyl |
| Propyl | 3-Methyl-2-Thienyl |
| Propyl | 3-Fluoro-4-methylphenyl |
| Propyl | 3-Fluorophenyl |
| Propyl | 3,4-Difluorophenyl |
| Allyl | 3-Chloro-4-fluorophenyl |
| Propyl | 5-Chloro-2-methoxyphenyl |
| Allyl | Phenyl |
| Allyl | 5-Fluoro-2-methylphenyl |
| Propyl | 4-Fluorophenyl |
| Allyl | 2,5-Difluorophenyl |
| Propyl | 3-Chloro-4-fluorophenyl |
| Methyl | 2,5-Dichlorophenyl |
| Propyl | Phenyl |
| Propyl | 5-Fluoro-2-methylphenyl |
| Allyl | 2-Fluorophenyl |
| Propyl | 2,5-Difluorophenyl |
| Methyl | 5-Chloro-2-methoxyphenyl |
| Allyl | 2,5-Dichlorophenyl |
| Allyl | 3-Methylphenyl |
| Allyl | 3-Chlorophenyl |
| Propyl | 2-Fluorophenyl |
| Allyl | 1,3-Benzodioxol-5-yl |
| Ethyl | 5-Chloro-2-methoxyphenyl |
| Propyl | 2,5-Dichlorophenyl |
| Propyl | 3-Methylphenyl |
| Propyl | 3-Chlorophenyl |
| Propyl | 4-Methylthiophenyl |
| Propyl | 3-Iodo-4-methylphenyl |
| Propyl | 2,3,6-Trifluorophenyl |
| 3-Methylbutyl | 2,3,6-Trifluorophenyl |
| 3-Methylbutyl | 3-(2-1,2,3,4-Teterahydroisoquinolinylmethyl)phenyl |
| 3-Methylbutyl | 3-(Diethylaminomethyl)phenyl |
| 3-Methylbutyl | 3-(Hexylmethylaminomethyl)phenyl |
| 3-Methylbutyl | 3-(Dibutylaminomethyl)phenyl |
| 3-Methylbutyl | 3-[(1-methylethyl)methylaminomethyl]phenyl |
| 3-Methylbutyl | 3-(Cyclohexylethylaminomethyl)phenyl |
| 3-Methylbutyl | 3-[bis(2-Methoxyethyl)aminomethyl]phenyl |
| 3-Methylbutyl | 3-[(3,3,5-Trimethylazaperhydroepinyl)methyl]phenyl. |

3. A compound of the formula

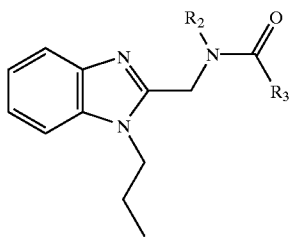

where $R_2$ and $R_3$ are defined in the following table:

| $R_2$ | $R_3$ |
|---|---|
| Methyl | 3-Fluorophenyl |
| Methyl | 5-Fluoro-2-methylphenyl |
| Methyl | 3-Chlorophenyl |
| Methyl | 5-Chloro-2-methoxyphenyl |
| 2-Methylpropyl | 2,3,6-Trifluorophenyl |
| Pentyl | 2,3,6-Trifluorophenyl |
| 3-Methylbutyl | 2,3,6-Trifluorophenyl |
| Butyl | Phenyl |
| 2-Methylpropyl | Phenyl |
| Pentyl | Phenyl |
| 3-Methylbutyl | Phenyl |
| Butyl | 3-Methylphenyl |
| 2-Methylpropyl | 3-Methylphenyl |
| 3-Methylbutyl | 3-Methylphenyl |
| 2-Methylpropyl | 4-Methylphenyl |
| Butyl | 3-Fluorophenyl |
| Pentyl | 3-Fluorophenyl |
| 3-Methylbutyl | 3-Fluorophenyl |
| 3-Methylbutyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 3,4-Dimethylphenyl |
| Butyl | 2-Chlorophenyl |
| Pentyl | 2-Chlorophenyl |
| 3-Methylbutyl | 2-Chlorophenyl |
| Butyl | 3,4-Difluorophenyl |
| 2-Methylpropyl | 3,4-Difluorophenyl |
| Pentyl | 3,4-Difluorophenyl |
| 3-Methylbutyl | 3,4-Difluorophenyl |
| Butyl | 2,3-Difluorophenyl |
| 2-Methylpropyl | 2,3-Difluorophenyl |
| Pentyl | 2,3-Difluorophenyl |
| 3-Methylbutyl | 2,3-Difluorophenyl |
| Butyl | 2,5-Difluorophenyl |
| 2-Methylpropyl | 2,5-Difluorophenyl |
| Pentyl | 2,5-Difluorophenyl |
| 3-Methylbutyl | 2,5-Difluorophenyl |
| Butyl | 2,4-Difluorophenyl |
| 2-Methylpropyl | 2,4-Difluorophenyl |
| 3-Methylbutyl | 2,4-Difluorophenyl |
| 2-Methylpropyl | 3-Ethoxyphenyl |
| Butyl | 1,3-Benzodioxol-5-yl |
| 2-Methylpropyl | 1,3-Benzodioxol-5-yl |
| 3-Methylbutyl | 1,3-Benzodioxol-5-yl |
| 2-Methylpropyl | 4-Methylthiophenyl |
| 3-Methylbutyl | 4-Methylthiophenyl |
| 2-Methylpropyl | 3-Fluoro-4-methoxyphenyl |
| 3-Methylbutyl | 3-Fluoro-4-methoxyphenyl |
| 2-Methylpropyl | 4-Chloro-3-methylphenyl |
| Butyl | 3-Chloro-4-fluorophenyl |
| 2-Methylpropyl | 3-Chloro-4-fluorophenyl |
| Pentyl | 3-Chloro-4-fluorophenyl |
| 3-Methylbutyl | 3-Chloro-4-fluorophenyl |
| 2-Methylpropyl | 3,4,5-Trifluorophenyl |
| 3-Methylbutyl | 3,4,5-Trifluorophenyl |
| 2-Methylpropyl | 4-Butylphenyl |
| 2-Methylpropyl | 4-Ethylthiophenyl |
| Cyclopropylmethyl | Phenyl |
| CyclopropylMethyl | 3-Methylphenyl |
| CyclopropylMethyl | 4-Methylphenyl |
| CyclopropylMethyl | 3-Fluorophenyl |
| CyclopropylMethyl | 2-Fluorophenyl |
| CyclopropylMethyl | 3-Methoxyphenyl |
| CyclopropylMethyl | 3-Fluoro-4-methylphenyl |
| Cyclopropylmethyl | 5-Fluoro-2-methylphenyl |
| CyclopropylMethyl | 5-Chloro-2-methoxyphenyl |
| CyclopropylMethyl | 2,5-Dichlorophenyl |
| CyclopropylMethyl | 3-Bromophenyl |
| 3-Methylbutyl | 5-Chloro-2-methoxyphenyl |
| Butyl | 2,5-Dichlorophenyl |
| 2-Methylpropyl | 2,5-Dichlorophenyl |
| Pentyl | 2,5-Dichlorophenyl |
| 3-Methylbutyl | 2,5-Dichlorophenyl |

-continued

| R₂ | R₃ |
|---|---|
| 2-Methylpropyl | 2,4-Dichlorophenyl |
| 2-Methylpropyl | 4-Pentylphenyl |
| Butyl | 3-Bromophenyl |
| 2-Methylpropyl | 3-Bromophenyl |
| Pentyl | 3-Bromophenyl |
| 3-Methylbutyl | 3-Bromophenyl |
| 2-Methylpropyl | 4-Bromophenyl |
| CyclopropylMethyl | 3,4-Difluorophenyl |
| CyclopropylMethyl | 2,4-Difluorophenyl |
| Propyl | 1,3-Benzodioxol-5-yl |
| Cyclopropylmethyl | 1,3-Benzodioxol-5-yl |
| Cyclopropylmethyl | 3-Chloro-4-fluorophenyl |
| 3-Methylbutyl | 3-Iodo-4-methylphenyl |
| 3-Methylbutyl | 2-Thienyl |
| 3-Methylbutyl | 3-Thienyl |
| 2-Methylpropyl | 5-Methyl-2-thienyl |
| Pentyl | 5-Methyl-2-thienyl |
| 3-Methylbutyl | 5-Methyl-2-thienyl |
| 3-Methylbutyl | 3-Fluorobenzyl |
| Methyl | 2,5-Difluorophenyl |
| Methyl | 2,5-Dichlorophenyl |
| 3-Methylbutyl | 5-Bromo-2-thienyl |
| Benzyl | 3-Fluorophenyl |
| Benzyl | 2-Fluorophenyl |
| Benzyl | 3,4-Dimethylphenyl |
| Benzyl | 3-Methoxyphenyl |
| Benzyl | 2-Methoxyphenyl |
| Benzyl | 5-Fluoro-2-methylphenyl |
| Benzyl | 3-Chlorophenyl |
| Benzyl | 3,4-Difluorophenyl |
| Benzyl | 2,3-Difluorophenyl |
| Benzyl | 2,5-Difluorophenyl |
| Benzyl | 5-Chloro-2-methoxyphenyl |
| Benzyl | 2,5-Dichlorophenyl |
| Benzyl | 3-Bromophenyl |
| Benzyl | 2-Bromophenyl |
| Benzyl | 3-Iodophenyl |
| Benzyl | 2,5-Dimethylpyrrol-3-yl |
| Benzyl | 3-Methylbutyl |
| 3-Methylbutyl | 3-(Methylaminomethyl)phenyl |
| 3-Methylbutyl | 3-(Ethylaminomethyl)phenyl |
| 3-Methylbutyl | 3-(Cyclobutylaminomethyl)phenyl |
| 3-Methylbutyl | 3-[(1-Methylpropyl)aminomethyl]phenyl |
| 3-Methylbutyl | 3-(Cyclopentylaminomethyl)phenyl |
| 3-Methylbutyl | 3-(Dibutylaminomethyl)phenyl |
| 3-Methylbutyl | 3-[bis(2-Methoxyethyl)aminomethyl]phenyl |
| 3-Methylbutyl | 3-[(3,3,5-Trimethylaza perhydroepinyl)methyl]phenyl |
| Methyl | 2,5-Difluorophenyl. |

4. A compound of the formula

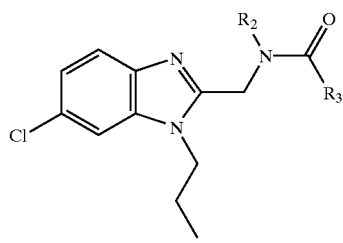

where R₂ and R₃ are defined in the following table:

| R₂ | R₃ |
|---|---|
| Propyl | 3-Fluorophenyl |
| Propyl | 1,3-Benzodioxol-5-yl |
| Propyl | 5-Fluoro-2-methylphenyl |
| Allyl | 2-Fluorophenyl |

-continued

| R₂ | R₃ |
|---|---|
| Propyl | 3-Chloro-4-fluorophenyl |
| Propyl | 3-Chlorophenyl |
| Propyl | 2-Fluorophenyl |
| Allyl | 5-Chloro-2-methoxyphenyl |
| Allyl | 3-Chlorophenyl |
| Methyl | 3-Fluorophenyl |
| Methyl | 2,5-Difluorophenyl |
| Propyl | Phenyl |
| Propyl | 3-Chlorophenyl |
| Allyl | 3-Fluorophenyl |
| Propyl | 2,5-Difluorophenyl |
| Propyl | 3-Fluoro-4-methylphenyl |
| Propyl | 4-Methylthiophenyl |
| 3-Methylbutyl | 3-Fluorophenyl |
| 2-Methylpropyl | 2-Fluorophenyl |
| Butyl | 3,4-Difluorophenyl |
| 2-Methylpropyl | 2,5-Difluorophenyl |
| 3-Methylbutyl | 1,3-Benzodioxol-5-yl |
| Butyl | 4-Fluorophenyl |
| Pentyl | 2-Fluorophenyl |
| 2-Methylpropyl | 3,4-Difluorophenyl |
| Pentyl | 2,5-Difluorophenyl |
| Butyl | 3-Chloro-4-fluorophenyl |
| Butyl | 3-Fluorophenyl |
| 2-Methylpropyl | 4-Fluorophenyl |
| 3-Methylbutyl | 2-Fluorophenyl |
| Pentyl | 3,4-Difluorophenyl |
| 3-Methylbutyl | 2,5-Difluorophenyl |
| 2-Methylpropyl | 3-Chloro-4-fluorophenyl |
| 2-Methylpropyl | 3-Fluorophenyl |
| 3-Methylbutyl | 4-Fluorophenyl |
| 2-Methylpropyl | 2,5-Dimethylphenyl |
| 3-Methylbutyl | 3,4-Difluorophenyl |
| Butyl | 1,3-Benzodioxol-5-yl |
| Pentyl | 3-Chloro-4-fluorophenyl |
| Pentyl | 3-Fluorophenyl |
| Butyl | 2-Fluorophenyl |
| 3-Methylbutyl | 2,5-Dimethylphenyl |
| Butyl | 2,5-Difluorophenyl |
| 2-Methylpropyl | 1,3-Benzodioxol-5-yl |
| 3-Methylbutyl | 3-Chloro-4-fluorophenyl |
| Butyl | 5-Chloro-2-methoxyphenyl |
| 2-Methylpropyl | 2,5-Dichlorophenyl |
| Pentyl | 5-Methyl-2-thienyl |
| 3-Methylbutyl | Phenyl |
| 2-Methylpropyl | 2-Methylphenyl |
| 3-Methylbutyl | 5-Fluoro-2-methylphenyl |
| 2-Methylpropyl | 5-Chloro-2-methoxyphenyl |
| Pentyl | 2,5-Dichlorophenyl |
| 3-Methylbutyl | 5-Methyl-2-thienyl |
| Butyl | 3-Methylphenyl |
| 3-Methylbutyl | 2-Methylphenyl |
| Butyl | 3-Chlorophenyl |
| Pentyl | 5-Chloro-2-methoxyphenyl |
| 3-Methylbutyl | 2,5-Dichlorophenyl |
| Butyl | Phenyl |
| 2-Methylpropyl | 3-Methylphenyl |
| 2-Methylpropyl | 3-Fluoro-4-methylphenyl |
| 2-Methylpropyl | 3-Chlorophenyl |
| 3-Methylbutyl | 5-Chloro-2-methoxyphenyl |
| Butyl | 5-Methyl-2-thienyl |
| 2-Methylpropyl | Phenyl |
| Pentyl | 3-Methylphenyl |
| 3-Methylbutyl | 3-Fluoro-4-methylphenyl |
| Pentyl | 3-Chlorophenyl |
| Butyl | 2,5-Dichlorophenyl |
| 2-Methylpropyl | 5-Methyl-2-thienyl |
| Pentyl | Phenyl |
| 3-Methylbutyl | 3-Methylphenyl |
| Pentyl | 5-Fluoro-2-methylphenyl |
| 3-Methylbutyl | 3-Chlorophenyl |
| 2-Methylpropyl | 4-Methylthiophenyl |
| 2-Methylpropyl | 3-Fluoro-4-methoxyphenyl |
| 3-Methylbutyl | 3-Fluoro-4-methoxyphenyl |
| 2-Methylpropyl | 2,4,6-Trifluorophenyl |
| Butyl | 2,3,6-Trifluorophenyl |
| 2-Methylpropyl | 2,3,6-Trifluorophenyl |

-continued

| R₂ | R₃ |
|---|---|
| Methyl | 2,3,6-Trifluorophenyl |
| Propyl | 2,3,6-Trifluorophenyl |
| Propyl | Phenyl |
| Propyl | 3-Fluorophenyl |
| Propyl | 4-Fluorophenyl |
| Allyl | 2-Fluorophenyl |
| Propyl | 2-Fluorophenyl |
| Butyl | 3-Chlorophenyl |
| 2-Methylpropyl | 3-Chlorophenyl |
| Pentyl | 3-Chlorophenyl |
| 3-Methylbutyl | 3-Chlorophenyl |
| Butyl | 3,4-Difluorophenyl |
| 2-Methylpropyl | 3,4-Difluorophenyl |
| Pentyl | 3,4-Difluorophenyl |
| 3-Methylbutyl | 3,4-Difluorophenyl |
| Butyl | 2,3-Difluorophenyl |
| 2-Methylpropyl | 2,3-Difluorophenyl |
| Pentyl | 2,3-Difluorophenyl |
| 3-Methylbutyl | 2,3-Difluorophenyl |
| Butyl | 2,5-Difluorophenyl |
| 2-Methylpropyl | 2,5-Difluorophenyl |
| Pentyl | 2,5-Difluorophenyl |
| 3-Methylbutyl | 2,5-Difluorophenyl |
| Butyl | 2,4-Difluorophenyl |
| 2-Methylpropyl | 2,4-Difluorophenyl |
| Pentyl | 2,4-Difluorophenyl |
| 3-Methylbutyl | 2,4-Difluorophenyl |
| 2-Methylpropyl | 4-Propylphenyl |
| 2-Methylpropyl | 4-Ethoxyphenyl |
| Butyl | 1,3-Benzodioxol-5-yl |
| 2-Methylpropyl | 1,3-Benzodioxol-5-yl |
| Pentyl | 1,3-Benzodioxol-5-yl |
| 3-Methylbutyl | 1,3-Benzodioxol-5-yl |
| Butyl | 4-Methylthiophenyl |
| 2-Methylpropyl | 4-Methylthiophenyl |
| Butyl | 3-Fluoro-4-methoxyphenyl |
| 2-Methylpropyl | 3-Fluoro-4-methoxyphenyl |
| 3-Methylbutyl | 3-Fluoro-4-methoxyphenyl |
| 2-Methylpropyl | 4-Chloro-3-methylphenyl |
| 3-Methylbutyl | 4-Chloro-3-methylphenyl |
| Butyl | 3-Chloro-4-fluorophenyl |
| 2-Methylpropyl | 3-Chloro-4-fluorophenyl |
| Pentyl | 3-Chloro-4-fluorophenyl |
| 3-Methylbutyl | 3-Chloro-4-fluorophenyl |
| 2-Methylpropyl | 3,4,5-Trifluorophenyl |
| 3-Methylbutyl | 3,4,5-Trifluorophenyl |
| 2-Methylpropyl | 4-Ethylthiophenyl |
| 3-Methylbutyl | 2,3,6-Trifluorophenyl |
| Allyl | 5-Chloro-2-methoxyphenyl |
| Propyl | 5-Chloro-2-methoxyphenyl |
| Propyl | 3-Trifluoromethylphenyl |
| Allyl | 2,5-Dichlorophenyl |
| Propyl | 2,5-Dichlorophenyl |
| Methyl | 3-Bromophenyl |
| Allyl | 3-Bromophenyl |
| Propyl | 3-Bromo-4-fluorophenyl |
| Methyl | 3-Iodophenyl |
| Allyl | 3-Iodophenyl |
| Propyl | 3-Iodophenyl |
| 2-Methoxyethyl | 2,5-Difluorophenyl |
| 2-Methoxyethyl | 2,5-Dichlorophenyl |
| 2-Methoxyethyl | 3-Bromophenyl |
| 2-Methylpropyl | 3-Chloro-4-methoxyphenyl |
| 3-Methylbutyl | 3-Chloro-4-methoxyphenyl |
| 2-Methylpropyl | 5-Chloro-2-methoxyphenyl |
| Pentyl | 5-Chloro-2-methoxyphenyl |
| 3-Methylbutyl | 5-Chloro-2-methoxyphenyl |
| Pentyl | 3-Trifluoromethylphenyl |
| 3-Methylbutyl | 3-Trifluoromethylphenyl |
| Butyl | 2-Trifluoromethylphenyl |
| 3-Methylbutyl | 2-Trifluoromethylphenyl |
| Butyl | 3,4-Dichlorophenyl |
| 2-Methylpropyl | 3,4-Dichlorophenyl |
| 3-Methylbutyl | 3,4-Dichlorophenyl |
| 2-Methylpropyl | 2,5-Dichlorophenyl |
| Pentyl | 2,5-Dichlorophenyl |
| 3-Methylbutyl | 2,5-Dichlorophenyl |
| 2-Methylpropyl | 2,4-Dichlorophenyl |
| 2-Methylpropyl | 3-Bromophenyl |
| Pentyl | 3-Bromophenyl |
| 3-Methylbutyl | 3-Bromophenyl |
| 2-Methylpropyl | 4-Bromophenyl |
| 2-Methylpropyl | 2-Bromophenyl |
| Pentyl | 2-Bromophenyl |
| 3-Methylbutyl | 2-Bromophenyl |
| 2-Methylpropyl | 3-Phenoxyphenyl |
| 2-Methylpropyl | 4-Phenoxyphenyl |
| Butyl | 3-Bromo-4-methylphenyl |
| 2-Methylpropyl | 3-Bromo-4-methylphenyl |
| Butyl | 3-Bromo-4-fluorophenyl |
| 2-Methylpropyl | 3-Bromo-4-fluorophenyl |
| Pentyl | 3-Bromo-4-fluorophenyl |
| 3-Methylbutyl | 3-Bromo-4-fluorophenyl |
| Butyl | 3-Iodophenyl |
| Pentyl | 3-Iodophenyl |
| 3-Methylbutyl | 3-Iodophenyl |
| 2-Methylpropyl | 4-Iodophenyl |
| Methyl | 3-Iodophenyl |
| Cyclopentyl | 4-Methylphenyl |
| Cyclopentyl | 3-Fluoro-4-methylphenyl |
| Cyclopropylmethyl | 5-Chloro-2-methoxyphenyl |
| Cyclopropylmethyl | 3-Trifluoromethylphenyl |
| Cyclopropylmethyl | 2,5-Dichlorophenyl |
| Cyclopropylmethyl | 3-Bromophenyl |
| Cyclopentyl | 3-Methoxybenzyl |
| Cyclopentyl | 2-(2-Chlorophenyl) ethenyl |
| Cyclopropylmethyl | 3-Bromo-4-methylphenyl |
| Cyclopropylmethyl | 3-Bromo-4-fluorophenyl |
| Cyclopropylmethyl | 3-Iodophenyl |
| Cyclopentyl | 3-Chloro-4-methoxyphenyl |
| Cyclopropylmethyl | 5-Chloro-2-methoxyphenyl |
| Cyclopentyl | 2,4-Dichlorophenyl |
| Cyclopentyl | 3-Fluorobenzyl |
| Cyclopentyl | 2-(2-Trifluoromethylphenyl) ethenyl |
| Cyclopentyl | 2-(2-Bromophenyl) ethenyl |
| Cyclopropylmethyl | 2,3,6-Trifluorophenyl |
| Cyclopentyl | 3-Chloro-4-methylphenyl |
| Cyclopropylmethyl | 2,4,5-Trifluorophenyl |
| Propyl | 3-Fluoro-4-methylphenyl |
| Propyl | 3-Chlorophenyl |
| Allyl | 3-Bromo-4-fluorophenyl |
| Propyl | 3-Bromo-4-fluorophenyl |
| Allyl | 3-Iodophenyl |
| Propyl | 3-Iodophenyl |
| Propyl | 3-Iodo-4-methylphenyl |
| Propyl | 3,4-Difluorophenyl |
| Propyl | 2,3-Difluorophenyl |
| Propyl | 2,4-Difluorophenyl |
| Propyl | 1,3-Benzodioxol-5-yl |
| Propyl | 3-Chloro-4-fluorophenyl |
| Propyl | 5-Chloro-2-methoxyphenyl |
| Methyl | 2,5-Dichlorophenyl |
| Allyl | 2,5-Dichlorophenyl |
| Propyl | 2,5-Dichlorophenyl |
| Propyl | 2,4-Dichlorophenyl |
| Methyl | 3-Bromophenyl |
| Allyl | 3-Bromophenyl |
| Propyl | 3-Bromophenyl |
| Propyl | 5-Methyl-2-thienyl |
| Propyl | 2,6-Difluorophenyl |
| 3-Methylbutyl | 4,5-Dimethyl-2-furyl |
| 3-Methylbutyl | 3-Chloro-4-methylphenyl |
| 3-Methylbutyl | 2,4,5-Trifluorophenyl |
| 3-Methylbutyl | 2,6-Difluorophenyl |
| 3-Methylbutyl | 2-Bromo-5-methoxyphenyl |
| 3-Methylbutyl | 3,5-Difluorophenyl |
| 3-Methylbutyl | 5-Bromo-2-thienyl |
| 3-Methylbutyl | 3-Bromo-2-thienyl. |

5. A compound of the formula

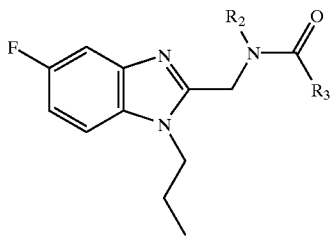

where $R_2$ and $R_3$ are defined in the following table:

| $R_2$ | $R_3$ |
|---|---|
| Propyl | Phenyl |
| Methyl | 3-Chlorophenyl |
| Allyl | 3-Chlorophenyl |
| Propyl | 3-Chlorophenyl |
| Propyl | 5-Chloro-2-methoxyphenyl |
| Propyl | 3-Trifluoromethylphenyl |
| Propyl | 2,5-Dichlorophenyl |
| Propyl | 3-Bromophenyl |
| Propyl | 3-Bromo-4-fluorophenyl |
| Methyl | 3-Iodophenyl |
| Allyl | 3-Iodophenyl |
| Propyl | 3-Iodophenyl |
| Allyl | 5-Chloro-2-methoxyphenyl |
| Propyl | 3-Fluorophenyl |
| Propyl | 2-Fluorophenyl |
| Propyl | 3-Fluorophenyl |
| Propyl | 2-Fluorophenyl |
| Allyl | 2,5-Difluorophenyl |
| Propyl | 2,5-Difluorophenyl |
| Propyl | 1,3-Benzodioxol-5-yl |
| Methyl | 5-Chloro-2-methoxyphenyl |
| Allyl | 5-Chloro-2-methoxyphenyl |
| Methyl | 2,5-Dichlorophenyl |
| Methyl | 5-Chloro-2-methoxyphenyl |
| Allyl | 5-Chloro-2-methoxyphenyl |
| Propyl | 5-Chloro-2-methoxyphenyl |
| Propyl | 3,4-Dichlorophenyl |
| Allyl | 2,5-Dichlorophenyl |
| Propyl | 2,5-Dichlorophenyl |
| Propyl | 2,4-Dichlorophenyl |
| Methyl | 3-Bromophenyl |
| Allyl | 3-Bromophenyl |
| Propyl | 3-Bromophenyl |
| Cyclopropylmethyl | 5-Chloro-2-methoxyphenyl |
| Cyclopropylmethyl | 2,5-Dichlorophenyl |
| Propyl | 3-Bromophenyl |
| Cyclopropylmethyl | 3-Bromophenyl |
| Pentyl | 3-Bromo-4-fluorophenyl |
| 3-Methylbutyl | 3-Bromo-4-fluorophenyl |
| Pentyl | 3-Iodophenyl |
| Cyclopropylmethyl | 3-Bromo-4-fluorophenyl |
| Cyclopropylmethyl | 3-Iodophenyl |
| Butyl | 2-Thienyl |
| 2-Methylpropyl | 2-Thienyl |
| Pentyl | 2-Thienyl |
| 3-Methylbutyl | 2-Thienyl |
| Butyl | 3-Thienyl |
| 2-Methylpropyl | 3-Thienyl |
| Pentyl | 3-Thienyl |
| 3-Methylbutyl | 3-Thienyl |
| 3-Methylbutyl | Benzyl |
| Butyl | 5-Methyl-2-thienyl |
| 2-Methylpropyl | 5-Methyl-2-thienyl |
| Pentyl | 5-Methyl-2-thienyl |
| 3-Methylbutyl | 5-Methyl-2-thienyl |
| 3-Methylbutyl | 3-Fluorobenzyl |
| 3-Methylbutyl | 4-Fluorobenzyl |
| 3-Methylbutyl | 3-Methoxybenzyl |
| 3-Methylbutyl | 2,3,6-Trifluorophenyl |
| 2-Methylpropyl | 2,3,6-Trifluorophenyl |

-continued

| $R_2$ | $R_3$ |
|---|---|
| 3-Methylbutyl | 2,3,6-Trifluorophenyl |
| 3-Methylbutyl | 2-Chloro-6-fluorophenyl |
| Butyl | Phenyl |
| 2-Methylpropyl | Phenyl |
| Pentyl | Phenyl |
| 3-Methylbutyl | Phenyl |
| Butyl | 3-Methylphenyl |
| 2-Methylpropyl | 3-Methylphenyl |
| Pentyl | 3-Methylphenyl |
| 3-Methylbutyl | 3-Methylphenyl |
| Butyl | 4-Methylphenyl |
| 2-Methylpropyl | 4-Methylphenyl |
| Butyl | 3-Fluorophenyl |
| 2-Methylpropyl | 3-Fluorophenyl |
| Pentyl | 3-Fluorophenyl |
| 3-Methylbutyl | 3-Fluorophenyl |
| Butyl | 4-Fluorophenyl |
| 3-Methylbutyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 4-Ethylphenyl |
| 2-Methylpropyl | 3,4-Dimethylphenyl |
| 3-Methylbutyl | 3-Methoxyphenyl |
| 2-Methylpropyl | 3-Fluoro-4-methylphenyl |
| 3-Methylbutyl | 3-Fluoro-4-methylphenyl |
| 2-Methylpropyl | 5-Fluoro-2-methylphenyl |
| Pentyl | 5-Fluoro-2-methylphenyl |
| 3-Methylbutyl | 5-Fluoro-2-methylphenyl |
| Butyl | 2,5-Dichlorophenyl |
| 2-Methylpropyl | 2,5-Dichlorophenyl |
| Pentyl | 2,5-Dichlorophenyl |
| 3-Methylbutyl | 2,5-Dichlorophenyl |
| 2-Methylpropyl | 4-Pentylphenyl |
| Butyl | 3-Bromophenyl |
| 2-Methylpropyl | 3-Bromophenyl |
| Pentyl | 3-Bromophenyl |
| 3-Methylbutyl | 3-Bromophenyl |
| 2-Methylpropyl | 4-Bromophenyl |
| Butyl | 3,4-Dimethylphenyl |
| 2-Methylpropyl | 3-Iodo-4-methylphenyl |
| 3-Methylbutyl | 3-Iodo-4-methylphenyl |
| Butyl | 4,5-Dimethyl-2-furyl |
| 2-Methylpropyl | 4,5-Dimethyl-2-furyl |
| 3-Methylbutyl | 4,5-Dimethyl-2-furyl |
| 3-Methylbutyl | 4-Methoxy-3-thienyl |
| Butyl | 3-Chloro-2-thienyl |
| 2-Methylpropyl | 3-Chloro-2-thienyl |
| Pentyl | 3-Chloro-2-thienyl |
| 3-Methylbutyl | 3-Chloro-2-thienyl |
| 2-Methylpropyl | 3-Chloro-4-methylphenyl |
| 3-Methylbutyl | 3-Chloro-4-methylphenyl |
| 3-Methylbutyl | 2,4,5-Trifluorophenyl |
| Pentyl | 2,6-Difluorophenyl |
| 3-Methylbutyl | 2,6-Difluorophenyl |
| Pentyl | 2-Bromo-5-methoxyphenyl |
| 3-Methylbutyl | 2-Bromo-5-methoxyphenyl |
| 3-Methylbutyl | 3,5-Difluorophenyl |
| 2-Methylpropyl | 5-Bromo-2-thienyl |
| 3-Methylbutyl | 5-Bromo-2-thienyl |
| Butyl | 5-Ethyl-2-thienyl |
| 2-Methylpropyl | 5-Ethyl-2-thienyl |
| 3-Methylbutyl | 5-Ethyl-2-thienyl |
| 2-Methylpropyl | 5-Propyl-2-thienyl |
| 2-Methylpropyl | 5-Butyl-2-thienyl |
| 2-Methylpropyl | 5-Pentyl-2-thienyl |
| 2-Methylpropyl | 5-Hexyl-2-thienyl. |

6. A compound of the formula

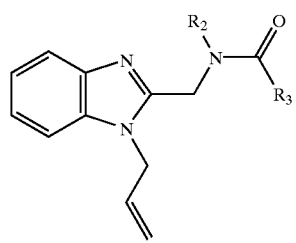

where R₂ and R₃ are defined in the following table:

| R₂ | R₃ |
|---|---|
| Methyl | 2,5-Difluorophenyl |
| Methyl | 2,5-Dichlorophenyl |
| Propyl | 3-Bromophenyl |
| Methyl | 3-Iodophenyl |
| Allyl | 3-Iodophenyl |
| Propyl | 3-Iodophenyl |
| Propyl | 2,5-Dichlorophenyl |
| Methyl | 3-Bromophenyl |
| Allyl | 3-Bromophenyl |
| Propyl | 3-Bromo-4-fluorophenyl |
| 2-Methylpropyl | 3-Fluorophenyl |
| 2-Methylpropyl | 3,4-Dimethylphenyl |
| 2-Methylpropyl | 3-Methoxyphenyl |
| 2-Methylpropyl | 3-Fluoro-4-methylphenyl |
| Cyclopentyl | 3-Fluoro-4-methylphenyl |
| 2-Methylpropyl | 5-Fluoro-2-methylphenyl |
| 2-Methylpropyl | 2-Fluoro-3-methylphenyl |
| 2-Methylpropyl | 3-Chlorophenyl |
| 2-Methylpropyl | 4-Chlorophenyl |
| 2-Methylpropyl | 1,3-Benzodioxol-5-yl |
| Cyclopentyl | 4-Methoxyphenyl |
| Cyclopentyl | 4-Butylphenyl |
| 3-Methylbutyl | 3-Chloro-4-methoxyphenyl |
| Cyclopentyl | 3-Chloro-4-methoxyphenyl |
| 2-Methylpropyl | 3,4-Dichlorophenyl |
| 3-Methylbutyl | 2,5-Dichlorophenyl |
| Cyclopentyl | 2,4-Dichlorophenyl |
| Cyclopentyl | 4-Pentylphenyl |
| 3-Methylbutyl | 3-Bromophenyl |
| 2-Methylpropyl | 4-Hexylphenyl |
| Cyclopentyl | 4-Hexylphenyl |
| 2-Methylpropyl | 3-Bromo-4-methylphenyl |
| 2-Methylpropyl | 3-Bromo-4-fluorophenyl |
| 3-Methylbutyl | 3-Bromo-4-fluorophenyl |
| 2-Methylpropyl | 3-Iodophenyl |
| 3-Methylbutyl | 3-Iodophenyl |
| 2-Methylpropyl | 3-Iodo-4-methylphenyl |
| 3-Methylbutyl | 2-Thienyl |
| 3-Methylbutyl | Benzyl |
| 2-Methylpropyl | 5-Methyl-2-thienyl |
| 3-Methylbutyl | 5-Methyl-2-thienyl |
| 3-Methylbutyl | 3-Fluorobenzyl |
| Cyclopentyl | 3-Fluorobenzyl |
| Cyclopentyl | 2-Chlorobenzyl |
| 2-Methylpropyl | 2-(2-Chlorophenyl)ethenyl |
| Cyclopentyl | 2-(2-Chlorophenyl)ethenyl |
| 2-Methylpropyl | 2,3,6-Trifluorophenyl |
| 2-Methylpropyl | 4,5-Dimethyl-2-furyl. |

7. A compound of the formula

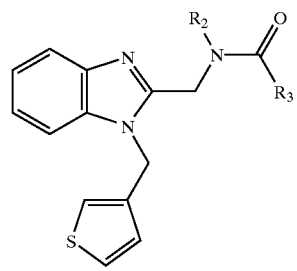

where R₂ and R₃ are defined in the following table:

| R₂ | R₃ |
|---|---|
| Propyl | 5-Bromo-2-thienyl |
| Propyl | 1,3-Benzodioxol-5-yl. |

8. A compound of the formula

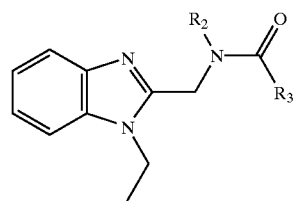

where R₂ and R₃ are defined in the following table:

| R₂ | R₃ |
|---|---|
| Propyl | 3-Bromo-4-fluorophenyl |
| Allyl | 3-Iodophenyl |
| Propyl | 3-Iodophenyl |
| Propyl | 3-Iodo-4-methylphenyl |
| Methyl | 2-Thienyl |
| Methyl | 5-Methyl-2-thienyl |
| Propyl | 3-Methylphenyl |
| Propyl | 5-Chloro-2-methoxyphenyl |
| Propyl | 2,5-Dichlorophenyl |
| Propyl | 3-Bromophenyl |
| 3-Methylbutyl | 3-Chloro-4-methylphenyl |
| 3-Methylbutyl | 2,4,5-Trifluorophenyl |
| 3-Methylbutyl | 3,5-Difluorophenyl |
| 3-Methylbutyl | 5-Bromo-2-thienyl |
| 2-(2-Fluorophenyl)ethyl | 2,5-Dichlorophenyl |
| 2-(2-Fluorophenyl)ethyl | 3-Bromophenyl |
| 2-(2-Fluorophenyl)ethyl | 3-Iodophenyl. |

9. A compound of the formula

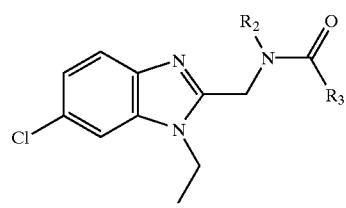

where $R_2$ and $R_3$ are defined in the following table:

| $R_2$ | $R_3$ |
|---|---|
| Allyl | 3-Bromo-4-methylphenyl |
| Propyl | 3-Bromo-4-methylphenyl |
| Allyl | 3-Bromo-4-fluorophenyl |
| Propyl | 3-Bromo-4-fluorophenyl |
| Methyl | 3-Iodophenyl |
| Allyl | 3-Iodophenyl |
| Propyl | 3-Iodophenyl |
| Propyl | 3-Iodo-4-methylphenyl |
| Methyl | 2-Thienyl |
| Methyl | 3-Thienyl |
| Methyl | 3-Methyl-2-thienyl |
| Propyl | 5-Methyl-2-thienyl |
| Propyl | Phenyl |
| Methyl | 3-Methylphenyl |
| Propyl | 3-Fluorophenyl |
| Propyl | 2-Fluorophenyl |
| Methyl | 5-Fluoro-2-methylphenyl |
| Allyl | 5-Fluoro-2-methylphenyl |
| Methyl | 3-Chlorophenyl |
| Propyl | 3-Chlorophenyl |
| Propyl | 2-Chlorophenyl |
| Allyl | 3,4-Difluorophenyl |
| Propyl | 3,4-Difluorophenyl |
| Methyl | 2,3-Difluorophenyl |
| Allyl | 2,3-Difluorophenyl |
| Propyl | 2,3-Difluorophenyl |
| Methyl | 2,5-Difluorophenyl |
| Allyl | 2,5-Difluorophenyl |
| Propyl | 2,5-Difluorophenyl |
| Propyl | 2,4-Difluorophenyl |
| Propyl | 1,3-Benzodioxol-5-yl |
| Allyl | 3-Chloro-4-fluorophenyl |
| Propyl | 3-Chloro-4-fluorophenyl |
| Allyl | 5-Chloro-2-methoxyphenyl |
| Propyl | 5-Chloro-2-methoxyphenyl |
| Allyl | 2,5-Dichlorophenyl |
| Propyl | 2,5-Dichlorophenyl |
| Allyl | 3-Bromophenyl |
| Propyl | 3-Bromophenyl |
| Methyl | 5-Ethoxy-2-thienyl |
| 2-Methylpropyl | 2,4,6-Trifluorophenyl |
| 2-Methylpropyl | 2,3,6-Trifluorophenyl |
| 3-Methylbutyl | 2,3,6-Trifluorophenyl |
| 2-Methylpropyl | 4,5-Dimethyl-2-furyl |
| 3-Methylbutyl | 4,5-Dimethyl-2-furyl |
| 2-Methylpropyl | 3-Chloro-2-thienyl |
| 3-Methylbutyl | 3-Chloro-2-thienyl |
| 2-Methylpropyl | 5-Methylthio-2-thienyl |
| 2-Methylpropyl | 3-Chlorophenyl |
| 3-Methylbutyl | 2,4,5-Trifluorophenyl |
| 2-Methylpropyl | 2,6-Difluorophenyl |
| 3-Methylbutyl | Phenyl |
| 2-Methylpropyl | 3-Methylphenyl |
| 3-Methylbutyl | 3-Methylphenyl |
| 2-Methylpropyl | 4-Methylphenyl |
| 3-Methylbutyl | 4-Methylphenyl |
| 2-Methylpropyl | 2-Methylphenyl |
| 3-Methylbutyl | 2-Methylphenyl |
| 2-Methylpropyl | 3-Fluorophenyl |
| 3-Methylbutyl | 3-Fluorophenyl |
| 2-Methylpropyl | 3-Fluorophenyl |
| 3-Methylbutyl | 4-Fluorophenyl |
| 2-Methylpropyl | 2-Fluorophenyl |
| 3-Methylbutyl | 2-Fluorophenyl |
| 2-Methylpropyl | 4-Ethylphenyl |
| 2-Methylpropyl | 3,4-Dimethylphenyl |
| 2-Methylpropyl | 3-Fluoro-4-methylphenyl |
| Cyclopentyl | 3-Fluoro-4-methylphenyl |
| 2-Methylpropyl | 4-Chlorophenyl |
| Cyclopentyl | 4-Methoxyphenyl |
| 3-Methylbutyl | 3-Chloro-4-fluorophenyl |
| 3-Methylbutyl | 2-Thienyl. |

10. A compound of the formula

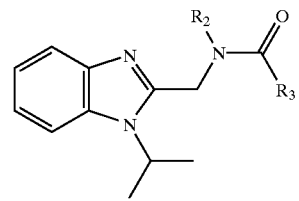

where $R_2$ and $R_3$ are defined in the following table:

| $R_2$ | $R_3$ |
|---|---|
| Methyl | 2,5-Difluorophenyl |
| Propyl | 2,5-Dichlorophenyl |
| Propyl | 3-Iodophenyl. |

11. A compound of the formula

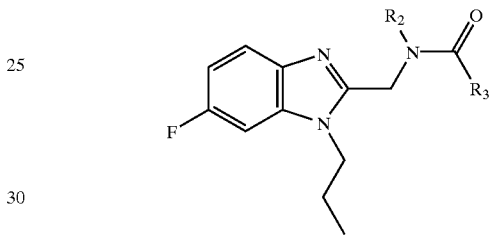

where $R_2$ and $R_3$ are defined in the following table:

| $R_2$ | $R_3$ |
|---|---|
| Propyl | 3-Fluorophenyl |
| Propyl | 2-Fluorophenyl |
| Propyl | 3,4-Difluorophenyl |
| Methyl | 2,5-Difluorophenyl |
| Allyl | 2,5-Difluorophenyl |
| Propyl | 2,5-Difluorophenyl |
| Propyl | 1,3-Benzodioxol-5-yl |
| Propyl | 3-Chloro-4-fluorophenyl |
| Methyl | 5-Chloro-2-methoxyphenyl |
| Ethyl | 5-Chloro-2-methoxyphenyl |
| Allyl | 5-Chloro-2-methoxyphenyl |
| Propyl | 5-Chloro-2-methoxyphenyl |
| Methyl | 2,5-Dichlorophenyl |
| Allyl | 2,5-Dichlorophenyl |
| Propyl | 2,5-Dichlorophenyl |
| Propyl | Phenyl |
| Propyl | 3-Fluoro-4-methylphenyl |
| Propyl | 5-Fluoro-2-methylphenyl |
| Methyl | 3-Chlorophenyl |
| Allyl | 3-Chlorophenyl |
| Propyl | 3-Chlorophenyl |
| Methyl | 5-Chloro-2-methoxyphenyl |
| Ethyi | 5-Chloro-2-methoxyphenyl |
| Allyl | 5-Chloro-2-methoxyphenyl |
| Propyl | 5-Chloro-2-methoxyphenyl |
| Methyl | 3-Trifluorophenyl |
| Propyl | 3-Trifluorophenyl |
| Methyl | 2,5-Dichlorophenyl |
| Allyl | 2,5-Dichlorophenyl |
| Propyl | 2,5-Dichlorophenyl |
| Methyl | 3-Bromophenyl |
| Allyl | 3-Bromophenyl |
| Propyl | 3-Bromophenyl |
| Propyl | 3-Bromo-4-fluorophenyl |
| Methyl | 3-Iodophenyl |

-continued

| R₂ | R₃ |
|---|---|
| Allyl | 3-Iodophenyl |
| Propyl | 3-Iodophenyl |
| Allyl | 2-Fluorophenyl |
| Propyl | 2-Fluorophenyl |
| Propyl | 2-Chlorophenyl |
| Propyl | 3,4-Difluorophenyl |
| Propyl | 2,3-Difluorophenyl |
| Methyl | 2,5-Difluorophenyl |
| Propyl | 4-Methylthiophenyl |
| Propyl | 3-Fluoro-4-methoxyphenyl |
| Propyl | 4-Chloro-3-methylphenyl |
| Methyl | 3-Chloro-4-fluorophenyl |
| Allyl | 3-Chloro-4-fluorophenyl |
| Propyl | 3-Chloro-4-fluorophenyl |
| Propyl | 3,4,5-Trifluorophenyl |
| Propyl | 4-Butylphenyl |
| Propyl | 4-Methylthiophenyl |
| Butyl | 2-Thienyl |
| 2-Methylpropyl | 2-Thienyl |
| Pentyl | 2-Thienyl |
| 3-Methylbutyl | 2-Thienyl |
| Butyl | 3-Thienyl |
| 2-Methylpropyl | 3-Thienyl |
| Pentyl | 3-Thienyl |
| 3-Methylbutyl | 3-Thienyl |
| 3-Methylbutyl | Benzyl |
| Butyl | 5-Methyl-2-thienyl |
| 2-Methylpropyl | 5-Methyl-2-thienyl |
| Pentyl | 5-Methyl-2-thienyl |
| 3-Methylbutyl | 5-Methyl-2-thienyl |
| 3-Methylbutyl | 3-Fluorobenzyl |
| 3-Methylbutyl | 3-Methoxybenzyl |
| Butyl | Phenyl |
| 2-Methylpropyl | Phenyl |
| Pentyl | Phenyl |
| 3-Methylbutyl | Phenyl |
| Butyl | 3-Methylphenyl |
| 2-Methylpropyl | 3-Methylphenyl |
| Pentyl | 3-Methylphenyl |
| 3-Methylbutyl | 3-Methylphenyl |
| Butyl | 4-Methylphenyl |
| 2-Methylpropyl | 4-Methylphenyl |
| 3-Methylbutyl | 4-Methylphenyl |
| Butyl | 3-Fluorophenyl |
| 2-Methylpropyl | 3-Fluorophenyl |
| Pentyl | 3-Fluorophenyl |
| 3-Methylbutyl | 3-Fluorophenyl |
| Butyl | 4-Fluorophenyl |
| 2-Methylpropyl | 4-Fluorophenyl |
| Pentyl | 4-Fluorophenyl |
| 3-Methylbutyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 4-Ethylphenyl |
| 2-Methylpropyl | 3,4-Dimethylphenyl |
| 3-Methylbutyl | 2,5-Dimethylphenyl |
| 2-Methylpropyl | 2,4-Dimethylphenyl |
| 2-Methylpropyl | 3-Methoxyphenyl |
| 3-Methylbutyl | 3-Methoxyphenyl |
| 3-Methylbutyl | 2-Methoxyphenyl |
| 2-Methylpropyl | 3-Fluoro-4-methylphenyl |
| 3-Methylbutyl | 3-Fluoro-4-methylphenyl |
| Butyl | 5-Fluoro-2-methylphenyl |
| 2-Methylpropyl | 5-Fluoro-2-methylphenyl |
| Pentyl | 5-Fluoro-2-methylphenyl |
| 3-Methylbutyl | 5-Fluoro-2-methylphenyl |
| 2-Methylpropyl | 4-Chlorophenyl |
| 3-Methylbutyl | 4-Chlorophenyl |
| 2-Methylpropyl | 2,5-Dichlorophenyl |
| Pentyl | 2,5-Dichlorophenyl |
| 3-Methylbutyl | 2,5-Dichlorophenyl |
| 2-Methylpropyl | 4-Pentylphenyl |
| 2-Methylpropyl | 3-Bromophenyl |
| Pentyl | 3-Bromophenyl |
| 3-Methylbutyl | 3-Bromophenyl |
| 2-Methylpropyl | 3-Iodo-4-methylphenyl |
| 3-Methylbutyl | 3-Iodo-4-methylphenyl |
| Butyl | 2-Chlorophenyl |
| 2-Methylpropyl | 2-Chlorophenyl |
| Pentyl | 2-Chlorophenyl |
| Butyl | 3,4-Difluorophenyl |
| 2-Methylpropyl | 3,4-Difluorophenyl |
| Pentyl | 3,4-Difluorophenyl |
| 3-Methylbutyl | 3,4-Difluorophenyl |
| Butyl | 2,3-Difluorophenyl |
| 2-Methylpropyl | 2,3-Difluorophenyl |
| Pentyl | 2,3-Difluorophenyl |
| 3-Methylbutyl | 2,3-Difluorophenyl |
| Butyl | 2,5-Difluorophenyl |
| 2-Methylpropyl | 2,5-Difluorophenyl |
| Pentyl | 2,5-Difluorophenyl |
| 3-Methylbutyl | 2,5-Difluorophenyl |
| Butyl | 2,4-Difluorophenyl |
| 2-Methylpropyl | 2,4-Difluorophenyl |
| Pentyl | 2,4-Difluorophenyl |
| 3-Methylbutyl | 2,4-Difluorophenyl |
| 2-Methylpropyl | 4-Propylphenyl |
| 2-Methylpropyl | 4-i-Propylphenyl |
| Butyl | 1,3-Benzodioxol-5-yl |
| 2-Methylpropyl | 1,3-Benzodioxol-5-yl |
| Pentyl | 1,3-Benzodioxol-5-yl |
| 3-Methylbutyl | 1,3-Benzodioxol-5-yl |
| Butyl | 3-Bromo-4-methylphenyl |
| 2-Methylpropyl | 3-Bromo-4-methylphenyl |
| Pentyl | 3-Bromo-4-methylphenyl |
| 3-Methylbutyl | 3-Bromo-4-methylphenyl |
| 2-Methylpropyl | 4-Heptylphenyl |
| Butyl | 3-Iodophenyl |
| 2-Methylpropyl | 3-Iodophenyl |
| Pentyl | 3-Iodophenyl |
| 3-Methylbutyl | 3-Iodophenyl |
| 2-Methylpropyl | 4-Iodophenyl |
| Butyl | 5-Ethyl-2-thienyl |
| 2-Methylpropyl | 5-Ethyl-2-thienyl |
| 3-Methylbutyl | 5-Ethyl-2-thienyl |
| 2-Methylpropyl | 5-Propyl-2-thienyl. |

12. A compound of the formula

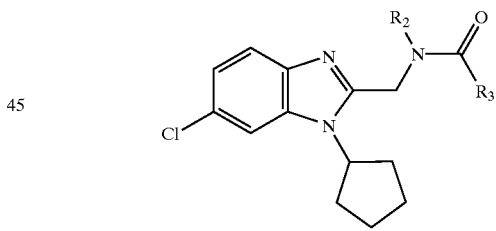

where R₂ and R₃ are defined in the following table:

| R₂ | R₃ |
|---|---|
| Methyl | 3-Fluorophenyl |
| Allyl | 3-Fluorophenyl |
| Propyl | 3-Fluorophenyl |
| Propyl | 4-Fluorophenyl |
| Methyl | 3-Chloro-4-methylphenyl |
| Allyl | 3-Chloro-4-methylphenyl |
| Propyl | 3-Chloro-4-methylphenyl |
| Allyl | 5-Bromo-2-thienyl |
| Propyl | 5-Bromo-2-thienyl |
| Propyl | 3-Fluoro-4-methylphenyl |
| Propyl | 5-Fluoro-2-methylphenyl |
| Propyl | 3-Methoxyphenyl |

-continued

| $R_2$ | $R_3$ |
|---|---|
| Propyl | 3-Bromo-4-methylphenyl |
| Allyl | 3-Bromo-4-fluorophenyl |
| Propyl | 3-Bromo-4-fluorophenyl |
| Allyl | 3-Iodophenyl |
| Propyl | 3-Iodophenyl |
| Allyl | 5-Chloro-2-methoxyphenyl |
| Propyl | 5-Chloro-2-methoxyphenyl |
| Propyl | 3,4-Dichlorophenyl |
| Ethyl | 2,5-Dichlorophenyl |
| Allyl | 2,5-Dichlorophenyl |
| Propyl | 2,5-Dichlorophenyl |
| Propyl | 2,4-Dichlorophenyl |
| Ethyl | 3-Bromophenyl |
| Allyl | 3-Bromophenyl |
| Propyl | 3-Bromophenyl |
| Propyl | 5-Methyl-2-thienyl |
| Propyl | 4-Chloro-3-methylphenyl |
| Propyl | 3-Chloro-4-fluorophenyl |
| 2-Methylpropyl | Phenyl |
| 3-Methylbutyl | Phenyl |
| 2-Methylpropyl | 3-Methylphenyl |
| 3-Methylbutyl | 3-Methylphenyl |
| 2-Methylpropyl | 4-Methylphenyl |
| Cyclopentyl | 4-Methylphenyl |
| 2-Methylpropyl | 2-Methylphenyl |
| 3-Methylbutyl | 2-Methylphenyl |
| 2-Methylpropyl | 3-Fluorophenyl |
| 3-Methylbutyl | 3-Fluorophenyl |
| 2-Methylpropyl | 4-Fluorophenyl |
| 3-Methylbutyl | 4-Fluorophenyl |
| 2-Methylpropyl | 2-Fluorophenyl |
| Cyclopentyl | 2-Fluorophenyl |
| 2-Methylpropyl | 4-Ethylphenyl |
| 2-Methylpropyl | 3,4-Dimethylphenyl |
| 2-Methylpropyl | 2,3-Dimethylphenyl |
| 2-Methylpropyl | 2,5-Dimethylphenyl |
| 3-Methylbutyl | 2,5-Dimethylphenyl |
| 2-Methylpropyl | 2,4-Dimethylphenyl |
| 3-Methylbutyl | 2,4-Dimethylphenyl |
| Cyclopentyl | 2,4-Dimethylphenyl |
| 2-Methylpropyl | 3 Methoxyphenyl |
| 3-Methylbutyl | 3-Methoxyphenyl |
| 2-Methylpropyl | 4-Methoxyphenyl |
| 3 Methylbutyl | 4-Methoxyphenyl |
| Cyclopentyl | 4-Methoxyphenyl |
| 2-Methylpropyl | 2-Methoxyphenyl |
| 3-Methylbutyl | 2-Methoxyphenyl |
| 2 Methylpropyl | 3-Fluoro-4-methylphenyl |
| Cyclopentyl | 3-Fluoro-4-methylphenyl |
| 2-Methylpropyl | 3-Fluoro-2-methylphenyl |
| 3 Methylbutyl | 3-Fluoro-2-methylphenyl |
| 2-Methylpropyl | 5-Fluoro-2-methylphenyl |
| 3-Methylbutyl | 5-Fluoro-2-methylphenyl |
| 2-Methylpropyl | 2-Fluoro-3-methylphenyl |
| 2-Methylpropyl | 3-Chlorophenyl |
| 3-Methylbutyl | 3-Chlorophenyl |
| Cyclopentyl | 3-Chlorophenyl |
| 2-Methylpropyl | 4-Chlorophenyl |
| Cyclopentyl | 4-Chlorophenyl |
| 3-Methylbutyl | 2-Chlorophenyl |
| Cyclopentyl | 2-Chlorophenyl |
| 2-Methylpropyl | 3,4-Difluorophenyl |
| 3-Methylbutyl | 3,4-Difluorophenyl |
| 2-Methylpropyl | 2,3-Difluorophenyl |
| 3-Methylbutyl | 2,3-Difluorophenyl |
| Cyclopentyl | 2,3-Difluorophenyl |
| 2-Methylpropyl | 2,5-Difluorophenyl |
| 3-Methylbutyl | 2,5-Difluorophenyl |
| 2-Methylpropyl | 2,4-Difluorophenyl |
| 3-Methylbutyl | 2,4-Difluorophenyl |
| Cyclopentyl | 2,4-Difluorophenyl |
| 2-Methylpropyl | 1,3-Benzodioxol-5-yl |
| 3-Methylbutyl | 1,3-Benzodioxol-5-yl |
| Cyclopentyl | 1,3-Benzodioxol-5-yl |
| 2-Methylpropyl | 4-Methylthiophenyl |
| 3-Methylbutyl | 4-Methylthiophenyl |
| Cyclopentyl | 3-Fluoro-4-methoxy |
| Cyclopentyl | 4-Butylphenyl |
| Cyclopentyl | 4-Ethylthiophenyl |
| 2-Methylpropyl | 3-Chloro-4-methoxyphenyl |
| 3-Methylbutyl | 3-Chloro-4-methoxyphenyl |
| Cyclopentyl | 3-Chloro-4-methoxyphenyl |
| 2-Methylpropyl | 2-Trifluoromethylphenyl |
| 3-Methylbutyl | 2-Trifluoromethylphenyl |
| 2-Methylpropyl | 3,4-Dichlorophenyl |
| 3-Methylbutyl | 3,4-Dichlorophenyl |
| 2-Methylpropyl | 2,3-Dichlorophenyl |
| 2-Methylpropyl | 2,5-Dichlorophenyl |
| 3-Methylbutyl | 2,5-Dichlorophenyl |
| 2-Methylpropyl | 2,4-Dichlorophenyl |
| Cyclopentyl | 2,4-Dichlorophenyl |
| 2-Methylpropyl | 3-Bromophenyl |
| 3-Methylbutyl | 3-Bromophenyl |
| Cyclopentyl | 3-Bromophenyl |
| 2-Methylpropyl | 4-Bromophenyl |
| Cyclopentyl | 4-Bromophenyl |
| 2-Methylpropyl | 2-Bromophenyl |
| 3-Methylbutyl | 2-Bromophenyl |
| 2-Methylpropyl | 3-Bromo-4-methylphenyl |
| 3-Methylbutyl | 3-Bromo-4-methylphenyl |
| Cyclopentyl | 3-Bromo-4-methylphenyl |
| 2-Methylpropyl | 3-Bromo-4-fluorophenyl |
| 3-Methylbutyl | 3-Bromo-4-fluorophenyl |
| 2-Methylpropyl | 3-Iodophenyl |
| 3-Methylbutyl | 3-Iodophenyl |
| 2-Methylpropyl | 4-Iodophenyl |
| 2-Methylpropyl | 3-Iodo-4-methylphenyl |
| 2-Methylpropyl | 4-Iodobenzyl |
| 2-Methylpropyl | 2-Thienyl |
| 3-Methylbutyl | 2-Thienyl |
| 2-Methylpropyl | Benzyl |
| 3-Methylbutyl | Benzyl |
| Cyclopentyl | Benzyl |
| 2-Methylpropyl | 5-Methyl-2-thienyl |
| 3-Methylbutyl | 5-Methyl-2-thienyl |
| Cyclopentyl | 5-Methyl-2-thienyl |
| Cyclopentyl | 3-Methylbenzyl |
| 2-Methylpropyl | 3-Fluorobenzyl |
| 3-Methylbutyl | 3-Fluorobenzyl |
| Cyclopentyl | 3-Fluorobenzyl |
| 3-Methylbutyl | 2-Methoxybenzyl |
| Cyclopentyl | 1-(4-Fluorophenyl)ethyl |
| Cyclopentyl | 2-Chlorobenzyl |
| Cyclopentyl | 2-(2-Chlorophenyl)ethenyl |
| 2-Methylpropyl | 2,4,6-Trifluorophenyl |
| 2-Methylpropyl | 2,3,6-Trifluorophenyl |
| 2-Methylpropyl | 2-Chloro-6-fluorophenyl |
| 2-Methylpropyl | 3-Chloro-4-methylphenyl. |

13. A compound of the formula

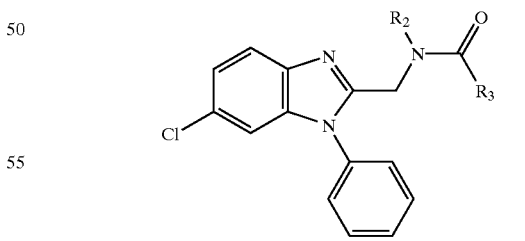

where $R_2$ and $R_3$ are defined in the following table:

| $R_2$ | $R_3$ |
|---|---|
| Propyl | Phenyl |
| Propyl | 3-Methylphenyl |

-continued

| $R_2$ | $R_3$ |
|---|---|
| Propyl | 4-Methylphenyl |
| Propyl | 3-Fluorophenyl |
| Methyl | 2-Fluorophenyl |
| Allyl | 2-Fluorophenyl |
| Propyl | 2-Fluorophenyl |
| Methyl | 2,3-Difluorophenyl |
| Methyl | 2,5-Difluorophenyl |
| Ethyl | 5-Chloro-2-methoxyphenyl |
| 3-Methylbutyl | 2,3,6-Trifluorophenyl. |

14. A compound of the formula

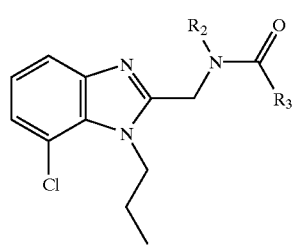

where $R_2$ and $R_3$ are defined in the following table:

| $R_2$ | $R_3$ |
|---|---|
| Methyl | Phenyl |
| Propyl | Phenyl |
| Methyl | 3-Methylphenyl |
| Propyl | 3-Methylphenyl |
| Methyl | 3-Fluorophenyl |
| Propyl | 3-Fluorophenyl |
| Methyl | 2-Fluorophenyl |
| Allyl | 2-Fluorophenyl |
| Propyl | 2-Fluorophenyl |
| Methyl | 5-Fluoro-2-methylphenyl |
| Methyl | 3-Chlorophenyl |
| Propyl | 3-Chlorophenyl |
| Propyl | 3-Chloro-4-fluorophenyl |
| Methyl | 2-Thienyl |
| Propyl | 2-Thienyl |
| Methyl | 3-Thienyl |
| Methyl | 3-Methyl-2-thienyl |
| Methyl | 5-Methyl-2-thienyl |
| Propyl | 5-Methyl-2-thienyl |
| Propyl | 5-Chloro-2-methoxyphenyl |
| Methyl | 3-Bromophenyl |
| Propyl | 3-Bromophenyl. |

15. A compound of the formula

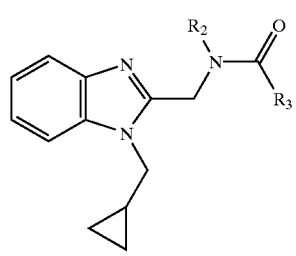

where $R_2$ and $R_3$ are defined in the following table:

| $R_2$ | $R_3$ |
|---|---|
| Propyl | Phenyl |
| Propyl | 3-Methylphenyl |
| Propyl | 4-Methylphenyl |
| Propyl | 3-Fluorophenyl |
| Propyl | 2-Fluorophenyl |
| Propyl | 5-Fluoro-2-methylphenyl |
| Ethyl | 3-Chlorophenyl |
| Allyl | 3-Chlorophenyl |
| Propyl | 3-Chlorophenyl |
| Propyl | 1,3-Benzodioxol-5-yl |
| Allyl | 3-Chloro-4-fluorophenyl |
| Propyl | 3-Chloro-4-fluorophenyl |
| Propyl | 5-Chloro-2-methoxyphenyl |
| Propyl | 3-Trifluoromethylphenyl |
| Propyl | 3,4-Dichlorophenyl |
| Allyl | 2,5-Dichlorophenyl |
| Allyl | 3-Bromophenyl |
| Propyl | 3-Bromophenyl |
| Propyl | 3-Bromo-4-methylphenyl |
| Methyl | 3-Bromo-4-fluorophenyl |
| Allyl | 3-Bromo-4-fluorophenyl |
| Propyl | 3-Bromo-4-fluorophenyl |
| Methyl | 3-Iodophenyl |
| Allyl | 3-Iodophenyl |
| Propyl | 3-Iodophenyl |
| Propyl | 3-Bromo-4-fluorophenyl |
| Methyl | 3-Bromo-4-fluorophenyl |
| Allyl | 3-Bromo-4-fluorophenyl |
| Propyl | 3-Bromo-4-fluorophenyl |
| Methyl | 3-Iodophenyl |
| Ethyl | 3-Iodophenyl |
| Allyl | 3-Iodophenyl |
| Propyl | 3-Iodophenyl |
| Propyl | 3-Iodo-4-methylphenyl |
| Methyl | 2-Thienyl |
| Propyl | 2-Thienyl |
| Allyl | 5-Methyl-2-thienyl |
| Propyl | 5-Methyl-2-thienyl. |

16. A compound of the formula

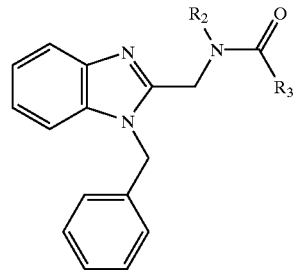

where $R_2$ and $R_3$ are defined in the following table:

| $R_2$ | $R_3$ |
|---|---|
| 2-Methylpropyl | Phenyl |
| 2-Methylpropyl | 3-Methylphenyl |
| 2-Methylpropyl | 4-Methylphenyl |
| 2-Methylpropyl | 2-Fluorophenyl |
| 2-Methylpropyl | 4-Ethylphenyl |
| 2-Methylpropyl | 3,4-Dimethylphenyl |
| 2-Methylpropyl | 2,5-Difluorophenyl |
| 2-Methylpropyl | 2,4-Difluorophenyl |
| 2-Methylpropyl | 1,3-Benzodioxol-5-yl |
| 2-Methylpropyl | 4-Bromophenyl |
| 2-Methylpropyl | 3-Bromo-4-methylphenyl |
| 2-Methylpropyl | 3-Chloro-4-methylphenyl |
| 2-Methylpropyl | 2,4,5-Trifluorophenyl. |

17. A compound of the formula

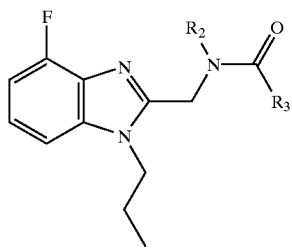

where $R_2$ and $R_3$ are defined in the following table:

| $R_2$ | $R_3$ |
|---|---|
| Propyl | 2-Fluorophenyl |
| Allyl | 5-Chloro-2-methoxyphenyl |
| Propyl | 5-Chloro-2-methoxyphenyl |
| Methyl | 2,5-Dichlorophenyl |
| Allyl | 2,5-Dichlorophenyl |
| Propyl | 2,5-Dichlorophenyl |
| Methyl | 3-Bromophenyl |
| Allyl | 3-Bromophenyl |
| Propyl | 3-Bromophenyl |
| Propyl | 3-Iodophenyl |
| 2-Methylpropyl | 2,3,6-Trifluorophenyl |
| 3-Methylbutyl | 2,3,6-Trifluorophenyl |
| 2-Methylpropyl | 3-Chloro-4-phenyl |
| 3-Methylbutyl | 3-Chloro-4-phenyl |
| 2-Methylpropyl | 2,4,5-Trifluorophenyl |
| 3-Methylbutyl | 2,4,5-Trifluorophenyl |
| 2-Methylpropyl | 2,6-Difluorophenyl |
| 3-Methylbutyl | 2,6-Difluorophenyl |
| Butyl | Phenyl |
| 2-Methylpropyl | Phenyl |
| Pentyl | Phenyl |
| 3-Methylbutyl | Phenyl |
| Butyl | 3-Methylphenyl |
| 2-Methylpropyl | 3-Methylphenyl |
| Pentyl | 3-Methylphenyl |
| 3-Methylbutyl | 3-Methylphenyl |
| 2-Methylpropyl | 4-Methylphenyl |
| 3-Methylbutyl | 4-Methylphenyl |
| Butyl | 3-Fluorophenyl |
| 2-Methylpropyl | 3-Fluorophenyl |
| Pentyl | 3-Fluorophenyl |
| 3-Methylbutyl | 3-Fluorophenyl |
| 2-Methylpropyl | 4-Fluorophenyl |
| 3-Methylbutyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 3,4-Dimethylphenyl |
| Butyl | 2-Chlorophenyl |
| 2-Methylpropyl | 2-Chlorophenyl |
| Pentyl | 2-Chlorophenyl |
| 3-Methylbutyl | 2-Chlorophenyl |
| Butyl | 3,4-Difluorophenyl |
| 2-Methylpropyl | 3,4-Difluorophenyl |
| Pentyl | 3,4-Difluorophenyl |
| 3-Methylbutyl | 3,4-Difluorophenyl |
| Butyl | 2,3-Difluorophenyl |
| 2-Methylpropyl | 2,3-Difluorophenyl |
| Pentyl | 2,3-Difluorophenyl |
| 3-Methylbutyl | 2,3-Difluorophenyl |
| Butyl | 2,5-Difluorophenyl |
| 2-Methylpropyl | 2,5-Difluorophenyl |
| Pentyl | 2,5-Difluorophenyl |
| 3-Methylbutyl | 2,5-Difluorophenyl |
| 2-Methylpropyl | 2,4-Difluorophenyl |
| 3-Methylbutyl | 2,4-Difluorophenyl |
| 2-Methylpropyl | 1,3-Benzodioxol-5-yl |
| 3-Methylbutyl | 1,3-Benzodioxol-5-yl |
| 3-Methylbutyl | 3-Iodo-4-methylphenyl |
| 2-Methylpropyl | 2-(2-Chlorophenyl)ethenyl |
| Butyl | 2-Thienyl |
| Pentyl | 2-Thienyl |
| 3-Methylbutyl | 2-Thienyl |
| Pentyl | 3-Thienyl |
| 3-Methylbutyl | 3-Thienyl |
| 3-Methylbutyl | Benzyl |
| Butyl | 5-Methyl-2-thienyl |
| 2-Methylpropyl | 5-Methyl-2-thienyl |
| Pentyl | 5-Methyl-2-thienyl |
| 3-Methylbutyl | 5-Methyl-2-thienyl |
| 3-Methylbutyl | 3-Fluorobenzyl |
| 3-Methylbutyl | 3-Methoxybenzyl. |

18. A compound of the formula

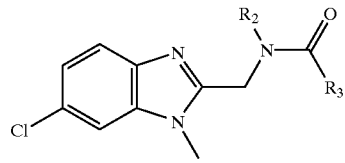

where $R_2$ and $R_3$ are defined in the following table:

| $R_2$ | $R_3$ |
|---|---|
| Propyl | 3-Iodophenyl |
| 2-Methylpropyl | 3-Chloro-4-fluorophenyl |
| 2-Methylpropyl | 3-Bromophenyl |
| 3-Methylbutyl | 3-Bromophenyl |
| 2-Methylpropyl | 3-Bromo-4-methylphenyl |
| 2-Methylpropyl | 3-Bromo-4-fluorophenyl |
| 3-Methylbutyl | 3-Bromo-4-fluorophenyl |
| 2-Methylpropyl | 3-Iodophenyl |
| 3-Methylbutyl | 3-Bromo-4-fluorophenyl |
| 2-Methylpropyl | Phenyl |
| 3-Methylbutyl | Phenyl |
| 2-Methylpropyl | 3-Methylphenyl |
| 3-Methylbutyl | 3-Methylphenyl |
| 2-Methylpropyl | 4-Methylphenyl |
| 2-Methylpropyl | 3-Fluorophenyl |
| 3-Methylbutyl | 3-Fluorophenyl |
| 2-Methylpropyl | 4-Fluorophenyl |
| 2-Methylpropyl | 2-Fluorophenyl |
| 3-Methylbutyl | 2-Fluorophenyl |
| 2-Methylpropyl | 3,4-Dimethylphenyl |
| 2-Methylpropyl | 3-Fluoro-4-methylphenyl |
| 2-Methylpropyl | 3-Chlorophenyl |
| 3-Methylbutyl | 3-Chlorophenyl |
| 2-Methylpropyl | 3-Iodo-4-methylphenyl |
| 2-Methylpropyl | 5-Methyl-2-thienyl |
| 3-Methylbutyl | 5-Methyl-2-thienyl |
| 3-Methylbutyl | 3-Fluorobenzyl |
| 2-Methylpropyl | 3-Chloro-4-methylphenyl |
| 2-Methylpropyl | 2,4,5-Trifluorophenyl |
| Butyl | 3,4-Dimethylphenyl |
| 2-Methylpropyl | 3,4-Dimethylphenyl |
| 3-Methylbutyl | 3,4-Dimethylphenyl |
| 3-Methylbutyl | 2,3-Dimethylphenyl |
| 2-Methylpropyl | 2,5-Dimethylphenyl |
| 3-Methylbutyl | 2,5-Dimethylphenyl |
| 2-Methylpropyl | 1,3-Benzodioxol-5-yl |
| 3-Methylbutyl | 3-Methoxybenzyl |
| Benzyl | 3-Chlorophenyl |
| Benzyl | 5-Chloro-2-methoxyphenyl |
| Benzyl | 3-Bromophenyl |
| Benzyl | 3-Iodophenyl. |

19. A compound of the formula

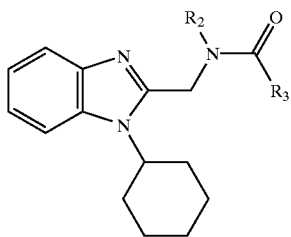

where $R_2$ and $R_3$ are defined in the following table:

| $R_2$ | $R_3$ |
|---|---|
| 2-Methylpropyl | Phenyl |
| Pentyl | Phenyl |
| 3-Methylbutyl | Phenyl |
| 3-Methylbutyl | 3-Methylphenyl |
| 2-Methylpropyl | 4-Methylphenyl |
| 2-Methylpropyl | 3-Fluorophenyl |
| 3-Methylbutyl | 3-Fluorophenyl |
| 2-Methylpropyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 3-Methoxyphenyl |
| 3-Methylbutyl | 3-Methoxyphenyl |
| 3-Methylbutyl | 4-Methoxyphenyl |
| 2-Methylpropyl | 3-Fluoro-4-methylphenyl |
| 3-Methylbutyl | 2-Fluoro-3-methylphenyl |
| Butyl | 3-Chlorophenyl |
| 2-Methylpropyl | 3-Chlorophenyl |
| Pentyl | 3-Chlorophenyl |
| 3-Methylbutyl | 3-Chlorophenyl |
| 2-Methylpropyl | 3,4-Difluorophenyl |
| 2-Methylpropyl | 2,3-Difluorophenyl |
| 3-Methylbutyl | 2,3-Difluorophenyl |
| 3-Methylbutyl | 2,5-Difluorophenyl |
| 2-Methylpropyl | 1,3-Benzodioxol-5-yl |
| 2-Methylpropyl | 1,3-Benzodioxol-5-yl |
| 3-Methylbutyl | 5-Chloro-2-methoxyphenyl |
| 3-Methylbutyl | 3-Bromophenyl |
| 2-Methylpropyl | 4-Bromophenyl |
| 2-Methylpropyl | 5-Methyl-2-thienyl |
| 3-Methylbutyl | 5-Methyl-2-thienyl |
| 3-Methylbutyl | 2,3,6-Trifluorophenyl. |

20. A compound of the formula

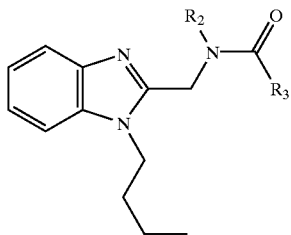

where $R_2$ and $R_3$ are defined in the following table:

| $R_2$ | $R_3$ |
|---|---|
| Butyl | Phenyl |
| 2-Methylpropyl | Phenyl |
| Pentyl | Phenyl |
| 3-Methylbutyl | Phenyl |
| Butyl | 3-Methylphenyl |
| 2-Methylpropyl | 3-Methylphenyl |
| Pentyl | 3-Methylphenyl |
| 3-Methylbutyl | 3-Methylphenyl |
| Butyl | 4-Methylphenyl |
| 2-Methylpropyl | 4-Methylphenyl |
| 3-Methylbutyl | 4-Methylphenyl |
| 3-Methylbutyl | 2-Methylphenyl |
| Butyl | 3-Fluorophenyl |
| 2-Methylpropyl | 3-Fluorophenyl |
| Pentyl | 3-Fluorophenyl |
| 3-Methylbutyl | 3-Fluorophenyl |
| 2-Methylpropyl | 4-Fluorophenyl |
| 3-Methylbutyl | 4-Fluorophenyl |
| Butyl | 2-Fluorophenyl |
| 2-Methylpropyl | 2-Fluorophenyl |
| Pentyl | 2-Fluorophenyl |
| 3-Methylbutyl | 2-Fluorophenyl |
| 2-Methylpropyl | 4-Ethylphenyl |
| Butyl | 3,4-Dimethylphenyl |
| 2-Methylpropyl | 3,4-Dimethylphenyl |
| 3-Methylbutyl | 3,4-Dimethylphenyl |
| 2-Methylpropyl | 2,4-Dimethylphenyl |
| Butyl | 3-Methoxyphenyl |
| 2-Methylpropyl | 3-Methoxyphenyl |
| Pentyl | 3-Methoxyphenyl |
| 3-Methylbutyl | 3-Methoxyphenyl |
| Butyl | 4-Methoxyphenyl |
| 2-Methylpropyl | 4-Methoxyphenyl |
| 3-Methylbutyl | 4-Methoxyphenyl |
| Pentyl | 2-Methoxyphenyl |
| 3-Methylbutyl | 2-Methoxyphenyl |
| Butyl | 3-Fluoro-4-methylphenyl |
| Pentyl | 3-Fluoro-4-methylphenyl |
| 3-Methylbutyl | 3-Fluoro-4-methylphenyl |
| 3-Methylbutyl | 3-Fluoro-2-methylphenyl |
| Butyl | 2-Fluoro-3-methylphenyl |
| 2-Methylpropyl | 2-Fluoro-3-methylphenyl |
| Pentyl | 2-Fluoro-3-methylphenyl |
| 3-Methylbutyl | 2-Fluoro-3-methylphenyl |
| Butyl | 3-Chlorophenyl |
| 2-Methylpropyl | 3-Chlorophenyl |
| Pentyl | 3-Chlorophenyl |
| 3-Methylbutyl | 3-Chlorophenyl |
| 2-Methylpropyl | 4-Chlorophenyl |
| Pentyl | 4-Chlorophenyl |
| 3-Methylbutyl | 4-Chlorophenyl |
| Butyl | 2-Chlorophenyl |
| 2-Methylpropyl | 2-Chlorophenyl |
| Pentyl | 2-Chlorophenyl |
| 3-Methylbutyl | 2-Chlorophenyl |
| Butyl | 3,4-Difluorophenyl |
| 2-Methylpropyl | 3,4-Difluorophenyl |
| Pentyl | 3,4-Difluorophenyl |
| 3-Methylbutyl | 3,4-Difluorophenyl |
| Butyl | 2,3-Difluorophenyl |
| 2-Methylpropyl | 2,3-Difluorophenyl |
| Pentyl | 2,3-Difluorophenyl |
| 3-Methylbutyl | 2,3-Difluorophenyl |
| Butyl | 2,5-Difluorophenyl |
| 2-Methylpropyl | 2,5-Difluorophenyl |
| Pentyl | 2,5-Difluorophenyl |
| 3-Methylbutyl | 2,5-Difluorophenyl |
| Butyl | 2,4-Difluorophenyl |
| 2-Methylpropyl | 2,4-Difluorophenyl |
| Pentyl | 2,4-Difluorophenyl |
| 3-Methylbutyl | 2,4-Difluorophenyl |
| 2-Methylpropyl | 3-Ethoxyphenyl |
| 3-Methylbutyl | 3-Ethoxyphenyl |
| Butyl | 1,3-Benzodioxol-5-yl |
| 2-Methylpropyl | 1,3-Benzodioxol-5-yl |
| Pentyl | 1,3-Benzodioxol-5-yl |
| 3-Methylbutyl | 1,3-Benzodioxol-5-yl |
| Butyl | 4-Methylthiophenyl |
| 2-Methylpropyl | 4-Methylthiophenyl |
| 3-Methylbutyl | 3-Fluoro-4-methoxyphenyl |
| Butyl | 3-Chloro-4-fluorophenyl |
| 2-Methylpropyl | 3-Chloro-4-fluorophenyl |
| 3-Methylbutyl | 3-Chloro-4-fluorophenyl |
| 3-Methylbutyl | 3-Chloro-4-methoxyphenyl |

-continued

| $R_2$ | $R_3$ |
|---|---|
| Pentyl | 5-Chloro-2-methoxyphenyl |
| 3-Methylbutyl | 5-Chloro-2-methoxyphenyl |
| 2-Methylpropyl | 3,4-Dichlorophenyl |
| 3-Methylbutyl | 3,4-Dichlorophenyl |
| Butyl | 2,5-Dichlorophenyl |
| 2-Methylpropyl | 2,5-Dichlorophenyl |
| Pentyl | 2,5-Dichlorophenyl |
| 3-Methylbutyl | 2,5-Dichlorophenyl |
| 2-Methylpropyl | 2,4-Dichlorophenyl |
| 3-Methylbutyl | 2,4-Dichlorophenyl |
| Butyl | 3-Bromophenyl |
| 2-Methylpropyl | 3-Bromophenyl |
| Pentyl | 3-Bromophenyl |
| 3-Methylbutyl | 3-Bromophenyl |
| 2-Methylpropyl | 4-Bromophenyl |
| 3-Methylbutyl | 4-Bromophenyl |
| 3-Methylbutyl | 2-Bromophenyl |
| 3-Methylbutyl | 3-Bromo-4-methylphenyl |
| Butyl | 3-Bromo-4-fluorophenyl |
| 2-Methylpropyl | 3-Bromo-4-fluorophenyl |
| Pentyl | 3-Bromo-4-fluorophenyl |
| 3-Methylbutyl | 3-Bromo-4-fluorophenyl |
| Butyl | 3-Iodophenyl |
| 2-Methylpropyl | 3-Iodophenyl |
| Pentyl | 3-Iodophenyl |
| 3-Methylbutyl | 3-Iodophenyl |
| Butyl | 5-Methyl-2-thienyl |
| 2-Methylpropyl | 5-Methyl-2-thienyl |
| Pentyl | 5-Methyl-2-thienyl |
| 3-Methylbutyl | 5-Methyl-2-thienyl |
| 3-Methylbutyl | 3-Fluorobenzyl |
| 3-Methylbutyl | 3-Methoxybenzyl |
| 3-Methylbutyl | 2-Methoxybenzyl |
| 2-Methylpropyl | 2,4,6-Trifluorophenyl |
| Butyl | 2,3,6-Trifluorophenyl |
| 2-Methylpropyl | 2,3,6-Trifluorophenyl |
| Pentyl | 2,3,6-Trifluorophenyl |
| 3-Methylbutyl | 2,3,6-Trifluorophenyl |
| 3-Methylbutyl | 2,5-Dimethyl-3-furyl |
| Butyl | 4,5-Dimethyl-2-furyl |
| 2-Methylpropyl | 4,5-Dimethyl-2-furyl |
| Pentyl | 4,5-Dimethyl-2-furyl |
| 3-Methylbutyl | 4,5-Dimethyl-2-furyl |
| 2-Methylpropyl | 2-(3-Thienyl)ethenyl |
| Pentyl | 3-Chloro-2-thienyl |
| 3-Methylbutyl | 3-Chloro-2-thienyl |
| 2-Methylpropyl | 5-Methylthio-2-thienyl |
| 3-Methylbutyl | 5-Methylthio-2-thienyl |
| Butyl | 3-Chloro-4-methylphenyl |
| 2-Methylpropyl | 3-Chloro-4-methylphenyl |
| 3-Methylbutyl | 3-Chloro-4-methylphenyl |
| 2-Methylpropyl | 2,4,5-Trichlorophenyl. |

21. A compound of the formula

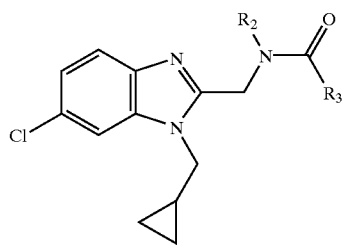

where $R_2$ and $R_3$ are defined in the following table:

| $R_2$ | $R_3$ |
|---|---|
| Methyl | Phenyl |
| Allyl | Phenyl |

-continued

| $R_2$ | $R_3$ |
|---|---|
| Propyl | Phenyl |
| Methyl | 3-Methylphenyl |
| Allyl | 3-Methylphenyl |
| Propyl | 3-Methylphenyl |
| Propyl | 4-Methylphenyl |
| Methyl | 3-Fluorophenyl |
| Allyl | 3-Fluorophenyl |
| Propyl | 3-Fluorophenyl |
| Propyl | 4-fluorophenyl |
| Methyl | 2-fluorophenyl |
| Allyl | 2-fluorophenyl |
| Propyl | 2-Fluorophenyl |
| Propyl | 3,4-Dimethylphenyl |
| Propyl | 3-Methoxyphenyl |
| Propyl | 3-Fluoro-4-methylphenyl |
| Allyl | 3-Chlorophenyl |
| Propyl | 3-Chlorophenyl |
| Propyl | 2-Chlorophenyl |
| Propyl | 3,4-Difluorophenyl |
| Methyl | 2,3-Difluorophenyl |
| Propyl | 2,3-Difluorophenyl |
| Methyl | 2,5-Difluorophenyl |
| Allyl | 2,5-Difluorophenyl |
| Propyl | 2,5-Difluorophenyl |
| Propyl | 2,4-Difluorophenyl |
| Propyl | 1,3-Benzodioxol-5-yl |
| Propyl | 3-Chloro-4-fluorophenyl |
| Methyl | 5-Chloro-2-methoxyphenyl |
| Methyl | 3-Trifluoromethylphenyl |
| Propyl | 3-Trifluoromethylphenyl |
| Methyl | 2,5-Dichlorophenyl |
| Propyl | 2,5-Dichlorophenyl |
| Methyl | 3-Bromophenyl |
| Allyl | 3-Bromophenyl |
| Propyl | 3-Bromophenyl |
| Propyl | 3-Bromo-4-methylphenyl |
| Methyl | 3-Bromo-4-fluorophenyl |
| Allyl | 3-Bromo-4-fluorophenyl |
| Propyl | 3-Bromo-4-fluorophenyl |
| Methyl | 3-Iodophenyl |
| Ethyl | 3-Iodophenyl |
| Allyl | 3-Iodophenyl |
| Propyl | 3-Iodophenyl |
| Propyl | 5-Methyl-2-thienyl |
| Propyl | 3-Fluorobenzyl |
| Methyl | 5-Ethoxy-2-thienyl. |

22. A compound of the formula

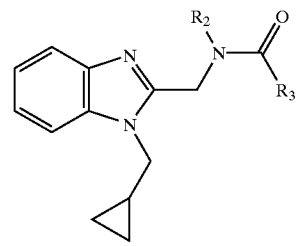

where $R_2$ and $R_3$ are defined in the following table:

| $R_2$ | $R_3$ |
|---|---|
| Propyl | 3-Chloro-4-methylphenyl |
| Propyl | 2,4,5-Trifluorophenyl |
| Benzyl | Phenyl |
| Benzyl | 3-Fluorophenyl |
| Benzyl | 4-Fluorophenyl |
| Benzyl | 2-Fluorophenyl |
| Benzyl | 3,4-Dimethylphenyl |

-continued

| R₂ | R₃ |
|---|---|
| Benzyl | 3,5-Dimethylphenyl |
| Benzyl | 2,3-Dimethylphenyl |
| Benzyl | 2,5-Dimethylphenyl |
| Benzyl | 2,4-Dimethylphenyl |
| Benzyl | 3-Methoxyphenyl |
| Benzyl | 2-Methoxyphenyl |
| Benzyl | 3-Fluoro-4-methylphenyl |
| Benzyl | 5-Fluoro-2-methylphenyl |
| Benzyl | 3-Chlorophenyl |
| Benzyl | 4-Chlorophenyl |
| Benzyl | 2-Chlorophenyl |
| Benzyl | 3,4-Difluorophenyl |
| Benzyl | 2,3-Difluorophenyl |
| Benzyl | 2,5-Difluorophenyl |
| Benzyl | 2,4-Difluorophenyl |
| Benzyl | 3-Ethoxyphenyl |
| Benzyl | 1,3-Benzodioxol-5-yl |
| Benzyl | 4-Chloro-3-methylphenyl |
| Benzyl | 3-Chloro-4-fluorophenyl |
| Benzyl | 3,4,5-Trifluorophenyl |
| Benzyl | 2,5-Dimethoxyphenyl |
| Benzyl | 5-Chloro-2-methoxyphenyl |
| Benzyl | 4-Chloro-2-methoxyphenyl |
| Benzyl | 3-Trifluoromethylphenyl |
| Benzyl | 2-Trifluoromethylphenyl |
| Benzyl | 3,4-Dichlorophenyl |
| Benzyl | 2,3-Dichlorophenyl |
| Benzyl | 2,5-Dichlorophenyl |
| Benzyl | 2,4-Dichlorophenyl |
| Benzyl | 3-Bromophenyl |
| Benzyl | 2-Bromophenyl |
| Benzyl | 3-Bromo-4-fluorophenyl |
| Benzyl | 3-Iodophenyl |
| Benzyl | 2-Methoxyphenyl |
| Benzyl | 2,5-Dimethylpyrrol-3-yl |
| Benzyl | 2,3,6-Trifluorphenyl |
| 3-Methylbutyl | 2-Chloro-6-fluorophenyl |
| 3-Methylbutyl | 3-(Methylaminomethyl)phenyl |
| 3-Methylbutyl | 3-(Ethylaminomethyl)phenyl |
| 3-Methylbutyl | 3-(allylaminomethyl)phenyl |
| 3-Methylbutyl | 3-(propylaminomethyl)phenyl |
| 3-Methylbutyl | 3-[(Cyclopropylmethyl)aminomethyl]phenyl |
| 3-Methylbutyl | 3-(butylaminomethyl)phenyl |
| 3-Methylbutyl | 3-[(2-Methylpropyl)aminomethyl]phenyl |
| 3-Methylbutyl | 3-(Pentylaminomethyl)phenyl |
| 3-Methylbutyl | 3-[(3-Methylbutyl)aminomethyl]phenyl |
| 3-Methylbutyl | 3-[(2-Methylbutyl)aminomethyl]phenyl |
| 3-Methylbutyl | 3-(Hexylaminomethyl)phenyl |
| 3-Methylbutyl | 3-(Cyclopropylaminomethyl)phenyl |
| 3-Methylbutyl | 3-[(1-Methylethyl)aminomethyl]phenyl |
| 3-Methylbutyl | 3-(Cyclobutylaminomethyl)phenyl |
| 3-Methylbutyl | 3-[(1-Methylpropyl)aminomethyl]phenyl |
| 3-Methylbutyl | 3-[(1,1-Dimethylethyl)aminomethyl]phenyl |
| 3-Methylbutyl | 3-(Cyclopentylaminomethyl)phenyl |
| 3-Methylbutyl | 3-[(1-Methylbutyl)aminomethyl]phenyl |
| 3-Methylbutyl | 3-[(1,2-Dimethylpropyl)aminomethyl]phenyl |
| 3-Methylbutyl | 3-[(1-Ethylpropyl) aminomethyl]phenyl |
| 3-Methylbutyl | 3-[(1,1-Dimethylpropyl)aminomethyl]phenyl |
| 3-Methylbutyl | 3-(Cyclohexylaminomethyl)phenyl |
| 3-Methylbutyl | 3-(Piperidylmethyl)phenyl |
| 3-Methylbutyl | 3-(Morpholin-4-ylmethyl)phenyl |
| 3-Methylbutyl | 3-(Azaperhydroepinylmethyl)phenyl |
| 3-Methylbutyl | 3-(Azaperhydroocinylmethyl)phenyl |
| 3-Methylbutyl | 3-(2-1,2,3,4-Tetrahydroisoquinolinylmethyl)phenyl |
| 3-Methylbutyl | 3-(Methylpropylaminomethyl)phenyl |
| 3-Methylbutyl | 3-(i-propylethylaminomethyl)phenyl |
| 3-Methylbutyl | 3-(Diethylaminomethyl)phenyl |
| 3-Methylbutyl | 3-(Butylethylaminomethyl)phenyl |
| 3-Methylbutyl | 3-[(Cyclopropylmethyl)-propylaminomethyl]phenyl |
| 3-Methylbutyl | 3-(Hexylmethylaminomethyl)phenyl |
| 3-Methylbutyl | 3-(Dibutylaminomethyl)phenyl |
| 3-Methylbutyl | 3-[(1-methylethyl)methylaminomethyl]phenyl |
| 3-Methylbutyl | 3-[(2-Methylpiperidyl)methyl]phenyl |
| 3-Methylbutyl | 3-[Ethyl(2-Methylprop-2-enyl)aminomethyl]phenyl |

-continued

| R₂ | R₃ |
|---|---|
| 3-Methylbutyl | 3-[(2-Ethylpiperidyl)methyl]phenyl |
| 3-Methylbutyl | 3-(Cyclohexylethylaminomethyl )phenyl |
| 3-Methylbutyl | 3-[bis(2-Methoxyethyl)aminomethyl]phenyl |
| 3-Methylbutyl | 3-[(3,3,5-Trimethylazaperhydroepinyl)methyl]phenyl |
| 3-Methylbutyl | 3-[(8-Aza-1,4-dioxaspiro[4.5]dec-8-yl)methyl]phenyl |
| 3-Methylbutyl | 3-(Dipentylaminomethyl)phenyl |
| 3-Methylbutyl | 3-(Dihexylaminomethyl)phenyl. |

23. A compound of the formula

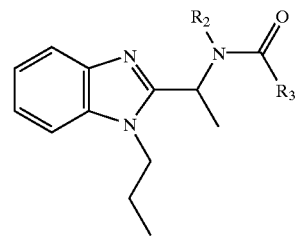

where R₂ is 2-Methylpropyl and R₃ is 2-(4-Chlorophenyl)ethenyl.

24. A compound of the formula

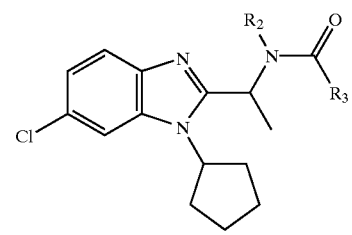

where R₂ and R₃ are defined in the following table:

| R₂ | R₃ |
|---|---|
| Methyl | 3-Thienyl |
| i-Propyl | 3-Methyl-2-thienyl |
| Methyl | 4-Methylbenzyl |
| Methyl | 2-Methylbenzyl |
| Methyl | 3-Fluorobenzyl. |

25. A compound of the formula

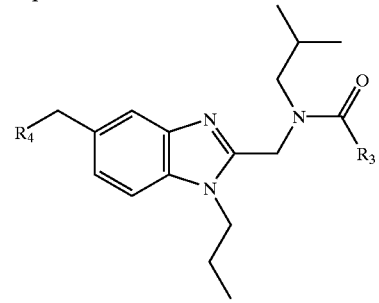

where R₂ and R₃ are defined in the following table:

| R₄ | R₃ |
|---|---|
| 3-Pyrrolinyl | 2,5-Difluorophenyl |
| 3-Pyrrolinyl | 3-Fluorophenyl |

-continued

| R₄ | R₃ |
|---|---|
| Pyrrolidinyl | 2,5-Difluorophenyl |
| Pyrrolidinyl | 3-Fluorophenyl |
| 1,2,5,6-Tetrahydropyridyl | 2,5-Difluorophenyl |
| 1,2,5,6-Tetrahydropyridyl | 3-Fluorophenyl |
| Piperidyl | 2,5-Difluorophenyl |
| Piperidyl | 3-Fluorophenyl |
| Morpholinyl | 2,5-Difluorophenyl |
| Morpholinyl | 3-Fluorophenyl |
| 4-Methylpiperidyl | 2,5-Difluorophenyl |
| 4-Methylpiperidyl | 3-Fluorophenyl |
| Azaperhydroepinyl | 2,5-Difluorophenyl |
| AzaperhydroEpinyl | 3-Fluorophenyl |
| 1,4-Thiazaperhydroin-4-yl | 2,5-Difluorophenyl |
| 1,4-Thiazaperhydroin-4-yl | 3-Fluorophenyl |
| 3,3-dimethylpiperidyl | 2,5-Difluorophenyl |
| 3,3-dimethylpiperidyl | 3-Fluorophenyl |
| Azaperhydroocinyl | 2,5-Difluorophenyl |
| AzaperhydroOcinyl | 3-Fluorophenyl |
| 2-(1,2,3,4-Tetrahydroisoquinolyl) | 2,5-Difluorophenyl |
| 2-(1,2,3,4-Tetrahydroisoquinolyl) | 3-Fluorophenyl |
| Methylprop-2-enylamino | 2,5-Difluorophenyl |
| Methylprop-2-enylamino | 3-Fluorophenyl |
| Diethylamino | 2,5-Difluorophenyl |
| Diethylamino | 3-Fluorophenyl |
| Methylpropylamino | 2,5-Difluorophenyl |
| MethylpropylAmino | 3-Fluorophenyl |
| Butylmethylamino | 2,5-Difluorophenyl |
| ButylmethylAmino | 3-Fluorophenyl |
| i-Propylethylamino | 2,5-Difluorophenyl |
| i-Propylethylamino | 3-Fluorophenyl |
| Diallylamino | 2,5-Difluorophenyl |
| Diallylamino | 3-Fluorophenyl |
| Dipropylamino | 2,5-Difluorophenyl |
| Dipropylamino | 3-Fluorophenyl |
| ButylethylAmino | 2,5-Difluorophenyl |
| Butyl ethylAmino | 3-Fluorophenyl |
| (Cyclopropylmethyl) propylamino | 2,5-Difluorophenyl |
| (Cyclopropylmethyl) propylamino | 3-Fluorophenyl |
| Hexylmethylamino | 2,5-Difluorophenyl |
| HexylmethylAmino | 3-Fluorophenyl |
| Dibutylamino | 2,5-Difluorophenyl |
| Dibutylamino | 3-Fluorophenyl |
| Methylamino | 2,5-Difluorophenyl |
| Methylamino | 3-Fluorophenyl |
| E thylamino | 2,5-Difluorophenyl |
| Ethylamino | 3-Fluorophenyl |
| Allylamino | 2,5-Difluorophenyl |
| Allylamino | 3-Fluorophenyl |
| Propylamino | 2,5-Difluorophenyl |
| Propylamino | 3-Fluorophenyl |
| (Cyclopropylmethyl)amino | 2,5-Difluorophenyl |
| (Cyclopropylmethyl)amino | 3-Fluorophenyl |
| Butyl | 2,5-Difluorophenyl |
| Butyl | 3-Fluorophenyl |
| (2-Methylpropyl)amino | 2,5-Difluorophenyl |
| (2-Methylpropyl)amino | 3-Fluorophenyl |
| Pentylamino | 2,5-Difluorophenyl |
| Pentylamino | 3-Fluorophenyl |
| (3-Methylbutyl)amino | 2,5-Difluorophenyl |
| (3-Methylbutyl)amino | 3-Fluorophenyl |
| (2-Methylbutyl)amino | 2,5-Difluorophenyl |
| (2-Methylbutyl)amino | 3-Fluorophenyl |
| Hexylamino | 2,5-Difluorophenyl |
| Hexylamino | 3-Fluorophenyl |
| [2-(Dimethylamino)ethyl]amino | 2,5-Difluorophenyl |
| [2-(Dimethylamino)ethyl]amino | 3-Fluorophenyl |
| [3-(Dimethylamino)propyl]amino | 2,5-Difluorophenyl |
| [3-(Dimethylamino)propyl]amino | 3-Fluorophenyl |
| (2-Pyrrolidinylethyl)amino | 2,5-Difluorophenyl |
| (2-Pyrrolidinylethyl)amino | 3-Fluorophenyl |
| [2-(Diethylamino)ethyl]amino | 2,5-Difluorophenyl |
| [2-(Diethylamino)ethyl]amino | 3-Fluorophenyl |
| (2-Piperidylethyl)amino | 2,5-Difluorophenyl |
| (2-Piperidylethyl)amino | 3-Fluorophenyl |
| [2-(1-Methylpyrrolidin-2-yl) ethyl]amino | 2,5-Difluorophenyl |

-continued

| R₄ | R₃ |
|---|---|
| [2-(1-Methylpyrrolidin-2-yl) ethyl]amino | 3-Fluorophenyl |
| [2-(Diethylamino)propyl]amino | 2,5-Difluorophenyl |
| [2-(Diethylamino)propyl]amino | 3-Fluorophenyl |
| (2-Morpholin-4-ylethyl)amino | 2,5-Difluorophenyl |
| (2-Morpholin-4-ylethyl)amino | 3-Fluorophenyl |
| (3-Morpholin-4-ylpropyl)amino | 2,5-Difluorophenyl |
| (3-Morpholin-4-ylpropyl)amino | 3-Fluorophenyl |
| [3-(2-Methylpiperidyl)propyl]amino | 2,5-Difluorophenyl |
| [3-(2-Methylpiperidyl)propyl]amino | 3-Fluorophenyl |
| [3-(2-Oxopyrrolidinyl)propyl]amino | 2,5-Difluorophenyl |
| [3-(2-Oxopyrrolidinyl)propyl]amino | 3-Fluorophenyl. |

26. A compound of the formula

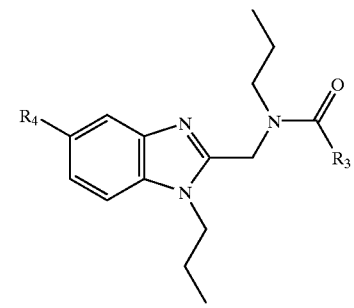

where R₂ and R₃ are defined in the following table:

| R₄ | R₃ |
|---|---|
| Pyrrolidinyl | 2,5-Difluorophenyl |
| Pyrrolidinyl | 3-Fluorophenyl |
| 1,2,5,6-Tetrahydropyridyl | 2,5-Difluorophenyl |
| 1,2,5,6-Tetrahydropyridyl | 3-Fluorophenyl |
| Piperidyl | 2,5-Difluorophenyl |
| Morpholinyl | 3-Fluorophenyl |
| 4-Methylpiperidyl | 2,5-Difluorophenyl |
| 4-Methylpiperidyl | 3-Fluorophenyl |
| AzaperhydroEpinyl | 3-Fluorophenyl |
| 1,4-Thiazaperhydroin-4-yl | 3-Fluorophenyl |
| 3,3-dimethylpiperidyl | 2,5-Difluorophenyl |
| 3,3-dimethylpiperidyl | 3-Fluorophenyl |
| Azaperhydroocinyl | 2,5-Difluorophenyl |
| Azaperhydrocinyl | 3-Fluorophenyl |
| 2-(1,2,3,4-Tetrahydroisoquinolyl) | 2,5-Difluorophenyl |
| 2-(1,2,3,4-Tetrahydroisoquinolyl) | 3-Fluorophenyl |
| Methylprop-2-enylamino | 2,5-Difluorophenyl |
| Methylprop-2-enylamino | 3-Fluorophenyl |
| Diethylamino | 3-Fluorophenyl |
| Methylpropylamino | 2,5-Difluorophenyl |
| MethylpropylAmino | 3-Fluorophenyl |
| Butylmethylamino | 2,5-Difluorophenyl |
| ButylmethylAmino | 3-Fluorophenyl |
| i-Propylethylamino | 2,5-Difluorophenyl |
| i-Propylethylamino | 3-Fluorophenyl |
| Diallylamino | 2,5-Difluorophenyl |
| Diallylamino | 3-Fluorophenyl |
| Dipropylamino | 2,5-Difluorophenyl |
| Dipropylamino | 3-Fluorophenyl |
| ButylethylAmino | 2,5-Difluorophenyl |
| ButylethylAmino | 3-Fluorophenyl |
| (Cyclopropylmethyl)propylamino | 2,5-Difluorophenyl |
| (Cyclopropylmethyl)propylamino | 3-Fluorophenyl |
| HexylmethylAmino | 2,5-Difluorophenyl |
| HexylmethylAmino | 3-Fluorophenyl |
| Dibutylamino | 2,5-Difluorophenyl |
| Dibutylamino | 3-Fluorophenyl |
| Methylamino | 3-Fluorophenyl |

-continued

| R₄ | R₃ |
|---|---|
| Ethylamino | 3-Fluorophenyl |
| Allylamino | 2,5-Difluorophenyl |
| Allylamino | 3-Fluorophenyl |
| Propylamino | 2,5-Difluorophenyl |
| Propylamino | 3-Fluorophenyl |
| (Cyclopropylmethyl)amino | 2,5-Difluorophenyl |
| (Cyclopropylmethyl)amino | 3-Fluorophenyl |
| Butyl | 2,5-Difluorophenyl |
| Butyl | 3-Fluorophenyl |
| (2-Methylpropyl)amino | 2,5-Difluorophenyl |
| (2-Methylpropyl)amino | 3-Fluorophenyl |
| Pentylamino | 2,5-Difluorophenyl |
| Pentylamino | 3-Fluorophenyl |
| (3-Methylbutyl)amino | 2,5-Difluorophenyl |
| (3-Methylbutyl)amino | 3-Fluorophenyl |
| (2-Methylbutyl)amino | 3-Fluorophenyl |
| Hexylamino | 2,5-Difluorophenyl |
| Hexylamino | 3-Fluorophenyl |
| (2-Pyrrolidinylethyl)amino | 3-Fluorophenyl |
| [2-(Diethylamino)ethyl]amino | 2,5-Difluorophenyl |
| [2-(Diethylamino)ethyl]amino | 3-Fluorophenyl |
| (2-Piperidylethyl)amino | 2,5-Difluorophenyl |
| (2-Piperidylethyl)amino | 3-Fluorophenyl |
| [2-(1-Methylpyrrolidin-2-yl)ethyl]amino | 3-Fluorophenyl |
| [2-(Diethylamino)propyl]amino | 2,5-Difluorophenyl |
| [2-(Diethylamino)propyl]amino | 3-Fluorophenyl |
| (2-Morpholin-4-ylethyl)amino | 2,5-Difluorophenyl |
| (2-Morpholin-4-ylethyl)amino | 3-Fluorophenyl |
| (3-Morpholin-4-ylpropyl)amino | 2,5-Difluorophenyl |
| (3-Morpholin-4-ylpropyl)amino | 3-Fluorophenyl |
| [3-(2-Methylpiperidyl)propyl]amino | 2,5-Difluorophenyl |
| [3-(2-Methylpiperidyl)propyl]amino | 3-Fluorophenyl |
| [3-(2-Oxopyrrolidinyl)propyl]amino | 2,5-Difluorophenyl |
| [3-(2-Oxopyrrolidinyl)propyl]amino | 3-Fluorophenyl. |

27. A compound of the formula

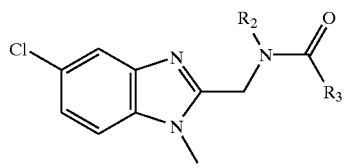

where $R_2$ and $R_3$ are defined in the following table:

| R₂ | R₃ |
|---|---|
| 3-Methylbutyl | 3-Chlorophenyl |
| 3-Methylbutyl | 3-Trifluoromethylphenyl |
| Butyl | 3-Broinophenyl |
| 2-Methylpropyl | 3-Bromophenyl |
| 3-Methylbutyl | 3-Bromophenyl. |

28. A compound of the formula

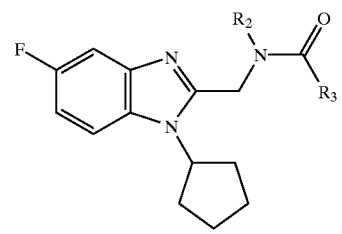

where $R_2$ and $R_3$ are defined in the following table:

| R₂ | R₃ |
|---|---|
| Butyl | 2,5-Dimethoxyphenyl |
| 2-Methylpropyl | 2,5-Dimethoxyphenyl |
| 3-Methylbutyl | 2,5-Dimethoxyphenyl |
| Butyl | 3-Chloro-4-methoxyphenyl |
| 2-Methylpropyl | 3-Chloro-4-methoxyphenyl |
| 3-Methylbutyl | 3-Chloro-4-methoxyphenyl |
| Butyl | 5-Chloro-2-methoxyphenyl |
| 2-Methylpropyl | 5-Chloro-2-methoxyphenyl |
| 3-Methylbutyl | 5-Chloro-2-methoxyphenyl |
| 2-Methylpropyl | 4-Chloro-2-methoxyphenyl |
| Butyl | 3-Trifluoromethylphenyl |
| 2-Methylpropyl | 3-Trifluoromethylphenyl |
| 3-Methylbutyl | 3-Trifluoromethylphenyl |
| Butyl | 2-Trifluoromethylphenyl |
| 3-Methylbutyl | 2-Trifluoromethylphenyl |
| Butyl | 3,4-Dichlorophenyl |
| 2-Methylpropyl | 3,4-Dichlorophenyl |
| 3-Methylbutyl | 3,4-Dichlorophenyl |
| Butyl | 2,5-Dichlorophenyl |
| 2-Methylpropyl | 2,5-Dichlorophenyl |
| Pentyl | 2,5-Dichlorophenyl |
| 3-Methylbutyl | 2,5-Dichlorophenyl |
| Butyl | 2,4-Dichlorophenyl |
| 2-Methylpropyl | 2,4-Dichlorophenyl |
| 3-Methylbutyl | 2,4-Dichlorophenyl |
| Butyl | 3-Bromophenyl |
| 2-Methylpropyl | 3-Bromophenyl |
| Pentyl | 3-Bromophenyl |
| 3-Methylbutyl | 3-Bromophenyl |
| 2-Methylpropyl | 4-Bromophenyl |
| Butyl | 2-Bromophenyl |
| 2-Methylpropyl | 2-Bromophenyl |
| 3-Methylbutyl | 2-Bromophenyl |
| 2-Methylpropyl | 3-Phenoxyphenyl |
| 2-Methylpropyl | 4-Phenoxyphenyl |
| 2-Methylpropyl | 3-Bromo-4-methylphenyl |
| Pentyl | 3-Bromo-4-methylphenyl |
| 3-Methylbutyl | 3-Bromo-4-methylphenyl |
| Butyl | 3-Bromo-4-methylphenyl |
| 2-Methylpropyl | 3-Bromo-4-methylphenyl |
| Pentyl | 3-Bromo-4-methylphenyl |
| 3-Methylbutyl | 3-Bromo-4-methylphenyl |
| Butyl | 3-Iodophenyl |
| 2-Methylpropyl | 3-Iodophenyl |
| Pentyl | 3-Iodophenyl |
| 3-Methylbutyl | 3-Iodophenyl |
| 2-Methylpropyl | 4-Iodophenyl |
| 2-Methylpropyl | 2,3,5,6-Tetrafluorophenyl |
| 2-Methylpropyl | 2,4,6-Trifluorophenyl |
| Butyl | 2,3,6-Trifluorophenyl |
| 2-Methylpropyl | 2,3,6-Trifluorophenyl |
| Pentyl | 2,3,6-Trifluorophenyl |
| 3-Methylbutyl | 2,3,6-Trifluorophenyl |
| Butyl | 3-Chloro-6-fluorophenyl |
| Pentyl | 3-Chloro-6-fluorophenyl |
| 3-Methylbutyl | 3-Chloro-6-fluorophenyl |
| Butyl | 2-Fluoro-6-trifluoromethylphenyl. |

29. A compound of the formula

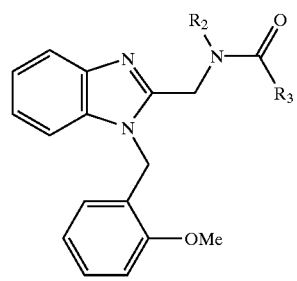

where $R_2$ is 2-methylpropyl and $R_3$ is 5-methyl-2-thienyl.

30. A compound of the formula

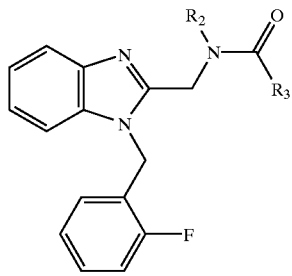

where $R_2$ and $R_3$ are defined in the following table:

| $R_2$ | $R_3$ |
|---|---|
| 2-Methylpropyl | 2,4-Difluorophenyl |
| 2-Methylpropyl | 2H-Benzo[d]1,3-dioxolane |
| 2-Methylpropyl | 3-Chloro-4-methylphenyl. |

31. A compound of the formula

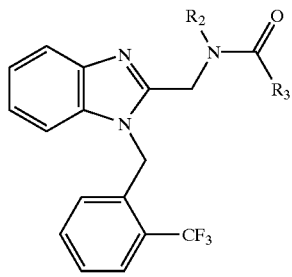

where $R_2$ is 2-methylpropyl and $R_3$ is 5-Methyl-2-thienyl.

32. A compound of the formula

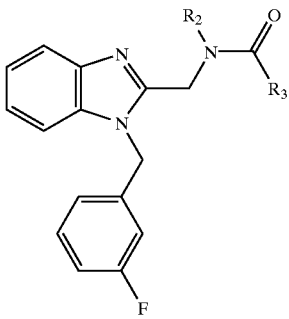

where $R_2$ and $R_3$ are defined in the following table:

| $R_2$ | $R_3$ |
|---|---|
| 2-Methylpropyl | 3-Chloro-4-methylphenyl |
| 2-Methylpropyl | 2,4-Difluorophenyl |
| 2-Methylpropyl | 2H-Benzo[d]1,3-dioxolane. |

33. A compound which is (3-fluoro-4-methylphenyl)-N-({1-[(2-methylphenyl)methyl]benzimidazol-2-yl}methyl-N-pentylcarboxamide.

* * * * *